US010130081B2

(12) United States Patent
McWhirter et al.

(10) Patent No.: US 10,130,081 B2
(45) Date of Patent: *Nov. 20, 2018

(54) HUMANIZED UNIVERSAL LIGHT CHAIN MICE

(75) Inventors: John McWhirter, Hastings-on-Hudson, NY (US); Lynn MacDonald, Harrison, NY (US); Sean Stevens, Del Mar, CA (US); Andrew J. Murphy, Croton-on-Hudson, NY (US); Margaret Karow, Santa Rosa, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 221 days.

This patent is subject to a terminal disclaimer.

(21) Appl. No.: 13/566,765

(22) Filed: Aug. 3, 2012

(65) Prior Publication Data

US 2013/0198879 A1    Aug. 1, 2013

Related U.S. Application Data

(60) Provisional application No. 61/515,374, filed on Aug. 5, 2011.

(51) Int. Cl.
| | |
|---|---|
| *A01K 67/027* | (2006.01) |
| *C12N 15/85* | (2006.01) |
| *C07K 16/00* | (2006.01) |
| *C12N 5/10* | (2006.01) |
| *C07K 16/28* | (2006.01) |
| *C07K 16/40* | (2006.01) |
| *C12N 9/64* | (2006.01) |

(52) U.S. Cl.
CPC .......... *A01K 67/0278* (2013.01); *C07K 16/00* (2013.01); *C07K 16/2833* (2013.01); *C07K 16/40* (2013.01); *C12N 9/6489* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/24* (2013.01); *C07K 2317/515* (2013.01); *C07K 2317/76* (2013.01); *C07K 2317/92* (2013.01); *C07K 2319/30* (2013.01); *C12N 2800/204* (2013.01); *C12N 2800/30* (2013.01)

(58) Field of Classification Search
CPC .......... A01K 67/0278; A01K 2227/105; A01K 2267/01; A01K 2217/15; A01K 2207/15; C12N 15/8509; C07K 16/00; C07K 2317/515; C07K 2317/24
USPC ................... 800/18, 4, 6; 435/326
See application file for complete search history.

(56) References Cited

U.S. PATENT DOCUMENTS

| | | | |
|---|---|---|---|
| 5,545,807 A | 8/1996 | Surani | |
| 5,574,205 A | 11/1996 | Kucherlapati et al. | |
| 5,667,988 A | 9/1997 | Barbas et al. | |
| 5,770,429 A | 6/1998 | Lonberg et al. | |
| 5,789,208 A | 8/1998 | Sharon | |
| 5,888,789 A | 3/1999 | Rodriguez | |
| 5,939,598 A | 8/1999 | Kucherlapati et al. | |
| 6,075,181 A | 6/2000 | Kucherlapati et al. | |
| 6,080,560 A | 6/2000 | Russell et al. | |
| 6,096,551 A | 8/2000 | Barbas et al. | |
| 6,114,598 A | 9/2000 | Kucherlapati et al. | |
| 6,139,835 A | 10/2000 | Kucherlapati et al. | |
| 6,150,584 A | 11/2000 | Kucherlapati et al. | |
| 6,162,963 A | 12/2000 | Kucherlapati | |
| 6,514,752 B1 | 2/2003 | Kucherlapati et al. | |
| 6,551,592 B2 | 4/2003 | Lindhofer et al. | |
| 6,586,251 B2 | 7/2003 | Economides et al. | |
| 6,596,541 B2 * | 7/2003 | Murphy et al. | 435/463 |
| 6,657,103 B1 | 12/2003 | Kucherlapati et al. | |
| 6,673,986 B1 | 1/2004 | Kucherlapati | |
| 6,713,610 B1 | 3/2004 | Kucherlapati et al. | |
| 6,914,128 B1 | 7/2005 | Salfeld et al. | |
| 6,998,514 B2 | 2/2006 | Bruggemann | |
| 7,052,873 B2 | 5/2006 | Tsuchiya | |

(Continued)

FOREIGN PATENT DOCUMENTS

| | | |
|---|---|---|
| CN | 1203922 A | 1/1999 |
| CN | 1277632 A | 12/2000 |

(Continued)

OTHER PUBLICATIONS

Green et al. (1994) Nat. Genetics., vol. 7, 13-21.*
Featherstone et al. (2010) J. Biol. Chem., vol. 285(13) 9327-9338.*
Han et al. (2009) Biol. Reprod., vol. 80, 1001-1008.*
Carter, P., Bispecific human IgG by design, Journal of Immunological Methods, 248(1-2):7-15 (2001).
Cascalho, M. et al., A quasi-monoclonal mouse, Science, 272(5268):1649-1652 (1996).

(Continued)

*Primary Examiner* — Anne Marie S Wehbe
(74) *Attorney, Agent, or Firm* — Choate, Hall & Stewart, LLP; Brenda Herschbach Jarrell; Stephanie L. Schonewald

(57) ABSTRACT

Mice, tissues, cells, and genetic material are provided that comprise a humanized heavy chain immunoglobulin locus, a humanized light chain locus that expresses a universal light chain, and a gene encoding an ADAM6 or ortholog or homolog or functional fragment thereof. Mice are provided that express humanized heavy chains comprising human variable domains, and that express humanized light chains comprising human variable domains wherein the light chains are derived from no more than one, or no more than two, light chain V and J or rearranged V/J sequences. Fertile male mice that express antibodies with universal light chains and humanized heavy chains are provided. Methods and compositions for making bispecific binding proteins are provided.

19 Claims, 46 Drawing Sheets

Specification includes a Sequence Listing.

(56) References Cited

U.S. PATENT DOCUMENTS

| | | |
|---|---|---|
| 7,064,244 B2 | 6/2006 | Jakobovits et al. |
| 7,067,284 B1 | 6/2006 | Barbas et al. |
| 7,084,260 B1 | 8/2006 | Lonberg et al. |
| 7,105,348 B2 | 9/2006 | Murphy et al. |
| 7,119,248 B1 | 10/2006 | Rajewsky et al. |
| 7,129,084 B2 | 10/2006 | Buelow et al. |
| 7,183,076 B2 | 2/2007 | Arathoon et al. |
| 7,262,028 B2 | 8/2007 | Van Berkel et al. |
| 7,435,871 B2 | 10/2008 | Green et al. |
| 7,491,392 B2 | 2/2009 | Gram et al. |
| 7,501,552 B2 | 3/2009 | Lonberg |
| 7,534,604 B2 | 5/2009 | Fandl et al. |
| 7,582,298 B2 | 9/2009 | Stevens et al. |
| 7,585,668 B2 | 9/2009 | Buelow et al. |
| 7,605,237 B2 | 10/2009 | Stevens et al. |
| 7,642,228 B2 | 1/2010 | Carter et al. |
| 7,704,498 B2 | 4/2010 | Gerritsen et al. |
| 7,879,985 B2 | 2/2011 | Urso et al. |
| 7,910,798 B2 | 3/2011 | Tanamachi |
| 8,158,419 B2 | 4/2012 | Lonberg |
| 8,502,018 B2 | 8/2013 | Murphy et al. |
| 8,592,562 B2 | 11/2013 | Kannan et al. |
| 8,642,835 B2 | 2/2014 | MacDonald et al. |
| 8,697,940 B2 | 4/2014 | Macdonald et al. |
| 8,771,960 B2 | 7/2014 | Breitling et al. |
| 9,248,182 B2 | 2/2016 | De Kruif et al. |
| 2002/0088016 A1 | 7/2002 | Bruggemann |
| 2002/0106628 A1 | 8/2002 | Economides et al. |
| 2002/0106629 A1 | 8/2002 | Murphy et al. |
| 2003/0017534 A1 | 1/2003 | Buelow et al. |
| 2003/0078385 A1 | 4/2003 | Arathoon et al. |
| 2003/0108925 A1 | 6/2003 | Dix |
| 2003/0109021 A1 | 6/2003 | Wu et al. |
| 2003/0138440 A1 | 7/2003 | Fang et al. |
| 2003/0217373 A1 | 11/2003 | Green et al. |
| 2004/0015880 A1 | 1/2004 | Floyd et al. |
| 2004/0018626 A1 | 1/2004 | Murphy |
| 2004/0052773 A1 | 3/2004 | Bogen et al. |
| 2004/0146991 A1 | 7/2004 | Tsuji et al. |
| 2005/0059082 A1 | 3/2005 | Breitling et al. |
| 2005/0153392 A1 | 7/2005 | Buelow et al. |
| 2005/0170398 A1 | 8/2005 | Van Berkel et al. |
| 2005/0229263 A1 | 10/2005 | Buelow |
| 2006/0015949 A1 | 1/2006 | Lonberg et al. |
| 2006/0015957 A1 | 1/2006 | Lonberg et al. |
| 2006/0015958 A1 | 1/2006 | Kuroiwa et al. |
| 2006/0021074 A1 | 1/2006 | Kellermann et al. |
| 2006/0026696 A1 | 2/2006 | Buelow et al. |
| 2006/0083747 A1 | 4/2006 | Winter et al. |
| 2006/0099207 A1 | 5/2006 | Wu et al. |
| 2006/0117398 A1 | 6/2006 | Buelow et al. |
| 2006/0153826 A1 | 7/2006 | Arnould et al. |
| 2006/0199204 A1 | 9/2006 | Dix |
| 2007/0009957 A1 | 1/2007 | Bowdish et al. |
| 2007/0280945 A1 | 12/2007 | Stevens et al. |
| 2008/0069822 A1 | 3/2008 | Jensen et al. |
| 2008/0196922 A1 | 8/2008 | Van Marion et al. |
| 2008/0267982 A1 | 10/2008 | Kiselev et al. |
| 2009/0083879 A1 | 3/2009 | Dhugga |
| 2009/0092582 A1 | 4/2009 | Bogin et al. |
| 2009/0093059 A1 | 4/2009 | Baszczynski et al. |
| 2009/0181855 A1 | 7/2009 | Vasquez et al. |
| 2009/0258392 A1 | 10/2009 | Gallo et al. |
| 2010/0069614 A1 | 3/2010 | Houtzager et al. |
| 2010/0146647 A1* | 6/2010 | Logtenberg et al. ............ 800/4 |
| 2010/0286374 A1 | 11/2010 | Kannan et al. |
| 2010/0310586 A1 | 12/2010 | Dolcetti et al. |
| 2010/0331527 A1 | 12/2010 | Davis et al. |
| 2011/0041370 A1 | 2/2011 | Saint et al. |
| 2011/0145937 A1 | 6/2011 | MacDonald et al. |
| 2011/0195454 A1 | 8/2011 | McWhirter et al. |
| 2011/0236378 A1 | 9/2011 | Green et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0070861 A1 | 3/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0222140 A1 | 8/2012 | Kuroiwa et al. |
| 2012/0272344 A1 | 10/2012 | Tanamachi et al. |
| 2012/0322108 A1 | 12/2012 | Macdonald et al. |
| 2013/0029125 A1 | 1/2013 | Tse et al. |
| 2013/0044257 A1 | 2/2013 | Chien et al. |
| 2013/0045492 A1 | 2/2013 | Babb et al. |
| 2013/0096020 A1 | 4/2013 | Throsby et al. |
| 2013/0096287 A1 | 4/2013 | Macdonald et al. |
| 2013/0145484 A1 | 6/2013 | Logtenberg et al. |
| 2013/0160153 A1 | 6/2013 | Macdonald et al. |
| 2013/0185821 A1 | 7/2013 | Babb et al. |
| 2013/0198879 A1 | 8/2013 | McWhirter et al. |
| 2013/0198880 A1 | 8/2013 | Babb et al. |
| 2013/0212719 A1 | 8/2013 | Macdonald et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0302836 A1 | 11/2013 | McWhirter et al. |
| 2013/0323235 A1 | 12/2013 | Craig et al. |
| 2013/0333057 A1 | 12/2013 | Macdonald et al. |
| 2014/0017228 A1 | 1/2014 | Macdonald et al. |
| 2014/0213773 A1 | 7/2014 | Macdonald et al. |
| 2014/0322756 A1 | 10/2014 | Arathoon et al. |
| 2015/0059009 A1 | 2/2015 | McWhirter et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2015/0313193 A1 | 11/2015 | McWhirter et al. |
| 2016/0219847 A1 | 8/2016 | McWhirter et al. |
| 2016/0238600 A1 | 8/2016 | Hoogenboom et al. |
| 2017/0369593 A1 | 12/2017 | McWhirter et al. |

FOREIGN PATENT DOCUMENTS

| | | |
|---|---|---|
| CN | 1468250 A | 1/2004 |
| CN | 1560081 A | 1/2005 |
| CN | 1852925 A | 10/2006 |
| CN | 101084317 A | 12/2007 |
| CN | 101506235 A | 8/2009 |
| CN | 101657535 A | 2/2010 |
| CN | 101962408 A | 2/2011 |
| CN | 101970491 A | 2/2011 |
| CN | 102292445 A | 12/2011 |
| EP | 0364096 A2 | 4/1990 |
| EP | 0695351 A1 | 2/1996 |
| EP | 0695351 B1 | 12/1999 |
| EP | 1439234 A1 | 7/2004 |
| EP | 1383891 B1 | 12/2005 |
| EP | 1662005 A1 | 5/2006 |
| EP | 1505148 B1 | 4/2009 |
| EP | 2050764 A1 | 4/2009 |
| EP | 1605058 B1 | 5/2009 |
| EP | 2147594 A1 | 1/2010 |
| EP | 1815001 B1 | 2/2011 |
| EP | 2427357 A1 | 3/2012 |
| EP | 2505654 A1 | 3/2012 |
| EP | 2501817 A1 | 9/2012 |
| EP | 2505654 A1 | 10/2012 |
| EP | 2517556 A2 | 10/2012 |
| EP | 2517557 A2 | 10/2012 |
| EP | 2556747 A2 | 2/2013 |
| EP | 2564695 A1 | 3/2013 |
| EP | 2582230 A1 | 4/2013 |
| GB | 2197322 A | 5/1988 |
| GB | 2197323 A | 5/1988 |
| GB | 2434578 A | 8/2007 |
| KR | 1020050042792 A | 5/2005 |
| RU | 010506 | 8/1999 |
| RU | 2434882 C2 | 11/2011 |
| TW | 201030143 A | 8/2010 |
| WO | WO-90/04036 A1 | 4/1990 |
| WO | WO-91/000906 A1 | 1/1991 |
| WO | WO-91/08216 A1 | 6/1991 |
| WO | WO-92/03918 A1 | 3/1992 |
| WO | WO-1994/02602 A1 | 2/1994 |

(56) References Cited

FOREIGN PATENT DOCUMENTS

| | | |
|---|---|---|
| WO | WO-94/04690 A1 | 3/1994 |
| WO | WO-94/12215 A1 | 6/1994 |
| WO | WO-94/25585 A1 | 11/1994 |
| WO | WO-1994/025585 A1 | 11/1994 |
| WO | WO-95/17085 A1 | 6/1995 |
| WO | WO-95/17500 A1 | 6/1995 |
| WO | WO-1995020042 A1 | 7/1995 |
| WO | WO-1995/028959 A1 | 11/1995 |
| WO | WO-97/13852 A1 | 4/1997 |
| WO | WO-1997/32603 A1 | 9/1997 |
| WO | WO-97/42313 A1 | 11/1997 |
| WO | WO-1998/24893 A2 | 6/1998 |
| WO | WO-98/39416 A1 | 9/1998 |
| WO | WO-98/46645 A2 | 10/1998 |
| WO | WO-1998/50431 A2 | 11/1998 |
| WO | WO-1999/018212 A1 | 4/1999 |
| WO | WO-99/45962 A1 | 9/1999 |
| WO | WO-00/26373 A1 | 5/2000 |
| WO | WO-00/63403 A2 | 10/2000 |
| WO | WO-00/073323 A2 | 12/2000 |
| WO | WO-01/64929 A1 | 9/2001 |
| WO | WO-2001/90192 A2 | 11/2001 |
| WO | WO-02/08409 A2 | 1/2002 |
| WO | WO-02/12437 A2 | 2/2002 |
| WO | WO-02/18948 A2 | 3/2002 |
| WO | WO-02/40685 A2 | 5/2002 |
| WO | WO-2002/0051780 A1 | 5/2002 |
| WO | WO-02/46237 A2 | 6/2002 |
| WO | WO-02/053596 A2 | 7/2002 |
| WO | WO-2002/066630 A1 | 8/2002 |
| WO | WO-02/085944 A2 | 10/2002 |
| WO | WO-02/085945 A2 | 10/2002 |
| WO | WO-2002/088353 A2 | 11/2002 |
| WO | WO-03/002609 A2 | 1/2003 |
| WO | WO-2003/002609 A2 | 1/2003 |
| WO | WO-03/047336 A2 | 6/2003 |
| WO | WO-03/052416 A2 | 6/2003 |
| WO | WO-03/061363 A2 | 7/2003 |
| WO | WO-2003/92611 A2 | 11/2003 |
| WO | WO-03/106495 A2 | 12/2003 |
| WO | WO-2004/006955 A1 | 1/2004 |
| WO | WO 2004/009618 A2 | 1/2004 |
| WO | WO-04/049794 A2 | 6/2004 |
| WO | WO-2004/049794 A2 | 6/2004 |
| WO | WO-2004/050838 A2 | 6/2004 |
| WO | WO-2004/058820 A2 | 7/2004 |
| WO | WO-2004/058822 A2 | 7/2004 |
| WO | WO-2004/106375 A1 | 12/2004 |
| WO | WO-2005/001087 A2 | 1/2005 |
| WO | WO-2005/019463 A1 | 3/2005 |
| WO | WO-2005/028510 A2 | 3/2005 |
| WO | WO-2005/038001 A2 | 4/2005 |
| WO | WO-2005078098 A1 | 8/2005 |
| WO | WO-2006/117699 A2 | 11/2006 |
| WO | WO-2006/122442 A1 | 11/2006 |
| WO | WO-2007/000668 A2 | 1/2007 |
| WO | WO-2007/003323 A1 | 1/2007 |
| WO | WO-2007/096779 A2 | 8/2007 |
| WO | WO-2007/117410 A2 | 10/2007 |
| WO | WO-2007149246 A2 | 12/2007 |
| WO | WO-2008/015418 A2 | 2/2008 |
| WO | WO-2008/022391 A1 | 2/2008 |
| WO | WO-2008/054606 A2 | 5/2008 |
| WO | WO-2008/076379 A2 | 6/2008 |
| WO | WO-2008/081197 A1 | 7/2008 |
| WO | WO-2008/112922 A2 | 9/2008 |
| WO | WO-2008112226 A2 | 9/2008 |
| WO | WO-08/122886 A2 | 10/2008 |
| WO | WO-2008/151081 A1 | 12/2008 |
| WO | WO-09/013620 A2 | 1/2009 |
| WO | WO-2009/013620 A2 | 1/2009 |
| WO | WO-2009/051974 A1 | 4/2009 |
| WO | WO-2009/089004 A1 | 7/2009 |
| WO | WO-2009/097006 A2 | 8/2009 |
| WO | WO-2009/114400 A1 | 9/2009 |
| WO | WO-2009/129247 A2 | 10/2009 |
| WO | WO-2009/143472 A2 | 11/2009 |
| WO | 2009157771 A2 | 12/2009 |
| WO | WO-2010/039900 A2 | 4/2010 |
| WO | WO-2010/053751 A1 | 5/2010 |
| WO | WO-2010/054007 A1 | 5/2010 |
| WO | WO-2010/070263 A1 | 6/2010 |
| WO | WO-2010/097385 A1 | 9/2010 |
| WO | WO-2010/128897 A1 | 11/2010 |
| WO | WO-2010/136598 A1 | 12/2010 |
| WO | WO-2010/151792 A1 | 12/2010 |
| WO | 2011004192 A1 | 1/2011 |
| WO | WO2011004192 A1 † | 1/2011 |
| WO | WO-2011/062207 A1 | 5/2011 |
| WO | 2011072204 A1 | 6/2011 |
| WO | WO-2011/097603 A1 | 8/2011 |
| WO | WO-2011/143545 A1 | 11/2011 |
| WO | 2011158009 A1 | 12/2011 |
| WO | WO-2011/158009 A1 | 12/2011 |
| WO | WO-2011/163311 A1 | 12/2011 |
| WO | WO2011158009 A1 † | 12/2011 |
| WO | WO-2012/018764 A1 | 2/2012 |
| WO | WO-2012/063048 A1 | 5/2012 |
| WO | WO 2012/141798 A1 | 10/2012 |
| WO | WO-2012/148873 A2 | 11/2012 |
| WO | WO-2013/022782 A1 | 2/2013 |
| WO | WO-2013/041844 A2 | 3/2013 |
| WO | WO-2013/041845 A2 | 3/2013 |
| WO | WO-2013/041846 A2 | 3/2013 |
| WO | WO-2013/045916 A1 | 4/2013 |
| WO | WO-2013/059230 A1 | 4/2013 |
| WO | WO-2013/061078 A1 | 5/2013 |
| WO | WO-2013/061098 A2 | 5/2013 |
| WO | WO-2013/079953 A1 | 6/2013 |
| WO | WO-2013/096142 A1 | 6/2013 |
| WO | WO-2013/116609 A1 | 8/2013 |
| WO | WO-2014/160179 A1 | 10/2014 |
| WO | WO-2014/160202 A1 | 10/2014 |

OTHER PUBLICATIONS

Davies, N. et al., Creation of Mice Expressing Human Antibody Light Chains by Introduction of a Yeast Artificial Chromosome Containing the Core Region of the Human Immunoglobulin κ Locus, Nature Biotechnology 11:911-914, (1993).

Desienhofer, J., Crystallographic Refinement and Atomic Models of a Human Fc Fragment and Its Complex with Fragment B of Protein A from *Staphylococcus aureus* at 2.9- and 2.8-Å Resolution, Biochemistry, 20(9):2361-2370 (1981).

European Communication for 12 173 456.0 (dated Dec. 5, 2012).

European Examination for 11 703 799.4 (dated Oct. 9, 2012).

European Search Report for 12 173 456.0 (dated Aug. 10, 2012).

Goletz, S. et al., Selection of Large Diversities of Antiidiotypic Antibody Fragments by Phage Display, J. Mol. Biol. 315:1087-97, (2002).

Goyenechea, B. et al., Modifying the sequence of an immunoglobulin V-gene alters the resulting pattern of hypermutation, PNAS USA, 93:13979-13984 (1996).

Hochedlinger, K. and R. Jaenisch, Monoclonal Mice Generated by Nuclear Transfer from Mature B and T Donor Cells, Nature, 415(6875):1035-1038, (2002).

Jakobovits, A. et al., From XenoMouse technology to panitumumab, the first fully human antibody product from transgenic mice, Nature Biotechnology, 25(10):1134-1143 (2007).

Jolly, C. et al., Rapid methods for the analysis of immunoglobulin gene hypermutation: application to transgenic and gene targeted mice, Nucleic Acids Research, 25(10):1913-1919 (1997).

Lefranc, M., Nomenclature of the Human Immunoglobulin Genes Current Protocols in Immunology, Supplement 40:A.1P.1-A.1P.37 (2001).

Lindhofer, H. et al., Preferential Species-Restricted Heavy/Light Chain Pairing in Rat/Mouse Quadromas, The Journal of Immunology, 155:219-225 (1995).

Lonberg, N. et al., Antigen-specific Human Antibodies from Mice Comprising Four Distinct Genetic Modifications, Nature, 368:856-859, (1994).

(56) References Cited

OTHER PUBLICATIONS

Marvin, J. et al., Recombinant approaches to IgG-like bispecific antibodies, Acta Pharmacologica Sinica, 26(6):649-658 (2005).
Merchant, A. et al., An efficient route to human bispecific IgG, Nature Biotechnology, 16(7):677-681 (1998).
Nicholson, I. et al., Antibody Repertoires of Four- and Five-Feature Translocus Mice Carrying Human Immunoglobulin Heavy Chain and κ and λ Light Chain Yeast Artificial Chromosomes, Journal of Immunology, 163:6898-6906 (1999).
Reply to Third Party Observations on EP2501817 (May 20, 2013).
Sirac, C. et al., Role of the monoclonal kappa chain V domain and reversibility of renal damage in a transgenic model of acquired Fanconi syndrome, Blood, 108(2):536-543 (2006).
Storb, U. et al., Transgenic Mice with μ and κ Genes Encoding Antiphosphorycholine Antibodies, J. Exp Med, 164:627-64 (1986).
Summons to Attend Oral Proceedings Arranged in Connection with EP2147594 (Mar. 6, 2013).
Taylor, L.D. et al., A Transgenic Mouse that Expresses a Diversity of Human Sequence Heavy and Light Chain Immunoglobulins, Nucleic Acid Research, 20(23):6287-6295 (1992).
Taylor, L.D. et al., Human immunoglobulin transgenes undergo rearrangement, somatic mutation and class switching in mice that lack endogenous IgM, Int. Immunol., 6:579-591 (1994).
Third Party Observations on EP2501817 (Feb. 28, 2013).
Third Party Observations Under Article 115 EPC against 09075279. 1, Oct. 25, 2012.
U.S. Non-Final Office Action for U.S. Appl. No. 13/022,759 (dated Sep. 7, 2012).
U.S. Non-Final Office Action for U.S. Appl. No. 13/093,156 (dated Sep. 6, 2012).
U.S. Non-Final Office Action for U.S. Appl. No. 13/412,936 (dated Sep. 6, 2012).
Written Opinion for PCT/US2012/034737 (dated Dec. 6, 2012).
Written Opinion for PCT/US2013/029125, (dated Jun. 20, 2013).
Bauer, S.R., et al. 1988. "Structure and pre-B lymphocyte restricted expression of the VpreB gene in humans and conservation of its structure in other mammalian species." The EMBO Journal. 7(1): 111-116.
Tsubata, T., et al. 1990. "The Products of Pre-B Cell-specific Genes(Lambda5 and VpreB) and the Immunoglobulin mu Chain Form a Comples That Is Transported onto the Cell Surface." Journal of Experimental Medicine. 172: 973-976.
Leitzgen, K., et al. 1997. "Assembly of Immunoglobulin Light Chains as a Prerequisite for Secretion." Journal of Biological Chemistry. 272(5): 3117-3123.
Donohoe, M.E., et al. 2000. "Transgenic Human Lambda5 Rescues the Murine Lambda5 Nullizygous Phenotype." Journal of Immunology. 164: 5269-5276.
Rojas, G., et al. 2002. "Phage antibody fragments library combining a single human light chain variable region with immune mouse heavy chain variable regions." Journal of Biotechnology. 94: 287-298.
Xu, L., et al. 2008. "Combinatorial surrobody libraries." Proceedings of the National Academy of Sciences USA. 105 (31): 10756-10761.
De Kruif, J., et al. 2009. "Human Immunoglobulin Repertoires against Tetanus Toxoid Contain a Large and Diverse Fraction of High-Affinity Promiscuous VH Genes." Journal of Molecular Biology. 387: 548-558.
Smith, B.P., et al. 2010. "The unique and immunoglobulin-like regions of surrogate light chain component lambda5 differentially interrogate immunoglobulin heavy-chain structure." Molecular Immunology. 47: 1195-1206.
International search report for PCT application No. PCT/US2011/023971, dated Apr. 11, 2011.
Written opinion of the International Searching Authority for PCT application No. PCT/US2011/023971, dated Apr. 11, 2011.
Brezinschek H.P., et al. 1998. "Pairing of variable heavy and variable kappa chains in individual naïve and memory B cells." J. Immunol. 160(10): 4762-4767.
Carmack, C.E., et al. 1991. "Influence of a V kappa 8 L chain transgene on endogenous rearrangements and the immune response to the HA(Sb) determinant on influenza virus." J. Immunol. (1991) 147(6): 2024-2033.
Cascalho M., et al. 1996. "A quasi-monoclonal mouse." Science. 272(5268): 1649-1652.
De Wildt R.M., et al. 1999. "Analysis of heavy and light chain pairings indicates that receptor editing shapes the human antibody repertoire." J. Mol. Biol. 285(3): 895-901.
Fraenkel S., et al. 2007. "Allelic 'choice' governs somatic hypermutation in vivo at the immunoglobulin kappa-chain locus." Nat. Immunol. 8(7): 715-722.
Gay D., et al. 1993. "Receptor editing: an approach by autoreactive B cells to escape tolerance." J. Exp. Med. 177(4): 999-1008.
Green L.L., et al. 1994. "Antigen-specific human monoclonal antibodies from mice engineered with human Ig heavy and light chain YACs." Nat. Genet. 7(1): 13-21.
Green L.L., et al. 1998. "Regulation of B cell development by variable gene complexity in mice reconstituted with human immunoglobulin yeast artificial chromosomes." J. Exp. Med. 188(3): 483-495.
O'Brien R.L., et al. 1987. "Somatic hypermutation of an immunoglobulin transgene in kappa transgenic mice." Nature. 326(6111): 405-409.
Pelanda R., et al. 1996. "A prematurely expressed Ig(kappa) transgene, but not V(kappa)J(kappa) gene segment targeted into the Ig(kappa) locus, can rescue B cell development in lambda5-deficient mice." Immunity. 5(3): 229-239.
Prak E.L., et al. 1995. "Light chain replacement: a new model for antibody gene rearrangement." J. Exp. Med. 182(2): 541-548.
Arnold, L.W., et al. 1994. "Development of B-1 cells: segregation of phosphatidyl choline-specific B cells to the B-1 population occurs after immunoglobulin gene expression." J. Exp. Med. 179: 1585-1595.
Hengstschlager, M., et al. 1994. "A lambda1 transgene under the control of a heavy chain promoter and enhancer does not undergo somatic hypermutation." Eur. J. Immunol. 24: 1649-1656.
Gonzalez-Fernandez, A., and C. Milstein. 1993. "Analysis of somatic hypermutation in mouse Peyer's patches using immunoglobulin kappa light-chain transgenes." PNAS USA. 90: 9862-9866.
Jolly, C.J., et al. 1997. "Rapid methods for the analysis of immunoglobulin gene hypermutation: application to transgenic and gene targeted mice." Nucleic Acids Research. 25(10): 1913-1919.
Goyenechea, B., and C. Milstein. 1996. "Modifying the sequence of an immunoglobulin V-gene alters the resulting pattern of hypermutation." PNAS USA. 93: 13979-13984.
Klotz, E.L., et al. 1998. "Somatic hypermutation of an artificial test substrate within an Ig kappa transgene." J. Immunol. 161: 782-790.
Klotz, E.L., and U. Storb. 1996. "Somatic hypermutation of a lambda2 transgene under the control of the lambda enhancer or the heavy chain intron enhancer." J. Immunol. 157: 4458-4463.
Kong, Q., et al. 1998. "A lambda 3' enhancer drives active and untemplated somatic hypermutation of a lambda1 transgene." J. Immunol. 161: 294-301.
Sirac, C., et al. 2006. "Role of the monoclonal kappa chain V domain and reversibility of renal damage in a transgenic model of acquired Fanconi syndrome." Blood. 108(2): 536-543.
Aucouturier, P., et al. 1993. "Monoclonal Ig L chain and L chain V domain fragment crystallization in myeloma-associated Fanconi's syndrome." J. Immunol. 150(8 Pt. 1): 3561-3568.
Mendez, M.J., et al. 1997. "Functional transplant of megabase human immunoglobulin loci recapitulates human antibody response in mice." Nat. Genet. 15(2): 146-156.
Seals, D.F. and S.A. Courtneidge. 2003. The ADAMs family of metalloproteases: multidomain proteins with multiple functions. Genes and Development 17:7-30.
Lonberg, N. 2005. Human antibodies from transgenic animals. Nature Biotechnology 23(9):1117-1125.
Kim, T. et al. 2006. Expression and relationship of male reproductive ADAMs in mouse. Biology of Reproduction 74:744-750.
Edwards, D.R. et al. 2008. The ADAM metalloproteinases. Molecular Aspects of Medicine 29:258-289.

(56) References Cited

OTHER PUBLICATIONS

Han, C. et al. 2009. Comprehensive analysis of reproductive ADAMs: Relationship of ADAM4 and ADAM6 with an ADAM complex required for fertilization in mice. Biology of Reproduction 80:1001-1008.
Featherstone. K. et al. 2010. The mouse immunoglobulin heavy chain V-D intergenic sequence contains insulators that may regulate ordered V(D)J recombination. Journal of Biological Chemistry 285(13):9327-9338.
Giallourakis, C.C. et al. 2010. Elements between the IgH variable (V) and diversity (D) clusters influence antisense transcription and lineage-specific V(D)J recombination. PNAS 107(51):22207-22212.
Hendricks, J. et al. 2010. Organization of the variable region of the immunoglobulin heavy-chain gene locus of the rat. Immunogenetics 62:479-486.
Communication in Cases for which No Other Form is Applicable for PCT/US2012/026416, 9 pages (dated Jun. 7, 2013).
Communication in Cases for which No Other Form is Applicable for PCT/US2012/069981, 18 pages (dated Jul. 3, 2013).
Edwards, DR et al., "The ADAM metalloproteinases," Molecular Aspects of Medicine, 29(5): 258-289, 2009.
Featherstone, Karen et al., "The Mouse Immunoglobulin Heavy Chain V-D Intergenic Sequence Contains Insulators That May Regulate Ordered V(D)J Recombination," *Journal of Biological Chemistry*, 285(13): 9327-9338, 2010.
Han, Cecil et al., "Comprehensive analysis of reproductive ADAMs: relationship of ADAM4 and ADAM6 with an ADAM complex required for fertilization in mice," *Biology of Reproduction*, 80(5): 1001-1008, 2009.
International Search Report for PCT/US12/49600, 7 pages (dated Nov. 23, 2012).
Written Opinion for PCT/US12/49600, 8 pages (dated Nov. 23, 2012).
Moran, Nuala, "Mouse platforms jostle for slice of humanized antibody market," Nature Biotechnology, vol. 31(4): 267-268, 2013.
Ray, Ectopic expression of a c-kitW42 minigene in transgenic mice: recapitulation of W phenotypes and evidence for c-kit function in melanoblast progenitors, Genes Dev., 5(12A): 2265-73, 1991.
Kaushik et al, "Stochastic pairing of heavy-chain and κ light-chain variable gene families occurs in polyclonally activated B cells," Proc. Natl. Acad. Sci. USA, vol. 87: 4932-4936 (1990).
Nagle (2007) Regeneron helps make Sanofi VelocImmune to its "weak pipeline", <http://www.outsourcing-pharma.com>—Published Dec. 3, 2007.
News in Brief Article (2007) Big Pharma vies for mice, *Nature Biotechnology* 2007, 25(6): 613—Published Jun. 2007.
Sasaki et al., "Canonical NF-κB Activity, Dispensable for B Cell Development, Replaces BAFF-Receptor Signals and Promotes B Cell Proliferation upon Activation," Immunity 24: 729-739 (2006).
Scott, Christopher T., "Mice with a human touch," Nature Biotechnology, 25(10): 1075-1077 (2007).
Author Not Known, Next generation transgenic mice for therapeutic human antibodies, Description of MeMoTM, filed by the Applicant/Patentee in prosecution for corresponding European application 09075279.1, now opposed patent EP 2147594 B1, 2 pages (Dec. 22, 2011).
Dechiara, T.M. et al., Chapter 16: VelociMouse: Fully ES Cell-Derived F0 Generation Mice Obtained from the Injection of ES Cells into 8-Cell Stage Embryos, Gene Knockout Protocols: Second Edition, vol. 530, Humana Press (2009).
GenBank Accession No. ABA26122, immunoglobulin light chain variable region, partial [*Homo sapiens*], Rabquer et al., 2 pages, first referenced Dec. 31, 2005.
GenBank Accession No. M87478, Human rearranged IgK mRNA VJC region, Aucouturier et al., 1 page, first referenced Mar. 3, 1992, first seen at NCBI Apr. 27, 1993.
Goodhardt et al., Rearrangement and Expression of rabbit immunoglobulin K light chain gene in transgenic mice; Jun. 1987; PNAS, 84: 4229-4233.

Goyenechea, B. et al., Cells strongly expressing Ig(kappa) transgenes show clonal recruitment of hypermutation: a role for both MAR and the enhancers, EMBO J., 16(13):3987-94 (1997).
Hardy, R.R and Hayakawa, K., B cell development pathways, Annu. Rev. Immunol., 19:595-621 (2001).
Hömig-Hölzel, C. et al., Constitutive CD40 signaling in B cells selectively activates the noncanonical NF-kappaB pathway and promotes lymphomagenesis, J. Exp. Med., 205(6):1317-29 (2008).
IMGT V-Quest Analysis of Sequence of GenBank M87478, 7 pages.
Inlay, M. et al., Essential roles of the kappa light chain intronic enhancer and 3' enhancer in kappa rearrangement and demethylation, Nat. Immunol., 3(5):463-8 (2002).
International Search Report for PCT/US2012/034737 (dated Dec. 6, 2012).
International Search Report for PCT/US2013/029125, (dated Jun. 20, 2013).
International Search Report for PCT/US2013/044257, 4 pages (dated Sep. 4, 2013).
International Search Report for PCT/US2014/025982 dated Jul. 22, 2014 (6 pages).
International Search Report for PCT/US2014/026040 dated Jul. 29, 2014 (5 pages).
Jakobovits, A., Production of fully human antibodies by transgenic mice, Curr. Opin. Biotechnol., 6(5):561-6 (1995).
Klöhn, P.C. et al., IBC's 23rd Annual Antibody Engineering, 10th Annual Antibody Therapeutics international conferences and the 2012 Annual Meeting of the Antibody Society: Dec. 3-6, 2012, San Diego, CA, Mabs, 5(2):178-201 (2013).
Logtenberg, T., Antibody cocktails: next-generation biopharmaceuticals with improved potency, Trends Biotechnol., 25(9):390-4 (2007).
Nemazee, D., Receptor editing in lymphocyte development and central tolerance, Nat. Rev. Immunol., 6(10):728-40 (2006).
Orban, P.C. et al., Tissue- and site-specific DNA recombination in transgenic mice, Proc. Natl. Acad. Sci. U S A., 89(15):6861-5 (1992).
Popov, A.V. et al., A human immunoglobulin lambda locus is similarly well expressed in mice and humans, J. Exp. Med., 189(10):1611-20 (1999).
Rickert, R.C. et al., B lymphocyte-specific, Cre-mediated mutagenesis in mice, Nucleic Acids Res., 25(6):1317-8 (1997).
Sharpe, M.J. et al., Somatic hypermutation of immunoglobulin kappa may depend on sequences 3' of C kappa and occurs on passenger transgenes, EMBO J., 10(8):2139-45 (1991).
Simon, T. and Rajewsky, K., Antibody domain mutants demonstrate autonomy of the antigen binding site, EMBO J., 9(4):1051-6 (1990).
Soriano, P., Generalized lacZ expression with the ROSA26 Cre reporter strain, Nat. Genet., 21(1):70-1 (1999).
Stevens et al., Human Antibody Discovery, VelocImmune—A novel platform, Pharma Focus Asia, Issue 8: 72-74 (2008).
Torres and Kuhn, Laboratory Protocols for Conditional Gene Targeting, 42-53 (1997).
Vaughan, T.J. et al., Human antibodies with sub-nanomolar affinities isolated from a large non-immunized phage display library, Nat. Biotechnol., 14(3):309-14 (1996).
Winter, D.B. et al., Insertion of 2 kb of bacteriophage DNA between an immunoglobulin promoter and leader exon stops somatic hypermutation in a kappa transgene, Mol. Immunol., 34(5):359-66 (1997).
Written Opinion for PCT/US2013/044257, 5 pages (dated Sep. 4, 2013).
Written Opinion for PCT/US2014/025982 dated Jul. 22, 2014 (7 pages).
Written Opinion for PCT/US2014/026040 dated Jul. 29, 2014 (8 pages).
Murphy, A., Declaration Under 37 C.F.R. §1.132, 4 pages (2014).
Murphy, D., BAC-based Modifications of the Mouse Genome: The Big and the Backward, Wellcome Trust Advanced Course: Genetic Manipulation of ES Cells, 58 pages (2009).
Sep. 14, 2015 Statement of Relatedness, ADAM6 Patents.
Sep. 14, 2015 Statement of Relatedness, Common Light Chain Mouse Patents.
Sirac, C. et al., Toward understanding renal Fanconi syndrome: step by step advances through experimental models, Contributions to Nephrology, 169:247-61 (2011).

(56) References Cited

OTHER PUBLICATIONS

Applicant's Written Submissions for AU2009263082, 49 pages (Sep. 6, 2016).
Brouwers, Brouwers, B. et al., Unexpected Phenotypes in Mouse Models Carrying the Human Growth Hormone Minigene to Enhance Transgene Expression, Journal of Steroids & Hormonal Science, 6(2): 2 pages (2015).
Choi, K. et al., Expression of the metabotropic glutamate receptor 5 (mGluR5) induces melanoma in transgenic mice, PNAS, 108(37):15219-15224 (2011).
Final Written Submissions for EP2147594, 40 pages (Aug. 26, 2016).
International Search Report for PCT/US2011/023971 (dated Apr. 11, 2011).
International Search Report for PCT/US2013/044257 dated Sep. 4, 2013 (4 pages).
Letter in Reply to Merus Response for EP2147594, 9 pages (Aug. 20, 2015).
Merus Final Written Submissions as filed in EP2147594 / 09075279. 1-1405, 32 pages (Aug. 26, 2016).
Murphy, L. and Silha, J., Unexpected and unexplained phenotypes in transgenic models, Growth Horm IGF Res., 10(5):233-235 (2000).
Response to Communication under Rule 79(1) EPC in EP2147594, 35 pages (dated Apr. 2, 2015).
Response to Opponents Submission dated Aug. 26, 2016 and in Preparation of the Hearing scheduled for Oct. 28, 2016 in EP2147594, 14 pages (Sep. 28, 2016).
Second Declaration of Meng (Amy) Li, Ph.D., 14 pages (Sep. 15, 2016).
Summary of Opponent's Submissions for AU2009263082, 35 pages (Aug. 30, 2016).
Yantha, J. et al., Unexpected Acceleration of Type 1 Diabetes by Transgenic Expression of B7—H1 in NOD Mouse Peri-Islet Glia, Diabetes, 59:2588-2596 (2010).
Appeal by Opponent for EP 12716101.6, 14 pages (Jun. 20, 2016).
Declaration of E-Chiang Lee, Ph.D., 8 pages (Jun. 20, 2016).
Declaration of Hui Liu, Ph.D., 4 pages (Jun. 20, 2016).
Declaration of Meng (Amy) Li, Ph.D., 4 pages (Jun. 20, 2016).
Declaration of Prof. Allan Bradley, Ph.D., 37 pages (Jun. 20, 2016).
Declaration of Wei Wang, Ph.D., 8 pages (Jun. 20, 2016).
Preliminary Opinion of Opposition Division on EP 2550363, 24 pages, Jul. 29, 2016.
Adderson, E.E. et al., Restricted Ig H Chain V Gene Usage in the Human Antibody Response to Haemophilus influenzae Type b Capsular Polysaccharide, The Journal of Immunology, 147:1667-1674 (1991).
Adderson, E.E. et al., Restricted Immunoglobulin VH Usage and VDJ Combinations in the Human Response to Haemophilus influenzae Type b Capsular Polysaccharide, Journal of Clinical Investigation, 91:2734-2743 (1993).
After Final Consideration Pilot Program Request as filed in U.S. Appl. No. 13/798,310 on Jul. 18, 2014 (2 pages).
Al-Lazikani, B. et al., Standard conformations for the canonical structures of immunoglobulins, J. Mol. Biol., 273(4):927-48 (1997).
Amit, M. and Itskovitz-Eldor, J., Embryonic Stem Cells: Isolation, Characterization and Culture, Adv Biochem Engin/Biotechnol, 114:173-184 (2009).
Arnaout, R. et al., High-resolution description of antibody heavy-chain repertoires in; humans PLoS One, 6(8):e22365 (2011).
Askew, G.R. et al., Site-directed point mutations in embryonic stem cells: a gene-targeting tag-and-exchange strategy, Mol. Cell Biol., 13(7):4115-24 (1993).
Astellas Negotiates $295M License Extension to Regeneron's VelocImmune mAb Platform, Gen News Highlights, Jul. 28, 2010.
Author Not Known, Additional post-filing data and letter filed by the Applicant/Patentee for corresponding European application 09075279.1, now opposed patent EP 2147594 B1, 4 pages (Jun. 13, 2013).
Author Not Known, Chapter 6: The Development of B Lymphocytes, Immuno Biology: The Immune System in Health and Disease, 4th Edition, Janeway et al. ed., pp. 195-208 (1999).
Author Not Known, Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4, (2011).
Author Not Known, Mouse strain, document #3 submitted with Third Party Observation, filed in GB2012052956, 4 pages (Mar. 26, 2014).
Author Not Known, V-BASE Sequence Directory, 6 pages, retrieved on Jun. 6, 2016 <http://www2.mrc-lmb.cam.ac.uk/vbase/list2.php.
Baeuerle, P.A. and Reinhardt, C., Bispecific T-cell engaging antibodies for cancer; therapy, Cancer Res., 69(12):4941-4 (2009).
Bando, Y. et al., Characterization of VH gene expressed in PBL from children with atopic diseases: detection of homologous VH1-69 derived transcripts from three unrelated patients, Immunology Letters, 94:99-106 (2004).
Baseggio, L. et al., CD5 expression identifies a subset of splenic marginal zone lymphomas with higher lymphocytosis: a clinicopathological, cytogenetic and molecular study of 24 cases, Haematologica, 95(4):604-612 (2010).
Berberian, L. et al., A VH Clonal Deficit in Human Immunodeficiency Virus-Positive Individuals Reflects a B-Cell Maturational Arrest, Blood, 78(1):175-179 (1991).
Billiard, F. et al., Ongoing Dll4-Notch signaling is required for T-cell homeostasis in the adult thymus, Eur. J. Immunol., 41(8):2207-16 (2011).
Blaas, L. et al., Bacterial artificial chromosomes improve recombinant protein production in mammalian cells, BMC Biotechnol., 9:3 (2009).
Bode, J. et al., The transgeneticist's toolbox: novel methods for the targeted modification of eukaryotic genomes, Biol. Chem., 381(9-10):801-13 (2000).
Bot, A. et al., V2-Light Chain Genes Reconstitute Immune Responses to Defined Carbohydrate Antigens or Haptens by Utilizing Different VH Genes, Molecular Immunology, 33(17/18):1359-1368 (1996).
Brezinschek, H.P. et al., Analysis of the Heavy Chain Repertoire of Human Peripheral B Cells Using Single-Cell Polymerase Chain Reaction, Journal of Immunology, 155:190-202 (1995).
Brezinschek, H.P. et al., Analysis of the human VH gene repertoire. Differential effects of selection and somatic hypermutation on human peripheral CD5(+)/IgM+ and CD5(−)/IgM+ B; Cells, J. Clin. Invest., 99(10):2488-501 (1997).
Brief comments on third party observations, EP 11703799.1-1410, submitted to EPO by David Power, 3 pages (Apr. 20, 2015).
Bruggemann, M. and Neuberger, M., Strategies for expressing human antibody repertoires in transgenic mice, Review Immunology Today, 192(17):391-397 (1996).
Bruggemann, M. et al., A repertoire of monoclonal antibodies with human heavy chains from transgenic mice, Proceedings of the National of Academy of Science USA, 86:6709-6713 (1989).
Bruggemann, M., Human Antibody Expression in Transgenic Mice, Archivum Immunologiae et Therapiae Experimentalis, 49:203-208 (2001).
Brüggemann, M. and Neuberger, M.S., Strategies for expressing human antibody repertoires in transgenic mice, Immunol. Today, 17(8):391-7 (1996).
Brüggemann, M., Human Monoclonal Antibodies from Translocus Mice, Molecular Biology of B Cells, Eds. Honjo, T. and Neuberger, M.S., New York, NY: Academic Press, pp. 547-561 (2004).
Butler, J.E., Immunoglobulin diversity, B-cell and antibody repertoire development in large farm animals, Rev. Sci. Tech. Off. Int. Epiz., 17(1):43-70(1998).
Campbell, K.H. et al., Sheep cloned by nuclear transfer from a cultured cell line, Nature, 380(6569):64-6 (1996).
Canadian Office Action for Application No. 2,820,824, 3 pages, dated Aug. 5, 2014.
Carbonari, M, et al., Hepatitis C Virus Drives the Unconstrained Monoclonal Expansion of VH1-69-Expressing Memory B Cells in Type II Cryoglobulinemia: A Model of Infection-Driven Lymphomagenesis, The Journal of Immunology, 174:6532-6539 (2005).

(56) References Cited

OTHER PUBLICATIONS

Casellas, R. et al., Contribution of receptor editing to the antibody repertoire, Science, 291(5508):1541-4 (2001).
Chan, C.H. et al., VH1-69 gene is preferentially used by hepatitis C virus-associated B cell lymphomas and by normal B cells responding to the E2 viral antigen, Blood, 97(4):1023-1026 (2001).
Charles, E.D. et al., A flow cytometry-based strategy to identify and express IgM from VH1-69+ clonal peripheral B cells, Journal of Immunological Methods, 363:210-220 (2011).
Chen, C. et al., Deletion and Editing of B Cells that Express Antibodies to DNA, Journal of Immunology, 152(4):1970-1982 (1994).
Cheval, L. et al., Of Mice and Men: Divergence of Gene Expression Patterns in Kidney, PLoS One, 7(10):e46876—12 pages (2012).
Cho, Chunghee, Testicular and epididymal ADAMs: expression and function during fertilization, Nat. Rev. Urol., 9:550-530 (2012).
Choi, H. et al., Identification and characterization of promotor and regulatory regions for mouse Adam2 gene expression, Mol Biol Rep, 40:787-796 (2013).
Choi, I. et al., Characterization and comparative genomic analysis of intronless Adams with testicular gene expression, Genomics, 83(4):636-46 (2004).
Chothia, C. and Lesk, A.M., Canonical structures for the hypervariable regions of; Immunoglobulins, J. Mol. Biol., 196(4):901-17 (1987).
Choulika, A. et al., Induction of homologous recombination in mammalian chromosomes by using the I-SceI system of *Saccharomyces cerevisiae*, Mol. Cell. Biol., 15:4 1968-73 (1995).
Cohen-Tannoudji, M. et al., I-SceI-induced gene replacement at a natural locus in; embryonic stem cells, Mol. Cell. Biol., 18(3):1444-8 (1998).
Combriato, G. and Klobeck, H.G., Regulation of human Ig lambda light chain gene expression by NF-kappa B, J. Immunol., 168(3):1259-66 (2002).
Communication in Cases for Which No Other Form Is Applicable for PCT/US2012/069981, 18 pages (Jul. 3, 2013).
Communication pursuant to Article 114(2) EPC, dated Jun. 21, 2013.
Communication pursuant to Article 94(3) EPC for EP 11 703 799.4, 6 pages (dated Oct. 9, 2012).
Communication pursuant to Article 94(3) EPC for EP 12 173 456.0, 5 pages (dated Dec. 5, 2012).
Communication Relating to the Results of the Partial International Search for PCT/US2013/029624, 9 pages, (dated May 17, 2013).
Corcos, D. et al, Pre-B-cell development in the absence of lambda 5 in transgenic mice expressing a heavy-chain disease protein, Curr. Biol., 5(10):1140-8 (1995).
Cowen, N.J. et al., Purification and Sequence Analysis of the mRNA Coding for an Immunoglobulin Heavy Chain, European J. of Biochem., 61(2): 355-368 (1976).
Davidkova, G. et al., Selective Usage of VH Genes in Adult Human B Lymphocyte Repertoires, Scandinavian Journal of Immunology, 45:62-73 (1997).
De Kruif, J. et al., Rapid selection of cell subpopulation-specific human monoclonal antibodies from a synthetic phage antibody library, Proc. Natl. Acad. Sci. U S A, 92(9):3938-42 (1995).
Declaration Appendix as filed in U.S. Appl. No. 13/798,310 on Jul. 18, 2014 (7 pages).
Declaration of Andrew M. Scharenberg, M.D., filed in prosecution of U.S. Appl. No. 12/130,818, 21 pages, signed Oct. 4, 2010.
Declaration of Brink dated Apr. 30, 2015, as filed in AU Application No. 2009263082, 34 pages.
Declaration of Brink dated Jun. 2, 2015, as filed in AU Application No. 2009263082, 38 pages.
Declaration of DeFranco dated Dec. 21, 2014, as filed in AU Application No. 2009263082, 56 pages.
Declaration of DeFranco dated Oct. 19, 2015, as filed in AU Application No. 2009263082, 31 pages.
Declaration of Denley dated May 1, 2015, as filed in AU Application No. 2009263082, 493 pages.
Declaration of Dr. Glenn Friedrich, 4 page (Mar. 3, 2016).
Declaration of Dr. Joel Martin, Opposition filed against European Patent No. EP 2314629 B1, 13 pages (May 18, 2016).
Declaration of Dr. Jürgen Roes, Ph.D., 14 pages (Jul. 19, 2014).
Declaration of Goodnow dated Oct. 19, 2015, as filed in AU Application No. 2009263082, 81 pages.
Declaration of Hudson dated Jun. 2, 2015, as filed in AU Application No. 2009263082, 81 pages.
Declaration of Hudson dated May 1, 2015, as filed in AU Application No. 2009263082, 52 pages.
Declaration of Lynn E. Macdonald, including Annexes 1-4, as together made publicly available at least upon submission to and online publication by the European Patent Office on Mar. 12, 2015, 13 pages, signed Mar. 3, 2015.
Declaration of Murphy dated Dec. 19, 2014, as filed in AU Application No. 2009263082, 18 pages.
Declaration of Tarlinton dated Dec. 21, 2014, as filed in AU Application No. 2009263082, 40 pages.
Declaration of Tarlinton dated Oct. 19, 2015, as filed in AU Application No. 2009263082, 24 pages.
Declaration under 37 CFR 1.131 as filed in U.S. Appl. No. 13/798,310 on Jul. 18, 2014 (21 Pages).
Deisenhofer, J., Crystallographic Refinement and Atomic Models of a Human Fc Fragment and Its Complex with Fragment B of Protein A from *Staphylococcus aureus* at 2.9- and 2.8-? Resolution, Biochemistry, 20(9):2361-2370 (1981).
Desmyter, A. et al., Crystal structure of a camel single-domain VH antibody fragment in complex with lysozyme, Nat. Struct. Biol., 3(9):803-11 (1996).
Dinnyés, A. et al., Somatic cell nuclear transfer: recent progress and challenges, Cloning Stem Cells, 4(1):81-90 (2002).
Donoho, G. et al., Analysis of gene targeting and intrachromosomal homologous recombination stimulated by genomic double-strand breaks in mouse embryonic stem cells, Mol. Cell. Biol., 18(7):4070-8 (1998).
Echelard, Y., Year of the ox, Nat. Biotechnol., 27(2):146-7 (2009).
Els Conrath, K. et al., Camel single-domain antibodies as modular building units in bispecific and bivalent antibody constructs, J. Biol. Chem., 276(10):7346-50 (2001).
English Translation of Arguments dated Jan. 14, 2014, as filed in Merus Japanese Patent No. 5749161, 6 pages.
English Translation of Arguments dated Jan. 5, 2015, as filed in Merus Japanese Patent No. 5749161, 9 pages.
Epinat, J.C., et al. A novel engineered meganuclease induces homologous recombination in yeast and mammalian cells, Nucleic Acids Res., 31(11):2952-62 (2003).
European Examination Report for EP 14154967.5, dated Sep. 9, 2014, 4 pages.
European Office Action for 12 716 101.6-1410, 5 pages, dated Jun. 17, 2014.
Ewert, S. et al., Biophysical properties of human antibody variable domains, J. Mol. Biol., 325(3):531-53 (2003).
Examination Report for EP Application 11 703 799.4, 6 pages (dated May 16, 2014).
Examination Report for EP Application 12 173 456.0, 5 pages (dated May 19, 2014).
Exhibit A as filed in U.S. Appl. No. 13/798,310 on Jul. 18, 2014 (2 pages).
Exhibit B as filed in U.S. Appl. No. 13/798,310 on Jul. 18, 2014 (2 pages).
Exhibit C as filed in U.S. Appl. No. 13/798,310 on Jul. 18, 2014 (1 page).
Exhibit D as filed in U.S. Appl. No. 13/798,310 on Jul. 18, 2014 (1 page).
Exhibit E as filed in U.S. Appl. No. 13/798,310 on Jul. 18, 2014 (3 pages).
Extended European Search Report for 12 173 456.0, 9 pages (dated Aug. 21, 2012).
Extended European Search Report for 12192727.1, 8 pages (dated Mar. 7, 2013).
Extended European Search Report for 14154918.8, 8 pages (dated Aug. 27, 2014).

(56) References Cited

OTHER PUBLICATIONS

Extended European Search Report for 14176593.3, 10 pages (dated Nov. 19, 2014).
Extended European Search Report for EP 15186515.1, 8 pages (dated Feb. 3, 2016).
Farner, N.L. et al., Molecular mechanisms and selection influence the generation of the human V lambda J lambda repertoire, J. Immunol., 162(4):2137-45 (1999).
Fell, H.P. et al., Homologous recombination in hybridoma cells: heavy chain chimeric antibody produced by gene targeting, Proc. Natl. Acad. Sci. U S A., 86(21):8507-11 (1989).
Final Written Submissions for Oral Proceedings Scheduled for Jun. 22, 2016, Opposition to Merus B.V.'s EP 2314629 B1, 13 pages (May 20, 2016).
Fischer, N. and Léger, O., Bispecific antibodies: molecules that enable novel therapeutic strategies, Pathobiology, 74(1):3-14 (2007).
Flavell, D.J., et al., Therapy of human T-cell acute lymphoblastic leukaemia with a combination of anti-CD7 and anti-CD38-Saporin immunotoxins is significantly better than therapy with each individual immunotoxin, Br. J. Cancer., 84(4):571-8 (2001).
Forrest, K. B., Opinion of the United States District Court, *Regeneron Pharmaceuticals, Inc.* v. *Merus B.V.*, 114 pages (Nov. 2, 2015).
Gallo, M.L. et al., The human immunoglobulin loci introduced into mice: V (D) and J gene segment usage similar to that of adult humans, Eur. J. Immunol., 30(2):534-40 (2000).
GenBank Accession No. X97051, GI:564822, first referenced Jan. 9, 1997, updated Nov. 14, 2006 (29 pages).
Giddings, G. et al., Transgenic plants as factories for biopharmaceuticals, Nat. Biotechnol., 18(11):1151-5 (2000).
Glick, B. and Pasternak, J., Molekulyarnaya biotekhnologiya. Printsipy i primeneniye, Moscow Mir., 45-47 (2002).
Gonzalez-Fernandez, A. and Milstein, C., Analysis of somatic hypermutation in mouse Peyer's patches using immunoglobulin kappa light-chain transgenes, PNAS USA, 90:9862-9866 (1993).
Goyenechea, B. and Milstein, C., Modifying the sequence of an immunoglobulin V-gene alters the resulting pattern of hypermutation, PNAS USA, 93:13979-13984 (1996).
Green, L. and Jakobovits, A., Regulation of B cell development by variable gene complexity in mice reconstituted with human immunoglobulin yeast artificial chromosomes, J. Exp. Med., 188(3):483-495 (1998).
Hagiwara, S., Transgenic expression of VpreB-3 under the control of the immunoglobulin heavy chain enhancer and SV40 promoter, Kobe J. Med. Sci., 42(1):43-59 (1996).
Harding, F.A. and Lonberg, N., Class switching in human immunoglobulin transgenic Mice, Ann. N Y Acad. Sci., 764:536-46 (1995).
Hartley, S. and Goodnow, C., Censoring of self-reactive B cells with a range of receptor affinities in transgenic mice expressing heavy chains for a lysozyme-specific antibody, International Immunology, 6:1417-1425 (1994).
Hiatt, A. et al. Production of antibodies in transgenic plants, Nature, 342(6245):76-8 (1989).
Hoiruchi, K. and Blobel, C., Studies from Adam Knockout Mice, in Hooper and Lendeckel, The ADAM family of proteases, Netherlands 2005, Springer (37 pages).
Houdebine, L.M. Transgenic Animals: Generation and Use. Amsterdam: Harwood Academic Publishers.pp. 397-403 (1997).
Huang, C. and Stoller, B.D., A Majority of Ig H Chain cDNA of Normal Human Adult Blood Lymphocytes Resembles cDNA for Fegal Ig and Natural Autoantibodies, The Journal of Immunology, 151(10):5290-5300 (1993).
Huls, G. et al., Antitumor immune effector mechanisms recruited by phage display-derived fully human IgG1 and IgA1 monoclonal antibodies, Cancer Res., 59(22):5778-84 (1999).
International Search Report and Written Opinion for PCT Application No. PCT/US2013/044257 dated Sep. 4, 2013.
International Search Report for PCT/US2011/023971, 5 pages (dated Apr. 11, 2011).
International Search Report for PCT/US2012/026416, 4 pages (dated Jun. 25, 2012).
International Search Report for PCT/US2012/060487, 7 pages (dated Feb. 1, 2013).
International Search Report for PCT/US2013/029624, 9 pages (dated Aug. 2, 2013).
Irving, R.A. et al., Ribosome display and affinity maturation: from antibodies to single V-domains and steps towards cancer therapeutics, J. Immunol. Methods, 248(1-2):31-45 (2001).
Jakobovits, Therapeutic Antibodies from XenoMouse Transgenic Mice, Recombinant Antibodies for Immunotherapy, Ed. Little, M., New York, NY: Cambridge University Press, Chapter 7, pp. 89-99 (2009).
Janeway's Immunobiology, Seventh Edition, Murphy, Travers and Walpot, eds., Garland Science, New York and London, Ch. 4, pp. 145-155, and Ch. 7, pp. 266-267 (2008).
Jendreyko, N. et al., Intradiabodies, bispecific, tetravalent antibodies for the simultaneous functional knockout of two cell surface receptors, J. Biol. Chem., 278(48):47812-9 (2003).
Johnson, T.A. et al., Ig VH1 Genes Expressed in B Cell Chronic Lymphocytic Leukemia Exhibit Distinctive Molecular Features, The Journal of Immunology, 158:235-246 (1997).
Jones, D. et al., High-level expression of recombinant IgG in the human cell line per.c6, Biotechnol. Prog., 19(1):163-8 (2003).
Joyner, A.L. ed., Gene Targeting: A Practical Approach, Second Edition, Oxford University Press, entire book, 193 pages (2000).
Kabat, E.A., and Wu, T.T., Identical V region amino acid sequences and segments of sequences in antibodies of different specificities. Relative contributions of VH and VL genes, minigenes, and complementarity-determining regions to binding of antibody-combining sites, J. Immunol., 147(5):1709-19 (1991).
Kantor, A.B. et al., An Unbiased Analysis of VH-D-JH Sequences from B-1a, B-1b, and Conventional B Cells, The Journal of Immunology, 158:1175-1186 (1997).
Kasprzyk, P.G. et al., Therapy of an animal model of human gastric cancer using a combination of anti-erbB-2 monoclonal antibodies, Cancer Res., 52(10):2771-6 (1992).
Knappik, A. et al., Fully synthetic human combinatorial antibody libraries (HuCAL) based on modular consensus frameworks and CDRs randomized with trinucleotides, J. Mol. Biol., 296(1):57-86 (2000).
Kong et al., Transgene expression is associated with copy number and cytomegalovirus promoter methylation in transgenic pigs, PLoS One 4(8):1-10 (2009).
Kontermann, R.E., Dual targeting strategies with bispecific antibodies, MAbs., 4(2):182-97 (2012).
Kroesen, B.J. et al., Bispecific antibodies for treatment of cancer in experimental animal models and man, Adv. Drug Deliv. Rev., 31(1-2):105-129 (1998).
Kunert, R. et al., Characterization of Molecular Features, Antigen-Binding, and in Vitro Properties of IgG and IgM Variants of 4E10, an Anti-HIV Type 1 Neutralizing Monoclonal Antibody, Aids Research and Human Retroviruses, 20(7):755-762 (2004).
Kuroiwa, Y. et al., Cloned transchromosomic calves producing human immunoglobulin, Nat. Biotechnol., 20(9):889-94 (2002).
Kuroiwa, Y. et al., Sequential targeting of the genes encoding immunoglobulin-µ and prion protein in cattle, Nature Genetics, 36:775-780 (2004).
Larrick, J.W. and Thomas, D.W., Producing proteins in transgenic plants and animals, Curr. Opin. Biotechnol., 12(4):411-8 (2001).
Le Gall, F. et al., Effect of linker sequences between the antibody variable domains on the formation, stability and biological activity of a bispecific tandem diabody, Protein Eng. Des. Sel., 17(4):357-66 (2004).
Lee, E.G. et al., Complete humanization of the mouse immunoglobulin loci enables efficient therapeutic antibody discovery, Nat. Biotechnol., 32(4):356-63 (2014).
Lee, H. et al., Human C5aR knock-in mice facilitate the production and assessment of anti-inflammatory monoclonal antibodies, Nat. Biotechnol., 24(10):1279-84 (2006).
Lefranc, M-P. and Lefranc, G., The Immunoblobulin Facts Books, San Diego, CA: Academic Press, entire book, pp. 1-457 (2001).

(56) References Cited

OTHER PUBLICATIONS

Lefranc, M.P. and Lefranc, G., Immunoglobulin Facts Book, London: Academic Press, pp. 3-44, 98-100, and 102 (2001).
Lefranc, M.P. Nomenclature of the human immunoglobulin heavy (IGH) genes, Exp. Clin. Immunogenet., 18(2):100-16 (2001).
Lefranc, M.P., Nomenclature of the human immunoglobulin kappa (IGK) genes, Exp. Clin. Immunogenet., 18(3):161-74 (2001).
Liao, M.J. and Van Dyke, T., Critical role for Atm in suppressing V(D)J recombination-driven thymic lymphoma, Genes Dev., 13(10):1246-50 (1999).
Lin, P. et al., Research of Immune Globulin in Mice, Guangzhou Medical Journal, 01:49-50 (1990).
Liu, Y. et al., Primary Genetic Investigation of a Hyperlipidemia Model: Molecular Characteristics and Variants of the Apolipoprotein E Gene in Mongolian Gerbil, Biomed Research International, 2014: 9 pages (2014).
Lonberg, N., Fully human antibodies from transgenic mouse and phage display platforms, Curr. Opin. Immunol., 20(4):450-9, and supplemental material, 16 pages (2008).
Lonberg, N., Human Monoclonal Antibodies from Transgenic Mice, Therapeutic Antibodies, Handbook of Experimental Pharmacology, Eds. Chernajovsky, Y and Nissim, A., Berlin Heidelberg: Springer-Verlag, 181: 69-97 (2008).
Lovell-Badge, Robin, Many ways to pluripotency, Nature Biotechnology, 25:1114-1116 (2007).
Luby, T.M. et al., The mu Switch Region Tandem Repeats Are Important, but Not Required, for Antibody Class Switch Recombination, J. Exp. Med., 193(2):159-168 (2001).
MacDonald, L. et al., Velocigene Technology Extended to Humanization of Several Megabases of Complex Gene Loci, First International MUGEN Conference of Animal Models for Human Immunological Disease, Sep. 10-13, 2006—Athens, Greece, Abstract 21 and Poster, 2 pages (2006).
Mageed, R.A. et al., Rearrangement of the human heavy chain variable region gene V3-23 in transgenic mice generates antibodies reactive with a range of antigens on the basis of VHCDR3 and residues intrinsic to the heavy chain variable region, Clinical and Experimental Immunology, 123(1):1-8 (2001).
Mahmoud, T.L. et al., Limiting CDR-H3 Diversity Abrogates the Antibody Response to the Bacterial Polysaccharide x 1→3 Dextran, The Journal of Immunology, 187:879-886 (2011).
Mahmoudi, M. et al., V region gene analysis of human IgM hybridoma monoclonal anti-Sm antibodies, Lupus, 6:578-589 (1997).
Manis, J.P. et al., Mechanism and control of class-switch recombination, Trends. Immunol., 23(1):31-9 (2002).
Marasca, R. et al., Immunoglobulin Gene Mutations and Frequent Use of VH1-69 and VH4-34 Segments in Hepatitis C Virus-Positive and Hepatitis C Virus-Negative Nodal Marginal Zone B-Cell Lymphoma, American Journal of Pathology, 159(1):253-261 (2001).
Mar. 3, 2016 Letter from H. Van Der Hoff, Opposition against EP 2550363 (2 pages).
Martinez-Jean, C. et al., Nomenclature and overview of the mouse (*Mus musculus* and *Mus* sp.) immunoglobulin kappa (IGK) genes, Exp. Clin. Immunogenet., 18(4):255-79 (2001).
Marvin, J. and Zhu, Z., Recombinant approaches to IgG-like bispecific antibodies, Acta Pharmacologica Sinica, 26(6):649-658 (2005).
Matsuda, F. et al., The Complete Nucleotide Sequence of the Human Immunoglobulin Heavy Chain Variable Region Locus, J. Exp. Med., 188(11): 2151-2162 (1998).
McGoldrick, P. et al., Roden models of amyotrophic lateral sclerosis, Biochimica et Biophysica Acta, 1832:1421-1436 (2013).
Miklos, J.A. et al., Salivary gland mucosa-associated lymphoid tissue lymphoma immunoglobulin VH genes show frequent use of V1-69 with distinctive CDR3 features, Blood, 95:3878-3884 (2000).
Mortari, F. et al., Human Cord Blood Antibody Repertoire, The Journal of Immunology, 150(4):1348-1357 (1993).
Muller, S. et al., B-Cell Abnormalities in AIDS: Stable and Clonally-Restricted Antibody Response in HIV-1 Infection, Scandinavian Journal of Immunology, 38:327-334 (1993).

Murphy, A., VelocImmune: Immunoglobulin Variable Region Humanized Mice, Recombinant Antibodies for Immunotherapy, Ed. Little, M., New York, NY: Cambridge University Press, Chapter 8, pp. 100-107 (2009).
Murphy, Kenneth, Janeway's Immunobiology, 8th Edition., New York: Garland Science, Chapter 5, Sections 5-1 to 5-4, pp. 157-162 (2012).
Muyldermans, S. et al., Sequence and structure of VH domain from naturally occurring camel heavy chain immunoglobulins lacking light chains, Protein Eng., 7(9):1129-35 (1994).
Muyldermans, S., Single domain camel antibodies: current status, J. Biotechnol., 74(4):277-302 (2001).
Nagle, Mike, Regeneron helps make Sanofi VelocImmune to its 'weak' pipeline, Breaking News on Contract Research, Manufacturing & Clinical Trials, 2 pages (2007).
Nelson, A.L. et al., Development trends for human monoclonal antibody therapeutics, Nat. Rev. Drug. Discov., 9(10):767-74 (2010).
Nemazee, D., Receptor editing in B cells, Adv. Immunol., 74:89-126 (2000).
Nguyen, V.K. et al., Heavy-chain only antibodies derived from dromedary are secreted and displayed by mouse B cells, Immunology, 109(1):93-101 (2003).
Nishimura, H. et al., Possible Function of the ADAM1a/ADAM2 Fertilin Complex in the Appearance of ADAM3 on the Sperm Surface, The Journal of Biological Chemistry, 279(33):34957-34962 (2004).
Nissim et al., Antibody fragments from a 'single pot' phage display library as immunochemical reagents, EMBO J., 13(3): 692-698 (1994).
Notice of Opposition for EP 2501817, 28 pages (May 25, 2016).
Notice of opposition to a European patent for EP 2314629, *Merus B.V. v. Regeneron Pharmaceuticals, Inc.*, 38 pages (Jul. 15, 2014).
Notice of Opposition to a European Patent for EP2550363, 28 pages (Dec. 10, 2014).
Nucleotide Sequence RID Y55HBK1 W114, last accessed Aug. 6, 2014 (2 pages).
Office Action for CN Application 201180013714.0 dated Jan. 30, 2014 (7 pages).
Office Action for CN Application 201180013714.0, 19 pages (dated May 15, 2013).
Office Action for U.S. Appl. No. 13/716,238, 7 pages (dated Jan. 4, 2016).
Office Action for U.S. Appl. No. 13/798,310 dated Sep. 11, 2013 (13 pages).
Office Action for U.S. Appl. No. 13/951,996, 7 pages (dated Dec. 17, 2015).
Office Action for U.S. Appl. No. 14/137,902, 23 pages (dated Oct. 30, 2015).
Office Action for U.S. Appl. No. 14/818,162, 30 pages (dated Dec. 11, 2015).
Office Action for U.S. Appl. No. 13/948,818 dated Jun. 26, 2014 (11 pages).
Office Action for U.S. Appl. No. 13/948,818 dated Sep. 11, 2013 (12 pages).
Opinion & Order between Regeneron Pharmaceuticals, Inc. and Merus B.V., 114 pages (Nov. 2, 2015).
Opposition dated Aug. 11, 2014, in EP Application No. 09075279.1, 983 pages.
Opposition dated Aug. 20, 2015, in EP Application No. 09075279.1, 25 pages.
Opposition dated Jan. 15, 2016, in JP Patent No. 5749161 and English translation, 188 pages.
Opposition dated Sep. 22, 2014, in AU Application No. 2009263082, 35 pages.
Opposition filed in European Application No. 10186063.3, 1351 pages (Jul. 15, 2014).
Pasqualini, R. and Arap, W., Hybridoma-free generation of monoclonal antibodies, Proceedings of the National Academy of Sciences USA, 101(1):257-259 (2004).
Peeters, K. et al., Production of antibodies and antibody fragments in plants, Vaccine, 19(17-19):2756-61 (2001).

(56) References Cited

OTHER PUBLICATIONS

Perez, M. et al., Primary cutaneous B-cell Lymphoma is associated with somatically hypermutated immunoglobulin variable genes and frequent use of VH1-69 and VH4-59 segments, British Journal of Dermatopathology, 162:611-618 (2010).
Phan, T. et al., Altered Migration, Recruitment, and Somatic Hypermutation in the Early Response of Marginal Zone B Cells to T Cell-Dependent Antigen, The Journal of Immunology, 174(8):4567-78 (2005).
Phan, T. et al., B Cell Receptor-independent Stimuli Trigger Immunoglobulin (Ig) Class Switch Recombination and Production of IgG Autoantibodies by Anergic Self-Reactive B Cells, The Journal of Experimental Medicine, 197(7):845-860 (2003).
Phan, T.G. et al., High affinity germinal center B cells are actively selected into the plasma cell compartment, J. Exp. Med., 203(11):2419-24 (2006).
Pollock, D.P. et al., Transgenic milk as a method for the production of recombinant antibodies, J. Immunol. Methods., 231(1-2):147-57 (1999).
Porteus, M.H. and Carroll, D., Gene targeting using zinc finger nucleases, Nat.; Biotechnol., 23(8):967-73 (2005).
Pos, W. et al., VH1-69 germline encoded antibodies directed towards ADAMTS13 in patients with acquired thrombotic thrombocytopenic purpura, Journal of Thrombosis and Haemostatis, 7:421-428 (2008).
Prak, E. and Weigert, M., Light chain replacement: a new model for antibody gene rearrangement, J. Exp. Med., 182(2):541-548 (1995).
Prelle, K. et al., Pluripotent stem cells—model of embryonic development, tool for gene targeting, and basis of cell therapy, Anat. Histol. Embryol., 31(3):169-86 (2002).
Radic, M.Z. et al., Ig H and L chain contributions to autoimmune specificities, J. Immunol., 146(1):176-82 (1991).
Ramsden, D.A. et al., Conservation of sequence in recombination signal sequence spacers. Nucleic Acids Res., 22(10):1785-96 (1994).
Ravetch, J.V., Structure of the human immunoglobulin mu locus: characterization of embryonic and rearranged J and D genes, Cell, 27(3 Pt 2):583-91 (1981).
Ray, Ectopic expression of a c-kitW42 minigene in transgenic mice: recapitulation of W phenotypes and evidence for c-kit function in melanoblast progenitors, Genes Dev., 5(12A): 2265-73 (1991).
Request to provoke an interference U.S. Appl. No. 13/750,753, filed Jan. 25, 2013.
Reusch, et al., Beyond mAbs with TandAbs, Innovations in Pharmaceutical Technology, 4 pages (Jun. 2011).
Riechmann, L. and Muyldermans, S., Single domain antibodies: comparison of camel VH and camelised human VH domains, J. Immunol. Methods., 231(1-2):25-38 (1999).
Ritchie, K. et al., Allelic exclusion and control of endogenous immunoglobulin gene rearrangement in kappa transgenic mice, Nature, 312:517-520 (1984).
Rodríguez, C.I., et al., High-efficiency deleter mice show that FLPe is an alternative to Cre-loxP, Nat. Genet., 25(2):139-40 (2000).
Rosner, K. et al., Third complementarity-determining region of mutated VH immunoglobulin genes contains shorter V, D, J, P, and N components than non-mutated genes, Immunology, 103(2):179-87 (2001).
Rouet, P., et al. Introduction of double-strand breaks into the genome of mouse cells by expression of a rare-cutting endonuclease, Mol. Cell. Biol., 14:12 8096-8106 (1994).
Rudikoff, S. et al., Single amino acid substitution altering antigen-binding specificity, Immunology, 79:1979-1983 (1982).
Sasso E.H. et al., A Fetally Expressed Immunoglobulin VH1 Gene Belongs to a Complex Set of Alleles, Journal of Clinical Investigation, 91:2358-2367 (1993).
Sasso E.H. et al., Expression of the Immunoglobulin VH Gene 51p1 is Proportional to its Germline Gene Copy Number, Journal of Clinical Investigation, 97(9):2074-2080 (1996).
Sasso, E.H. et al., Prevalence and Polymorphism of Human VH3 Genes, The Journal of Immunology, 145(8):2751-2757 (1990).
Schelonka, R.L. et al., A Single DH Gene Segment Creates Its Own Unique CDR-H3 Repertoire and Is Sufficient for B Cell Development and Immune Function, The Journal of Immunology, 175:6624-6632 (2005).
Schnieke, A.E. et al., Human factor IX transgenic sheep produced by transfer of nuclei from transfected fetal fibroblasts, Science, 278(5346):2130-3 (1997).
Schroeder, H.W. Jr., Similarity and divergence in the development and expression; of the mouse and human antibody repertoires, Dev. Comp. Immunol., 30(1-2):119-35 (2006).
Schulze, M. et al., Derivation, Maintenance, and Characterization of Rat Embryonic Stem Cells In Vitro, Methods in Molecular Biology, 329:45-58 (2006).
Segal, D. et al., Introduction: bispecific antibodies, Journal of Immunological Methods, 248(12):1-6 (2001).
Sekiguchi, et al. Mechanism of V(D)J Recombination, Molecular Biology of B Cells, Eds. Honjo, Alt, and Neuberger, London, UK: Elsevier Academic Press, pp. 61-82 (2004).
Shih, H.H., Discovery Process for Antibody-Based Therapeutics, Development of Antibody-Based Therapeutics 426, Eds. Tabrizi, M.A. et al., Springer New York, pp. 9-32 (2012).
Shmerling et al., Strong and ubiquitous expression of transgenes targeted into the β-actin locus by Cre/lox cassette replacement, Genesis 42(5):229-235 (2005).
Sibilia, J. et al., Structural Analsys of Human Antibodies to Proteinase 3 from Patients with Wegener Granulomatosis, The Journal of Immunology, 159:712-719 (1997).
Sigmund, Curt D., Viewpoint: Are Studies in Genetically Altered Mice Out of Control?, Arterioscler Thromb Vasc Biol, 20(6):1425-1429 (2000).
Sirac, C. et al., Light chain inclusion permits terminal B cell differentiation and does not necessarily result in autoreactivity, Proc. Natl. Acad. Sci, U S A, 103(20):7747-52 (2006), and Supplemental information, 4 pages, retrieved Jul. 7, 2016: <http://www.pnas.org/content/103/20/7747.long?tab=ds#F6>.
Smith, E.J. et al., A novel, native-format bispecific antibody triggering T-cell killing of B-cells is robustly active in mouse tumor models and cynomolgus monkeys, Sci. Rep., 5:17943 (2015).
Souroujon, M.C. et al., Polymorphisms in Human H Chain V Region Genes from the VHIII Gene Family, The Journal fo Immunology, 143(2):706-711 (1989).
Steipe, B., et al. Sequence statistics reliably predict stabilizing mutations in a protein domain, J. Mol. Biol., 240(3):188-92 (1994).
Stevens, S. et al., Velocimmune: Humanization of Immunoglobulin Loc Using Velocigene Technology, First International MUGEN Conference of Animal Models for Human Immunological Disease, Sep. 10-13, 2006—Athens, Greece, Abstract 4 and Poster, 2 pages (2006).
Storb, U. et al., Transgenic Mice with μ nd κ Genes Encoding Antiphosphorycholine Antibodies, J. Exp Med, 164:627-41 (1986).
Su, Q. et al., A DNA transposon-based approach to validate oncogenic mutations in the mouse, Proc. Natl. Acad. Sci. USA, 105(50):19904-9 (2008).
Sui, J. et al., Structural and functional bases for broad-spectrum neutralization of avian and human influenza A viruses, Nature Structural and Molecular Biology, 16(3):265-273 (2009).
Summons to attend oral proceedings dated Jan. 19, 2016, in EP Application 09075279.1, 20 pages.
Suzuki, I. et al., Representation of Rearranged VH Gene Segments in the Human Adult Antibody Repertoire, The Journal of Immunology, 154:3902-3911 (1995).
Taki, S. et al., Targeted insertion of a variable region gene into the immunoglobulin heavy chain locus, Science, 262(5137):1268-71 (1993).
Tanha, J. et al., Optimal design features of camelized human single-domain antibody libraries, J. Biol. Chem., 276(27):24774-80 (2001).
Third Party Observation dated Apr. 8, 2014, in CA Application No. 2729095, 16 pages.
Third Party Observation dated Apr. 10, 2015, in EP Application No. 11703799.4, 248 pages.
Third Party Observation dated Apr. 25, 2012, in EP Application No. 09075279.1, 145 pages.

(56) References Cited

OTHER PUBLICATIONS

Third Party Observation dated Feb. 28, 2013, in EP Application No. 11703799.4, 43 pages.
Third Party Observation dated Jul. 1, 2013, in EP Application No. 09075279.1, 6 pages.
Third Party Observation dated Jun. 24, 2013, in EP Application No. 09075279.1, 15 pages.
Third Party Observation dated May 16, 2013, in EP Application No. 09075279.1, 82 pages.
Third Party Observation dated May 4, 2015, in EP Application No. 12717033.0, 151 pages.
Third Party Observation dated Nov. 18, 2014, in EP Application No. 11703799.4, 132 pages.
Third Party Observation dated Nov. 3, 2014, in EP Application No. 12173456.0, 274 pages.
Third Party Observation dated Oct. 3, 2013, in EP Application No. 09075279.1, 3 pages.
Third Party Observation dated Oct. 21, 2013, in AU Application No. 2009263082, 24 pages.
Third Party Observation dated Oct. 25, 2012, in EP Application No. 09075279.1, 27 pages.
Third Party Observation dated Sep. 12, 2013, in EP Application No. 09075279.1, 5 pages.
Third Party Observation dated Sep. 16, 2015, in CA Application No. 2729095, 15 pages.
Third Party Observation dated Sep. 5, 2013, in EP Application No. 09075279.1, 11 pages.
Third Party Observation dated Sep. 7, 2015, in EP Application No. 12173456.0, 68 pages.
Third Party Observation pursuant to Article 115 EPC for EP 14170196.1, 6 pages (Jul. 1, 2015).
Third Party Observations on European Patent Application No. 12192727.1, 17 pages (Jun. 18, 2013).
Third Party Observations on European Patent Application No. 12192727.1, 3 pages (Feb. 25, 2014).
Third Party Observations on European Patent Application No. 12192727.1, 5 pages (Nov. 17, 2014).
Third Party Observations on European Patent Application No. 12192727.1, 7 pages (Apr. 8, 2015).
Third Party Observations on European Patent Application No. 12192727.1, 9 pages (Aug. 11, 2015).
Third Party Observations on European Patent Application No. 12716101.6, 4 pages (Feb. 25, 2014).
Third Party Observations on European Patent Application No. 12716101.6, 4 pages (Jul. 31, 2014).
Third Party Observations on European Patent Application No. 12716101.6, 4 pages (Sep. 4, 2013).
Third Party Observations on European Patent Application No. 12716101.6, 5 pages (Jun. 27, 2014).
Third Party Observations on European Patent Application No. 12809955.3, 3 pages (Aug. 6, 2015).
Third Party Observations on European Patent Application No. 12809955.3, 4 pages (Jun. 24, 2014).
Third Party Observations on European Patent Application No. 14154918.8, 5 pages (Nov. 26, 2014).
Third Party Observations on European Patent Application No. 14154918.8, 289 pages (Apr. 20, 2015).
Third Party Observations on European Patent Application No. 14154967.5, 5 pages (Nov. 18, 2014).
Third Party Observations on European Patent Application No. 14154967.5, 7 pages (Apr. 23, 2015).
Third Party Observations on European Patent Application Nos. 12192727.1, 14154918.8, 14154967.5, 14176593.3 and 12809955.3, 3 pages (Nov. 12, 2015).
Third Party Observations on U.S. Appl. No. 13/890,519, 27 pages (Oct. 23, 2013).
Third Party Observations pursuant to Art. 115 EPC and R. 114 EPC against EP Application No. 12717033.0, 11 pages (May 4, 2015).
Third Party Observations pursuant to Article 115 EPC and R. 114 EPC against European Application No. 11703799.4, 5 pages (Apr. 10, 2015).
Third Party Observations Under Article 115 EPC against European Application No. 09075279.1 in the name of Merus BV, 12 pages (Oct. 25, 2012).
Third Party Observations under Article 115 EPC for EP 12 173 456.0, 8 pages (Nov. 3, 2014).
Third Party Submission dated Feb. 18, 2013, in U.S. Appl. No. 13/093,156, 179 pages.
Third Party Submission dated Feb. 19, 2014, in U.S. Appl. No. 13/750,753, 282 pages.
Third Party Submission dated Feb. 24, 2014, in U.S. Appl. No. 13/750,753, 97 pages.
Third Party Submission dated Feb. 27, 2014, in U.S. Appl. No. 13/948,818, 10 pages.
Third Party Submission dated Jan. 28, 2013, in U.S. Appl. No. 12/589,181, 13 pages.
Third Party Submission dated Jun. 12, 2013, in U.S. Appl. No. 13/750,753, 100 pages.
Third Party Submission filed in U.S. Appl. No. 13/795,637, 117 pages (Mar. 18, 2014).
Tiegs, S. et al., Receptor Editing in Self-reactive Bone Marrow B Cells, The Journal of Experimental Medicine, 177:1009-1020 (1993).
Timetable for Mouse ES Cells course at Wellcome Trust Sanger Institute Oct. 26, 2009-Nov. 8, 2009 (greyscale).
Tomizuka, K. et al., Double trans-chromosomic mice: maintenance of two individual human chromosome fragments containing Ig heavy and kappa loci and expression of fully human antibodies, Proc. Natl. Acad. Sci. U S A., 97(2):722-7 (2000).
Tonegawa, S., Somatic generation of antibody diversity, Nature, 302(5909):575-81 (1983).
Tsubata, T. and Reth, M., The Products of the Pre-B Cell-specific Genes(Lambda5 and VpreB) and the Immunoglobulin mu Chain Form a Complex that is Transported onto the Cell Surface, Journal of Experimental Medicine, 172:973-976 (1990).
Tuaillon, N. et al., Human immunoglobulin heavy-chain minilocus recombination in transgenic mice: Gene-segment use in u and y transcripts, Proceeding of the National Academy of Science USA, 90:3720-3724 (1993).
Tuaillon, N., Repertoire analysis in human immunoglobulin heavy chain minilocus transgenic, [mu]MT/[mu]MT mice, Molecular Immunology, 37(5):221-231(2000).
UniProt Entry Q5QGZ9, retrieved Jan. 21, 2015 from <http://www.uniprot.org/uniprot/Q5QGZ9>(16 pages).
Van Spriel, A.B. et al., Immunotherapeutic perspective for bispecific antibodies, Immunol. Today, 21(8):391-7 (2000).
Vasquez, K.M. et al., Manipulating the mammalian genome by homologous recombination, Proc. Natl. Acad. Sci. U S A., 98(15):8403-10 (2001).
Vieira, P. and Rajewsky, K., The half-lives of serum immunoglobulins in adult mice,; Eur. J. Immunol., 18(2):313-6 (1988).
Wagner et al., "The Diversity of Antigen-Specific Monoclonal Antibodies from Transgenic Mice Bearing Human Immunoglobulin Gene Miniloci," European Journal of Immunology, 24: 2672-2681, 1994.
Wagner, S.D. et al., Antibodies generated from human immunoglobulin miniloci in transgenic mice, Nucleic Acids Research, 22(8):1389-1393 (1994).
Wang, T.T. and Palese, P., Universal epitopes of influenza virus hemagglutinins?, Nature Structural & Molecular Biology, 16(3):233-234 (2009).
Waterfield, M.D. et al., Restricted Structural Heterogeneity in Antibodies: Might Different Heavy Chains have a Common Light Chain? Nature New Biology, vol. 240:215-217 (1972).
Wilmut, I. and Clark, A.J., Basic techniques for transgenesis, J. Reprod. Fertil. Suppl., 43:265-75 (1991).
Wilmut, I. et al., Viable offspring derived from fetal and adult mammalian cells, Nature, 385(6619):810-3 (1997).
Written Opinion for PCT/US2011/023971 (dated Apr. 11, 2011).
Written Opinion for PCT/US2012/026416 (8 pages), dated Jun. 25, 2012.

(56) References Cited

OTHER PUBLICATIONS

Written Opinion for PCT/US2012/060487, 5 pages (dated Feb. 1, 2013).
Written Opinion for PCT/US2013/029624 (12 pages), dated Aug. 2, 2013.
Wu, H. et al., Double replacement: strategy for efficient introduction of subtle mutations into the murine Col1a-1 gene by homologous recombination in embryonic stem cells, Proc. Natl. Acad. Sci. U S A., 91(7):2819-23 (1994).
Xu, J. and Davis, M. Diversity in the CDR3 Region of VH Is Sufficient for Most Antibody Specificities, Immunity, 13:37-45 (2000).
Yamada, M. et al., Preferential Utilization of Specific Immunoglobulin Heavy Chain Diversity and Joining Segments in Adult Human Peripheral Blood B Lymphocytes, Journal of Experimental Medicine, 173:395-407 (1991).
Yang, X.W. et al., Homologous recombination based modification in *Escherichia coli* and germline transmission in transgenic mice of a bacterial artificial chromosome, Nat. Biotechnol. 15(9):859-65 (1997).
Zemlin, M. et al., Expressed Murine and Human CDR-H3 Intervals of Equal Length Exhibit Distinct Repertoires that Differ in their Amino Acid Composition and Predicted Range of Structures, JMB, 334:733-749 (2003).
Zheng, J. et al., Immunoglobulin gene transcripts have distinct VHDJH recombination characteristics in human epithelial cancer cells, J. Biol. Chem., 284(20):13610-9 (2009).
Zou, Y.R. et al., Cre-loxP-mediated gene replacement: a mouse strain producing humanized antibodies, Curr. Biol., 4(12):1099-103 (1994).
Collins, A. et al., The reported germline repertoire of human immunoglobulin kappa chain genes is relatively complete and accurate, Immunogenetics, 60:669-676 (2008).
Corrected Claims in JP5749161 (English and Japanese), 6 pages.
Cover Letter—Applicant Post-Hearing Submissions in AU2009263082, 1 page (Oct. 19, 2016).
Declaration of Dr. Ton Logtenberg filed in U.S. Appl. No. 13/750,753, 10 pages (Dec. 18, 2015).
Declaration of Dr. Ton Logtenberg filed in U.S. Appl. No. 13/750,753, 4 pages (Sep. 15, 2015).
Declaration of Professor Dr. Roland Kontermann, Ph.D. For EP2505654 B1, 4 pages (May 19, 2017).
Declaration of Professor Ton Logtenberg for EP2314629, 7 pages (May 4, 2016).
Declaration of Robert Brink dated Sep. 27, 2016, as filed against EP Patent No. 2,147,594 B1 (European patent application No. 09075279.1), 33 pages.
Declaration of Robert Brink in AU 2009263082, 19 pages (Oct. 19, 2016).
Final Post-Hearing Submission—DeFranco Declaration Annexure in AU2009263082, 10 pages (Oct. 18, 2016).
Final Post-Hearing Submission—Opponent in AU2009263082, 4 pages (Oct. 19, 2016).
Final Response to Opposition in EP2501817, 27 pages (Dec. 23, 2016).
Fussenegger, M. et al., Genetic optimization of recombinant glycoprotein production by mammalian cells, Tibtech, 17:35-42 (1999).
Initial Determination in EP Application No. 10186063.3, 11 pages (Nov. 19, 2015).
Initial Post-Hearing Submissions (Applicant) Brink Declaration Annex for Australian patent application No. 2009263082, 36 pages (Oct. 4, 2016).
Initial Post-Hearing Submissions (Applicant) for Australian patent application No. 2009263082, 5 pages (Oct. 5, 2016).
Initial Post-Hearing Submissions (Opponent's Initial Supplementary Submissions) for Australian patent application No. 2009263082, 7 pages (Oct. 5, 2016).
Initial Post-Hearing Submissions—DeFranco Declaration Annexure for Australian patent application No. 2009263082, 41 pages (Oct. 4, 2016).
Initial Post-Hearing Submissions—Goodnow Declaration Annexure for Australian patent application No. 2009263082, 13 pages (Oct. 4, 2016).
Interlocutory decision in Opposition proceedings (Art. 101(3)(a) and 106(2) EPC) for EP12716101.6, 36 pages (May 26, 2017).
Jendeberg, L. et al., Engineering of Fc1 and Fc3 from human immunoglobulin G to analyse subclass specificity for staphylococcal protein A1, Journal of Immunological Methods, 201:25-34 (1997).
Johnston, C. et al., Complete Sequence Assembly and Characterization of the C57BL/6 Mouse Ig Heavy Chain V Region, The Journal of Immunology, 176:4221-4234 (2006).
JP Opposition Decision in JP5749161 (English and Japanese), 54 pages (Sep. 7, 2016).
Lam, K. et al., In Vivo Ablation of Surface Immunoglobulin on Mature B Cells by Inducible Gene Targeting Results in Rapid Cell Death, Cell, 90:1073-1083 (1997).
Lantto, J. et al., Capturing the natural diversity of the human antibody response against vaccinia virus, J Virol, 85(4):1820-33 (2011).
Letter Accompanying Initial Post-Hearing Submissions (Applicant) for Australian patent application No. 2009263082, 1 page (Oct. 5, 2016).
Merus Response to REGN Opposition in EP2147594, 35 pages (Apr. 2, 2015).
Minutes of the taking of evidence by hearing of witnesses recorded in the oral proceedings before the Opposition Division for EP12716101.6, 25 pages (May 26, 2017).
Notice of Opposition in EP2505654, 39 pages (May 24, 21017).
Notice of Opposition in EP2701499, 27 pages (Nov. 10, 2016).
Notice of Opposition in JP5749161 (English and Japanese), 188 pages (Jan. 15, 2016).
Notice of Reasons for Revocation in JP5749161, (English and Japanese), 18 pages (Mar. 17, 2016).
Notice of Receipt of Correction Request in JP5749161 (English and Japanese), 2 pages (Jul. 1, 2016).
Opponent Reply to Patentee Submissions in EP2501817, 5 pages (Mar. 17, 2017).
Opponent Final Submissions for EP2550363, 15 pages (Jan. 27, 2017).
Opposition's rebuttal to Proprietor's submissions in Opposition No. 700031/2016 (English and Japanese), 64 pages (Aug. 22, 2016).
Patent Owner Final Submissions in response to the Summons to attend Oral Proceedings dated Nov. 19, 2015 and in preparation of the Hearing of Jun. 22, 2016 for EP2314629, 16 pages (May 20, 2016).
Patentee Final Submissions for EP12716101.6, 4 pages (Jan. 27, 2017).
Patentee's Arguments against Opposition No. 700031/2016 (English and Japanese), 29 pages (Jun. 21, 2016).
Patentee's Exhibit 1 submitted with Argument against Opposition No. 700031/2016 on Jun. 21, 2016, "Really Essential Medical Immunology", Blackwell Science Ltd. Cover, colophon, Contents and Chapter 3 (pp. 23-25) (English and Japanese), 17 pages (2000).
Patentee's Exhibit 2 submitted with Argument against Opposition No. 700031/2016 on Jun. 21, 2016, Communication to the EPO submitted by the Opponent in connection with prosecution of EP2505654 (English and Japanese), 7 pages (Sep. 29, 2014).
Patentee's Exhibit 3 submitted with Argument against Opposition No. 700031/2016 on Jun. 21, 2016, Declaration of Peter Hudson (English and Japanese), 15 pages (Jun. 17, 2016).
Phelps, J. et al., Expression and Characterization of a Chimeric Bifunctional Antibody with Therapeutic Applications, The Journal of Immunology, 145:1200-1204 (1990).
Provision of the minutes in accordance with Rule 124(4) EPC for EP1276101.6, 62 pages (May 26, 2017).
Reply to Communication in EP12173456.0, 12 pages (dated Apr. 12, 2013).
Request for Correction in JP5749161 (English and Japanese), 29 pages (Jun. 21, 2016).
Response Post-Hearing Submissions by Applicant in AU2009263082, 15 pages (Oct. 19, 2016).

(56) References Cited

OTHER PUBLICATIONS

Response to Notice of Opposition dated Aug. 22, 2014 for EP2314629, 20 pages (Feb. 24, 2015).
Response to Opposition in EP2701499, 22 pages (Apr. 28, 2017).
Response to Summons to attend Oral Proceedings for EP255036, 1 page (Feb. 28, 2017).
Rickert, R. et al., Impairment of T-cell-dependent B-cell responses and B-1 cell development in CD19-deficient mice, Nature, 376(6538):352-5 (1995).
Statement of Facts and Arguments in Support of Opposition for EP2147594, 57 pages (Aug. 11, 2014).
Summons to Opposition in EP2501817, 12 pages (May 17, 2017).
Tada, H. et al., Expression and characterization of a chimeric bispecific antibody against fibrin and against urokinase-type plasminogen activator, Journal of Biotechnology, 33:157-174 (1994).
Verma, R. et al., Antibody engineering: Comparison of bacterial, yeast, insect and mammalian expression systems, Journal of Immunological Methods, 216:165-181 (1998).
Alfandari, D. et al., Xenopus ADAM 13 is a metalloprotease required for cranial neural crest-cell migration, Current Biology, 11:918-930 (2001).
Austin, C. et al., The Knockout Mouse Project, Nat. Genet., 36(9):921-924 (2004).
Blobel, Carl P., ADAMS: Key Components in EGFR Signalling and Development, Nature Reviews, Molecular Cell Biology, 6:32-43 (2005).
Borghei, A. et al., Targeted Disruption of Tyrosylprotein Sulfotransferase-2, an Enzyme That Catalyzes Post-translational Protein Tyrosine O-Sulfation, Causes Male Infertility, The Journal of Biological Chemistry, 281(14):9423-9431 (2006).
Cho, C. et al., Analysis of Mouse Fertilin in Wild-Type and Fertilin β-/- Sperm: Evidence for C-terminal Modification, αβDimerization, and Lack of Essential Role of Fertilin α in Sperm-Egg Fusion, Developmental Biology, 222:289-295 (2000).
Cho, C. et al., Fertilization Defects in Sperm from Mice Lacking Fertilin β, Science, 281:1857-1859 (1998).
Cho, Chunghee, Mammalian ADAMS with Testis-Specific or-Predominant Expression, The ADAM Family of Proteases, 239-259 (2005).
Declaration of Brink dated Sep. 27, 2016, as filed against EP Patent No. 2,147,594 B1 (European patent application No. 09075279.1), 33 pages.
Declaration of Dr. Kosuke Yusa and associated Annexes, 7 pages (Oct. 2, 2017).
Declaration of Professor Michel Cogné, 26 pages (Jul. 17, 2017).
Declaration of Dr. Liang in EP 2550363, 9 pages (Feb. 1, 2018).
Engel, P. et al., Abnormal B Lymphocyte Development, Activation, and Differentiation in Mice that Lack or Overexpress the CD19 Signal Transduction Molecule, Immunity, 3:39-50 (1995).
Ensembl database entries for the heavy and light chain immunoglobulin loci, as submitted in EP 2550363 on Oct. 16, 2017, 3 pages.
Final Written Submissions Oral Proceedings Scheduled for Oct. 28, 2016 in EP2147594, 40 pages.
Fishwild, D. et al., High-avidity human IgGk monoclonal antibodies from a novel strain of minilocus transgenic mice, Nature Biotechnology, 14:845-851 (1996).
Gaultier, A. et al., ADAM13 Disintegrin and Cysteine-rich Domains Bind to the Second Heparin-binding Domain of Fibronectin, The Journal of Biological Chemistry, 277(26):23336-23344 (2002).
Glassey, B. and Civetta, A., Positive Selection at Reproductive ADAM Genes with Potential Intercellular Binding Activity, Molecular Biology and Evolution, 21(5):851-859 (2004).
Gorman, et al., The LGK 3' Enhancer Influences the Ratio of LGK Versus LGL B Lymphocytes, Immunity, 5(3): 241-252(1996).
Hagaman, J. et al., Angiotensin-covering enzyme and male fertility, Proc. Natl. Acad. Sci. USA, 95:2552-2557 (1998).
Han, C. et al., Impaired sperm aggregation in Adam2 and Adam3 null mice, Fertility and Sterility, 93(8):2754-2756 (2010).
Huovila, A. et al., ADAMs and cell fusion, Current Opinion in Cell Biology, 8:692-699 (1996).
Ikawa, M. et al., Calsperin Is a Testis-specific Chaperone Required for Sperm Fertility, The Journal of Biological Chemistry, 286(7):5639-5646 (2011).
Immler, S. et al., By Hook or by Crook? Morphometry, Competition and Cooperation in Rodent Sperm, PLoS ONE, Issue 1(e170) 5 pages (2007).
Immler, Simone, Sperm competition and sperm cooperation: the potential role of diploid and haploid expression, Reproduction, 135:275-283 (2008).
International Search Report for PCT/US2011/041366, 5 pages (dated Sep. 22, 2011).
Kim, E. et al., Differential localization of ADAM1a and ADAM1b in the endoplasmic reticulum of testicular germ cells and on the surface of epididymal sperm, Biochemical and Biophysical Research Communications, 304:313-309 (2003).
Kim, E. et al., Mouse Sperm Lacking ADAM1b/ADAM2 Fertilin Can Fuse with the Egg Plasma Membrane and Effect Fertilization, The Journal of Biological Chemistry, 281(9):5634-5639 (2006).
Kim, E. et al., Synthesis, Processing, and Subcellular Localization of Mouse ADAM3 during Spermatogenesis and Epididymal Sperm Transport, Journal of Reproduction and Development, 50(5):571-578 (2004).
Krutskikh, A. et al., Epididymal protein Rnase10 is required for post-testicular sperm maturation and male fertility, The FASEB Journal, 26(10):4198-4209 (2012).
Linder, B. et al., Delayed Translation and Posttranslational Processing of Cyritestin, an Integral Transmembrane Protein of the Mouse Acrosome, Experimental Cell Research, 221:66-72 (1995).
Long, J. et al., Phylogenetic and molecular evolution of the ADAM (A Disintegrin and Metalloprotease) gene family from Xenopus tropicalis, to *Mus musculus*, *Rattus norvegicus*, and *Homo sapiens*, Gene, 507:36-43 (2012).
Longo, N. et al., Characterization of immunoglobulin gene somatic hypermutation in the absence of activation-induced cytidine deaminase, J. Immunol., 181(2):1299-1306 (2008).
Marcello, M. et al., Lack of Tyrosylprotein Sulfotransferase-2 Activity Results in Altered Sperm-Egg Interactions and Loss of ADAM3 and ADAM6 in Epididymal Sperm, The Journal of Biological Chemistry, 286(15):13060-13070 (2011).
Melton, David W., Chapter 8: Gene-Targeting Strategies, Methods in Molecular Biology, Transgenesis Techniques, 2nd Edition, Principles and Protocols, 180:19 pages (2002).
Moore, H. et al., Exceptional sperm cooperation in the wood mouse, Nature, 418:174-177 (2002).
Murphy, Andrew, Chapter 8: VelocImmune: Immunoglobulin Variable Region Humanized Mice, Recombinant Antibodies for Immunotherapy, Part III, 14 pages (2009).
Nakanishi, T. et al., Selective Passage Through the Uterotubal Junction of Sperm from a Mixed Population Produced by Chimeras of Calmegin-Knockout and Wild-Type Male Mice, Biology of Reproduction, 71:959-965 (2004).
Nishimura, H. et al., Analysis of Loss of Adhesive Function in Sperm Lacking Cyritestin or Fertilin β, Developmental Biology, 233:204-213 (2001).
Nishimura, H. et al., Identification of an ADAM2-ADAM3 Complex on the Surface of Mouse Testicular Germ Cells and Cauda Epididymal Sperm, The Journal of Biological Chemistry, 282(24):17900-17907 (2007).
Patent Oppositions—Decision in for AU2009263082, 53 pages (May 5, 2017).
Pizzari, T. and Foster, K., Sperm Sociality: Cooperation, Altruism, and Spite, PLoS Biology, 6(5)(e130):0925-0931 (2008).
Poueymirou, W. et al., F0 generation mice fully derived from gene-targeted embryonic stem cells allowing immediate phenotypic analyses, Nature Biotechnology, 25(1):91-99 (2007).
Preliminary Opinion of the Opposition Division in EP2147594, 11 pages (Jan. 19, 2016).
Primakoff, P. and Myles, D., The ADAM gene family: surface proteins with adhesion and protease activity, Trends Genet, 16(2):83-87 (2000).
Roebroek, A. et al., Chapter 10: Knockin Approaches, Methods in Molecular Biology, Transgenic Mouse Methods and Protocols, 209:16 pages (2003).

(56) References Cited

OTHER PUBLICATIONS

Roychaudhuri, R. et al., ADAM9 Is a Novel Product of Polymorphonuclear Neutrophils: Regulation of Expression and Contributions to Extracellular Matrix Protein Degradation during Acute Lung Injury, The Journal of Immunology, 193:2469-2482 (2014).
Schwartz, D. and Cantor, C., Separation of Yeast Chromosome-Sized DNAs by Pulsed Field Gradient Gel Electrophoresis, Cell, 37:67-75 (1984).
Shamsadin, R. et al., Male Mice Deficient for Germ-Cell Cyritestin Are Infertile, Biology of Reproduction, 61:1445-1451 (1999).
Sorrell, D. and Kolb, A., Chapter XI: Targeted Modification of Mammalian Genomes, Focus on Genome Research, 6 pages (2004).
Statement of Grounds of Appeal for U.S. Pat. No. 2,147,594, 82 pages (2017).
Suarez, Susan S., Sperm Transport and Motility in the Mouse Oviduct: Observations in Situ, Biology of Reproduction, 36:203-210 (1987).
Swanson, W. and Vacquier, V., The Rapid Evolution of Reproductive Proteins, Nature Reviews, Genetics, 3:137-144 (2002).
Tokuhiro, K. et al., Protein disulfide isomerase homolog PDILT is required for quality control of sperm membrane protein ADAM3 and male fertility, PNAS, 109(10):3850-3855 (2012).
Valenzuela, D. et al., High-throughput engineering of the mouse genome coupled with high-resolution expression analysis, Nature Biotechnology, 21(6):652-659 (2003).
White, Judith M., ADAMS: modulators of cell-cell and cell-matrix interactions, Current Opinion in Cell Biology, 15:598-606 (2003).
Wolfsberg, T. et al., ADAM, a Widely Distributed and Developmentally Regulated Gene Family Encoding Membrane Proteins with a Disintegrin and Metalloprotease Domain, Developmental Biology, 169:378-383 (1995).

Yamaguchi, R. et al., Aberrant Distribution of ADAM3 in Sperm from Both Angiotensin-Converting Enzyme (Ace)- and Calmegin (Clgn)-Deficient Mice, Biology of Reproduction, 75:760-766 (2006).
Yamaguchi, R. et al., Disruption of ADAM3 Impairs the Migration of Sperm into Oviduct in Mouse, Biology of Reproduction, 81:142-146 (2009).
Yamaguchi, R. et al., Mice expressing aberrant sperm-specific protein PMIS2 produce normal-looking but fertilization-incompetent spermatozoa, MBoC, 23:2671-2679 (2012).
Zhang, Y. et al., A new logic for DNA engineering using recombination in *Escherichia coli*, Nature Genetics, 20:123-128 (1998).
Zhu, G. et al., Testase 1 (ADAM 24) a plasma membrane-anchored sperm protease implicated in sperm function during epididymal maturation or fertilization, Journal of Cell Science, 114:1787-1794 (2001).
Goodhardt et al. Rarrangement and Expression of rabbit immunoglobulin K light chain gene in transgenic mice; Jun. 1987;PNAS;84;4229-4233.†
Nicholson et al. Antibody repertoires of four and five-feature translocus mice carrying human immunoglobulin heavy chain and kappa and lambda light chain yeast artificial chromosomes; The Journal of Immunology, 1999; 163:6898-6906.†
Featherstone et al. The mouse immunoglobulin heavy chain V-D intergenic sequence contains insulaters that may regulate ordered V(D)J recombination. J. Biol. Chem. Mar. 26, 2010; 285 (13):9327-38.†
Choi et al., Characterization and comparative genomic analysis of intronless Adams with testicular gene expression: Apr. 2004; Genomics 83(4): 636-646.†

\* cited by examiner
† cited by third party

|  | A | B | C | D | E | F | G | H |
|---|---|---|---|---|---|---|---|---|
| Parental ES | Theoretical copy number | 2 | 2 | 2 | 2 | 2 | 2 | 0 | 0 |
| | Observed copy number | 1.9 | 1.8 | 2.1 | 1.8 | 1.9 | 1.8 | <0.01 | <0.04 |
| Modified ES | Theoretical copy number | 2 | 2 | 1 | 1 | 2 | 2 | 1 | 1 |
| | Observed copy number | 1.9 | 2.4 | 1.0 | 1.0 | 2.0 | 1.9 | + | + |

FIG. 3B

| | copy number | D | H |
|---|---|---|---|
| WT Mice | Theoretical | 2 | 0 |
| | Observed 1 | 1.71 | <0.01 |
| | Observed 2 | 2.07 | <0.01 |
| | Observed 3 | 2.16 | <0.01 |
| | Observed 4 | 1.88 | <0.01 |
| Het Mice | Theoretical | 1 | 1 |
| | Observed 1 | 1.22 | 1.04 |
| | Observed 2 | 0.94 | 1.02 |
| | Observed 3 | 0.85 | 0.95 |
| | Observed 4 | 1.02 | 1.00 |
| Homo Mice | Theoretical | 0 | 2 |
| | Observed 1 | <0.01 | 2.37 |
| | Observed 2 | <0.01 | 2.22 |
| | Observed 3 | <0.01 | 2.43 |
| | Observed 4 | <0.01 | 1.93 |

FIG. 3C

| 3'V$_H$ | N | D$_H$ | N | 5' J$_H$ |
|---|---|---|---|---|
| | | (D$_H$ 1-26) | | |
| (3-72) GCTAG | | GGTATAGTGGGAGCTACTAC | | |
| (3-9) GCAAAAG | CCCAGGGG | TAGTGGGgcCTAC | AGGC | CTTTTGATATC(3) |
| (3-7) GCGAGAGA | G | AGTGGGAGCTACTAC | ACCT | ATGCTTTTGATATC(3) |
| (4-59) GCGAGAG | GGAC | GGTATAGTGGGAaCTACT | GAGG | ACTTTGAtTAC(4) |
| (3-23) GCGAAAA | CC | AGTGGGAGC | CCT | CTTTGACTAC(4) |
| | | TAGTGGGAGCTACT | C | CTGGTTCGACCCC(5) |
| | | (D$_H$ 1-7) | | |
| (4-34) GCGAGAGG | AGGAG | GGTATAACTGGAACTGGAACT | | |
| (1-2) GCGAGAG | GA | GGTATAACTGGAACT | CGA | ATGCTTTTGATATC(3) |
| (3-23) GCGAAAGA | | TATAACTGGA | | ACTACTTTGACTAC(4) |
| (3-7) GCGAGAGA | G | GTATAACTGGAACCAC | TGG | TACTTTGACTAC(4) |
| (4-59) GCGAG | GGGA | ATAACTGGAAC | CCC | CTTTGACTAC(4) |
| (4-39) GCGAGA | GG | TATAACTGGAACT | TTTCTTTT | TTTGACTAC(4) |
| | | TAACTGGAACT | CTCTGGG | CTTTGACTAC(4) |
| | | (D$_H$ 3-10) | | |
| (3-30) GCGA | AAAGGGC | GTATTACTATGGTTCGGGGAGTTATTATAAC | | |
| (1-2) GCGAGAGA | | TACTATGGTTCGGGGAG | CTC | TTGACTAC(4) |
| | | TATTACTATGGTTCGGGGAGTTATTATAAC | GAAGGT CTACGGTATGGACGTC(6) | |
| | | (D$_H$ 6-6) | | |
| (1-2) GCGAGAGA | | GAGTATAGCAGCTCGTCC | | |
| (3-48) GCGAGA | GA | GTATAGCAG | | CTTTGACTAC(4) |
| (3-13) GCAAGAGA | GG | GAGTATAGCAGCTCGT | TG | TGACTAC(4) |
| | | ATAGgAGCTCGCCC | CTCGGG | TACTTTGACTAC(4) |
| | | (D$_H$ 7-27) | | |
| (3-7) GCGAGAGA | TCT | CTAACTGGGGA | | |
| (3-15) ACCAC | CCA | TGGGGA | AGG | CTAC(4) |
| (3-48) GCGAGA | GATA | TAACTGGGGA | GGG | TTTGACTAC(4) |
| | | GGGGA | | CCg(5) |

FIG. 7A

| 3'Vκ | N | 5' Jκ |
|---|---|---|
| (1-6) CAACAGAGTTAtAGTACCCCTCC | GGA | GACG(1) |
| (1-9) CAACAGCTTAATAGTTACCCTC | | GGACG(1) |
| (1-9) CAACAGCTTAATAGTTACC | | ATTCACT(3) |
| (1-9) CAACAtTTTAATAGTTACCC | | GCTCACT(4) |
| (3-15) CAGCAGTATAATAACTGGCCTC | | TCACT(4) |
| (1-17) CTACAGCATAATAGTTACCC | | GTGGACG(1) |
| (1-17) CTACAGCATAATAGTTACCCTC | | GGACG(1) |
| (3-20) CAGCAGTATGGTAGCTCACCTC | | GGACG(1) |
| (2-30) ATGCAAGGTACACACTGGCC | | GTGGACG(1) |
| (2-30) ATGCAAGGTtCACACTGGCC | | GTACACT(2) |
| (2-30) ATGCAAGGTACACACTGGCC | | GCTCACT(4) |
| (1-33) CAACAGTATGATAATCTCCCTCC | | CACT(3) |
| (1-33) CAACAGTATGATAATCTCCC | CG | ATTCACT(3) |
| (1-33) CAACAGTATGATAATCTCCC | | TCACT(4) |
| (1-33) CAACAGTATGATAATCTCCC | | GATCACC(5) |
| (1-37) CAACGGAtTTACAATGCC | GA | CACC(5) |
| (1-39) CAACAGAGTTACAGTACCCC | CA | TGTACACT(2) |
| (1-39) CAACAGAGTTACAGTACCCCTC | | TCACT(4) |
| (1-39) CAACAGAGTTACAGTACtCCTCC | | CACT(4) |

FIG. 7B

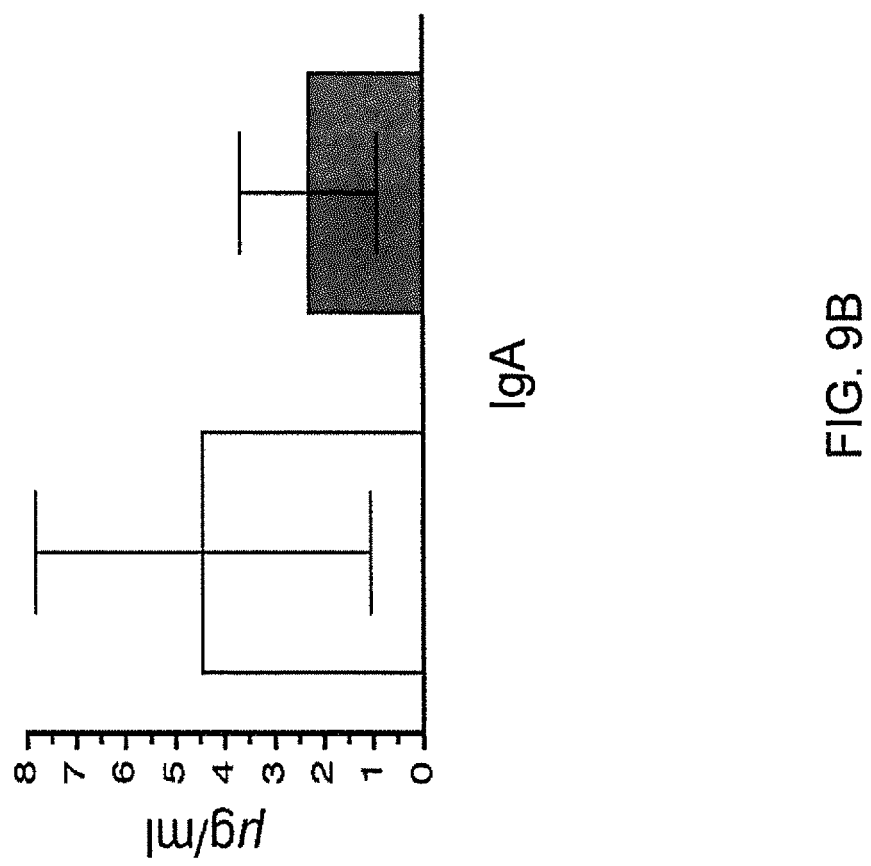

SEQUENCE LISTING

```
<160> NUMBER OF SEQ ID NOS: 91

<210> SEQ ID NO 1
<211> LENGTH: 754
<212> TYPE: PRT
<213> ORGANISM: Mus musculus

<400> SEQUENCE: 1

Met Leu Ser Leu Thr Trp Gly Met Arg Leu Val Glu Arg Pro Val Val
 1               5                  10                  15

Pro Arg Val Leu Leu Leu Leu Phe Ala Leu Trp Leu Leu Leu Leu Val
            20                  25                  30

Pro Val Trp Cys Ser Gln Gly His Pro Thr Trp Arg Tyr Ile Ser Ser
        35                  40                  45

Glu Val Val Ile Pro Arg Lys Glu Ile Tyr His Thr Lys Gly Leu Gln
    50                  55                  60

Ala Gln Arg Leu Leu Ser Tyr Ser Leu Arg Phe Arg Gly Gln Arg His
65                  70                  75                  80

Ile Ile His Leu Arg Arg Lys Thr Leu Ile Trp Pro Arg His Leu Leu
                85                  90                  95

Leu Thr Thr Gln Asp Asp Gln Gly Ala Leu Gln Met Glu Tyr Pro Phe
            100                 105                 110

Phe Pro Val Asp Cys Tyr Tyr Ile Gly Tyr Leu Glu Gly Ile Leu Gln
        115                 120                 125

Ser Met Val Thr Val Asp Thr Cys Tyr Gly Gly Leu Ser Gly Val Ile
    130                 135                 140

Lys Leu Asp Asn Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Leu Ser Ser Lys
        195                 200                 205

Asn Tyr Ala Thr His Pro Ala Ala Ile Lys Gly His Phe Gln Ala Thr
    210                 215                 220

His Ser Val Tyr Ser Ala Ser Gly Gly Asp Lys Leu Ser Ser Thr Val
225                 230                 235                 240

Glu Tyr Leu Phe Lys Val Ile Ser Leu Met Asp Thr Tyr Leu Thr Asn
                245                 250                 255

Leu His Met Arg Tyr Tyr Val Phe Leu Met Thr Val Tyr Thr Glu Ala
            260                 265                 270

Asp Pro Phe Ser Gln Asp Phe Arg Val Pro Gly Gly Gln Ala His Thr
        275                 280                 285

Phe Tyr Glu Arg Val Phe Tyr Ala His Phe Arg Pro Asp Ala Gly Ala
    290                 295                 300
```

-continued

| | | | | | | | | | | | |
|---|---|---|---|---|---|---|---|---|---|---|---|
|Ile|Ile|Asn|Lys|Asn|Ser|Pro|Gly|Asp|Asp|Ala|Val|Asn|Pro|Ala|Glu|
|305| | | |310| | | |315| | | |320|

Arg Ser Ile Cys Ser Pro Ser Ala Leu Ile Cys Leu Gly Gln His Gly
    325                 330                 335

Arg Asn Pro Leu Phe Leu Ser Ile Ile Ile Thr Asn Arg Val Gly Arg
            340                 345                 350

Ser Leu Gly Leu Lys His Asp Glu Gly Tyr Cys Ile Cys Gln Arg Arg
355                 360                 365

Asn Thr Cys Ile Met Phe Lys Asn Pro Gln Leu Thr Asp Ala Phe Ser
        370                 375                 380

Asn Cys Ser Leu Ala Glu Ile Ser Asn Ile Leu Asn Thr Pro Asp Leu
385                 390                 395                 400

Met Pro Cys Leu Phe Tyr Asp Arg His Val Tyr Tyr Asn Thr Ser Leu
                405                 410                 415

Thr Tyr Lys Phe Cys Gly Asn Phe Lys Val Asp Asn Asn Glu Gln Cys
            420                 425                 430

Asp Cys Gly Ser Gln Lys Ala Cys Tyr Ser Asp Pro Cys Cys Gly Asn
        435                 440                 445

Asp Cys Arg Leu Thr Pro Gly Ser Ile Cys Asp Lys Glu Leu Cys Cys
450                 455                 460

Ala Asn Cys Thr Tyr Ser Pro Ser Gly Thr Leu Cys Arg Pro Ile Gln
465                 470                 475                 480

Asn Ile Cys Asp Leu Pro Glu Tyr Cys Ser Gly Ser Lys Phe Ile Cys
                485                 490                 495

Pro Asp Asp Thr Tyr Leu Gln Asp Gly Thr Pro Cys Ser Glu Glu Gly
            500                 505                 510

Tyr Cys Tyr Lys Gly Asn Cys Thr Asp Arg Asn Ile Gln Cys Met Glu
        515                 520                 525

Ile Phe Gly Val Ser Ala Lys Asn Ala Asn Ile Lys Cys Tyr Asp Ile
530                 535                 540

Asn Lys Gln Arg Phe Arg Phe Gly His Cys Thr Arg Ala Glu Glu Ser
545                 550                 555                 560

Leu Thr Phe Asn Ala Cys Ala Asp Gln Asp Lys Leu Cys Gly Arg Leu
                565                 570                 575

Gln Cys Thr Asn Val Thr Asn Leu Pro Phe Leu Gln Glu His Val Ser
        580                 585                 590

Phe His Gln Ser Val Ile Ser Gly Val Thr Cys Phe Gly Leu Asp Glu
            595                 600                 605

His Arg Gly Thr Glu Thr Ala Asp Ala Gly Leu Val Arg His Gly Thr
610                 615                 620

Pro Cys Ser Arg Gly Lys Phe Cys Asp Arg Gly Ala Cys Asn Gly Ser
625                 630                 635                 640

Leu Ser Arg Leu Gly Tyr Asp Cys Thr Pro Glu Lys Cys Asn Phe Arg
                645                 650                 655

Gly Val Cys Asn Asn Arg Arg Asn Cys His Cys His Phe Gly Trp Ser
        660                 665                 670

Pro Pro Lys Cys Lys Glu Glu Gly His Ser Gly Ser Ile Asp Ser Gly
            675                 680                 685

Ser Pro Pro Val Gln Arg Ile Ile Lys Gln Asn Leu Glu Pro Val
690                 695                 700

Val Tyr Leu Arg Ile Leu Phe Gly Arg Ile Tyr Phe Leu Phe Val Ala
705                 710                 715                 720

Leu Leu Phe Gly Ile Ala Thr Arg Val Gly Val Thr Lys Ile Phe Arg

```
                    725                 730                 735
Phe Glu Asp Leu Gln Ala Ala Leu Arg Ser Trp Gln Glu Gln Ala Lys
            740                 745                 750

Asp Lys

<210> SEQ ID NO 2
<211> LENGTH: 756
<212> TYPE: PRT
<213> ORGANISM: Mus musculus

<400> SEQUENCE: 2

Met Leu Ser Leu Thr Trp Gly Met Arg Leu Val Glu Arg Pro Val Val
 1               5                  10                  15

Pro Arg Val Leu Leu Leu Phe Ala Leu Trp Leu Leu Leu Val
            20                  25                  30

Pro Val Trp Cys Ser Gln Gly His Pro Thr Trp Arg Tyr Ile Ser Ser
            35                  40                  45

Glu Val Val Ile Pro Arg Lys Glu Ile Tyr His Thr Lys Gly Leu Gln
         50                  55                  60

Ala Gln Arg Leu Leu Ser Tyr Ser Leu His Phe Arg Gly Gln Arg His
65                   70                  75                  80

Ile Ile His Leu Arg Arg Lys Thr Leu Ile Trp Pro Arg His Leu Leu
                 85                  90                  95

Leu Thr Thr Gln Asp Asp Gln Gly Ala Leu Gln Met Asp Tyr Pro Phe
                100                 105                 110

Phe Pro Val Asp Cys Tyr Tyr Ile Gly Tyr Leu Glu Gly Ile Pro Gln
            115                 120                 125

Ser Met Val Thr Val Asp Thr Cys Tyr Gly Gly Leu Ser Gly Val Met
130                 135                 140

Lys Leu Asp Asp Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Ile Ser Ser Lys
        195                 200                 205

Asn Tyr Ala Thr His Pro Ala Ala Ile Lys Gly His Phe Gln Ala Thr
210                 215                 220

Asn Ser Val Tyr Asn Ser Ala Ala Gly Asp Lys Leu Ser Ser Thr Val
225                 230                 235                 240

Gly Tyr Leu Phe Gln Val Ile Ser Leu Met Asp Thr Tyr Leu Thr Asn
                245                 250                 255

Leu His Met Arg Tyr Tyr Val Phe Leu Met Thr Val Tyr Thr Asn Ser
            260                 265                 270

Asp Pro Phe Arg Leu Glu Phe Ala Val Pro Gly Gly Ser Ala Tyr Asn
        275                 280                 285

Tyr Tyr Val Ser Val Phe Tyr Asn Lys Phe Lys Pro Asp Ala Gly Val
    290                 295                 300

Leu Leu Asn Lys Tyr Gly Pro Gln Asp Asn Gln Val Asn Pro Ala Glu
305                 310                 315                 320

Arg Ser Ile Cys Ser Ser Leu Ala Leu Ile Cys Ile Gly Lys Tyr Asp
                325                 330                 335

Arg Asn Pro Leu Phe Leu Ser Pro Ile Ile Thr Asn Arg Val Gly Arg
```

```
              340                 345                 350
Ser Leu Gly Leu Lys Tyr Asp Glu Gly Tyr Cys Val Cys Gln Arg Arg
            355                 360                 365
Asn Thr Cys Ile Met Phe Arg His Pro Gln Leu Thr Asp Ala Phe Ser
370                 375                 380
Asn Cys Ser Leu Ala Glu Ile Ser Asn Ile Leu Asn Thr Pro Gly Leu
385                 390                 395                 400
Met Pro Cys Leu Phe Tyr Asp Arg His Val Tyr Tyr Asn Thr Ser Leu
                405                 410                 415
Thr Tyr Lys Phe Cys Gly Asn Phe Lys Val Asp Asn Asp Glu Gln Cys
                420                 425                 430
Asp Cys Gly Ser Gln Lys Ala Cys Tyr Ser Asp Pro Cys Cys Gly Asn
            435                 440                 445
Asp Cys Arg Leu Thr Pro Gly Ser Ile Cys Asp Lys Glu Leu Cys Cys
        450                 455                 460
Ala Asn Cys Thr Tyr Ser Pro Ser Gly Thr Leu Cys Arg Pro Ile Gln
465                 470                 475                 480
Asn Ile Cys Asp Leu Pro Glu Tyr Cys Asn Gly Thr Lys Tyr Ile Cys
                485                 490                 495
Pro Asp Asp Thr Tyr Leu Gln Asp Gly Thr Pro Cys Ser Glu Asp Gly
                500                 505                 510
Tyr Cys Tyr Lys Gly Asn Cys Thr Asp Arg Asn Ile Gln Cys Met Glu
            515                 520                 525
Ile Phe Gly Val Ser Ala Lys Asn Ala Asn Ile Lys Cys Tyr Asp Ile
            530                 535                 540
Asn Lys Gln Arg Phe Arg Phe Gly His Cys Thr Arg Ala Glu Glu Ser
545                 550                 555                 560
Leu Thr Phe Asn Ala Cys Ala Asp Gln Asp Lys Leu Cys Gly Arg Leu
                565                 570                 575
Gln Cys Thr Asn Val Thr Asn Leu Pro Tyr Leu Gln Glu His Val Ser
            580                 585                 590
Phe His Gln Ser Ile Ile Ser Gly Phe Thr Cys Phe Gly Leu Asp Glu
            595                 600                 605
His Arg Gly Thr Glu Thr Thr Asp Ala Gly Met Val Arg His Gly Thr
        610                 615                 620
Pro Cys Ser Lys Ser Lys Phe Cys Asp Gln Gly Ala Cys Ser Gly Ser
625                 630                 635                 640
Leu Ser His Leu Gly Tyr Asp Cys Thr Pro Glu Lys Cys Ser Phe Arg
                645                 650                 655
Gly Val Cys Asn Asn His Arg Asn Cys His Cys His Phe Gly Trp Lys
                660                 665                 670
Pro Pro Glu Cys Lys Glu Glu Gly Leu Ser Gly Ser Ile Asp Ser Gly
            675                 680                 685
Ser Pro Pro Val Gln Arg His Thr Ile Lys Gln Lys Gln Glu Pro Val
            690                 695                 700
Val Tyr Leu Arg Ile Leu Phe Gly Arg Ile Tyr Phe Leu Phe Val Ala
705                 710                 715                 720
Leu Leu Phe Gly Ile Ala Thr Arg Val Gly Val Thr Lys Ile Phe Arg
                725                 730                 735
Phe Glu Asp Leu Gln Ala Thr Leu Arg Ser Gly Gln Gly Pro Ala Arg
                740                 745                 750
Asp Lys Pro Lys
            755
```

<210> SEQ ID NO 3
<211> LENGTH: 13894
<212> TYPE: DNA
<213> ORGANISM: Artificial Sequence
<220> FEATURE:
<223> OTHER INFORMATION: synthetic

<400> SEQUENCE: 3

```
gtcctaaggt agcgagggat gacagattct ctgttcagtg cactcagggt ctgcctccac      60
gagaatcacc atgcccttc tcaagactgt gttctgtgca gtgccctgtc agtggaaatc      120
tggagagcat gcttccatga gcttgtgagt agtatatcta gtaagccatg ctttgtgtt     180
aatggtgatg ttctacatac cagttctctg cttaataat gaggtgatga ttctatgttc     240
ctgtaacgct cctcaactg gtcctaagt ctttcttcac tccatctatt cctctaagga      300
atgatcctga aaatcccatc acaaactata ggagatggga accatcaaaa aacacagtga    360
caaagaggtg ggaacgcatc agggttcagg aaccatattt taaaaagata tcgtaaataa    420
cttcttaaaa gagatataga caaatctcca ttaatacgga gaccagaggc ctaaggctaa    480
gaaccaatgg tggctcaagg tctcctgcta cccgaggagc aaacgtagag cagtttctaa    540
tgatttattt aaaatataga atcaaaagta ccagtttgca attttgaaag atttatttca    600
gcaatgcaac aacatcaggt ggtgccgagt ccaacacgtc ttatgtccca tgatataaac    660
aaaggccatc cagaactgtg gactggagtt ctaccttgtc ccctaatgac attcagattt    720
tttttccatt ctctttatct tagaggagac aggggctaa ctcattttac ttgtcctttg    780
cttgttcttg ccaagaacgt aaagcagctt gcaagtcttc aaacctaaat atcttagtaa    840
ctcctacacg agtggcaatg ccaaagagca gtgcaacaaa gaggaagtaa atacgaccaa    900
agagtattct taaatacact actggctcta ggttctgttt tattatgcgc ctttgaaccg    960
gaggggaccc actgtctatg ctcccactgt gtccctcttc tttgcacttt ggagggctcc   1020
aaccaaaatg gcaatggcaa ttccgacgat tgttacacac tcctctgaaa ttgcattttt   1080
ctggggtgca gtcataaccc aaacgagata aacttccatt gcaagctcct cgatcacaga   1140
acttacccct tgaacacggg gtaccatgtc tcaccaatcc agcatctgct gtttctgtcc   1200
cacgatgttc atcaagccca aagcaggtaa ccccagagat aaccgattga tggaatgaaa   1260
catgttcttg caaaaatgga agattggtga cattggtaca ctgcaacctt ccacacagct   1320
tgtcctgatc agcacaagca ttgaatgtga ggctttcttc tgctctagta caatgcccaa   1380
atcgaaaccg ttgtttgttg atgtcatagc acttaatatt agcattctta gcacttacac   1440
caaagatttc catgcattgt atgttgcgat cagtgcagtt acctttatag cagtaaccct   1500
cttctgagca tggtgtccca tcttgcagat aagtgtcatc tgggcaaatg aacttagagc   1560
cactacagta ctctggaaga tcacatatgt tctggatagg tctgcagagt gtcccagaag   1620
gactgtaagt gcaatttgca cagcataatt ctttatcaca aatgctacca ggtgttaacc   1680
tgcaatcatt tccacagcag ggatctgaat aacatgcctt tgggagcca cagtcacact   1740
gctcattgtt atctactttg aagtttccac aaaacttata agtcaatgat gtattataat   1800
aaacatgacg tcatagaaa agacatgca tcagatcagg agtattaagt atgttgctta    1860
tctctgcaag ggaacaattg ctgaaagcat ctgttaattg aggattttg aacatgatgc    1920
aggtgttcct tctctggcag atacagtacc cctcatcatg ttttaggcct aaactccttc   1980
caacacgatt ggttattata atagataaaa ataaaggatt tcgaccatgt tgaccaagac   2040
```

```
aaattagggc tgagggagaa catatactcc tctcagctgg attaacagca tcatctcctg    2100
gcgaattctt gttaattata gctcctgcat caggcctaaa atgagcataa aatactctct    2160
catagaaagt atgagcctgc cctcctggaa ctcgaaaatc ttgtgaaaat ggatcagcct    2220
cggtatacac agtcatgaga aagacatagt accgcatatg aagattggtc agataggtgt    2280
ccattaaact aatgacttta aacaaatact caacagtaga tgaaagtttg tcacctccag    2340
aagcactata tacagaatgg gttgcttgaa agtggccttt tatagcagct ggatgtgtag    2400
cgtaattctt actagatagt ctgggagctc catctgcata ttccaatctg gaggagggag    2460
aacctgtatt atggctccag tgcttccatg cattcatagg ccctgtgtca tcagactcag    2520
atactatctg agaaacaagg tgttcaaagc tctgtgaatc attgaggggt ttgatttcat    2580
aggtaaggtt atccaacttt atgacccctg acaggccccc ataacaagta tccacagtga    2640
ccatggattg caggatcccc tccaggtagc caatatagta acaatctaca ggaaaaaagg    2700
ggtactccat ctgtaaggct ccttggtcat cttgagttgt cagcaacaag tgtctgggcc    2760
aaatgagtgt cttctccgc aggtggatga tatgtctctg gccccgaaaa cgcaagctat    2820
acgagagcag tctttgtgct tgaagtcctt tggtatggta gatctccttc cgaggaataa    2880
ccacctccga tgagatgtaa cgccaagtgg gatggccttg agaacaccag actggaacca    2940
ggaggagcag ccagagtgca aatagcaaga ggaggaccct ggggaccaca ggtctttcca    3000
ctagcctcat gccccaggtc agagataaca tcctgggtgg agctaactcc ctctgctgtg    3060
gccactgcct ggtctagaaa atactgacag aggactaaaa acctcctcag gctcccaacc    3120
taagtggtta cccagacaac tggagttagg taacagtcac tgggtgtggc aggaattgag    3180
tctgaatgtg ttagctgagg ttgaggttaa atattgtcaa aagggatgtc tataaatgtg    3240
cctggacaag aaaagtcaga agcagcaagg agtgtctctg acaggctcaa tcctttcttt    3300
tctttttttg aagttcaaaa tatcatttcc acgtgaatgt atttggttcc cagtgtgact    3360
ctgggtctct ttctaggagt caatatttct ttatatcttg gctcatgttt ttcacagttg    3420
ttctaacttc ttgttttgtt ttgtttgttt gtttgtttga aagttagaag taaatactgt    3480
ctatattagc cttttagcta taaatgattg ttttttatttc ttctaatcat gttttgtttg    3540
agttttggtt aaactattta caaatgagtt ttttttttcc ttttgggtgt tgctcgaaag    3600
tttggagctt tctgttaata ttgtgttgtt gtttctccaa tattattaga cctgagaatt    3660
ctacctgggt acctgtgaac tccagaattt ttaaaaattc catctcttgg gaacattatc    3720
tctgaccccg tctgaggccg aagtggctgt ccccctccaa cctttagtat ctttctttcc    3780
tgactattgg gatttcttca agcaatcagg ctgatgggtt ctcagcagtg agaccagtag    3840
actgtcggta tgaacgtcga agagtctgcc acacactccg ggttcatcaa cagtgctttc    3900
gcgtctctta cttttgtaga aggaaatgca gcctctgagt tttctccaag aaatcattga    3960
tgaaagggtg aaaagatggg tatcacccgg agttcatgac aagccctggc tcagacacgt    4020
gagcaaggtc tacagcccca agataggct gccctgcaac atgtatttat aagataggag    4080
aaaaaaatgg gtagttggag ggttgatcaa cttacttcct ctcaaacata tatatctcat    4140
ctaagtgtgc aggggaaaac tctgtagaac tactgggata cctgctcacc cccaggagcc    4200
tcatgaataa gtctctgctt ctgccttgta gccatgagca ttactgcacc tgatacccct    4260
gcagcttcct agggaagagg gaggaagtga cttggcccct gtctggttaa ggtaagagga    4320
gataaatccc ttctcattga ttagggtgag aggggtcatg tgctctatca ttggtgaccc    4380
agttgggaca tgggtttata ccaaagtcat cactctgagg ttctgtgtac caccaggctg    4440
```

```
aactcccata tcctacatgg acataggaca acaccaagca gaaggaggtt ttaggactaa    4500
actgaaggac agagatgcgg tttctaaaca actagggagt gccagggcca gcctctctaa    4560
ccactatagg acactgtgga gtctggttac aaagagagat tactcaaggt ccttagcact    4620
gattacagag catatctcag atgccttctg ctgaccagat gtatctttgc ataatctgcc    4680
tatccagatt cagaaaattg atgccacata gccaagtgga ctttcaggaa cagacgattt    4740
aaaaacaggc agagagatgt gagagaaagg agaaggagag agagaaggga gagggagaga    4800
agagagaggg agacggagaa ggaaagaggg agaaggagaa ggagagaagg ggcatggaca    4860
gagggaggga cagaaggaga gaggagatag agagggggat aaggaagaag ggagggaggg    4920
agagagagag aaggctaagt cttctccatac ctgggtccca atacctctta taacccaagc    4980
acatggtttc acatatcaca atgcggttgg gatatagata actgtaaata cttgtgaaaa    5040
taatggggct gagatctggg gttttcatga tagtttcaaa gtcaccgtac tgactaaaac    5100
cttccactgg cccatctcca gcttcctaat ctgagggtat caaatttccc actaagtgtg    5160
tttagaaaga tctccacctt tttgcccttg tcttccagtg ccccacctac gttctggtct    5220
cccacatctg atgtcttctc agtgattctg gccctgcctg ctccacagct acaaacccct    5280
tcctataatg agctctgtgc tgagccatca tcctgaatca atccacctta agcagatgtt    5340
ttgcttattt ttcctgtgtc catactacag aggaaaggta ggcatgtaga agctgaagca    5400
tctcacctca ttccaagcac cctcagtctc taaatgtgcc cccttgtttc cagaagtgca    5460
acctcaagca tcttttattc attcatctta gagggccaca tgtgctgtag tgttataaga    5520
tgaaatttaa agcattaatt attcctaaca agccaattaa acaagccaaa acattcatc     5580 agtcattccc atggaacctc tgaagcatct tcctgctcta accttgggtt ttccagggct    5640
gctctgggat cacaggagct gtcctgtcta ccagccatat aaaggcagac ctatcagaat    5700
tacaccagac ttctcaccat agactataaa agcagaata tcctggacag atgttataca    5760
gaaactaaga gaacacaaat gccagcccag gctactatac ccagcaaaac tctcaattac    5820
catcgatgaa gaaaccaaga tattccatta caagtccaaa tttacacaat atctttccat    5880
aaatccagcc ctacaaagga tagcagatgg aaaactccaa cacaggtagg aaaactacac    5940
cctagaaaga gcactaaagt aatcatcttt caacacactc aaaagaagat aaccacacaa    6000
acataattcc acctctaaca acaaaaataa agtaggcaac aatcactatt ccttaatatc    6060
tcttttaaca tcaatggact caattctcca ataaaaagac atagactaac agactgaata    6120
cataaacagg acacagcatt ttgctgcata agcaaacac agcgttactt ttttttttct     6180
aaatgacatt ttttattaga tattgtcttt attgacattt caaatgttat cccctttcct    6240
ggtttaccct ctgaaatccc ctatctcctc cccctcccccc tgctcaccaa tccacccact    6300
cccacttcca ggccctggca atcccctata tttgggcata gagccttcac aggaccaagg    6360
tactctcctt gcattgatga ccaactagtc cattctctgc tacaaatgca gctagatcta    6420
tgagtcccac catgttttct tttgttggtg gtttcatgcc agggagctct ggagtactg     6480 attggttcat attgttgttc tccctatggg gttacaaaac ccttcaactt cttgggtcct    6540
ttctctggct gcctcattgg ggaccttgtg cgaagtccaa tggatgactg tgagcatcca    6600
cttctgtatt tgccaggcac tggcagagcc tctcagaaga cagctatatc aagatcctgg    6660
cagcaagctc ttgttggtat ccacaaaagt gtcggtggt tgtctatggg atggatcccc     6720
aaaggggcag tctctggatg gtcattcctt cagtctctgt tccacacttt gtctctttaa    6780
```

```
ctccttccat gactatttta ttcctccctc taagaaggac cgaagtattc atactttggt    6840
cttccttctt gaaattcatg tgttttgtga attgtatctt tgatattccg aacttctggg    6900
ctaatatcca cttatcagtg agtgaatatc atgtgtgttc ttatgtgatt gagttacctc    6960
actcaggatg atatcctcca gaaccatcca tttgtctaag aatttaatga attcattgtt    7020
tttaatagct gaggagtact ccattgtgta aatgtaccac attttctgta cccattgttc    7080
tcttgaggga catctggggtt ctttaaagct tctggacatt aaatataagg ctgctatgga    7140
aatagtggag aatgtgtcct tattacatgt tggagcatct tctgggtata tgcccaggag    7200
tgctattgct ggatcctctg atagtactat gtccaatttt ctgaggaact gccaaactga    7260
tttacagagt ggttgtacca gcttgcaatt ccaccagcaa tggagaaatg ttccccttcc    7320
tccacatcct caccaacatc tgctgtcacc tcaatttgtt cttagtgatt cagacaggtg    7380
tgaggtggaa tatcagggtt gttttggcatt tccctgatga ctagtgatat tgaaaaaaat    7440
tttaagtgtt tctcagccat tcagtattct tcagttgaga attcactgtt tagctctgta    7500
ctcaggtttt tttaataggg ttatttggtt ttctggagtc taacgtcttg aattcttcct    7560
atatattgga tattagccct ctgtcatatt taggattggt aaagatcttt cccaatatgt    7620
tggctgcctt tttgtgtcct ttgccttaca gaacctttt aattttatga ggtcccattt    7680
gctaattctt cattttacag cacaagccat tggtgttctg ttcaaaaatc ttcccctg    7740 aaccctatct tcgaggatct tccccacttt ctcctctata agtttcagtg tctctattat    7800
tgtgctgagg ggtaccgaag ttcctattcc gaagttccta ttctctagaa agtataggaa    7860 cttcccctagg gtttaaaccc gcggtggagc tctgatgtgg gaacgcttca gtgttcagga    7920
accatatgat ttattaaaa tatagaatca aaagtaccaa tttgcagttt tgaaagattt    7980
attccagtgt aagcattagc aatgcaccaa catcaggtga tttctgaatc caacacgtct    8040
tatgtcctca tgatattaaa aaaaaaaaaa ggccatccag aactgtgaac ttgagttcta    8100
ccttgttccc tactgacatt cagattttct ttttttgcatt ctcttatct tacaggagac    8160 aggagggggag ggctaactca ttttactttg gcttgtccct tgctggtcct tgcccagaac    8220
gtaaagtagc ttgcaagtct tcaaatctaa aaatcttagt aactcctaca cgagtggcaa    8280
tgccaaagag cagtgcaaca aagaggaagt aaatacgacc aaagagtatt cttaaataca    8340
ccactggctc ttgttttttgt tttattgtgt gcctttgaac tggagggggac ccactgtcta    8400 tgctcccact tagtccctct tcttttgcact ctggaggctt ccaaccaaaa tgacaatggc    8460
aattccgatg attgttacac actcctctaa aactgcattt ttctggggtg cagtcataac    8520
ccaaatgaga taaacttcca ctgcaagctc cttgatcaca gaacttactt ttggagcagg    8580
gggtaccatg tctcaccatt ccagcatctg ttgtttctgt cccacgatgt tcatcaagcc    8640
caaagcaggt aaacccagag ataatcgatt gatggaatga acatgttct tgcaaatatg    8700 gaagattggt gacattggta cactgcaacc ttccacacag cttgtcctga tcagcacaag    8760
cattgaatgt gaggctttct tctgctctag tacaatgccc aaatcgaaac cgttgtttgt    8820
tgatgtcata gcacttaata ttagcattct tagcacttac accaaagatt tccatgcatt    8880
gtatgttgcg atcagtgcag ttacctttat agcagtaacc atcttctgag catggtgtcc    8940
catcttgcag ataagtgtca tctgggcaaa tgtatttagt cccattacag tactctggaa    9000
gatcacatat gttctggata ggtctgcaga gtgtcccaga aggactgtaa gtgcaatttg    9060
cacagcataa ttctttatca caaatgctac caggtgttaa cctgcaatca tttccacagc    9120
agggatctga ataacatgcc ttttgggagc cacagtcaca ctgctcatcg ttatctactt    9180
```

```
tgaagtttcc acaaaactta taagtcaatg atgtattata ataaacatga cggtcataga    9240
aaagacatgg catcagacca ggagtattaa gtatgttgct tatctctgca agggaacaat    9300
tgctgaaagc atctgttaat tgaggatgtc tgaacataat gcaggtgttc cttctctggc    9360
agacacagta cccctcatca tattttaagc ctaaactcct tccaacacga ttggttatta    9420
taggagataa aaataaagga tttcgatcat atttaccaat acaaattagg gctaaggaag    9480
aacatatact cctctcagct ggattaacct ggttatcttg tggcccatac ttattaagta    9540
aaactcctgc atcaggctta aatttattat aaaagactga cacatagtaa ttataagccg    9600
accctcctgg aactgcaaac tcaagtcgaa atggatcaga attggtgtac acagtcatga    9660
gaaagacata gtaccgcata tgaagattgg tcagataggt gtccattaaa ctaatgactt    9720
gaaacaaata cccaacagta gatgaaagtt tgtcacctgc agcagaatta tatacagaat    9780
tggttgcttg aaagtggcct tttatagcag ctggatgtgt agcgtagttc ttactagata    9840
ttctgggagc tccatctgca tattccaatc tggaggaggg agaacctgta ttatggctcc    9900
agtgcttcca tgcattcata ggccctgtgt catcagactc agatactatc tgagaaacaa    9960
ggtgttcaaa gctctgtgaa tcattgaggg gtttgatttc ataggtaagg tcatctaact   10020
tcatgacccc tgacaggccc ccataacaag tatccacagt gaccatggat tgtgggatcc   10080
cctccaggta gccaatatag taacaatcta caggaaaaaa ggggtaatcc atctgtaagg   10140
ctccttggtc atcttgagtt gtcagcaaca agtgtctggg ccaaatgagt gtctttctcc   10200
gcaggtggat gatatgtctc tggccccgaa aatgcaagct atatgagagc agtctttgtg   10260
cttgaagtcc tttggtatgg tagatctcct tccgaggaat aaccacctcc gatgagatgt   10320
aacgccaagt aggatggcct tgagaacacc agactggaac caggaggagc agccagagtg   10380
caaatagcaa gaggaggacc ctggggacca caggtctttc cactagcctc atgccccagg   10440
tcagagataa catcctgggt ggagctaaat ccctctgctg tggccactgc ctggtctaga   10500
aaatactgac agaggactaa aaacctcctc aggctcccaa cctaagtggt tacccagaca   10560
actggagtta ggtaacagtc actgggtgtg gcaggaattg agtctgaatg tgttagctga   10620
ggttgaggtt aaatattgtc aaaagggatg tctataaatg tgcctggaca agaaaagtca   10680
gaagcagcaa ggagtgtctc tgacaggctc aatcctttct tttctttttt tgaagttcaa   10740
aatatcattt ccacgtgaat gtatttggtt cccagtgtga ctctgggtct ctttctagga   10800
gtcaatattt ctttatatct tggctcatgt ttctcacagt tgttctaatt tcttgttttg   10860
ttttgttgt ttgtttgaac gttagtagta aatactgtct atattagcct tttagctata   10920
aatgattgtt tttatttctt ctaatcatat tttgtttgag ttttggttaa actatttaca   10980
aatgagtttt tttttttttcc ttttgggtgt tgctcgaaag tttggagctt tctgttaata   11040
ttgtgttgtt attttccaa tattattaga cctgagaatt ctatctgggt acctgtgaac   11100
tctagaattt ttaaaaattc catctcttgg gaacattacc tctgacccccg tctgaggccg   11160
aagtggctgt ccccctccaa cctttagtat cttctttcc tgactattgg gatttcttca   11220
agcaatcagg ctgatgggtt ctcagcagtg agaccagtag actgccggta tgaacgtcga   11280
agagactgcc acacactcca ggttcatcaa cagtgctttc gcgtctctta cttttgtaga   11340
aggaaaagca gcctctgagt tatctccaag aaatcattaa tgaaagagtt aaaagatggg   11400
tatcacccgg agttcatgac aagccctggc tcagacacgt gagcaaggtc tacagcccca   11460
aagataggct gccctgcaac atgtatttat aagatagaag aaaaaaatgg gtggttggag   11520
```

```
ggttgatcaa cttacttcct ctcaaacata tatatctcat ctaagtgtgc aggggaaaac    11580
tctgtaggac tactgggatt gttattatca ttattattat tattattatt attattatta    11640
ttattattat tattaactta aggcatttta ttagatattt tcttcattta gttttcaaat    11700 gttatcccg gaacctccta tactctctcc ctgccctgct ccccaaccca cccactccta     11760
catcctggcc ctggcattcc cctatactgt ggcagatgat cttcgtaaga ccaagagcct    11820
ttcctcccat tgatggccta ctaggctatc ctcttttaca tatgcaacta gagtcacagc    11880
tctggggagg tattgcttag ttcatattgt ttttcctcct atagggttgc agatcccttt    11940
agctccttgg gtactttctc tagctcctcc attgggggcc ctgtgttcca tccaatagat    12000
gactgtgagc atccacttct gtatttgcca ggtattggca tggatcttac tgcaccttct    12060
gaactctcta agcagctttc ctggtcacct ccaggagcct catgaataag tctctgcttc    12120 cccttgtgg ctatgagcat tactgcacct gatacaccct gcagcttcct agggaagagg     12180
gaggaagtgg cttggcccct gtctggttaa ggtaagagga gataaatccc ttctcatgaa    12240
ttagggtgag aagggtcatg tgctctatca ttggtgacca acttggggac atgggcttat    12300
acagtcatca ctctgaggct ctgtgtacca ccagactgaa ctcccatatc ctacatgcac    12360
ataggacaac accaagtaga aggaggtttt aggactaaac tgaaggacag agatgggtt     12420 tctaaacaac tagggagtgc cagggccagc ctctctaacc actataggac actatggagt    12480
ctggttacaa agagagatta ctcaaggtcc ttagcactga ttacagagca tatctcagat    12540
gccttctgct gaccagatgt atctttgcat aatctgccta tccagattca gaaaattgat    12600
gccacatagc caagtggact ttcaggaaca gacgatttaa aaacaggcag agagatgtga    12660
gagaaaggag aaggagagag agaagggaga gggagagaag agagagggag acggagaagg    12720
aaagagggag aaggagaagg agagaagggg catggacaga gggagggaca gaaggagaga    12780
ggagatagag aggggataa ggaagaaagg agggagggag agagagagaa ggctaagtct     12840 ttccataccct gggtcccaat acctcttata acccaagcac atggtttcag atatcacaat    12900
gcggttggga tatagataac tgtaaatact tgtgaaaata atggggctga gatctggggt    12960
tttcatgata gtttcaaagt cactgtactg actaaaacct tccactggcc catctccagc    13020
ttgttaatct gagggtatca aatttcccac taagtgtgtt tagaaagatc tccaccttt     13080 tgccctagtc ttccagtgcc ccacctacgt tctggtctcc cacatctgat gtcttctcag    13140
tgattctggc cctgcctgct ccacagctac aaaccccttc ctataatgag ctctgtgctg    13200
agccatcatc ctgaatcaat ccaccttaag cagatgtttt gcttattttt cctgtgtcca    13260
tactacagag gaagggtagg catgtagaag ctgaggcatc tcatctcact ctaagcaccc    13320
tcagtctcta aatgtgcccc tttgtttcca gcagttcagc ctcaagcatc ttttattcac    13380
tcgtcttaga gggacacatg tgctgtagtg ttataagatg aaatttaaag cattagttat    13440
tcccaacaag ccaattaaac aagccaaaaa cattcatcag tcattcccat ggaacctctg    13500
aagcatcttc ctgctctaac cttgagtttc ctagggctgc tgtgggatca caggagctgt    13560
cctgtttacc agcctatcct gtcccacggg attcagttat tagtgggtgc gaggggacc     13620 gcaaacctgg aagaaaatgg gattggaaga gaaagagaa acgaagacca agtagatctt      13680
ttcctatcaa ggtcttcgtt tattaggctg aggtgcctgg tgtaaagcat gcatcgcggg    13740
gaataggaag gggtcgaggg ggaatttac aaagaacaaa gaagcgggca tctgctgaca      13800
tgagggccga agtcaggctc caggcagcgg gagctccacc gcggtggcgc catttcatta    13860
cctctttctc cgcacccgac atagataaag ctta                                13894
```

<210> SEQ ID NO 4
<211> LENGTH: 251
<212> TYPE: DNA
<213> ORGANISM: Artificial Sequence
<220> FEATURE:
<223> OTHER INFORMATION: synthetic

<400> SEQUENCE: 4

```
ccagcttcat tagtaatcgt tcatctgtgg taaaaaggca ggatttgaag cgatggaaga    60
tgggagtacg gggcgttgga agacaaagtg ccacacagcg cagccttcgt ctagaccccc   120
gggctaacta taacggtcct aaggtagcga ggggatgaca gattctctgt tcagtgcact   180
cagggtctgc ctccacgaga atcaccatgc cctttctcaa gactgtgttc tgtgcagtgc   240
cctgtcagtg g                                                       251
```

<210> SEQ ID NO 5
<211> LENGTH: 245
<212> TYPE: DNA
<213> ORGANISM: Artificial Sequence
<220> FEATURE:
<223> OTHER INFORMATION: synthetic

<400> SEQUENCE: 5

```
aggggtcgag ggggaatttt acaaagaaca aagaagcggg catctgctga catgagggcc    60
gaagtcaggc tccaggcagc gggagctcca ccgcggtggc gccatttcat tacctctttc   120
tccgcacccg acatagataa agcttatccc ccaccaagca aatcccccta cctggggccg   180
agcttcccgt atgtgggaaa atgaatccct gaggtcgatt gctgcatgca atgaaattca   240
actag                                                              245
```

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6

```
caggtacagc tgcagcagtc a                                             21
```

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7

```
ggagatggca caggtgagtg a                                             21
```

<210> SEQ ID NO 8
<211> LENGTH: 17
<212> TYPE: DNA
<213> ORGANISM: Artificial Sequence
<220> FEATURE:
<223> OTHER INFORMATION: synthetic

<400> SEQUENCE: 8

```
tccaggactg gtgaagc                                                  17
```

<210> SEQ ID NO 9

```
<211> LENGTH: 24
<212> TYPE: DNA
<213> ORGANISM: Artificial Sequence
<220> FEATURE:
<223> OTHER INFORMATION: synthetic

<400> SEQUENCE: 9
tagtcccagt gatgagaaag agat                                          24

<210> SEQ ID NO 10
<211> LENGTH: 24
<212> TYPE: DNA
<213> ORGANISM: Artificial Sequence
<220> FEATURE:
<223> OTHER INFORMATION: synthetic

<400> SEQUENCE: 10
gagaacacag aagtggatga gatc                                          24

<210> SEQ ID NO 11
<211> LENGTH: 17
<212> TYPE: DNA
<213> ORGANISM: Artificial Sequence
<220> FEATURE:
<223> OTHER INFORMATION: synthetic

<400> SEQUENCE: 11
tgagtccagt ccaggga                                                  17

<210> SEQ ID NO 12
<211> LENGTH: 28
<212> TYPE: DNA
<213> ORGANISM: Artificial Sequence
<220> FEATURE:
<223> OTHER INFORMATION: synthetic

<400> SEQUENCE: 12
aaaaattgag tgtgaatgga taagagtg                                      28

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
aaccctggtc agaaactgcc a                                             21

<210> SEQ ID NO 14
<211> LENGTH: 19
<212> TYPE: DNA
<213> ORGANISM: Artificial Sequence
<220> FEATURE:
<223> OTHER INFORMATION: synthetic

<400> SEQUENCE: 14
agagaaacag tggatacgt                                                19

<210> SEQ ID NO 15
<211> LENGTH: 22
<212> TYPE: DNA
<213> ORGANISM: Artificial Sequence
<220> FEATURE:
<223> OTHER INFORMATION: synthetic

<400> SEQUENCE: 15
```
aactacgcac agaagttcca gg                                              22

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
gctcgtggat ttgtccgc                                                   18

<210> SEQ ID NO 17
<211> LENGTH: 16
<212> TYPE: DNA
<213> ORGANISM: Artificial Sequence
<220> FEATURE:
<223> OTHER INFORMATION: synthetic

<400> SEQUENCE: 17
cagagtcacg attacc                                                     16

<210> SEQ ID NO 18
<211> LENGTH: 19
<212> TYPE: DNA
<213> ORGANISM: Artificial Sequence
<220> FEATURE:
<223> OTHER INFORMATION: synthetic

<400> SEQUENCE: 18
tgagcagcac cctcacgtt                                                  19

<210> SEQ ID NO 19
<211> LENGTH: 23
<212> TYPE: DNA
<213> ORGANISM: Artificial Sequence
<220> FEATURE:
<223> OTHER INFORMATION: synthetic

<400> SEQUENCE: 19
gtggcctcac aggtatagct gtt                                             23

<210> SEQ ID NO 20
<211> LENGTH: 18
<212> TYPE: DNA
<213> ORGANISM: Artificial Sequence
<220> FEATURE:
<223> OTHER INFORMATION: synthetic

<400> SEQUENCE: 20
accaaggacg agtatgaa                                                   18

<210> SEQ ID NO 21
<211> LENGTH: 33
<212> TYPE: DNA
<213> ORGANISM: Artificial Sequence
<220> FEATURE:
<223> OTHER INFORMATION: synthetic

<400> SEQUENCE: 21
gctagtagtg gggcctacag gccttttgat atc                                  33

<210> SEQ ID NO 22
<211> LENGTH: 48
<212> TYPE: DNA

```
<213> ORGANISM: Artificial Sequence
<220> FEATURE:
<223> OTHER INFORMATION: synthetic

<400> SEQUENCE: 22
gcaaaagccc aggggagtgg gagctactac acctatgctt ttgatatc                48

<210> SEQ ID NO 23
<211> LENGTH: 42
<212> TYPE: DNA
<213> ORGANISM: Artificial Sequence
<220> FEATURE:
<223> OTHER INFORMATION: synthetic

<400> SEQUENCE: 23
gcgagagagg gtatagtggg aactactgag gactttgatt ac                      42

<210> SEQ ID NO 24
<211> LENGTH: 33
<212> TYPE: DNA
<213> ORGANISM: Artificial Sequence
<220> FEATURE:
<223> OTHER INFORMATION: synthetic

<400> SEQUENCE: 24
gcgagaggga cagtgggagc cctctttgac tac                                33

<210> SEQ ID NO 25
<211> LENGTH: 36
<212> TYPE: DNA
<213> ORGANISM: Artificial Sequence
<220> FEATURE:
<223> OTHER INFORMATION: synthetic

<400> SEQUENCE: 25
gcgaaaccta gtgggagcta ctcctggttc gacccc                             36

<210> SEQ ID NO 26
<211> LENGTH: 45
<212> TYPE: DNA
<213> ORGANISM: Artificial Sequence
<220> FEATURE:
<223> OTHER INFORMATION: synthetic

<400> SEQUENCE: 26
gcgagaggag gagggtataa ctggaactcg aatgcttttg atatc                   45

<210> SEQ ID NO 27
<211> LENGTH: 33
<212> TYPE: DNA
<213> ORGANISM: Artificial Sequence
<220> FEATURE:
<223> OTHER INFORMATION: synthetic

<400> SEQUENCE: 27
gcgagaggat ataactggaa ctactttgac tac                                33

<210> SEQ ID NO 28
<211> LENGTH: 39
<212> TYPE: DNA
<213> ORGANISM: Artificial Sequence
<220> FEATURE:
<223> OTHER INFORMATION: synthetic

<400> SEQUENCE: 28
gcgaaagagt ataactggaa ccactggtac tttgactac                          39
```

<210> SEQ ID NO 29
<211> LENGTH: 33
<212> TYPE: DNA
<213> ORGANISM: Artificial Sequence
<220> FEATURE:
<223> OTHER INFORMATION: synthetic

<400> SEQUENCE: 29
gcgagagaga taactggaac cccctttgac tac       33

<210> SEQ ID NO 30
<211> LENGTH: 39
<212> TYPE: DNA
<213> ORGANISM: Artificial Sequence
<220> FEATURE:
<223> OTHER INFORMATION: synthetic

<400> SEQUENCE: 30
gcgaggggat ataactggaa cttttctttt tttgactac       39

<210> SEQ ID NO 31
<211> LENGTH: 36
<212> TYPE: DNA
<213> ORGANISM: Artificial Sequence
<220> FEATURE:
<223> OTHER INFORMATION: synthetic

<400> SEQUENCE: 31
gcgagaggta actggaactc tctgggcttt gactac       36

<210> SEQ ID NO 32
<211> LENGTH: 39
<212> TYPE: DNA
<213> ORGANISM: Artificial Sequence
<220> FEATURE:
<223> OTHER INFORMATION: synthetic

<400> SEQUENCE: 32
gcgaaaaggg ctactatggt tcggggagct cttgactac       39

<210> SEQ ID NO 33
<211> LENGTH: 60
<212> TYPE: DNA
<213> ORGANISM: Artificial Sequence
<220> FEATURE:
<223> OTHER INFORMATION: synthetic

<400> SEQUENCE: 33
gcgagagata ttactatggt tcggggagtt attataacga aggtctacgg tatggacgtc       60

<210> SEQ ID NO 34
<211> LENGTH: 27
<212> TYPE: DNA
<213> ORGANISM: Artificial Sequence
<220> FEATURE:
<223> OTHER INFORMATION: synthetic

<400> SEQUENCE: 34
gcgagagagt atagcagctt tgactac       27

<210> SEQ ID NO 35
<211> LENGTH: 33
<212> TYPE: DNA
<213> ORGANISM: Artificial Sequence
<220> FEATURE:

<223> OTHER INFORMATION: synthetic

<400> SEQUENCE: 35
gcgagagaga gtatagcagc tcgttgtgac tac                          33

<210> SEQ ID NO 36
<211> LENGTH: 42
<212> TYPE: DNA
<213> ORGANISM: Artificial Sequence
<220> FEATURE:
<223> OTHER INFORMATION: synthetic

<400> SEQUENCE: 36
gcaagagagg ataggagctc gcccctcggg tactttgact ac                42

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
gcgagagatc ttggggaagg ctac                                    24

<210> SEQ ID NO 38
<211> LENGTH: 30
<212> TYPE: DNA
<213> ORGANISM: Artificial Sequence
<220> FEATURE:
<223> OTHER INFORMATION: synthetic

<400> SEQUENCE: 38
accacccata actggggagg gtttgactac                              30

<210> SEQ ID NO 39
<211> LENGTH: 18
<212> TYPE: DNA
<213> ORGANISM: Artificial Sequence
<220> FEATURE:
<223> OTHER INFORMATION: synthetic

<400> SEQUENCE: 39
gcgagagata ggggaccg                                           18

<210> SEQ ID NO 40
<211> LENGTH: 30
<212> TYPE: DNA
<213> ORGANISM: Artificial Sequence
<220> FEATURE:
<223> OTHER INFORMATION: synthetic

<400> SEQUENCE: 40
caacagagtt atagtacccc tccggagacg                              30

<210> SEQ ID NO 41
<211> LENGTH: 27
<212> TYPE: DNA
<213> ORGANISM: Artificial Sequence
<220> FEATURE:
<223> OTHER INFORMATION: synthetic

<400> SEQUENCE: 41
caacagctta atagttaccc tcggacg                                 27

<210> SEQ ID NO 42
<211> LENGTH: 26
<212> TYPE: DNA
<213> ORGANISM: Artificial Sequence
<220> FEATURE:
<223> OTHER INFORMATION: synthetic

<400> SEQUENCE: 42
caacagctta atagttacca ttcact                                              26

<210> SEQ ID NO 43
<211> LENGTH: 27
<212> TYPE: DNA
<213> ORGANISM: Artificial Sequence
<220> FEATURE:
<223> OTHER INFORMATION: synthetic

<400> SEQUENCE: 43
caacatttta atagttaccc gctcact                                             27

<210> SEQ ID NO 44
<211> LENGTH: 27
<212> TYPE: DNA
<213> ORGANISM: Artificial Sequence
<220> FEATURE:
<223> OTHER INFORMATION: synthetic

<400> SEQUENCE: 44
cagcagtata ataactggcc tctcact                                             27

<210> SEQ ID NO 45
<211> LENGTH: 27
<212> TYPE: DNA
<213> ORGANISM: Artificial Sequence
<220> FEATURE:
<223> OTHER INFORMATION: synthetic

<400> SEQUENCE: 45
ctacagcata atagttaccc gtggacg                                             27

<210> SEQ ID NO 46
<211> LENGTH: 27
<212> TYPE: DNA
<213> ORGANISM: Artificial Sequence
<220> FEATURE:
<223> OTHER INFORMATION: synthetic

<400> SEQUENCE: 46
ctacagcata atagttaccc tcggacg                                             27

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
cagcagtatg gtagctcacc tcggacg                                             27

<210> SEQ ID NO 48
<211> LENGTH: 27
<212> TYPE: DNA
<213> ORGANISM: Artificial Sequence
<220> FEATURE:
<223> OTHER INFORMATION: synthetic

```
<400> SEQUENCE: 48
atgcaaggta cacactggcc gtggacg                                              27

<210> SEQ ID NO 49
<211> LENGTH: 27
<212> TYPE: DNA
<213> ORGANISM: Artificial Sequence
<220> FEATURE:
<223> OTHER INFORMATION: synthetic

<400> SEQUENCE: 49
atgcaaggtt cacactggcc gtacact                                              27

<210> SEQ ID NO 50
<211> LENGTH: 27
<212> TYPE: DNA
<213> ORGANISM: Artificial Sequence
<220> FEATURE:
<223> OTHER INFORMATION: synthetic

<400> SEQUENCE: 50
atgcaaggta cacactggcc gctcact                                              27

<210> SEQ ID NO 51
<211> LENGTH: 27
<212> TYPE: DNA
<213> ORGANISM: Artificial Sequence
<220> FEATURE:
<223> OTHER INFORMATION: synthetic

<400> SEQUENCE: 51
caacagtatg ataatctccc tcccact                                              27

<210> SEQ ID NO 52
<211> LENGTH: 27
<212> TYPE: DNA
<213> ORGANISM: Artificial Sequence
<220> FEATURE:
<223> OTHER INFORMATION: synthetic

<400> SEQUENCE: 52
caacagtatg ataatctccc attcact                                              27

<210> SEQ ID NO 53
<211> LENGTH: 27
<212> TYPE: DNA
<213> ORGANISM: Artificial Sequence
<220> FEATURE:
<223> OTHER INFORMATION: synthetic

<400> SEQUENCE: 53
caacagtatg ataatctccc cgtcact                                              27

<210> SEQ ID NO 54
<211> LENGTH: 27
<212> TYPE: DNA
<213> ORGANISM: Artificial Sequence
<220> FEATURE:
<223> OTHER INFORMATION: synthetic

<400> SEQUENCE: 54
caacagtatg ataatctccc gatcacc                                              27

<210> SEQ ID NO 55
<211> LENGTH: 24
```

```
<212> TYPE: DNA
<213> ORGANISM: Artificial Sequence
<220> FEATURE:
<223> OTHER INFORMATION: synthetic

<400> SEQUENCE: 55
caacggattt acaatgccga cacc                                           24

<210> SEQ ID NO 56
<211> LENGTH: 30
<212> TYPE: DNA
<213> ORGANISM: Artificial Sequence
<220> FEATURE:
<223> OTHER INFORMATION: synthetic

<400> SEQUENCE: 56
caacagagtt acagtacccc catgtacact                                     30

<210> SEQ ID NO 57
<211> LENGTH: 27
<212> TYPE: DNA
<213> ORGANISM: Artificial Sequence
<220> FEATURE:
<223> OTHER INFORMATION: synthetic

<400> SEQUENCE: 57
caacagagtt acagtacccc tctcact                                        27

<210> SEQ ID NO 58
<211> LENGTH: 27
<212> TYPE: DNA
<213> ORGANISM: Artificial Sequence
<220> FEATURE:
<223> OTHER INFORMATION: synthetic

<400> SEQUENCE: 58
caacagagtt acagtactcc tcccact                                        27

<210> SEQ ID NO 59
<211> LENGTH: 3155
<212> TYPE: DNA
<213> ORGANISM: Artificial Sequence
<220> FEATURE:
<223> OTHER INFORMATION: Synthetic

<400> SEQUENCE: 59
ggcgcgccgt agctttgaat tttaaacatc tatttgacaa gaaatgcata gttccttctc    60
tttaaaataa tgtaatgttt ctttcaagaa taagcttggt ttgatgcctc tctccccaac   120
atgatagaag tgtagcataa atctatgaaa aattccattt ccctgtgcct acaacaacta   180
cctgggattg aaaacttctt cccttgctct agtcctttct tctacaccta cttccacatc   240
atctgtgact caaaacaata cttgtcagga agatcccgg aaagagcaaa aaagacttcc    300
ttagaggtgt cagagattcc tatgccacta tctgtcatct ctagaagggg ttgtgagtat   360
gaggaagagc agagcttgta aatttttctac ttgctttgac ttccactgta tttcctaaca  420
acaacaacca cagcaacacc cataacatca caggacaaac ttctagtact tccaaggctt   480
tagtctcagt aaatcttctc tacctccatc acagcagcta aaggtttga tactcataca    540 aatagtactg tagcttttctg ttcataattg gaaaaataga caagacccaa tgtaatacag   600
gctttccttc agccagttag cgttcagttt ttggatcacc attgcacaca tatcccagc    660 atatgtctaa tatatatgta gaaatccgtg aagcaagagt tataatagct tgtgttttct   720
```

```
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga agaaggaca    1020 gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttca cttttaact    1560 caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tgacatccag atgacccagt ctccatcctc cctgtctgca   2400
tctgtaggag acagagtcac catcacttgc cgggcaagtc agagcattag cagctattta   2460
aattggtatc agcagaaacc agggaaagcc cctaagctcc tgatctatgc tgcatccagt   2520
ttgcaaagtg gggtcccatc aaggttcagt ggcagtggat ctgggacaga tttcactctc   2580
accatcagca gtctgcaacc tgaagatttt gcaacttact actgtcaaca gagttacagt   2640 accccctccga tcaccttcgg ccaagggaca cgactggaga ttaaacgtaa gtaattttc    2700 actattgtct tctgaaattt gggtctgatg gccagtattg acttttagag gcttaaatag   2760
gagtttggta agattggta aatgagggca tttaagattt gccatgggtt gcaaaagtta    2820
aactcagctt caaaaatgga tttggagaaa aaaagattaa attgctctaa actgaatgac   2880
acaaagtaaa aaaaaaagt gtaactaaaa aggaaccctt gtatttctaa ggagcaaaag    2940
taaatttatt tttgttcact cttgccaaat attgtattgg ttgttgctga ttatgcatga   3000
tacagaaaag tggaaaaata cattttttag tctttctccc ttttgtttga taaattattt   3060
tgtcagacaa caataaaaat caatagcacg ccctaagatc tagatgcatg ctcgagtgcc   3120
```

-continued atttcattac ctctttctcc gcacccgaca tagat      3155

<210> SEQ ID NO 60
<211> LENGTH: 28
<212> TYPE: DNA
<213> ORGANISM: Artificial Sequence
<220> FEATURE:
<223> OTHER INFORMATION: Synthetic

<400> SEQUENCE: 60
aggtgagggt acagataagt gttatgag      28

<210> SEQ ID NO 61
<211> LENGTH: 27
<212> TYPE: DNA
<213> ORGANISM: Artificial Sequence
<220> FEATURE:
<223> OTHER INFORMATION: Synthetic

<400> SEQUENCE: 61
tgacaaatgc cctaattata gtgatca      27

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
gggcaagtca gagcattagc a      21

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
tgcaaactgg atgcagcata g      21

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
ggtggagagg ctattcggc      19

<210> SEQ ID NO 65
<211> LENGTH: 17
<212> TYPE: DNA
<213> ORGANISM: Artificial Sequence
<220> FEATURE:
<223> OTHER INFORMATION: Synthetic

<400> SEQUENCE: 65
gaacacggcg gcatcag      17

<210> SEQ ID NO 66
<211> LENGTH: 23
<212> TYPE: DNA

<213> ORGANISM: Artificial Sequence
<220> FEATURE:
<223> OTHER INFORMATION: Synthetic

<400> SEQUENCE: 66
tgggcacaac agacaatcgg ctg                                              23

<210> SEQ ID NO 67
<211> LENGTH: 29
<212> TYPE: DNA
<213> ORGANISM: Artificial Sequence
<220> FEATURE:
<223> OTHER INFORMATION: Synthetic

<400> SEQUENCE: 67
ccattatgat gctccatgcc tctctgttc                                        29

<210> SEQ ID NO 68
<211> LENGTH: 26
<212> TYPE: DNA
<213> ORGANISM: Artificial Sequence
<220> FEATURE:
<223> OTHER INFORMATION: Synthetic

<400> SEQUENCE: 68
atcagcagaa accagggaaa gcccct                                           26

<210> SEQ ID NO 69
<211> LENGTH: 3166
<212> TYPE: DNA
<213> ORGANISM: Artificial Sequence
<220> FEATURE:
<223> OTHER INFORMATION: Synthetic

<400> SEQUENCE: 69
ggcgcgccgt agctttgaat tttaaacatc tatttgacaa gaaatgcata gttccttctc      60
tttaaaataa tgtaatgttt ctttcaagaa taagcttggt ttgatgcctc tctcccaac      120 atgatagaag tgtagcataa atctatgaaa aattccattt ccctgtgcct acaacaacta     180
cctgggattg aaaacttctt cccttgctct agtcctttct tctacaccta cttccacatc     240
atctgtgact caaaacaata cttgtcagga agatcccgg aaagagcaaa aaagacttcc      300
ttagaggtgt cagagattcc tatgccacta tctgtcatct ctagaagggg ttgtgagtat     360
gaggaagagc agagcttgta aattttctac ttgctttgac ttccactgta tttcctaaca    420
acaacaacca cagcaacacc cataacatca caggacaaac ttctagtact tccaaggctt    480
tagtctcagt aaatcttctc tacctccatc acagcagcta gaaggtttga tactcataca     540
aatagtactg tagcttttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgtttcct    720
attgtattgt attttcctct tatatcatct tcttcttcgt tcattaaaaa aaaaccgttc     780
aagtaggtct aaattaatta ttggatcata agtagataaa atatttatt tcataacaca    840 ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga agaaggaca    1020 gcaacaggac atgggaacct tttatagagt aacatttga taatgatga tgagaattaa    1080 tgagttagac agggatgggt gggaatgatt gaaggtgtga gtactttagc acagattaag   1140

```
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttca cttttaact    1560 caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tataccaccg gagaaattgt gttgacgcag tctccaggca   2400
ccctgtcttt gtctccaggg gaaagagcca ccctctcctg cagggccagt cagagtgtta   2460
gcagcagcta cttagcctgg taccagcaga aacctggcca ggctcccagg ctcctcatct   2520
atggtgcatc cagcagggcc actggcatcc cagacaggtt cagtggcagt gggtctggga   2580
cagacttcac tctcaccatc agcagactgg agcctgaaga ttttgcagtg tattactgtc   2640
agcagtatgg tagctcacct tggacgttcg gccaagggac caaggtggaa atcaaacgta   2700
agtaattttt cactattgtc ttctgaaatt tgggtctgat ggccagtatt gacttttaga   2760
ggcttaaata ggagtttggt aaagattggt aaatgagggc atttaagatt tgccatgggt   2820
tgcaaaagtt aaactcagct tcaaaaatgg atttggagaa aaaagatta aattgctcta   2880 aactgaatga cacaaagtaa aaaaaaaaag tgtaactaaa aggaaccct tgtatttcta    2940 aggagcaaaa gtaaatttat ttttgttcac tcttgccaaa tattgtattg gttgttgctg   3000
attatgcatg atacagaaaa gtggaaaaat acatttttta gtctttctcc cttttgtttg   3060
ataaattatt ttgtcagaca acaataaaaa tcaatagcac gccctaagat ctagatgcat   3120
gctcgagtgc catttcatta cctctttctc cgcacccgac atagat              3166
```

<210> SEQ ID NO 70
<211> LENGTH: 19
<212> TYPE: DNA
<213> ORGANISM: Artificial Sequence
<220> FEATURE:
<223> OTHER INFORMATION: Synthetic

<400> SEQUENCE: 70

| | |
|---|---|
| tccaggcacc ctgtctttg | 19 |

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71

| | |
|---|---|
| aagtagctgc tgctaacact ctgact | 26 |

<210> SEQ ID NO 72
<211> LENGTH: 24
<212> TYPE: DNA
<213> ORGANISM: Artificial Sequence
<220> FEATURE:
<223> OTHER INFORMATION: Synthetic

<400> SEQUENCE: 72

| | |
|---|---|
| aaagagccac cctctcctgc aggg | 24 |

<210> SEQ ID NO 73
<211> LENGTH: 3187
<212> TYPE: DNA
<213> ORGANISM: Artificial Sequence
<220> FEATURE:
<223> OTHER INFORMATION: Synthetic

<400> SEQUENCE: 73

| | |
|---|---|
| ggcgcgccgt agctttgaat tttaaacatc tatttgacaa gaaatgcata gttccttctc | 60 |
| tttaaaataa tgtaatgttt ctttcaagaa taagcttggt ttgatgcctc tctccccaac | 120 |
| atgatagaag tgtagcataa atctatgaaa aattccattt ccctgtgcct acaacaacta | 180 |
| cctgggattg aaaacttctt cccttgctct agtcctttct tctacaccta cttccacatc | 240 |
| atctgtgact caaacaata cttgtcagga aagatcccgg aaagagcaaa aaagacttcc | 300 |
| ttagaggtgt cagagattcc tatgccacta tctgtcatct ctagaagggg ttgtgagtat | 360 |
| gaggaagagc agagcttgta aattttctac ttgctttgac ttccactgta tttcctaaca | 420 |
| acaacaacca cagcaacacc cataacatca caggacaaac ttctagtact tccaaggctt | 480 |
| tagtctcagt aaatcttctc tacctccatc acagcagcta gaaggtttga tactcataca | 540 |
| aatagtactg tagctttctg ttcataattg gaaaaataga caagacccaa tgtaatacag | 600 |
| gctttccttc agccagttag cgttcagttt ttggatcacc attgcacaca tatacccagc | 660 |
| atatgtctaa tatatatgta gaaatccgtg aagcaagagt tataatagct tgtgttttct | 720 |
| attgtattgt attttcctct tatatcatct tcttcttcgt tcattaaaaa aaaaccgttc | 780 |
| aagtaggtct aaattaatta ttggatcata agtagataaa atattttatt tcataacaca | 840 |
| ttgacccgat gaatatgttt ctttgccaga catagtcctc atttccaagg taacaagcct | 900 |
| gaaaaaatta tactggagca agtcaacagg taatgatggt agcttttcct tattgtcctg | 960 |
| gggcaagaat aagacaaaag ataacagggt agaataaaga ttgtgtaaga aagaaggaca | 1020 |
| gcaacaggac atgggaacct tttatagagt aacattttga taatgatga tgagaattaa | 1080 |
| tgagttagac agggatgggt gggaatgatt gaaggtgtga gtactttagc acagattaag | 1140 |
| accaaatcat taggatttaa agagttgtgt agagttagtg aaggaaaagc cttagaatta | 1200 |
| aatttggctg cggataaaac attccttgga t tagactgaag actcttttct gtgctaagta | 1260 |
| agtatatttta tgataatgat gatgactgta gtgctgaata tttaataaat aaaaacaaaa | 1320 |

```
ttaattgccg catacataat gtcctgaata ctattgtaaa tgttttatct tatttccttt    1380
aaactgtcta cagcactata aggtaggtac cagtattgtc acagttacac agatatggaa    1440
accgagacac agggaagtta agttacttga tcaatttcaa gcaatcggca agccatggag    1500
catctatgtc agggctgcca ggacatgtga ctgtaaacag aagttttca cttttaact     1560 caaagagggt atgtggctgg gttaatggaa agcttcagga ccctcagaaa acattactaa    1620
caagcaaatg aaaggtgtat ctggaagatt aagttttaac agactcttca tttccatcga    1680
tccaataatg cacttaggga gatgactggg catattgagg ataggaagag agaagtgaaa    1740
acacagcttt ttatattgtt cttaacaggc ttgtgccaaa catcttctgg gtggatttag    1800
gtgattgagg agaagaaaga cacaggagcg aaattctctg agcacaaggg aggagttcta    1860
cactcagact gagccaacag acttttctgg cctgacaacc agggcggcgc aggatgctca    1920
gtgcagagag gaagaagcag gtggtctttg cagctgaaag ctcagctgat ttgcatatgg    1980
agtcattata caacatccca gaattcttta agggcagctg ccaggaagct aagaagcatc    2040
ctctcttcta gctctcagag atggagacag acacactcct gctatgggtg ctgctgctct    2100
gggttccagg tgagggtaca gataagtgtt atgagcaacc tctgtggcca ttatgatgct    2160
ccatgcctct ctgttcttga tcactataat tagggcattt gtcactggtt ttaagtttcc    2220
ccagtcccct gaattttcca ttttctcaga gtgatgtcca aaattattct taaaaattta    2280
aatgaaaagg tcctctgctg tgaaggcttt taaagatata taaaaataat ctttgtgttt    2340
atcattccag gtgccagatg tgttgtggtc ctcagccggt gctgcatcag ccgccggcca    2400
tgtcctcggc ccttggaacc acaatccgcc tcacctgcac cctgaggaac gaccatgaca    2460
tcggtgtgta cagcgtctac tggtaccagc agaggccggg ccaccctccc aggttcctgc    2520
tgagatattt ctcacaatca gacaagagcc agggccccca ggtccccct cgcttctctg     2580 gatccaaaga tgtggccagg aacagggggt atttgagcat ctctgagctg cagcctgagg    2640
acgaggctat gtattactgt gctatgcata actcagtgac gcatgtgttt ggcagcggga    2700
cccagctcac cgttttaagt aagtaatttt tcactattgt cttctgaaat ttgggtctga    2760
tggccagtat tgacttttag aggcttaaat aggagtttgg taaagattgg taaatgaggg    2820
catttaagat ttgccatggg ttgcaaaagt taaactcagc ttcaaaaatg gatttggaga    2880 aaaaagatt aaattgctct aaactgaatg acacaaagta aaaaaaaaa gtgtaactaa      2940 aaaggaaccc ttgtatttct aaggagcaaa agtaaattta tttttgttca ctcttgccaa    3000
atattgtatt ggttgttgct gattatgcat gatacagaaa agtggaaaaa tacattttt    3060 agtctttctc ccttttgttt gataaattat tttgtcagac aacaataaaa atcaatagca    3120
cgccctaaga tctagatgca tgctcgagtg ccatttcatt acctctttct ccgcacccga    3180
catagat                                                              3187
```

<210> SEQ ID NO 74
<211> LENGTH: 17
<212> TYPE: DNA
<213> ORGANISM: Artificial Sequence
<220> FEATURE:
<223> OTHER INFORMATION: Synthetic

<400> SEQUENCE: 74

```
tgtcctcggc ccttgga                                                     17
```

<210> SEQ ID NO 75

```
<211> LENGTH: 20
<212> TYPE: DNA
<213> ORGANISM: Artificial Sequence
<220> FEATURE:
<223> OTHER INFORMATION: Synthetic

<400> SEQUENCE: 75
ccgatgtcat ggtcgttcct                                          20

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
acaatccgcc tcacctgcac cct                                      23

<210> SEQ ID NO 77
<211> LENGTH: 23
<212> TYPE: DNA
<213> ORGANISM: Artificial Sequence
<220> FEATURE:
<223> OTHER INFORMATION: synthetic

<400> SEQUENCE: 77
agcagtctgc aacctgaaga ttt                                      23

<210> SEQ ID NO 78
<211> LENGTH: 24
<212> TYPE: DNA
<213> ORGANISM: Artificial Sequence
<220> FEATURE:
<223> OTHER INFORMATION: synthetic

<400> SEQUENCE: 78
gtttaatctc cagtcgtgtc cctt                                     24

<210> SEQ ID NO 79
<211> LENGTH: 15
<212> TYPE: DNA
<213> ORGANISM: Artificial Sequence
<220> FEATURE:
<223> OTHER INFORMATION: synthetic

<400> SEQUENCE: 79
cctccgatca ccttc                                               15

<210> SEQ ID NO 80
<211> LENGTH: 20
<212> TYPE: DNA
<213> ORGANISM: Artificial Sequence
<220> FEATURE:
<223> OTHER INFORMATION: synthetic

<400> SEQUENCE: 80
aaaccaggga agcccctaa                                           20

<210> SEQ ID NO 81
<211> LENGTH: 18
<212> TYPE: DNA
<213> ORGANISM: Artificial Sequence
<220> FEATURE:
<223> OTHER INFORMATION: synthetic
```

<400> SEQUENCE: 81
atgggacccc actttgca                                                    18

<210> SEQ ID NO 82
<211> LENGTH: 19
<212> TYPE: DNA
<213> ORGANISM: Artificial Sequence
<220> FEATURE:
<223> OTHER INFORMATION: synthetic

<400> SEQUENCE: 82
ctcctgatct atgctgcat                                                   19

<210> SEQ ID NO 83
<211> LENGTH: 21
<212> TYPE: DNA
<213> ORGANISM: Artificial Sequence
<220> FEATURE:
<223> OTHER INFORMATION: synthetic

<400> SEQUENCE: 83
cagcagactg gagcctgaag a                                                21

<210> SEQ ID NO 84
<211> LENGTH: 21
<212> TYPE: DNA
<213> ORGANISM: Artificial Sequence
<220> FEATURE:
<223> OTHER INFORMATION: synthetic

<400> SEQUENCE: 84
tgatttccac cttggtccct t                                                21

<210> SEQ ID NO 85
<211> LENGTH: 18
<212> TYPE: DNA
<213> ORGANISM: Artificial Sequence
<220> FEATURE:
<223> OTHER INFORMATION: synthetic

<400> SEQUENCE: 85
tagctcacct tggacgtt                                                    18

<210> SEQ ID NO 86
<211> LENGTH: 22
<212> TYPE: DNA
<213> ORGANISM: Artificial Sequence
<220> FEATURE:
<223> OTHER INFORMATION: synthetic

<400> SEQUENCE: 86
ctcctcatct atggtgcatc ca                                               22

<210> SEQ ID NO 87
<211> LENGTH: 20
<212> TYPE: DNA
<213> ORGANISM: Artificial Sequence
<220> FEATURE:
<223> OTHER INFORMATION: synthetic

<400> SEQUENCE: 87
gacccactgc cactgaacct                                                  20

<210> SEQ ID NO 88
<211> LENGTH: 13

```
<212> TYPE: DNA
<213> ORGANISM: Artificial Sequence
<220> FEATURE:
<223> OTHER INFORMATION: synthetic

<400> SEQUENCE: 88
ccactggcat ccc                                                        13

<210> SEQ ID NO 89
<211> LENGTH: 19
<212> TYPE: DNA
<213> ORGANISM: Artificial Sequence
<220> FEATURE:
<223> OTHER INFORMATION: synthetic

<400> SEQUENCE: 89
tgagcagcac cctcacgtt                                                  19

<210> SEQ ID NO 90
<211> LENGTH: 23
<212> TYPE: DNA
<213> ORGANISM: Artificial Sequence
<220> FEATURE:
<223> OTHER INFORMATION: synthetic

<400> SEQUENCE: 90
gtggcctcac aggtatagct gtt                                             23

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
accaaggacg agtatgaa                                                   18
```

HUMANIZED UNIVERSAL LIGHT CHAIN MICE

CROSS-REFERENCE TO RELATED APPLICATIONS

This application claims the benefit under 35 U.S.C. § 119(e) of U.S. provisional application No. 61/515,374, filed on Aug. 5, 2011, which application is hereby incorporated by reference in its entirety.

FIELD OF INVENTION

Genetically modified mice, cells, embryos, tissues, and isolated nucleic acids for making antibodies and sequences encoding human immunoglobulin heavy chain variable domains, including bispecific antibodies, and including bispecific antibodies that comprise universal light chains. Compositions and methods include genetically modified mice with germline replacements at the endogenous mouse heavy chain variable locus, which comprise modified light chain loci that express light chains derived from no more than one or two different light chain V gene segments, wherein the mice are further genetically modified in their germline such that male mice bearing these modifications are fertile. Genetically modified mice that express universal light chains and humanized heavy chain variable domains are provided, wherein the mice comprise an ADAM6 activity that is functional in a male mouse.

BACKGROUND

The development of antibodies for use as human therapeutics has a long and complex history. One significant advance has been the ability to make essentially fully human antibody sequences to use in designing effective human therapeutics with reduced potential for immunogenicity. Mice now exist that are modified in their germline to generate human antibody sequences derived from unrearranged gene segments (heavy and light) either as transgenes or as replacements at endogenous mouse immunoglobulin loci. Replacement of mouse variable sequences with human variable sequences at endogenous loci in mice, as with VELOCIMMUNE® humanized mice, allow for the mouse immune system to function essentially normally. As a result, exposing these mice to an antigen of choice generates a marvelously diverse, rich population of clonally selected B cells that express high affinity somatically mutated human variable domains that can be used in making fully human antibodies directed against the antigen of choice.

Human variable domains made in humanized mice can be used to design fully human bispecific antibodies, i.e., binding proteins that are heterodimers of heavy chains, where the identities and binding specificities of the heavy chain variable domains differ. But selecting light chains that can effectively associate and express with the heavy chain heterodimers has no facile solution. Developing human light chain variable domains for use in human therapeutics is certainly possible in humanized mice, but there are no easy solutions to selecting which light chains will effectively associate and express with heavy chains having desired binding characteristics, where the light chains are not detrimental to the expression or binding behavior of both heavy chains.

Thus, there remains a need in the art for compositions and methods for developing human immunoglobulin variable regions for use in human therapeutics, including human immunoglobulin variable regions generated from nucleic acid sequences at endogenous mouse immunoglobulin loci.

SUMMARY

Mice are described that express human immunoglobulin variable domains that are suitable for use in bispecific binding proteins, including bispecific antibodies, wherein the mice comprise a humanization of an endogenous mouse heavy chain variable locus, wherein male mice comprising the humanization are fertile, and wherein the mice further comprise a humanization of an endogenous immunoglobulin light chain locus that results in the mouse expressing an immunoglobulin light chain repertoire that is derived from no more than one, or no more than two, λ and/or κ V gene segments.

Genetically engineered mice are provided that select suitable affinity-matured human immunoglobulin heavy chain variable domains derived from a repertoire of unrearranged human heavy chain V, D, and J segments, wherein the affinity-matured human heavy chain variable domains associate and express with a humanized universal light chain. The humanized universal light chain is expressed from a locus that comprises either no more than one or no more than two human light chain V segments and a human J segment operably linked to a light chain constant gene, or no more than one or no more than two rearranged (Vλ/Jλ, Vκ/Jκ, Vλ/Jκ, or Vκ/Jλ) human nucleic acid sequences encoding a light chain variable domain operably linked to a light chain constant gene. In various embodiments the universal humanized light chain domain pairs with a plurality of affinity-matured human heavy chain variable domains, wherein the plurality of heavy chain variable domains specifically bind different epitopes or antigens.

In one aspect, nucleic acid constructs, cells, embryos, mice, and methods are provided for making mice that comprise a humanized heavy chain immunoglobulin variable locus and a humanized light chain immunoglobulin variable locus, wherein the mouse expresses one of no more than two universal light chains, and mice that are males exhibit wild-type fertility.

In one aspect, a modified mouse is provided that comprises in its germline a humanized heavy chain immunoglobulin variable locus at an endogenous mouse heavy chain locus, and a humanized light chain immunoglobulin variable locus, wherein the mouse expresses a universal light chain, and wherein the mouse comprises a nucleic acid sequence encoding a mouse ADAM6 or ortholog or homolog or functional fragment thereof. In various embodiments the humanized light chain immunoglobulin variable locus is at an endogenous mouse light chain locus.

In one embodiment, the humanized heavy chain immunoglobulin variable locus comprises a replacement at the endogenous mouse heavy chain variable locus of all or substantially all functional mouse immunoglobulin heavy chain V, D, and J gene segments with one or more human V, human D, and human J gene segments, wherein the one or more human V, D, and J segments are operably linked and capable of rearranging to form a rearranged V/D/J gene that is operably linked to a heavy chain constant sequence.

In one embodiment, the mouse comprises a light chain locus that this engineered to make a universal light chain, wherein the universal light chain is a light chain that is derived from a light chain locus that comprises no more than one light chain V segment and no more than one light chain J segment, or a light chain locus that comprises a single rearranged light chain V/J sequence. In one embodiment, the mouse comprises an immunoglobulin light chain locus that comprises single human immunoglobulin light chain V segment that is capable of rearranging with a human light chain J gene segment (selected from one or a plurality of J segments) and encoding a human light chain variable domain. In another embodiment, the mouse comprises no more than two human light chain V segments at the light chain locus, each V segment of which is capable of rearranging with a human J gene segment (selected from one or a plurality of light chain J segments) and encoding a rearranged human light chain variable domain.

In one embodiment, the single human light chain V segment is operably linked to a human light chain J segment selected from Jκ1, Jκ3, Jκ4, and Jκ5, wherein the single human light chain V segment is capable of rearranging to form a sequence encoding a light chain variable region gene with any of the one or more human light chain J segments.

In one embodiment, the mouse comprises an endogenous light chain locus that comprises a replacement of all or substantially all mouse V and J gene segments with no more than one, or no more than two, rearranged (V/J) nucleic acid sequences. In one embodiment, the no more than one or no more than two rearranged (V/J) nucleic acid sequences are selected from a human Vκ1-39Jκ5, a Vκ3-20Jκ1, and a combination thereof.

In one embodiment, the mouse lacks a functional endogenous light chain locus that is capable of expressing a mouse light chain variable domain. In one embodiment, the mouse comprises a nucleic acid sequence encoding a variable domain of a universal light chain at a λ locus. In one embodiment, the mouse comprises a nucleic acid sequence encoding a variable domain of a universal light chain at a λ locus.

In one embodiment, the human V segment (or rearranged V/J sequence) is operably linked to a human or mouse leader sequence. In one embodiment, the leader sequence is a mouse leader sequence. In a specific embodiment, the mouse leader sequence is a mouse Vκ3-7 leader sequence.

In one embodiment, the human V segment (or rearranged V/J sequence) is operably linked to an immunoglobulin promoter sequence. In one embodiment, the promoter sequence is a human promoter sequence. In a specific embodiment, the human immunoglobulin promoter is a human Vκ3-15 promoter.

In one embodiment, the unrearranged V and J segments or the rearranged (V/J) sequence is operably linked to a light chain immunoglobulin constant region gene. In a specific embodiment, the constant region gene is a mouse Cκ gene.

In one embodiment, the unrearranged V and J segments or the rearranged (V/J) sequence are present at a κ light chain locus, and the κ light chain locus comprises a mouse κ intronic enhancer, a mouse κ 3' enhancer, or both an intronic enhancer and a 3' enhancer. In a specific embodiment, the κ locus is an endogenous κ locus.

In one embodiment, the mouse comprises a κ locus comprising a sequence encoding a variable domain of a universal light chain, and the mouse comprises a nonfunctional immunoglobulin lambda (λ) light chain locus. In a specific embodiment, the λ light chain locus comprises a deletion of one or more sequences of the locus, wherein the one or more deletions renders the λ light chain locus incapable of rearranging to form a light chain gene. In another embodiment, all or substantially all of the V segments of the λ light chain locus are deleted. In one another embodiment, the mouse comprises a deletion of all, or substantially all, of the endogenous light chain variable locus.

In one embodiment, the mouse further comprises in its germline a sequence selected from a mouse κ intronic enhancer 5' with respect to rearranged immunoglobulin light chain sequence or the unrearranged gene segments, a mouse κ 3' enhancer, and a combination thereof.

In one embodiment, the universal light chain variable domain sequence of the mouse comprises one or more somatic hypermutations; in one embodiment, the variable domain sequence comprises a plurality of somatic hypermutations.

In one embodiment, the mouse makes a universal light chain that comprises a somatically mutated human variable domain. In one embodiment, the light chain comprises a somatically mutated human variable domain derived from a human V segment, a human J segment, and a mouse Cκ gene. In one embodiment, the mouse does not express a λ light chain.

In one embodiment, the human variable sequence is a rearranged human Vκ1-39Jκ5 sequence, and the mouse expresses a reverse chimeric light chain comprising (i) a variable domain derived from Vκ1-39Jκ5 and (ii) a mouse $C_L$; wherein the light chain is associated with a reverse chimeric heavy chain comprising (i) a mouse $C_H$ and (ii) a somatically mutated human heavy chain variable domain. In one embodiment, the mouse expresses a light chain that is somatically mutated. In one embodiment the $C_L$ is a mouse Cκ.

In one embodiment, the human variable sequence is a rearranged human Vκ3-20Jκ1 sequence, and the mouse expresses a reverse chimeric light chain comprising (i) a variable domain derived from Vκ3-20Jκ1, and (ii) a mouse $C_L$; wherein the light chain is associated with a reverse chimeric heavy chain comprising (i) a mouse $C_H$, and (ii) a somatically mutated human heavy chain variable domain.

In one embodiment, the mouse comprises both a rearranged human Vκ1-39Jκ5 sequence and a rearranged human Vκ3-20Jκ1 sequence, and the mouse expresses a reverse chimeric light chain comprising (i) a light chain comprising a variable domain derived from the Vκ1-39Jκ5 sequence or the Vκ3-20Jκ1 sequence, and (ii) a mouse $C_L$; wherein the light chain is associated with a reverse chimeric heavy chain comprising (i) a mouse $C_H$, and (ii) a somatically mutated human heavy chain variable domain. In one embodiment, the mouse expresses a light chain that is somatically mutated. In one embodiment the $C_L$ is a mouse Cκ.

In one embodiment, the mouse expresses a reverse chimeric antibody comprising a light chain that comprises a mouse Cκ and a somatically mutated human variable domain derived from a rearranged human Vκ1-39Jκ5 sequence or a rearranged human Vκ3-20Jκ1 sequence, and a heavy chain that comprises a mouse $C_H$ and a somatically mutated human heavy chain variable domain, wherein the mouse does not express a fully mouse antibody and does not express a fully human antibody. In one embodiment the mouse comprises a κ light chain locus that comprises a replacement of endogenous mouse κ light chain gene segments with the rearranged human Vκ1-39Jκ5 sequence or the rearranged human Vκ3-20Jκ1 sequence, and comprises a replacement of all or substantially all endogenous mouse heavy chain V, D, and J gene segments with a complete or substantially complete repertoire of human heavy chain V, D, and J gene segments.

In one aspect, a genetically modified mouse is provided that expresses a single κ light chain derived from no more than one, or no more than two, rearranged κ light chain sequences, wherein the mouse, upon immunization with antigen, exhibits a serum titer that is comparable to a wild type mouse immunized with the same antigen. In a specific embodiment, the mouse expresses a single κ light chain sequence, wherein the single κ light chain sequence is derived from no more than one rearranged κ light chain sequence. In one embodiment, the serum titer is characterized as total immunoglobulin. In a specific embodiment, the serum titer is characterized as IgM specific titer. In a specific embodiment, the serum titer is characterized as IgG specific titer. In a more specific embodiment, the rearranged κ light chain sequence is selected from a Vκ1-39Jκ5 and Vκ3-20Jκ1 sequence. In one embodiment, the rearranged κ light chain sequence is a Vκ1-39Jκ5 sequence. In one embodiment, the rearranged κ light chain sequence is a Vκ3-20Jκ1 sequence.

In one aspect, a genetically modified mouse is provided that expresses a plurality of immunoglobulin heavy chains associated with a single light chain sequence. In one embodiment, the heavy chain comprises a human sequence. In various embodiments, the human sequence is selected from a variable sequence, a CH1, a hinge, a CH2, a CH3, and a combination thereof. In one embodiment, the single light chain comprises a human sequence. In various embodiments, the human sequence is selected from a variable sequence, a constant sequence, and a combination thereof. In one embodiment, the mouse comprises a disabled endogenous immunoglobulin locus and expresses the heavy chain and/or the light chain from a transgene or extrachromosomal episome. In one embodiment, the mouse comprises a replacement at an endogenous mouse locus of some or all endogenous mouse heavy chain gene segments (i.e., V, D, J), and/or some or all endogenous mouse heavy chain constant sequences (e.g., CH1, hinge, CH2, CH3, or a combination thereof), and/or some or all endogenous mouse light chain sequences (e.g., V, J, constant, or a combination thereof), with one or more human immunoglobulin sequences.

In one embodiment, the mouse, following rearrangement of the one or more V, D, and J gene segments, or one or more V and J gene segments, the mouse comprises in its genome at least one nucleic acid sequence encoding a mouse ADAM6 gene or homolog or ortholog or functional fragment thereof. In one embodiment, following rearrangement the mouse comprises in its genome at least two nucleic acid sequences encoding a mouse ADAM6 gene or homolog or ortholog or functional fragment thereof. In one embodiment, following rearrangement the mouse comprises in its genome at least one nucleic acid sequence encoding a mouse ADAM6 gene or homolog or ortholog or functional fragment thereof. In one embodiment, the mouse comprises the ADAM6 gene or homolog or ortholog or functional fragment thereof in a B cell.

In one embodiment, the male mice comprise a single unmodified endogenous ADAM6 allele or ortholog of homolog or functional fragment thereof at an endogenous ADAM6 locus.

In one embodiment, the male mice comprise an ADAM6 sequence or homolog or ortholog or functional fragment thereof at a location in the mouse genome that approximates the location of the endogenous mouse ADAM6 allele, e.g., 3' of a final V gene segment sequence and 5' of an initial D gene segment.

In one embodiment, the male mice comprise an ADAM6 sequence or homolog or ortholog or functional fragment thereof flanked upstream, downstream, or upstream and downstream (with respect to the direction of transcription of the ADAM6 sequence) of a nucleic acid sequence encoding an immunoglobulin variable region gene segment. In a specific embodiment, the immunoglobulin variable region gene segment is a human gene segment. In one embodiment, the immunoglobulin variable region gene segment is a human gene segment, and the sequence encoding the mouse ADAM or ortholog or homolog or fragment thereof functional in a mouse is between human V gene segments; in one embodiment, the mouse comprises two or more human V gene segments, and the sequence is at a position between the final V gene segment and the penultimate V gene segment; in one embodiment, the sequence is at a position following the final V gene segment and the first D gene segment.

In one embodiment, the humanized heavy chain immunoglobulin variable locus lacks an endogenous mouse ADAM6 gene. In one embodiment, the humanized heavy chain immunoglobulin variable locus comprises an ADAM6 gene that is functional in a male mouse. In a specific embodiment, the ADAM6 gene that is functional in the male mouse is a mouse ADAM6 gene, and the mouse ADAM6 gene is placed within or immediately adjacent to the humanized heavy chain immunoglobulin variable locus.

In one embodiment, the humanized heavy chain immunoglobulin variable locus lacks an endogenous mouse ADAM6 gene, and the mouse comprises an ectopic ADAM6 sequence that is functional in a male mouse. In one embodiment, the ectopic ADAM6 gene that is functional in the male mouse is a mouse ADAM6 gene. In one embodiment, the mouse ADAM6 gene is on the same chromosome as the humanized heavy chain immunoglobulin variable locus. In one embodiment, the mouse ADAM6 gene is on a different chromosome than the humanized heavy chain immunoglobulin variable locus. In one embodiment, the mouse ADAM6 gene is on an episome.

In one embodiment, the mouse comprises a first endogenous heavy chain allele and a second endogenous heavy chain allele, and the first endogenous heavy chain allele comprises a deletion of a mouse ADAM6 locus, and the first endogenous heavy chain allele comprises a replacement of all or substantially all functional mouse V, D, and J segments with one or more human V, D, and J segments. In one embodiment, the first and the second endogenous heavy chain alleles each comprise a deletion of an endogenous mouse ADAM6 locus, and the first and the second endogenous heavy chain alleles comprise a replacement of all or substantially all functional mouse V, D, and J segments with one or more human V, D, and J segments. In one embodiment, the first and/or the second allele comprises an ectopic nucleic acid sequence that encodes a mouse ADAM6 or ortholog or homolog or functional fragment thereof. In one embodiment, the ectopic nucleic acid sequence is located 3' (with respect to the transcriptional directionality of the heavy chain variable locust) of a final mouse V gene segment and located 5' (with respect to the transcriptional directionality of the constant sequence) of a mouse (or chimeric human/mouse) heavy chain constant gene or fragment thereof (e.g., a nucleic acid sequence encoding a human and/or mouse: $C_H1$ and/or hinge and/or $C_H2$ and/or $C_H3$). In one embodiment, the ectopic nucleic acid sequence is located downstream (with respect to direction of transcription of the V segment locus) of a V segment and upstream of a D segment. In one embodiment, the ectopic nucleic acid sequence is located between the penultimate 3'-most V segment and the ultimate 3'-most V segment. In a specific embodiment, the ectopic nucleic acid sequence is located between human V segment $V_H1$-2 and human V segment $V_H6$-1. In one embodiment, the nucleotide sequence between the two human V gene segments is placed in opposite transcription orientation with respect to the human V gene segments. In a specific embodiment, nucleotide sequence encodes, from 5' to 3' with respect to the direction of transcription of ADAM6 genes, and ADAM6a sequence followed by an ADAM6b sequence. In a specific embodiment, the ADAM6 gene(s) is oriented in opposite transcriptional orientation as compared with the upstream and downstream flanking V segments.

In one embodiment, the nucleic acid sequence comprises a sequence encoding mouse ADAM6a or functional fragment thereof and/or a sequence encoding mouse ADAM6b or functional fragment thereof, wherein the ADAM6a and/or ADAM6b or functional fragment(s) thereof is operably linked to a promoter. In one embodiment, the promoter is a human promoter. In one embodiment, the promoter is the mouse ADAM6 promoter. In a specific embodiment, the ADAM6 promoter comprises sequence located between the first codon of the first ADAM6 gene closest to the mouse 5'-most $D_H$ gene segment and the recombination signal sequence of the 5'-most $D_H$ gene segment, wherein 5' is indicated with respect to direction of transcription of the mouse immunoglobulin genes. In one embodiment, the promoter is a viral promoter. In a specific embodiment, the viral promoter is a cytomegalovirus (CMV) promoter. In one embodiment, the promoter is a ubiquitin promoter.

In one embodiment, the mouse ADAM6a and/or ADAM6b are selected from the ADAM6a of SEQ ID NO:1 and/or ADAM6b of sequence SEQ ID NO:2. In one embodiment, the mouse ADAM6 promoter is a promoter of SEQ ID NO:3. In a specific embodiment, the mouse ADAM6 promoter comprises the nucleic acid sequence of SEQ ID NO:3 directly upstream (with respect to the direction of transcription of ADAM6a) of the first codon of ADAM6a and extending to the end of SEQ ID NO:3 upstream of the ADAM6 coding region. In another specific embodiment, the ADAM6 promoter is a fragment extending from within about 5 to about 20 nucleotides upstream of the start codon of ADAM6a to about 0.5 kb, 1 kb, 2 kb, or 3 kb or more upstream of the start codon of ADAM6a.

In one embodiment, the nucleic acid sequence comprises SEQ ID NO:3 or a fragment thereof that when placed into a mouse that is infertile or that has low fertility due to a lack of ADAM6, improves fertility or restores fertility to about a wild-type fertility. In one embodiment, SEQ ID NO:3 or a fragment thereof confers upon a male mouse the ability to produce a sperm cell that is capable of traversing a female mouse oviduct in order to fertilize a mouse egg.

In one embodiment, the mice comprise a nucleic acid sequence that encodes an ADAM6 protein, or ortholog or homolog or fragment thereof, that is functional in a male mouse. In a specific embodiment, the nucleic acid sequence is within or adjacent to a human nucleic acid sequence that comprises one or more immunoglobulin variable region gene segment. In one embodiment, the one or more immunoglobulin variable region gene segments is at a modified endogenous mouse immunoglobulin heavy chain variable locus. In one embodiment, the modification comprises a replacement of all or substantially all functional mouse immunoglobulin heavy chain variable gene segments with a plurality of unrearranged human heavy chain gene segments that are operably linked to an endogenous mouse constant region gene. In a specific embodiment, the nucleic acid sequence is between two human V segments. In a specific embodiment, the nucleic acid sequence is between a human V segment and a human D segment. In a specific embodiment, the nucleic acid sequence is between a human D segment and a human J segment. In a specific embodiment, the nucleic acid sequence is upstream of the 5'-most (with respect to direction of transcription of the V segment) human. V segment. In a specific embodiment, the nucleic acid sequence is between a human J segment and an endogenous mouse heavy chain constant region gene sequence.

In one embodiment, the male mice are capable of generating offspring by mating, with a frequency that is about the same as a wild-type mouse. In one embodiment, the male mice produce sperm that can transit from a mouse uterus through a mouse oviduct to fertilize a mouse egg; in a specific embodiment, sperm of the mice transit through the oviduct about as efficiently as sperm from a wild-type mouse. In one embodiment, about 50% or more of the sperm produced in the mouse exhibit the ability to enter and/or transit an oviduct to fertilize a mouse egg.

In one embodiment, the mouse lacks a functional endogenous ADAM6 locus, wherein the mouse comprises an ectopic nucleotide sequence that complements the loss of mouse ADAM6 function in a male mouse. In one embodiment, the ectopic nucleotide sequence confers upon the male mouse an ability to produce offspring that is comparable to a corresponding wild-type male mouse that contains a functional endogenous ADAM6 gene. In one embodiment, the sequence confers upon the mouse an ability to form a complex of ADAM2 and/or ADAM6 and/or ADAM6 on the surface of sperm cell of the mouse. In one embodiment, the sequence confers upon the mouse an ability to travel from a mouse uterus through a mouse oviduct to a mouse ovum to fertilize the ovum.

In one embodiment, the mouse lacks a functional endogenous ADAM6 locus and comprises an ectopic nucleotide sequence encoding an ADAM6 or ortholog or homolog or fragment thereof that is functional in a male mouse and wherein the male mouse produces at least about 50%, 60%, 70%, 80%, or 90% of the number of litters a wild-type mouse of the same age and strain produces in a six-month time period.

In one embodiment, the mouse lacking the functional endogenous ADAM6 gene and comprising the ectopic nucleotide sequence produces at least about 1.5-fold, about 2-fold, about 2.5-fold, about 3-fold, about 4-fold, about 6-fold, about 7-fold, about 8-fold, or about 10-fold or more progeny when bred over a six-month time period than a mouse of the same age and the same or similar strain that lacks the functional endogenous ADAM6 gene and that lacks the ectopic nucleotide sequence that is bred over substantially the same time period and under substantially the same conditions.

In one embodiment, the mouse lacking the functional endogenous ADAM6 gene and comprising the ectopic nucleotide sequence produces an average of at least about 2-fold, 3-fold, or 4-fold higher number of pups per litter in a 4- or 6-month breeding period than a mouse that lacks the functional endogenous ADAM6 gene and that lacks the ectopic nucleotide sequence, and that is bred for the same period of time.

In one embodiment, the mouse lacking the functional endogenous ADAM6 gene and comprising the ectopic nucleotide sequence is a male mouse, and the male mouse produces sperm that when recovered from oviducts at about 5-6 hours post-copulation reflects an oviduct migration that is at least 10-fold, at least 20-fold, at least 30-fold, at least 40-fold, at least 50-fold, at least 60-fold, at least 70-fold, at least 80-fold, at least 90-fold, 100-fold, 110-fold, or 120-fold or higher than sperm of a mouse that lacks the functional endogenous ADAM6 gene and that lacks the ectopic nucleotide sequence.

In one embodiment, the mouse lacking the functional endogenous ADAM6 gene and comprising the ectopic nucleotide sequence when copulated with a female mouse generates sperm that is capable of traversing the uterus and entering and traversing the oviduct within about 6 hours at an efficiency that is about equal to sperm from a wild-type mouse.

In one embodiment, the mouse lacking the functional endogenous ADAM6 gene and comprising the ectopic nucleotide sequence produces about 1.5-fold, about 2-fold, about 3-fold, or about 4-fold or more litters in a comparable period of time than a mouse that lacks the functional ADAM6 gene and that lacks the ectopic nucleotide sequence.

In one aspect, a mouse is provided that comprises a humanized endogenous mouse heavy chain variable immunoglobulin locus and a modification of a mouse light chain immunoglobulin locus, wherein the mouse expresses a B cell that comprises a rearranged human heavy chain immunoglobulin sequence operably linked to a human or mouse heavy chain constant region gene sequence, and the B cell comprises in its genome (e.g., on a B cell chromosome) a gene encoding an ADAM6 or ortholog or homolog or fragment thereof that is functional in a male mouse (e.g., a mouse ADAM6 gene, e.g., mouse ADAM6a and/or mouse ADAM6b), wherein the variable domains of immunoglobulin λ or κ light chains of the mice are derived from no more than one or no more than two light chain V gene segments.

In one embodiment, the rearranged immunoglobulin sequence operably linked to the heavy chain constant region gene sequence comprises a human heavy chain V, D, and/or J sequence; a mouse heavy chain V, D, and/or J sequence; a human or mouse light chain V and/or J sequence. In one embodiment, the heavy chain constant region gene sequence comprises a human or a mouse heavy chain sequence selected from the group consisting of a $C_H1$, a hinge, a $C_H2$, a $C_H3$, and a combination thereof.

In one aspect, a mouse suitable for making antibodies that have the same light chain is provided, wherein all or substantially all antibodies made in the mouse are expressed with the same light chain, wherein the light chain comprises a human variable domain, and wherein the antibodies comprise a heavy chain that comprises a human variable domain.

In one aspect, a mouse is provided that is characterized by an inability of the mouse to make a B cell that expresses an immunoglobulin light chain variable domain that is derived from a rearranged light chain sequence that is not a human Vκ1-39Jκ5 or a human Vκ3-20Jκ1 sequence.

In one embodiment, the mouse exhibits a κ:λ light chain ratio that is about the same as a mouse that comprises a wild type complement of immunoglobulin light chain V and J gene segments.

In one aspect, a mouse as described herein is provided that expresses an immunoglobulin light chain derived from a human Vκ1-39Jκ5 or a human Vκ3-20Jκ1 sequence, wherein the mouse comprises a replacement of all or substantially all endogenous mouse heavy chain variable region gene segments with one or more human heavy chain variable region gene segments, and the mouse exhibits a ratio of (a) $CD19^+$ B cells that express an immunoglobulin having a λ light chain, to (b) $CD19^+$ B cells that express an immunoglobulin having a κ light chain, of about 1 to about 20.

In one embodiment, the mouse expresses a single κ light chain, wherein the single κ light chain is derived from a human Vκ1-39Jκ5 sequence, and the ratio of $CD19^+$ B cells that express an immunoglobulin having a λ light chain to B cells that express an immunoglobulin having a κ light chain is about 1 to about 20; in one embodiment, the ratio is about 1 to at least about 66; in a specific embodiment, the ratio is about 1 to 66.

In one embodiment, the mouse expresses a single κ light chain, wherein the single κ light chain is derived from a human Vκ3-20Jκ5 sequence, and the ratio of $CD19^+$ B cells that express an immunoglobulin having a λ light chain to $CD19^+$ B cells that express an immunoglobulin having a κ light chain is about 1 to about 20; in one embodiment, the ratio is about 1 to about 21. In specific embodiments, the ratio is 1 to 20, or 1 to 21.

In one embodiment, the percent of $Igκ^+Igλ^+$ B cells in the mouse is about the same as in a wild type mouse. In a specific embodiment, the percent of $Igκ^+Igλ^+$ B cells in the mouse is about 2 to about 6 percent. In a specific embodiment, the percent of $Igκ^+Igλ^+$ B cells in a mouse wherein the single rearranged κ light chain is derived from a Vκ1-39Jκ5 sequence is about 2 to about 3; in a specific embodiment, about 2.6. In a specific embodiment, the percent of $Igκ^+Igλ^+$ B cells in a mouse wherein the single rearranged κ light chain is derived from a Vκ3-20Jκ1 sequence is about 4 to about 8; in a specific embodiment, about 6.

In one embodiment, the mouse is does not comprise a modification that reduces or eliminates an ability of the mouse to somatically mutate any functional light chain locus of the mouse. In one embodiment, the only functional light chain locus in the mouse expresses a light chain that comprises a human variable domain derived from a rearranged sequence selected from a human Vκ1-39Jκ5 sequence, a human Vκ3-20Jκ1 sequence, and a combination thereof.

In one aspect, a genetically modified mouse is provided that expresses a single κ light chain derived from no more than one, or no more than two, rearranged κ light chain sequences, wherein the mouse exhibits usage of the κ light chain that is about 100-fold or more, at least about 200-fold or more, at least about 300-fold or more, at least about 400-fold or more, at least about 500-fold or more, at least about 600-fold or more, at least about 700-fold or more, at least about 800-fold or more, at least about 900-fold or more, at least about 1000-fold or more greater than the usage of the same κ light chain (i.e., derived from the same V segment and the same J segment, or derived from the same rearranged V/J segment) exhibited by a mouse bearing a complete or substantially complete human κ light chain locus. In a specific embodiment, the mouse bearing a complete or substantially complete human κ light chain locus lacks a functional unrearranged mouse κ light chain sequence. In a specific embodiment, the mouse expresses the single κ light chain from no more than one rearranged κ light chain sequence. In one embodiment, the mouse comprises one copy of a rearranged κ light chain sequence (e.g., a heterozygote). In one embodiment, the mouse comprises two copies of a rearranged κ light chain sequence (e.g., a homozygote). In a more specific embodiment, the rearranged κ light chain sequence is selected from a Vκ1-39Jκ5 and Vκ3-20Jκ1 sequence. In one embodiment, the rearranged κ light chain sequence is a Vκ1-39Jκ5 sequence. In one embodiment, the rearranged κ light chain sequence is a Vκ3-20Jκ1 sequence.

In one aspect, a genetically modified mouse is provided that expresses a single light chain derived from no more than one, or no more than two, rearranged κ light chain sequences, wherein the light chain in the genetically modified mouse exhibits a level of expression that is at least 10-fold to about 1,000-fold, 100-fold to about 1,000-fold, 200-fold to about 1,000-fold, 300-fold to about 1,000-fold, 400-fold to about 1,000-fold, 500-fold to about 1,000-fold, 600-fold to about 1,000-fold, 700-fold to about 1,000-fold, 800-fold to about 1,000-fold, or 900-fold to about 1,000-fold higher than expression of the same rearranged light chain exhibited by a mouse bearing a complete or substantially complete human κ light chain variable locus. In one embodiment, the light chain comprises a human sequence. In one embodiment, the single light chain is derived from a rearranged κ light chain sequence selected from a human Vκ1-39Jκ5, a human Vκ3-20Jκ1, and a combination thereof.

In one embodiment, the level of expression of the light chain, for the purpose of comparing the expression of the light chain with expression in a mouse comprising a substantially completely humanized light chain variable locus, is characterized by quantitating mRNA of transcribed light chain sequence (from the one or two rearranged sequences), and comparing it to transcribed light chain sequence of a mouse bearing a complete or substantially complete light chain locus.

In one aspect, a method for making an antibody is provided, comprising expressing in a cell (a) a first human heavy chain variable domain nucleic acid sequence of an immunized mouse as described herein fused with a human $C_H$ gene sequence; (b) a human light chain variable domain nucleic acid sequence of an immunized mouse as described herein fused with a human $C_L$ gene sequence; and, (c) maintaining the cell under conditions sufficient to express a fully human antibody, and isolating the antibody. In one embodiment, the cell comprises a second human heavy chain variable domain nucleic acid sequence of a second immunized mouse as described herein fused with a human $C_H$ gene sequence, the first heavy chain nucleic acid sequence encodes a first heavy chain variable domain that recognizes a first epitope, and the second heavy chain nucleic acid sequence encodes a second heavy chain variable domain that recognizes a second epitope, wherein the first epitope and the second epitope are not identical.

In one aspect, a method for making an epitope-binding protein is provided, comprising exposing a mouse as described herein with an antigen that comprises an epitope of interest, maintaining the mouse under conditions sufficient for the mouse to generate an immunoglobulin molecule that specifically binds the epitope of interest, and isolating the immunoglobulin molecule that specifically binds the epitope of interest; wherein the epitope-binding protein comprises a heavy chain that comprises a somatically mutated human variable domain and a mouse $C_H$, associated with a light chain comprising a mouse $C_L$ and a human variable domain derived from a rearranged human Vκ1-39Jκ5 or a rearranged human Vκ3-20Jκ1.

In one aspect, a method for making a bispecific antigen-binding protein is provided, comprising exposing a first mouse as described herein to a first antigen of interest that comprises a first epitope, exposing a second mouse as described herein to a second antigen of interest that comprises a second epitope, allowing the first and the second mouse to each mount immune responses to the antigens of interest, identifying in the first mouse a first human heavy chain variable region that binds the first epitope of the first antigen of interest, identifying in the second mouse a second human heavy chain variable region that binds the second epitope of the second antigen of interest, making a first fully human heavy chain gene that encodes a first heavy chain that binds the first epitope of the first antigen of interest, making a second fully human heavy chain gene that encodes a second heavy chain that binds the second epitope of the second antigen of interest, expressing the first heavy chain and the second heavy chain in a cell that expresses a single fully human light chain derived from a human Vκ1-39 or a human Vκ3-20 gene segment to form a bispecific antigen-binding protein, and isolating the bispecific antigen-binding protein.

In one embodiment, the first antigen and the second antigen are not identical.

In one embodiment, the first antigen and the second antigen are identical, and the first epitope and the second epitope are not identical. In one embodiment, binding of the first heavy chain variable region to the first epitope does not block binding of the second heavy chain variable region to the second epitope.

In one embodiment, the first antigen is selected from a soluble antigen and a cell surface antigen (e.g., a tumor antigen), and the second antigen comprises a cell surface receptor. In a specific embodiment, the cell surface receptor is an immunoglobulin receptor. In a specific embodiment, the immunoglobulin receptor is an Fc receptor. In one embodiment, the first antigen and the second antigen are the same cell surface receptor, and binding of the first heavy chain to the first epitope does not block binding of the second heavy chain to the second epitope.

In one embodiment, the light chain variable domain of the light chain comprises 2 to 5 somatic mutations. In one embodiment, the light chain variable domain is a somatically mutated cognate light chain expressed in a B cell of the first or the second immunized mouse with either the first or the second heavy chain variable domain.

In one aspect, a cell that expresses an epitope-binding protein is provided, wherein the cell comprises: (a) a human nucleotide sequence encoding a human light chain variable domain that is derived from a rearranged human Vκ1-39Jκ5 or a rearranged human Vκ3-20Jκ1, wherein the human nucleic acid sequence is fused (directly or through a linker) to a human immunoglobulin light chain constant domain nucleic acid sequence (e.g., a human κ constant domain DNA sequence); and, (b) a first human heavy chain variable domain nucleic acid sequence encoding a human heavy chain variable domain derived from a first human heavy chain variable domain nucleotide sequence, wherein the first human heavy chain variable domain nucleotide sequence is fused (directly or through a linker) to a human immunoglobulin heavy chain constant domain nucleic acid sequence (e.g., a human IgG1, IgG2, IgG3, IgG4, or IgE sequence); wherein the epitope-binding protein recognizes a first epitope. In one embodiment, the epitope-binding protein binds the first epitope with a dissociation constant of lower than $10^{-6}$ M, lower than $10^{-8}$M, lower than $10^{-9}$M, lower than $10^{-10}$ M, lower than $10^{-11}$ M, or lower than $10^{-12}$ M. In one embodiment, the cell comprises a second human nucleotide sequence encoding a second human heavy chain variable domain, wherein the second human sequence is fused (directly or through a linker) to a human immunoglobulin heavy chain constant domain nucleic acid sequence, and wherein the second human heavy chain variable domain does not specifically recognize the first epitope (e.g., displays a dissociation constant of, e.g., $10^{-6}$ M, $10^{-5}$ M, $10^{-4}$ M, or higher), and wherein the epitope-binding protein binds both the first epitope and the second epitope, and wherein the first and the second immunoglobulin heavy chains each associate with a light chain according to (a). In one embodiment, the second $V_H$ domain binds the second epitope with a dissociation constant that is lower than $10^{-6}$ M, lower than $10^{-7}$M, lower than $10^{-8}$ M, lower than $10^{-9}$ M, lower than $10^{-10}$ M, lower than $10^{-11}$ M, or lower than $10^{-12}$ M.

In one embodiment, the epitope-binding protein comprises a first immunoglobulin heavy chain and a second immunoglobulin heavy chain, each associated with a universal light chain (e.g., a light chain derived from a rearranged human light chain variable sequence selected from a human Vκ1-39Jκ5 or a human Vκ3-20Jκ1), wherein the first immunoglobulin heavy chain binds a first epitope with a dissociation constant in the nanomolar (e.g., 1 nM to 100 nM) to picomolar range (e.g., 1 pM to 100 pM), the second immunoglobulin heavy chain binds a second epitope with a dissociation constant in the nanomolar to picomolar range (e.g., 1 pM to 100 nM), the first epitope and the second epitope are not identical, the first immunoglobulin heavy chain does not bind the second epitope or binds the second epitope with a dissociation constant weaker than the micromolar range (e.g., the millimolar range), the second immunoglobulin heavy chain does not bind the first epitope or binds the first epitope with a dissociation constant weaker than the micromolar range (e.g., the millimolar range), and one or more of the variable domains (i.e., one or more of the light chain variable domain, the heavy chain variable domain of the first immunoglobulin heavy chain, and the heavy chain variable domain) of the second immunoglobulin heavy chain is somatically mutated. In one embodiment, binding of the epitope-binding protein to the first epitope does not block binding of the epitope-binding protein to the second epitope.

In one embodiment, the first immunoglobulin heavy chain comprises a wild type protein A binding determinant, and the second heavy chain lacks a wild type protein A binding determinant. In one embodiment, the first immunoglobulin heavy chain binds protein A under isolation conditions, and the second immunoglobulin heavy chain does not bind protein A or binds protein A at least 10-fold, a hundred-fold, or a thousand-fold weaker than the first immunoglobulin heavy chain binds protein A under isolation conditions. In a specific embodiment, the first and the second heavy chains are IgG1 isotypes, wherein the second heavy chain comprises a modification selected from 95R (EU 435R), 96F (EU 436F), and a combination thereof, and wherein the first heavy chain lacks such modification.

In aspect, a mouse, embryo, or cell as described herein comprises a κ light chain locus that retains endogenous regulatory or control elements, e.g., a mouse κ intronic enhancer, a mouse κ 3' enhancer, or both an intronic enhancer and a 3' enhancer, wherein the regulatory or control elements facilitate somatic mutation and affinity maturation of an expressed sequence of the κ light chain locus.

In one aspect, a mouse cell is provided that is isolated from a mouse as described herein. In one embodiment, the cell is an ES cell. In one embodiment, the cell is a lymphocyte. In one embodiment, the lymphocyte is a B cell. In one embodiment, the B cell expresses a chimeric heavy chain comprising a variable domain derived from a human V gene segment; and a light chain derived from (a) a rearranged human Vκ1-39/J sequence, (b) a rearranged human Vκ3-20/J sequence, or (c) a combination thereof; wherein the heavy chain variable domain is fused to a mouse constant region and the light chain variable domain is fused to a mouse or a human constant region. In one embodiment, the mouse cell comprises at least one gene that encodes a mouse ADAM6 or ortholog or homolog or functional fragment thereof. In one embodiment, the cell is a B cell and the B cell comprises a sequence encoding a rearranged human heavy chain immunoglobulin variable domain and a sequence encoding a universal light chain variable domain, wherein the B cell comprises on a chromosome a nucleic acid sequence encoding an ADAM6 protein or ortholog or homolog or fragment thereof that is functional in a male mouse; in one embodiment, the mouse B cell comprises two alleles of the nucleic acid sequence.

In one aspect, a mouse cell is provided, comprising a first chromosome that comprises a humanized immunoglobulin heavy chain locus comprising unrearranged human V, D, and J segments; a second chromosome that comprises a humanized immunoglobulin light chain locus that encodes or is capable of rearranging to encode a light chain, wherein the light chain locus comprises no more than one V segment (or no more than two V segments) and no more than one J segment (or no more than two J segments) operably linked to a light chain constant region gene, or no more than one or no more than two rearranged light chain V/J sequences operably linked to a light chain constant gene; and a third chromosome that comprises nucleic acid sequence encoding a mouse ADAM6 or ortholog or homolog or fragment thereof that is functional in a male mouse. In one embodiment, the first and third chromosomes are the same. In one embodiment, the second and third chromosomes are the same. In one embodiment, the first, the second, and the third chromosomes are each different. In one embodiment, the nucleic acid sequence encoding the mouse ADAM6 or ortholog or homolog or functional fragment thereof is present in two copies. In one embodiment, the cell is a somatic cell. In a specific embodiment, the somatic cell is a B cell. In one embodiment, the cell is a germ cell.

In one aspect, a hybridoma is provided, wherein the hybridoma is made with a B cell of a mouse as described herein. In a specific embodiment, the B cell is from a mouse as described herein that has been immunized with an antigen comprising an epitope of interest, and the B cell expresses a binding protein that binds the epitope of interest, the binding protein has a somatically mutated human heavy chain variable domain and a mouse heavy chain constant region, and has a human light chain variable domain derived from a rearranged human Vκ1-39Jκ5 or a rearranged human Vκ3-20Jκ1 and a mouse $C_L$.

In one aspect, a cell is provided that comprises a fully human heavy chain gene comprising a nucleic acid sequence encoding a first heavy chain variable domain of a mouse as described herein, and a fully human light chain gene comprising a nucleic acid sequence encoding a universal light chain sequence as described herein. In one embodiment, the cell further comprises a nucleic acid sequence encoding a second heavy chain variable domain of a mouse as described herein, wherein the first and the second heavy chain variable domains are different. In one embodiment, the cell is selected from CHO, COS, 293, HeLa, and a retinal cell expressing a viral nucleic acid sequence (e.g., a PERC.6™ cell).

In one aspect, a mouse embryo is provided, wherein the embryo comprises a donor ES cell that is derived from a mouse as described herein.

In one aspect, use of a mouse embryo that comprises a genetic modification as described herein is provided, wherein the use comprises making a genetically modified mouse as described herein.

In one aspect, a human heavy chain variable domain and a human light chain variable domain amino acid sequence of an antibody made in a mouse as described herein are provided.

In one aspect, a human heavy chain variable domain nucleotide sequence and a human light chain variable domain nucleotide sequence of an antibody made in a mouse as described herein is provided.

In one aspect, an antibody or antigen-binding protein or antigen-binding fragment thereof (e.g., Fab, F(ab)$_2$, scFv) made in a mouse as described herein is provided.

In one aspect, a mouse made using a targeting vector, nucleotide construct, or cell as described herein is provided.

In one aspect, a progeny of a mating of a first mouse as described herein with a second mouse that is a wild-type mouse or genetically modified is provided.

In one aspect, use of a mouse as described herein to make a fully human antibody, or a fully human antigen-binding protein comprising an immunoglobulin variable domain or functional fragment thereof, is provided.

In one aspect, use of a mouse or tissue or cell as described herein to make a fully human bispecific antibody is provided.

In one aspect, use of a nucleic acid sequence made by a mouse as described herein is provided, wherein the use comprises expressing the nucleic acid sequence in the manufacture of a human therapeutic.

In one aspect, use of a mouse as described herein to make an immortalized cell line is provided.

In one aspect, use of a mouse as described herein to make a hybridoma or quadroma is provided.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multispecific antibody (e.g., a bispecific antibody), an scFv, a bis-scFV, a diabody, a triabody, a tetrabody, a V-NAR, a VHH, a VL, an F(ab), an F(ab)$_2$, a DVD (i.e., dual variable domain antigen-binding protein), an SVD (i.e., single variable domain antigen-binding protein), or a bispecific T-cell engager (BiTE).

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE FIGURES

FIG. 3B shows a representative calculation of observed probe copy number in parental and modified ES cells for the first insertion of human immunoglobulin heavy chain gene segments. Observed probe copy number for probes A through F were calculated as 2/2ΔΔCt. ΔΔCt is calculated as ave[ΔCt(sample)−medΔCt(control)] where ΔCt is the difference in Ct between test and reference probes (between 4 and 6 reference probes depending on the assay). The term medΔCt(control) is the median ΔCt of multiple (>60) nontargeted DNA samples from parental ES cells. Each modified ES cell clone was assayed in sextuplicate. To calculate copy numbers of IgH probes G and H in parental ES cells, these probes were assumed to have copy number of 1 in modified ES cells and a maximum Ct of 35 was used even though no amplification was observed.

FIG. 3C shows a representative calculation of copy numbers for four mice of each genotype were calculated in a similar manner using only probes D and H. Wild-type mice: WT Mice; Mice heterozygous for the first insertion of human immunoglobulin gene segments: HET Mice; Mice homozygous for the first insertion of human immunoglobulin gene segments: Homo Mice.

FIG. 7A shows representative heavy chain CDR3 sequences of randomly selected VELOCIMMUNE® antibodies around the $V_H$-$D_H$-$J_H$ (CDR3) junction, demonstrating junctional diversity and nucleotide additions. Heavy chain CDR3 sequences are grouped according to DH gene segment usage, the germline of which is provided above each group in bold. $V_H$ gene segments for each heavy chain CDR3 sequence are noted within parenthesis at the 5' end of each sequence (e.g. 3-72 is human $V_H$3-72). $J_H$ gene segments for each heavy chain CDR3 are noted within parenthesis at the 3' end of each sequence (e.g. 3 is human $J_H$3). SEQ ID NOs for each sequence shown are as follows proceeding from top to bottom: SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39.

FIG. 7B shows representative light chain CDR3 sequences of randomly selected VELOCIMMUNE® antibodies around the Vκ-Jκ (CDR3) junction, demonstrating junctional diversity and nucleotide additions. Vκ gene segments for each light chain CDR3 sequence are noted within parenthesis at the 5' end of each sequence (e.g. 1-6 is human Vκ1-6). Jκ gene segments for each light chain CDR3 are noted within parenthesis at the 3' end of each sequence (e.g. 1 is human Jκ1). SEQ ID NOs for each sequence shown are as follows proceeding from top to bottom: SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58.

FIG. 9B shows levels of serum immunoglobulin for IgA isotype in wild type (open bars) or VELOCIMMUNE® mice (closed bars).

DETAILED DESCRIPTION

Figure 1A:
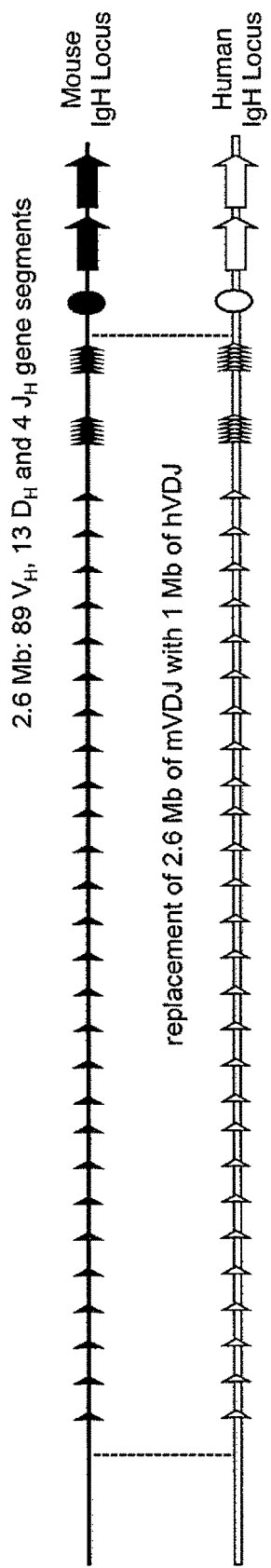
FIG. 1A shows a general illustration, not to scale, for direct genomic replacement of about three megabases (Mb) of the mouse immunoglobulin heavy chain variable gene locus (closed symbols) with about one megabase (Mb) of the human immunoglobulin heavy chain variable gene locus (open symbols).

The term "antibody", as used herein, includes immunoglobulin molecules comprising four polypeptide chains, two heavy (H) chains and two light (L) chains inter-connected by disulfide bonds. Each heavy chain comprises a heavy chain variable ($V_H$) region and a heavy chain constant region ($C_H$). The heavy chain constant region comprises three domains, $C_H1$, $C_H2$ and $C_H3$. Each light chain comprises a light chain variable ($V_L$) region and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding or one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or a functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1 \times 10^{-6}$ M, $1 \times 10^{-7}$ M, $1 \times 10^{-9}$ M, $1 \times 10^{-9}$ M, $1 \times 10^{-10}$ M, $1 \times 10^{-11}$ M, or about $1 \times 10^{-12}$ M). Therapeutic epitope-binding proteins (e.g., therapeutic antibodies) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" includes reference to an immunoglobulin nucleic acid sequence in a non-somatically mutated cell, e.g., a non-somatically mutated B cell or pre-B cell or hematopoietic cell.

The phrase "heavy chain," or "immunoglobulin heavy chain" includes an immunoglobulin heavy chain constant region sequence from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR.

The term "identity" when used in connection with sequence, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one $C_H1$ domain of a human or a mouse. In the case of a $C_H1$ domain, the length of sequence should contain sequence of sufficient length to fold into a $C_H1$ domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human κ and λ light chains and a VpreB, as well as surrogate light chains. Light chain variable ($V_L$) domains typically include three light chain CDRs and four framework (FR) regions, unless otherwise specified. Generally, a full-length light chain includes, from amino terminus to carboxyl terminus, a $V_L$ domain that includes FR1-CDR1-FR2-CDR2-FR3-CDR3-FR4, and a light chain constant domain. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

Universal light chains, or common light chains, refer to light chains made in mice as described herein, wherein the mice are highly restricted in the selection of gene segments available for making a light chain variable domain. As a result, such mice make a light chain derived from, in one embodiment, no more than one or two unrearranged light chain V segments and no more than one or two unrearranged light chain J segments (e.g., one V and one J, two V's and one J, one V and two J's, two V's and two J's). In one embodiment, no more than one or two rearranged light chain V/J sequences, e.g., a rearranged human Vκ1-39Jκ5 sequence or a rearranged human Vκ3-20Jκ1 sequence. In various embodiments universal light chains include somatically mutated (e.g., affinity matured) versions.

The phrase "somatically mutated" includes reference to a nucleic acid sequence from a B cell that has undergone class-switching, wherein the nucleic acid sequence of an immunoglobulin variable region (e.g., a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

Mice with Humanized Immunoglobulin Loci

The mouse as a genetic model has been greatly enhanced by transgenic and knockout technologies, which have allowed for the study of the effects of the directed overexpression or deletion of specific genes. Despite all of its advantages, the mouse still presents genetic obstacles that render it an imperfect model for human diseases and an imperfect platform to test human therapeutics or make them. First, although about 99% of human genes have a mouse homolog (Waterston, R. H., et. al. (2002). Initial sequencing and comparative analysis of the mouse genome. Nature 420, 520-562.), potential therapeutics often fail to cross-react, or cross-react inadequately, with mouse orthologs of the intended human targets. To obviate this problem, selected target genes can be "humanized," that is, the mouse gene can be eliminated and replaced by the corresponding human orthologous gene sequence (e.g., U.S. Pat. No. 6,586,251, U.S. Pat. No. 6,596,541 and U.S. Pat. No. 7,105,348, incorporated herein by reference). Initially, efforts to humanize mouse genes by a "knockout-plus-transgenic humanization" strategy entailed crossing a mouse carrying a deletion (i.e., knockout) of the endogenous gene with a mouse carrying a randomly integrated human transgene (see, e.g., Bril, W. S., et al. (2006). Tolerance to factor VIII in a transgenic mouse expressing human factor VIII cDNA carrying an Arg(593) to Cys substitution. Thromb Haemost 95, 341-347; Homanics, G. E., et al. (2006). Production and characterization of murine models of classic and intermediate maple syrup urine disease. BMC Med Genet 7, 33; Jamsai, D., et al. (2006). A humanized BAC transgenic/knockout mouse model for HbE/beta-thalassemia. Genomics 88(3):309-15; Pan, Q., et al. (2006). Different role for mouse and human CD3delta/epsilon heterodimer in preT cell receptor (preTCR) function: human CD3delta/epsilon heterodimer restores the defective preTCR function in CD3gamma- and CD3gammadelta-deficient mice. Mol Immunol 43, 1741-1750). But those efforts were hampered by size limitations; conventional knockout technologies were not sufficient to directly replace large mouse genes with their large human genomic counterparts. A straightforward approach of direct homologous replacement, in which an endogenous mouse gene is directly replaced by the human counterpart gene at the same precise genetic location of the mouse gene (i.e., at the endogenous mouse locus), is rarely attempted because of technical difficulties. Until now, efforts at direct replacement involved elaborate and burdensome procedures, thus limiting the length of genetic material that could be handled and the precision with which it could be manipulated.

Exogenously introduced human immunoglobulin transgenes rearrange in precursor B-cells in mice (Alt, F. W., Blackwell, T. K., and Yancopoulos, G. D. (1985). Immunoglobulin genes in transgenic mice. Trends Genet 1, 231-236). This finding was exploited by engineering mice using the knockout-plus-transgenic approach to express human antibodies (Green, L. L. et al. (1994). Antigen-specific human monoclonal antibodies from mice engineered with human Ig heavy and light chain YACs. Nat Genet 7, 13-21; Lonberg, N. (2005). Human antibodies from transgenic animals. Nat Biotechnol 23, 1117-1125; Lonberg, N., et al. (1994). Antigen-specific human antibodies from mice comprising four distinct genetic modifications. Nature 368, 856-859; Jakobovits, A., et al. (2007). From XenoMouse technology to panitumumab, the first fully human antibody product from transgenic mice. Nat Biotechnol 25, 1134-1143). The endogenous mouse immunoglobulin heavy chain and κ light chain loci were inactivated in these mice by targeted deletion of small but critical portions of each endogenous locus, followed by introducing human immunoglobulin gene loci as randomly integrated large transgenes, as described above, or minichromosomes (Tomizuka, K., et al. (2000). Double trans-chromosomic mice: maintenance of two individual human chromosome fragments containing Ig heavy and kappa loci and expression of fully human antibodies. Proc Natl Acad Sci USA 97, 722-727). Such mice represented an important advance in genetic engineering; fully human monoclonal antibodies isolated from them yielded promising therapeutic potential for treating a variety of human diseases (Gibson, T. B., et al., (2006). Randomized phase III trial results of panitumumab, a fully human anti-epidermal growth factor receptor monoclonal antibody, in metastatic colorectal cancer. Clin Colorectal Cancer 6, 29-31; Jakobovits et al., 2007; Kim, Y. H., et al. (2007). Clinical efficacy of zanolimumab (HuMax-CD4): two Phase II studies in refractory cutaneous T-cell lymphoma. Blood 109(11):4655-62; Lonberg, 2005; Maker, A. V., et al., (2005). Tumor regression and autoimmunity in patients treated with cytotoxic T lymphocyte-associated antigen 4 blockade and interleukin 2: a phase I/II study. Ann Surg Oncol 12, 1005-1016; McClung, MR., et al. (2006). Denosumab in postmenopausal women with low bone mineral density. N Engl J Med 354, 821-831). But, as discussed above, these mice exhibit compromised B cell development and immune deficiencies when compared to wild type mice. Such problems potentially limit the ability of the mice to support a vigorous humoral response and, consequently, generate fully human antibodies against some antigens. The deficiencies may be due to: (1) inefficient functionality due to the random introduction of the human immunoglobulin transgenes and resulting incorrect expression due to a lack of upstream and downstream control elements (Garrett, F. E., et al. (2005). Chromatin architecture near a potential 3' end of the igh locus involves modular regulation of histone modifications during B-Cell development and in vivo occupancy at CTCF sites. Mol Cell Biol 25, 1511-1525; Manis, J. P., et al. (2003). Elucidation of a downstream boundary of the 3' IgH regulatory region. Mol Immunol 39, 753-760; Pawlitzky, I., et al. (2006). Identification of a candidate regulatory element within the 5' flanking region of the mouse Igh locus defined by pro-B cell-specific hypersensitivity associated with binding of PU.1, Pax5, and E2A. J Immunol 176, 6839-6851); (2) inefficient interspecies interactions between human constant domains and mouse components of the B-cell receptor signaling complex on the cell surface, which may impair signaling processes required for normal maturation, proliferation, and survival of B cells (Hombach, J., et al., (1990). Molecular components of the B-cell antigen receptor complex of the IgM class. Nature 343, 760-762); and (3) inefficient interspecies interactions between soluble human immunoglobulins and mouse Fc receptors that might reduce affinity selection (Rao, S. P., et al. (2002). Differential expression of the inhibitory IgG Fc receptor FcgammaRIIB on germinal center cells: implications for selection of high-affinity B cells. J Immunol 169, 1859-1868) and immunoglobulin serum concentrations (Brambell, F. W., et al. (1964). A Theoretical Model of Gamma-Globulin Catabolism. Nature 203, 1352-1354; Junghans, R. P., and Anderson, C. L. (1996). The protection receptor for IgG catabolism is the beta2-microglobulin-containing neonatal intestinal transport receptor. Proc Natl Acad Sci USA 93, 5512-5516; Rao et al., 2002; Hjelm, F., et al. (2006). Antibody-mediated regulation of the immune response. Scand J Immunol 64, 177-184; Nimmerjahn, F., and Ravetch, J. V. (2007). Fc-receptors as regulators of immunity. Adv Immunol 96, 179-204). These deficiencies can be corrected by in situ humanization of only the variable regions of the mouse immunoglobulin loci within their natural locations at the endogenous heavy and light chain loci. This would effectively result in mice that make reverse chimeric (i.e., human V: mouse C) antibodies that would be capable of normal interactions and selection with the mouse environment based on retaining mouse constant regions. Further, such reverse chimeric antibodies are readily reformatted into fully human antibodies for therapeutic purposes.

A method for a large in situ genetic replacement of the mouse germline immunoglobulin variable genes with human germline immunoglobulin variable genes while maintaining the ability of the mice to generate offspring is described. Specifically, the precise replacement of six megabases of both the mouse heavy chain and κ light chain immunoglobulin variable gene loci with their human counterparts while leaving the mouse constant regions intact is described. As a result, mice have been created that have a precise replacement of their entire germline immunoglobulin variable repertoire with equivalent human germline immunoglobulin variable sequences, while maintaining mouse constant regions. The human variable regions are linked to mouse constant regions to form chimeric human-mouse immunoglobulin loci that rearrange and express at physiologically appropriate levels. The antibodies expressed are "reverse chimeras," i.e., they comprise human variable region sequences and mouse constant region sequences. These mice having humanized immunoglobulin variable regions that express antibodies having human variable regions and mouse constant regions are called VELCOIMMUNE® humanized mice.

VELOCIMMUNE® humanized mice exhibit a fully functional humoral immune system that is essentially indistinguishable from that of wild-type mice. They display normal cell populations at all stages of B cell development. They exhibit normal lymphoid organ morphology. Antibody sequences of VELOCIMMUNE® humanized mice exhibit normal variable segment rearrangement and normal somatic hypermutation. Antibody populations in these mice reflect isotype distributions that result from normal class switching (e.g., normal isotype cis-switching). Immunizing VELOCIMMUNE® humanized mice results in robust humoral responses that generate a large diversity of antibodies having human immunoglobulin variable domains suitable as therapeutic candidates. This platform provides a plentiful source of affinity-matured human immunoglobulin variable region sequences for making pharmaceutically acceptable antibodies and other antigen-binding proteins.

It is the precise replacement of mouse immunoglobulin variable sequences with human immunoglobulin variable sequences that allows for making VELOCIMMUNE® humanized mice. Yet even a precise replacement of endogenous mouse immunoglobulin sequences at heavy and light chain loci with equivalent human immunoglobulin sequences, by sequential recombineering of very large spans of human immunoglobulin sequences, may present certain challenges due to divergent evolution of the immunoglobulin loci between mouse and man. For example, intergenic sequences interspersed within the immunoglobulin loci are not identical between mice and humans and, in some circumstances, may not be functionally equivalent. Differences between mice and humans in their immunoglobulin loci can still result in abnormalities in humanized mice, particularly when humanizing or manipulating certain portions of endogenous mouse immunoglobulin heavy chain loci. Some modifications at mouse immunoglobulin heavy chain loci are deleterious. Deleterious modifications can include, for example, loss of the ability of the modified mice to mate and produce offspring.

A precise, large-scale, in situ replacement of six megabases of the variable regions of the mouse heavy and light chain immunoglobulin loci ($V_H$-$D_H$-$J_H$ and Vκ-Jκ) with the corresponding 1.4 megabases human genomic sequences was performed, while leaving the flanking mouse sequences intact and functional within the hybrid loci, including all mouse constant chain genes and locus transcriptional control regions (FIG. 1). Specifically, the human $V_H$, $D_H$, $J_H$, Vκ and Jκ gene sequences were introduced through stepwise insertion of 13 chimeric BAC targeting vectors bearing overlapping fragments of the human germline variable loci into mouse ES cells using VELOCIGENE® genetic engineering technology (see, e.g., U.S. Pat. No. 6,586,251 and Valenzuela, D. M., et al., (2003). High-throughput engineering of the mouse genome coupled with high-resolution expression analysis. Nat Biotechnol 21, 652-659).

Humanization of the mouse immunoglobulin genes represents the largest genetic modification to the mouse genome to date. While previous efforts with randomly integrated human immunoglobulin transgenes have met with some success (discussed above), direct replacement of the mouse immunoglobulin genes with their human counterparts dramatically increases the efficiency with which fully-human antibodies can be efficiently generated in otherwise normal mice. Further, such mice exhibit a dramatically increased diversity of fully-human antibodies that can be obtained after immunization with virtually any antigen, as compared with mice bearing disabled endogenous loci and fully human antibody transgenes. Multiple versions of replaced, humanized loci exhibit completely normal levels of mature and immature B cells, in contrast to mice with randomly integrated human transgenes, which exhibit significantly reduced B cell populations at various stages of differentiation. While efforts to increase the number of human gene segments in human transgenic mice have reduced such defects, the expanded immunoglobulin repertoires have not altogether corrected reductions in B cell populations as compared to wild-type mice.

Notwithstanding the near wild-type humoral immune function observed in mice with replaced immunoglobulin loci, there are other challenges encountered when employing a direct replacement of the immunoglobulin that is not encountered in some approaches that employ randomly integrated transgenes. Differences in the genetic composition of the immunoglobulin loci between mice and humans has lead to the discovery of sequences beneficial for the propagation of mice with replaced immunoglobulin gene segments. Specifically, mouse ADAM genes located within the endogenous immunoglobulin locus are optimally present in mice with replaced immunoglobulin loci, due to their role in fertility.

Genomic Location and Function of Mouse ADAM6

Male mice that lack the ability to express any functional ADAM6 protein exhibit a severe defect in the ability of the mice to mate and to generate offspring. The mice lack the ability to express a functional ADAM6 protein by virtue of a replacement of all or substantially all mouse immunoglobulin variable region gene segments with human variable region gene segments. The loss of ADAM6 function results because the ADAM6 locus is located within a region of the endogenous mouse immunoglobulin heavy chain variable region gene locus, proximal to the 3' end of the $V_H$ gene segment locus that is upstream of the $D_H$ gene segments. In order to breed mice that are homozygous for a replacement of all or substantially all endogenous mouse heavy chain variable gene segments with human heavy chain variable gene segments, it is generally a cumbersome approach to set up males and females that are each homozygous for the replacement and await a productive mating. Successful litters are relatively rare, and average litter size is very low. Instead, males heterozygous for the replacement have been employed to mate with females homozygous for the replacement to generate progeny that are heterozygous for the replacement, then breed a homozygous mouse therefrom. The inventors have determined that the likely cause of the loss in fertility in the mate mice is the absence in homozygous male mice of a functional ADAM6 protein.

The ADAM6 protein is a member of the ADAM family of proteins, where ADAM is an acronym for A Disintegrin And Metalloprotease. The ADAM family of proteins is large and diverse, with diverse functions. Some members of the ADAM family are implicated in spermatogenesis and fertilization. For example, ADAM2 encodes a subunit of the protein fertilin, which is implicated in sperm-egg interactions. ADAM3, or cyritestin, appears necessary for sperm binding to the zona pellucida. The absence of either ADAM2 or ADAM3 results in infertility. It has been postulated that ADAM2, ADAM3, and ADAM6 form a complex on the surface of mouse sperm cells.

Figure 11A:
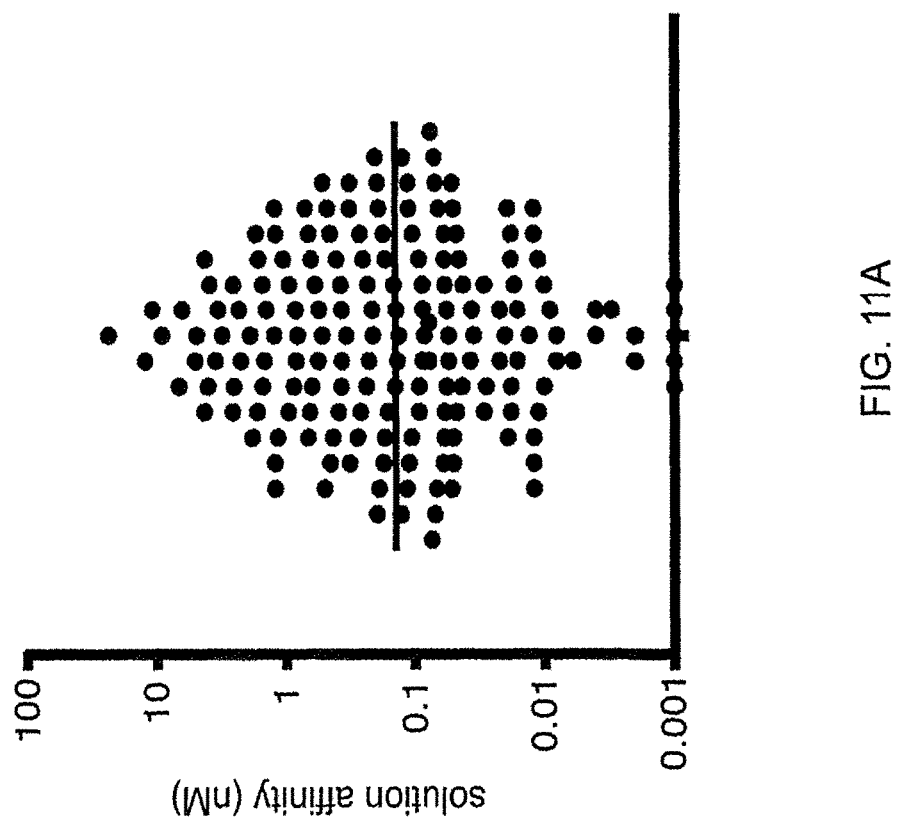
FIG. 11A shows the affinity distribution of anti-interleukin-6 receptor monoclonal antibodies generated in VELOCIMMUNE® mice.
Figure 11B:
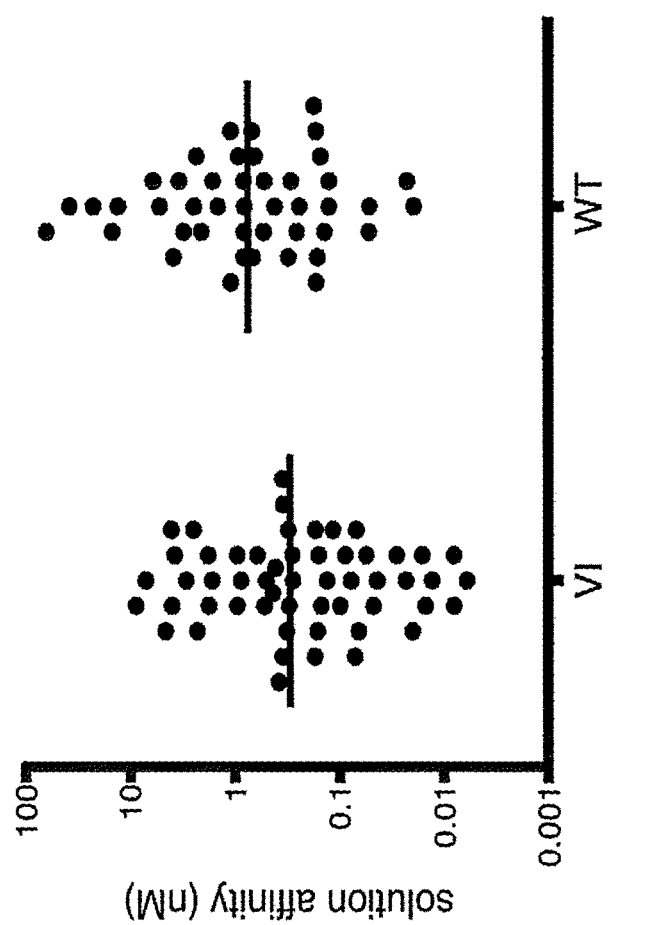
FIG. 11B shows the antigen-specific blocking of anti-interleukin-6 receptor monoclonal antibodies generated in VELOCIMMUNE® (VI) and wild type (WT) mice.
Figure 12:
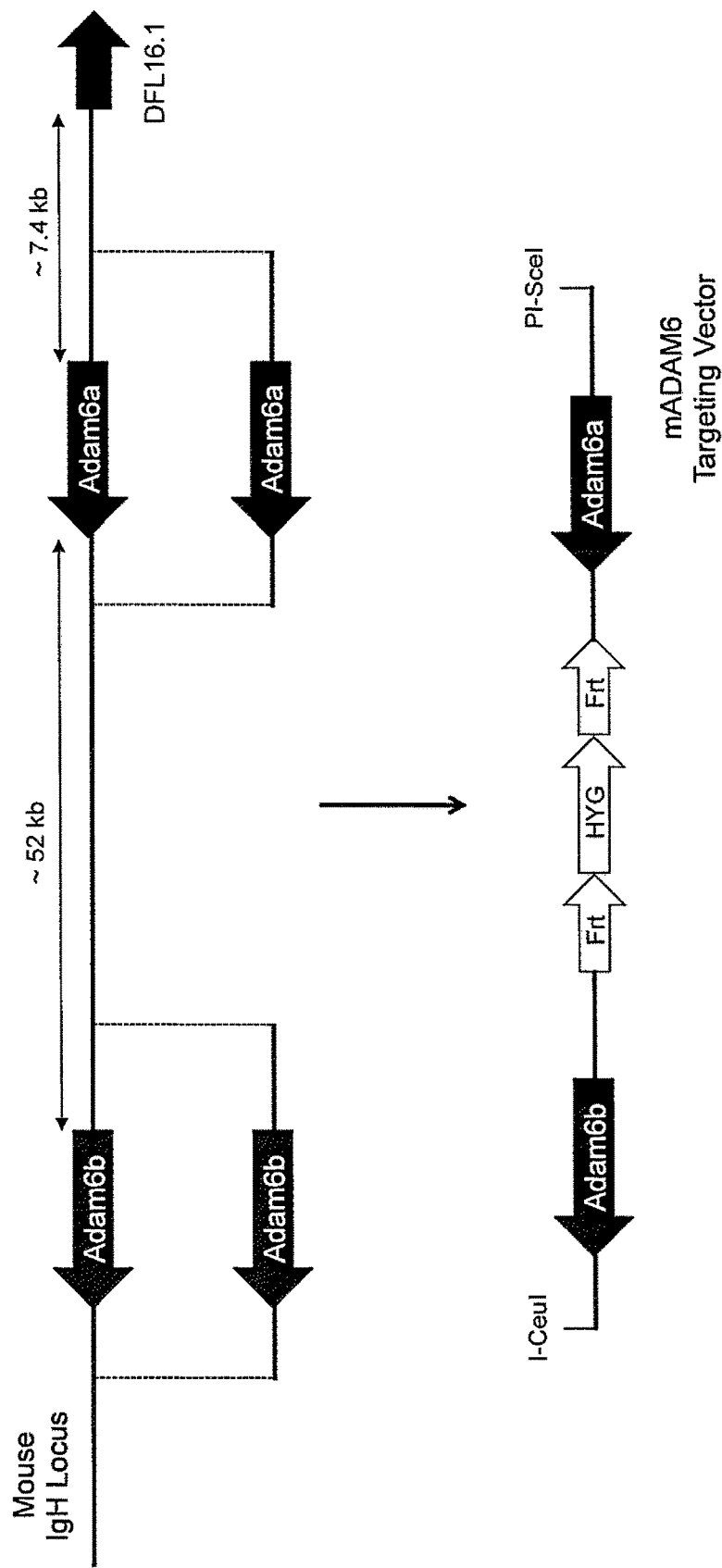
FIG. 12 shows a schematic illustration, not to scale, of mouse ADAM6a and ADAM6b genes in the mouse immunoglobulin heavy chain locus. A targeting vector (mADAM6 Targeting Vector) used for the insertion of mouse ADAM6a and ADAM6b into a humanized endogenous heavy chain locus is shown with a selection cassette (HYG: hygromycin) flanked by site-specific recombination sites (Frt) including engineered restriction sites on the 5' and 3' ends.

The human ADAM6 gene, normally found between human $V_H$ gene segments $V_H$1-2 and $V_H$6-1, appears to be a pseudogene (FIG. 12). In mice, there are two ADAM6 genes—ADAM6a and ADAM6b—that are found in an intergenic region between mouse $V_H$ and $D_H$ gene segments, and in the mouse the a and b genes are oriented in a transcriptional orientation opposite to that of the transcription orientation of the surrounding immunoglobulin gene segments (FIG. 11). In mice, a functional ADAM6 locus is apparently required for normal fertilization. A functional ADAM6 locus or sequence, then, refers to an ADAM6 locus or sequence that can complement, or rescue, the drastically reduced fertilization exhibited in male mice with missing or damaged endogenous ADAM6 loci.

The position of the intergenic sequence in mice that encodes ADAM6a and ADAM6b renders the intergenic sequence susceptible to modification when modifying an endogenous mouse heavy chain. When $V_H$ gene segments are deleted or replaced, or when $D_H$ gene segments are deleted or replaced, there is a high probability that a resulting mouse will exhibit a severe deficit in fertility. In order to compensate for the deficit, the mouse is modified to include a nucleotide sequence that encodes a protein that will complement the loss in ADAM6 activity due to a modification of the endogenous mouse ADAM6 locus. In various embodiments, the complementing nucleotide sequence is one that encodes a mouse ADAM6a, a mouse ADAM6b, or a homolog or ortholog or functional fragment thereof that rescues the fertility deficit.

The nucleotide sequence that rescues fertility can be placed at any suitable position. It can be placed in the intergenic region, or in any suitable position in the genome (i.e., ectopically). In one embodiment, the nucleotide sequence can be introduced into a transgene that randomly integrates into the mouse genome. In one embodiment, the sequence can be maintained episomally, that is, on a separate nucleic acid rather than on a mouse chromosome. Suitable positions include positions that are transcriptionally permissive or active, e.g., a ROSA26 locus.

The term "ectopic" is intended to include a displacement, or a placement at a position that is not normally encountered in nature (e.g., placement of a nucleic acid sequence at a position that is not the same position as the nucleic acid sequence is found in a wild-type mouse). The term in various embodiments is used in the sense of its object being out of its normal, or proper, position. For example, the phrase "an ectopic nucleotide sequence encoding . . . " refers to a nucleotide sequence that appears at a position at which it is not normally encountered in the mouse. For example, in the case of an ectopic nucleotide sequence encoding a mouse ADAM6 protein (or an ortholog or homolog or fragment thereof that provides the same or similar fertility benefit on male mice), the sequence can be placed at a different position in the mouse's genome than is normally found in a wild-type mouse. A functional homolog or ortholog of mouse ADAM6 is a sequence that confers a rescue of fertility loss (e.g., loss of the ability of a male mouse to generate offspring by mating) that is observed in an $ADAM6^{-/-}$ mouse. Functional homologs or orthologs include proteins that have at least about 89% identity or more, e.g., up to 99% identity, to the amino acid sequence of ADAM6a and/or to the amino acid sequence of ADAM6b, and that can complement, or rescue ability to successfully mate, of a mouse that has a genotype that includes a deletion or knockout of ADAM6a and/or ADAM6b.

The ectopic position can be anywhere (e.g., as with random insertion of a transgene containing a mouse ADAM6 sequence), or can be, e.g., at a position that approximates (but is not precisely the same as) its location in a wild-type mouse (e.g., in a modified endogenous mouse immunoglobulin locus, but either upstream or downstream of its natural position, e.g., within a modified immunoglobulin locus but between different gene segments, or at a different position in a mouse V-D intergenic sequence). One example of an ectopic placement is placement within a humanized immunoglobulin heavy chain locus. For example, a mouse comprising a replacement of one or more endogenous $V_H$ gene segments with human $V_H$ gene segments, wherein the replacement removes an endogenous ADAM6 sequence, can be engineered to have a mouse ADAM6 sequence located within sequence that contains the human $V_H$ gene segments. The resulting modification would generate an (ectopic) mouse ADAM6 sequence within a human gene sequence, and the (ectopic) placement of the mouse ADAM6 sequence within the human gene sequence can approximate the position of the human ADAM6 pseudogene (i.e., between two V segments) or can approximate the position of the mouse ADAM6 sequence (i.e., within the V-D intergenic region).

In various aspects, mice that comprise deletions or replacements of the endogenous heavy chain variable region locus or portions thereof can be made that contain an ectopic nucleotide sequence that encodes a protein that confers similar fertility benefits to mouse ADAM6 (e.g., an ortholog or a homolog or a fragment thereof that is functional in a male mouse). The ectopic nucleotide sequence can include a nucleotide sequence that encodes a protein that is an ADAM6 homolog or ortholog (or fragment thereof) of a different mouse strain or a different species, e.g., a different rodent species, and that confers a benefit in fertility, e.g., increased number of litters over a specified time period, and/or increased number of pups per litter, and/or the ability of a sperm cell of a male mouse to traverse through a mouse oviduct to fertilize a mouse egg.

In one embodiment, the ADAM6 is a homolog or ortholog that is at least 89% to 99% identical to a mouse ADAM6 protein (e.g., at least 89% to 99% identical to mouse ADAM6a or mouse ADAM6b). In one embodiment, the ectopic nucleotide sequence encodes one or more proteins independently selected from a protein at least 89% identical to mouse ADAM6a, a protein at least 89% identical to mouse ADAM6b, and a combination thereof. In one embodiment, the homolog or ortholog is a rat, hamster, mouse, or guine pig protein that is or is modified to be about 89% or more identical to mouse ADAM6a and/or mouse ADAM6b. In one embodiment, the homolog or ortholog is 90%, 91%, 92%, 93%, 94%, 95%, 96%, 97%, 98%, or 99% identical to a mouse ADAM6a and/or mouse ADAM6b.

Ectopic ADAM6 in Humanized Heavy Chain Mice

Mice that make human antibodies have been available for some time now. Although they represent an important advance in the development of human therapeutic antibodies, these mice display a number of significant abnormalities that limit their usefulness. For example, they display compromised B cell development. The compromised development may be due to a variety of differences between the transgenic mice and wild-type mice.

Human antibodies might not optimally interact with mouse pre B cell or B cell receptors on the surface of mouse cells that signal for maturation, proliferation, or survival during clonal selection. Fully human antibodies might not optimally interact with a mouse Fc receptor system; mice express Fc receptors that do not display a one-to-one correspondence with human Fc receptors. Finally, various mice that make fully human antibodies do not include all genuine mouse sequences, e.g., downstream enhancer elements and other locus control elements, which may be required for wild-type B cell development.

Mice that make fully human antibodies generally comprise endogenous immunoglobulin loci that are disabled in some way, and human transgenes that comprise variable and constant immunoglobulin gene segments are introduced into a random location in the mouse genome. As long as the endogenous locus is sufficiently disabled so as not to rearrange gene segments to form a functional immunoglobulin gene, the goal of making fully human antibodies in such a mouse can be achieved—albeit with compromised B cell development.

Although compelled to make fully human antibodies from the human transgene locus, generating human antibodies in a mouse is apparently an unfavored process. In some mice, the process is so unfavored as to result in formation of chimeric human variable/mouse constant heavy chains (but not light chains) through the mechanism of trans-switching. By this mechanism, transcripts that encode fully human antibodies undergo isotype switching in trans from the human isotype to a mouse isotype. The process is in trans, because the fully human transgene is located apart from the endogenous locus that retains an undamaged copy of a mouse heavy chain constant region gene. Although in such mice trans-switching is readily apparent the phenomenon is still insufficient to rescue B cell development, which remains frankly impaired. In any event, trans-switched antibodies made in such mice retain fully human light chains, since the phenomenon of trans-switching apparently does not occur with respect to light chains; trans-switching presumably relies on switch sequences in endogenous loci used (albeit differently) in normal isotype switching in cis. Thus, even when mice engineered to make fully human antibodies select a trans-switching mechanism to make antibodies with mouse constant regions, the strategy is still insufficient to rescue normal B cell development.

A primary concern in making antibody-based human therapeutics is making a sufficiently large diversity of human immunoglobulin variable region sequences to identify useful variable domains that specifically recognize particular epitopes and bind them with a desirable affinity, usually—but not always—with high affinity. Prior to the development of VELOCIMMUNE® humanized mice, there was no indication that mice expressing human variable regions with mouse constant regions would exhibit any significant differences from mice that made human antibodies from a transgene. That supposition, however, was incorrect.

VELOCIMMUNE® humanized mice, which contain a precise replacement of mouse immunoglobulin variable regions with human immunoglobulin variable regions at the endogenous mouse loci, display a surprising and remarkable similarity to wild-type mice with respect to B cell development. In a surprising and stunning development, VELOCIMMUNE® humanized mice displayed an essentially normal, wild-type response to immunization that differed only in one significant respect from wild-type mice—the variable regions generated in response to immunization are fully human.

VELOCIMMUNE® humanized mice contain a precise, large-scale replacement of germline variable regions of mouse immunoglobulin heavy chain (IgH) and immunoglobulin light chain (e.g., κ light chain, Igκ) with corresponding human immunoglobulin variable regions, at the endogenous loci. In total, about six megabases of mouse loci are replaced with about 1.4 megabases of human genomic sequence. This precise replacement results in a mouse with hybrid immunoglobulin loci that make heavy and light chains that have a human variable regions and a mouse constant region. The precise replacement of mouse $V_H$-$D_H$-$J_H$ and Vκ-Jκ segments leave flanking mouse sequences intact and functional at the hybrid immunoglobulin loci. The humoral immune system of the mouse functions like that of a wild-type mouse. B cell development is unhindered in any significant respect and a rich diversity of human variable regions is generated in the mouse upon antigen challenge.

VELOCIMMUNE® humanized mice are possible because immunoglobulin gene segments for heavy and κ light chains rearrange similarly in humans and mice, which is not to say that their loci are the same or even nearly so—clearly they are not. However, the loci are similar enough that humanization of the heavy chain variable gene locus can be accomplished by replacing about 3 million base pairs of contiguous mouse gene sequence that contains all the $V_H$, $D_H$, and $J_H$ gene segments with about 1 million bases of contiguous human genomic sequence covering basically the equivalent sequence from a human immunoglobulin locus.

In some embodiments, further replacement of certain mouse constant region gene sequences with human gene sequences (e.g., replacement of mouse $C_H1$ sequence with human $C_H1$ sequence, and replacement of mouse $C_L$ sequence with human $C_L$ sequence) results in mice with hybrid immunoglobulin loci that make antibodies that have human variable regions and partly human constant regions, suitable for, e.g., making fully human antibody fragments, e.g., fully human Fab' s. Mice with hybrid immunoglobulin loci exhibit normal variable gene segment rearrangement, normal somatic hypermutation, and normal class switching. These mice exhibit a humoral immune system that is indistinguishable from wild type mice, and display normal cell populations at all stages of B cell development and normal lymphoid organ structures—even where the mice lack a full repertoire of human variable region gene segments. Immunizing these mice results in robust humoral responses that display a wide diversity of variable gene segment usage.

The precise replacement of mouse germline variable region gene segments allows for making mice that have partly human immunoglobulin loci. Because the partly human immunoglobulin loci rearrange, hypermutate, and class switch normally, the partly human immunoglobulin loci generate antibodies in a mouse that comprise human variable regions. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

Large-scale humanization by recombineering methods were used to modify mouse embryonic stem (ES) cells to precisely replace up to 3 megabases of the mouse heavy chain immunoglobulin locus that included essentially all of the mouse $V_H$, $D_H$, and $J_H$ gene segments with equivalent human gene segments with up to a 1 megabase human genomic sequence containing some or essentially all human $V_H$, $D_H$, and $J_H$ gene segments. Up to a 0.5 megabase segment of the human genome comprising one of two repeats encoding essentially all human Vκ and Jκ gene segments was used to replace a 3 megabase segment of the mouse immunoglobulin κ light chain locus containing essentially all of the mouse Vκ and Jκ gene segments.

Mice with such replaced immunoglobulin loci can comprise a disruption or deletion of the endogenous mouse ADAM6 locus, which is normally found between the 3'-most $V_H$ gene segment and the 5'-most $D_H$ gene segment at the mouse immunoglobulin heavy chain locus. Disruption in this region can lead to reduction or elimination of functionality of the endogenous mouse ADAM6 locus. If the 3'-most $V_H$ gene segments of the human heavy chain repertoire are used in a replacement, an intergenic region containing a pseudogene that appears to be a human ADAM6 pseudogene is present between these $V_H$ gene segments, i.e., between human $V_H1-2$ and $V_H1-6$. However, male mice that comprise this human intergenic sequence exhibit little or no fertility.

Mice are described that comprise the replaced loci as described above, and that also comprise an ectopic nucleic acid sequence encoding a mouse ADAM6, where the mice exhibit essentially normal fertility. In one embodiment, the ectopic nucleic acid sequence is SEQ ID NO:3, placed between human $V_H1-2$ and $V_H1-6$ at the modified endogenous mouse heavy chain locus. The direction of transcription of the ADAM6 genes of SEQ ID NO:3 are opposite with respect to the direction of transcription of the surrounding human $V_H$ gene segments. Although examples herein show rescue of fertility by placing the ectopic sequence between the indicated human $V_H$ gene segments, skilled persons will recognize that placement of the ectopic sequence at any suitable transcriptionally-permissive locus in the mouse genome (or even extrachromosomally) will be expected to similarly rescue fertility in a male mouse.

The phenomenon of complementing a mouse that lacks a functional ADAM6 locus with an ectopic sequence that comprises a mouse ADAM6 gene or ortholog or homolog or functional fragment thereof is a general method that is applicable to rescuing any mice with nonfunctional or minimally functional endogenous ADAM6 loci. Thus, a great many mice that comprise an ADAM6-disrupting modification of the immunoglobulin heavy chain locus can be rescued with the compositions and methods of the invention. Accordingly, the invention comprises mice with a wide variety of modifications of immunoglobulin heavy chain loci that compromise endogenous ADAM6 function. Some (non-limiting) examples are provided in this description. In addition to the VELOCIMMUNE® humanized mice described, the compositions and methods related to ADAM6 can be used in a great many applications, e.g., when modifying a heavy chain locus in a wide variety of ways.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_H$ gene segments, a replacement of all or substantially all mouse $D_H$ gene segments and $J_H$ gene segments with human $D_H$ and human $J_H$ gene segments; wherein the mouse lacks a $C_H1$ and/or hinge region. In one embodiment, the mouse makes a single variable domain binding protein that is a dimer of immunoglobulin chains selected from: (a) human $V_H$-mouse $C_H1$-mouse $C_H2$-mouse $C_H3$; (b) human $V_H$-mouse hinge-mouse $C_H2$-mouse $C_H3$; and, (c) human $V_H$-mouse $C_H2$-mouse $C_H3$.

In one aspect, the nucleotide sequence that rescues fertility is placed within a human immunoglobulin heavy chain variable region sequence (e.g., between human $V_H1-2$ and $V_H1-6$ gene segments) in a mouse that has a replacement of all or substantially all mouse immunoglobulin heavy chain variable gene segments ($mV_H$'s, $mD_H$'s, and $mJ_H$'s) with one or more human immunoglobulin heavy chain variable gene segments ($hV_H$'s, $hD_H$'s, and $hJ_H$'s), and the mouse further comprises a replacement of all or substantially all mouse immunoglobulin κ light chain variable gene segments (mVκ's, mJκ's) with one or more human immunoglobulin κ light chain variable gene segments (hVκ's and hJκ's). In one embodiment, the nucleotide sequence is placed between a human $V_H1-2$ gene segment and a human $V_H1-6$ gene segment in a VELOCIMMUNE® humanized mouse (U.S. Pat. No. 6,596,541 and U.S. Pat. No. 7,105,348, incorporated herein by reference). In one embodiment, the VELOCIMMUNE® humanized mouse so modified comprises a replacement with all or substantially all human immunoglobulin heavy chain variable gene segments (all $hV_H$'s, $hD_H$'s, and $hJ_H$'s) and all or substantially all human immunoglobulin κ light chain variable gene segments (hVκ's and hJκ's).

In one aspect, a functional mouse ADAM6 locus (or ortholog or homolog or functional fragment thereof) can be placed in the midst of human $V_H$ gene segments that replace endogenous mouse $V_H$ gene segments. In one embodiment, all or substantially all mouse $V_H$ gene segments are removed and replaced with one or more human $V_H$ gene segments, and the mouse ADAM6 locus is placed immediately adjacent to the 3' end of the human $V_H$ gene segments, or between two human $V_H$ gene segments. In a specific embodiment, the mouse ADAM6 locus is placed between two $V_H$ gene segments near the 3' terminus of the inserted human $V_H$ gene segments. In a specific embodiment, the replacement includes human $V_H$ gene segments $V_H1$-2 and $V_H6$-1, and the mouse ADAM6 locus is placed downstream of the $V_H1$-2 gene segment and upstream of the $V_H6$-1 gene segment. In a specific embodiment, the arrangement of human $V_H$ gene segments is then the following (from upstream to downstream with respect to direction of transcription of the human $V_H$ gene segments): human $V_H1$-2-mouse ADAM6 locus-human $V_H6$-1. In a specific embodiment, the ADAM6 pseudogene between human $V_H1$-2 and human $V_H6$-1 is replaced with the mouse ADAM6 locus. In one embodiment, the orientation of one or more of mouse ADAM6a and mouse ADAM6b of the mouse ADAM6 locus is opposite with respect to direction of transcription as compared with the orientation of the human $V_H$ gene segments. Alternatively, the mouse ADAM6 locus can be placed in the intergenic region between the 3'-most human $V_H$ gene segment and the 5'-most $D_H$ gene segment. This can be the case whether the 5'-most $D_H$ segment is mouse or human.

Similarly, a mouse modified with one or more human $V_L$ gene segments (e.g., Vκ or Vλ segments) replacing all or substantially all endogenous mouse $V_H$ gene segments can be modified so as to either maintain the endogenous mouse ADAM6 locus, as described above, e.g., by employing a targeting vector having a downstream homology arm that includes a mouse ADAM6 locus or functional fragment thereof, or to replace a damaged mouse ADAM6 locus with an ectopic sequence positioned between two human $V_L$ gene segments or between the human $V_L$ gene segments and a $D_H$ gene segment (whether human or mouse, e.g., Vλ+m/h$D_H$), or a J gene segment (whether human or mouse, e.g., Vκ+$J_H$). In one embodiment, the replacement includes two or more human $V_L$ gene segments, and the mouse ADAM6 locus or functional fragment thereof is placed between the two 3'-most $V_L$ gene segments. In a specific embodiment, the arrangement of human $V_L$ gene segments is then the following (from upstream to downstream with respect to direction of transcription of the human gene segments): human $V_L3$'-1-mouse ADAM6 locus-human $V_L3$'. In one embodiment, the orientation of one or more of mouse ADAM6a and mouse ADAM6b of the mouse ADAM6 locus is opposite with respect to direction of transcription as compared with the orientation of the human $V_L$ gene segments. Alternatively, the mouse ADAM6 locus can be placed in the intergenic region between the 3'-most human $V_L$ gene segment and the 5'-most $D_H$ gene segment. This can be the case whether the 5'-most $D_H$ segment is mouse or human.

In one aspect, a mouse is provided with a replacement of one or more endogenous mouse $V_H$ gene segments, and that comprises at least one endogenous mouse $D_H$ gene segment. In such a mouse, the modification of the endogenous mouse $V_H$ gene segments can comprise a modification of one or more of the 3'-most $V_H$ gene segments, but not the 5'-most $D_H$ gene segment, where care is taken so that the modification of the one or more 3'-most $V_H$ gene segments does not disrupt or render the endogenous mouse ADAM6 locus nonfunctional. For example, in one embodiment the mouse comprises a replacement of all or substantially all endogenous mouse $V_H$ gene segments with one or more human $V_H$ gene segments, and the mouse comprises one or more endogenous $D_H$ gene segments and a functional endogenous mouse ADAM6 locus.

In another embodiment, the mouse comprises the modification of endogenous mouse 3'-most $V_H$ gene segments, and a modification of one or more endogenous mouse $D_H$ gene segments, and the modification is carried out so as to maintain the integrity of the endogenous mouse ADAM6 locus to the extent that the endogenous ADAM6 locus remains functional. In one example, such a modification is done in two steps: (1) replacing the 3'-most endogenous mouse $V_H$ gene segments with one or more human $V_H$ gene segments employing a targeting vector with an upstream homology arm and a downstream homology arm wherein the downstream homology arm includes all or a portion of a functional mouse ADAM6 locus; (2) then replacing and endogenous mouse $D_H$ gene segment with a targeting vector having an upstream homology arm that includes a all or a functional portion of a mouse ADAM6 locus.

In various aspects, employing mice that contain an ectopic sequence that encodes a mouse ADAM6 protein or an ortholog or homolog or functional homolog thereof are useful where modifications disrupt the function of endogenous mouse ADAM6. The probability of disrupting endogenous mouse ADAM6 function is high when making modifications to mouse immunoglobulin loci, in particular when modifying mouse immunoglobulin heavy chain variable regions and surrounding sequences. Therefore, such mice provide particular benefit when making mice with immunoglobulin heavy chain loci that are deleted in whole or in part, are humanized in whole or in part, or are replaced (e.g., with Vκ or Vλ sequences) in whole or in part. Methods for making the genetic modifications described for the mice described below are known to those skilled in the art.

Mice containing an ectopic sequence encoding a mouse ADAM6 protein, or a substantially identical or similar protein that confers the fertility benefits of a mouse ADAM6 protein, are particularly useful in conjunction with modifications to a mouse immunoglobulin heavy chain variable region gene locus that disrupt or delete the endogenous mouse ADAM6 sequence. Although primarily described in connection with mice that express antibodies with human variable regions and mouse constant regions, such mice are useful in connection with any genetic modifications that disrupt the endogenous mouse ADAM6 gene. Persons of skill will recognize that this encompasses a wide variety of genetically modified mice that contain modifications of the mouse immunoglobulin heavy chain variable region gene locus. These include, for example, mice with a deletion or a replacement of all or a portion of the mouse immunoglobulin heavy chain gene segments, regardless of other modifications. Non-limiting examples are described below.

In some aspects, genetically modified mice are provided that comprise an ectopic mouse, rodent, or other ADAM6 gene (or ortholog or homolog or fragment) functional in a mouse, and one or more human immunoglobulin variable and/or constant region gene segments.

In one aspect, a mouse is provided that comprises an ectopic ADAM6 sequence that encodes a functional ADAM6 protein, a replacement of all or substantially all mouse $V_H$ gene segments with one or more human $V_H$ gene segments; a replacement of all or substantially all mouse $D_H$ gene segments with one or more human $D_K$ gene segments;

and a replacement of all or substantially all mouse $J_H$ gene segments with one or more human $J_H$ gene segments.

In one embodiment, the mouse further comprises a replacement of a mouse $C_H1$ nucleotide sequence with a human $C_H1$ nucleotide sequence. In one embodiment, the mouse further comprises a replacement of a mouse hinge nucleotide sequence with a human hinge nucleotide sequence. In one embodiment, the mouse further comprises a replacement of an immunoglobulin light chain variable locus ($V_L$ and $J_L$) with a human immunoglobulin light chain variable locus. In one embodiment, the mouse further comprises a replacement of a mouse immunoglobulin light chain constant region nucleotide sequence with a human immunoglobulin light chain constant region nucleotide sequence. In a specific embodiment, the $V_L$, $J_L$, and $C_L$ are immunoglobulin κ light chain sequences. In a specific embodiment, the mouse comprises a mouse $C_H2$ and a mouse $C_H3$ immunoglobulin constant region sequence fused with a human hinge and a human $C_H1$ sequence, such that the mouse immunoglobulin loci rearrange to form a gene that encodes a binding protein comprising (a) a heavy chain that has a human variable region, a human $C_H1$ region, a human hinge region, and a mouse $C_H2$ and a mouse $C_H3$ region; and (b) a gene that encodes, an immunoglobulin light chain that comprises a human variable domain and a human constant region.

In one aspect, a mouse is provided that comprises an ectopic ADAM6 sequence that encodes a functional ADAM6 protein, a replacement of all or substantially all mouse $V_H$ gene segments with one or more human $V_L$ gene segments, and optionally a replacement of all or substantially all $D_H$ gene segments and/or $J_H$ gene segments with one or more human $D_H$ gene segments and/or human $J_H$ gene segments, or optionally a replacement of all or substantially all $D_H$ gene segments and $J_H$ gene segments with one or more human $J_L$ gene segments.

In one embodiment, the mouse comprises a replacement of all or substantially all mouse $V_H$, $D_H$, and $J_H$ gene segments with one or more $V_L$, one or more $D_H$, and one or more J gene segments (e.g., Jκ or Jλ), wherein the gene segments are operably linked to an endogenous mouse hinge region, wherein the mouse forms a rearranged immunoglobulin chain gene that contains, from 5' to 3' in the direction of transcription, human $V_L$-human or mouse $D_H$-human or mouse J-mouse hinge-mouse $C_H2$-mouse $C_H3$. In one embodiment, the J region is a human Jκ region. In one embodiment, the J region is a human $J_H$ region. In one embodiment, the J region is a human Jλ region. In one embodiment, the human $V_1$ region is selected from a human Vλ region and a human Vκ region.

In specific embodiments, the mouse expresses a single variable domain antibody having a mouse or human constant region and a variable region derived from a human Vκ, a human $D_H$ and a human Jκ; a human Vκ, a human $D_H$, and a human $J_H$; a human Vλ, a human $D_H$, and a human Jλ; a human Vλ, a human $D_H$, and a human $J_H$; a human Vκ, a human $D_H$, and a human Jλ; a human Vλ, a human $D_H$, and a human Jκ. In specific embodiment, recombination recognition sequences are modified so as to allow for productive rearrangements to occur between recited V, D, and J gene segments or between recited V and J gene segments.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ gene segment and $J_H$ gene segments with human $J_1$ gene segments; wherein the mouse lacks a $C_H1$ and/or hinge region.

In one embodiment, the mouse lacks a sequence encoding a $C_H1$ domain. In one embodiment, the mouse lacks a sequence encoding a hinge region. In one embodiment, the mouse lacks a sequence encoding a $C_H1$ domain and a hinge region.

In a specific embodiment, the mouse expresses a binding protein that comprises a human immunoglobulin light chain variable domain (λ or κ) fused to a mouse $C_H2$ domain that is attached to a mouse $C_H3$ domain.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ and $J_H$ gene segments with human $J_L$ gene segments.

In one embodiment, the mouse comprises a deletion of an immunoglobulin heavy chain constant region gene sequence encoding a $C_H1$ region, a hinge region, a $C_H1$ and a hinge region, or a $C_H1$ region and a hinge region and a $C_H2$ region.

In one embodiment, the mouse makes a single variable domain binding protein comprising a homodimer selected from the following: (a) human $V_L$-mouse $C_H1$-mouse $C_H2$-mouse $C_H3$; (b) human $V_1$-mouse hinge-mouse $C_H2$-mouse $C_H3$; (c) human $V_L$-mouse $C_H2$-mouse $C_H3$.

In one aspect, a mouse is provided with a disabled endogenous heavy chain immunoglobulin locus, comprising a disabled or deleted endogenous mouse ADAM6 locus, wherein the mouse comprises a nucleic acid sequence that expresses a human or mouse or human/mouse or other chimeric antibody. In one embodiment, the nucleic acid sequence is present on a transgene integrated that is randomly integrated into the mouse genome. In one embodiment, the nucleic acid sequence is on an episome (e.g., a chromosome) not found in a wild-type mouse.

Common, or Universal, Light Chain

Prior efforts to make useful multispecific epitope-binding proteins, e.g., bispecific antibodies, have been hindered by variety of problems that frequently share a common paradigm: in vitro selection or manipulation of sequences to rationally engineer, or to engineer through trial-and-error, a suitable format for pairing a heterodimeric bispecific human immunoglobulin. Unfortunately, most if not all of the in vitro engineering approaches provide largely ad hoc fixes that are suitable, if at all, for individual molecules. On the other hand, in vivo methods for employing complex organisms to select appropriate pairings that are capable of leading to human therapeutics have not been realized.

Generally, native mouse sequences are frequently not a good source for human therapeutic sequences. For at least that reason, generating mouse heavy chain immunoglobulin variable regions that pair with a common human light chain is of limited practical utility. More in vitro engineering efforts would be expended in a trial-and-error process to try to humanize the mouse heavy chain variable sequences while hoping to retain epitope specificity and affinity while maintaining the ability to couple with the common human light chain, with uncertain outcome. At the end of such a process, the final product may maintain some of the specificity and affinity, and associate with the common light chain, but ultimately immunogenicity in a human would likely remain a profound risk.

Therefore, a suitable mouse for making human therapeutics would include a suitably large repertoire of human heavy chain variable region gene segments in place of endogenous mouse heavy chain variable region gene segments. The human heavy chain variable region gene segments should be able to rearrange and recombine with an endogenous mouse heavy chain constant domain to form a reverse chimeric heavy chain (i.e., a heavy chain comprising a human variable domain and a mouse constant region). The heavy chain should be capable of class switching and somatic hypermutation so that a suitably large repertoire of heavy chain variable domains are available for the mouse to select one that can associate with the limited repertoire of human light chain variable regions.

A mouse that selects a common light chain for a plurality of heavy chains has a practical utility. In various embodiments, antibodies that express in a mouse that can only express a common light chain will have heavy chains that can associate and express with an identical or substantially identical light chain. This is particularly useful in making bispecific antibodies. For example, such a mouse can be immunized with a first immunogen to generate a B cell that expresses an antibody that specifically binds a first epitope. The mouse (or a mouse genetically the same) can be immunized with a second immunogen to generate a B cell that expresses an antibody that specifically binds the second epitope. Variable heavy regions can be cloned from the B cells and expresses with the same heavy chain constant region, and the same light chain, and expressed in a cell to make a bispecific antibody, wherein the light chain component of the bispecific antibody has been selected by a mouse to associate and express with the light chain component.

The inventors have engineered a mouse for generating immunoglobulin light chains that will suitably pair with a rather diverse family of heavy chains, including heavy chains whose variable regions depart from germline sequences, e.g., affinity matured or somatically mutated variable regions. In various embodiments, the mouse is devised to pair human light chain variable domains with human heavy chain variable domains that comprise somatic mutations, thus enabling a route to high affinity binding proteins suitable for use as human therapeutics.

The genetically engineered mouse, through the long and complex process of antibody selection within an organism, makes biologically appropriate choices in pairing a diverse collection of human heavy chain variable domains with a limited number of human light chain options. In order to achieve this, the mouse is engineered to present a limited number of human light chain variable domain options in conjunction with a wide diversity of human heavy chain variable domain options. Upon challenge with an antigen, the mouse maximizes the number of solutions in its repertoire to develop an antibody to the antigen, limited largely or solely by the number or light chain options in its repertoire. In various embodiments, this includes allowing the mouse to achieve suitable and compatible somatic mutations of the light chain variable domain that will nonetheless be compatible with a relatively large variety of human heavy chain variable domains, including in particular somatically mutated human heavy chain variable domains.

To achieve a limited repertoire of light chain options, the mouse is engineered to render nonfunctional or substantially nonfunctional its ability to make, or rearrange, a native mouse light chain variable domain. This can be achieved, e.g., by deleting the mouse's light chain variable region gene segments. The endogenous mouse locus can then be modified by an exogenous suitable human light chain variable region gene segment of choice, operably linked to the endogenous mouse light chain constant domain, in a manner such that the exogenous human variable region gene segments can combine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. For example, in modifying a mouse κ light chain locus to replace endogenous mouse κ light chain gene segments with human κ light chain gene segments, the mouse κ intronic enhancer and mouse κ 3' enhancer are functionally maintained, or undisrupted.

A genetically engineered mouse is provided that expresses a limited repertoire of reverse chimeric (human variable, mouse constant) light chains associated with a diversity of reverse chimeric (human variable, mouse constant) heavy chains. In various embodiments, the endogenous mouse κ light chain gene segments are deleted and replaced with a single (or two) rearranged human light chain region, operably linked to the endogenous mouse Cκ gene. In embodiments for maximizing somatic hypermutation of the rearranged human light chain region, the mouse κ intronic enhancer and the mouse κ 3' enhancer are maintained. In various embodiments, the mouse also comprises a nonfunctional λ light chain locus, or a deletion thereof or a deletion that renders the locus unable to make a λ light chain.

A genetically engineered mouse is provided that, in various embodiments, comprises a light chain variable region locus lacking endogenous mouse light chain $V_L$ and $J_L$ gene segments and comprising a rearranged human light chain variable region, in one embodiment a rearranged human $V_L/J_L$ sequence, operably linked to a mouse constant region, wherein the locus is capable of undergoing somatic hypermutation, and wherein the locus expresses a light chain comprising the human $V_L/J_L$ sequence linked to a mouse constant region. Thus, in various embodiments, the locus comprises a mouse K 3' enhancer, which is correlated with a normal, or wild type, level of somatic hypermutation.

The genetically engineered mouse in various embodiments when immunized with an antigen of interest generates B cells that exhibit a diversity of rearrangements of human immunoglobulin heavy chain variable regions that express and function with one or with two rearranged light chains, including embodiments where the one or two light chains comprise human light chain variable regions that comprise, e.g., 1 to 5 somatic mutations. In various embodiments, the human light chains so expressed are capable of associating and expressing with any human immunoglobulin heavy chain variable region expressed in the mouse.

Epitope-Binding Proteins that Bind More than One Epitope

The compositions and methods of described herein can be used to make binding proteins that bind more than one epitope with high affinity, e.g., bispecific antibodies. Advantages of the invention include the ability to select suitably high binding (e.g., affinity matured) heavy chain immunoglobulin chains each of which will associate with a single light chain.

Synthesis and expression of bispecific binding proteins has been problematic, in part due to issues associated with identifying a suitable light chain that can associate and express with two different heavy chains, and in part due to isolation issues. The methods and compositions described herein allow for a genetically modified mouse to select, through otherwise natural processes, a suitable light chain that can associate and express with more than one heavy chain, including heavy chains that are somatically mutated (e.g., affinity matured). Human $V_L$ and $V_H$ sequences from suitable B cells of immunized mice as described herein that express affinity matured antibodies having reverse chimeric heavy chains (i.e., human variable and mouse constant) can be identified and cloned in frame in an expression vector with a suitable human constant region gene sequence (e.g., a human IgG1). Two such constructs can be prepared, wherein each construct encodes a human heavy chain variable domain that binds a different epitope. One of the human $V_L$S (e.g., human Vκ1-39Jκ5 or human Vκ3-20Jκ1), in germline sequence or from a B cell wherein the sequence has been somatically mutated, can be fused in frame to a suitable human constant region gene (e.g., a human κ constant gene). These three fully-human heavy and light constructs can be placed in a suitable cell for expression. The cell will express two major species: a homodimeric heavy chain with the identical light chain, and a heterodimeric heavy chain with the identical light chain. To allow for a facile separation of these major species, one of the heavy chains is modified to omit a Protein A-binding determinant, resulting in a differential affinity of a homodimeric binding protein from a heterodimeric binding protein. Compositions and methods that address this issue are described in U.S. Ser. No. 12/832,838, filed 25 Jun. 2010, entitled "Readily Isolated Bispecific Antibodies with Native Immunoglobulin Format," published as US 2010/0331527A1, hereby incorporated by reference.

In one aspect, an epitope-binding protein as described herein is provided, wherein human $V_L$ and $V_H$ sequences are derived from mice described herein that have been immunized with an antigen comprising an epitope of interest.

In one embodiment, an epitope-binding protein is provided that comprises a first and a second polypeptide, the first polypeptide comprising, from N-terminal to C-terminal, a first epitope-binding region that selectively binds a first epitope, followed by a constant region that comprises a first $C_H3$ region of a human IgG selected from IgG1, IgG2, IgG4, and a combination thereof; and, a second polypeptide comprising, from N-terminal to C-terminal, a second epitope-binding region that selectively binds a second epitope, followed by a constant region that comprises a second $C_H3$ region of a human IgG selected from IgG1, IgG2, IgG4, and a combination thereof, wherein the second $C_H3$ region comprises a modification that reduces or eliminates binding of the second $C_H3$ domain to protein A.

In one embodiment, the second $C_H3$ region comprises an H95R modification (by IMGT exon numbering; H435R by EU numbering). In another embodiment, the second $C_H3$ region further comprises a Y96F modification (IMGT; Y436F by EU).

In one embodiment, the second $C_H3$ region is from a modified human IgG1, and further comprises a modification selected from the group consisting of D16E, L18M, N44S, K52N, V57M, and V82I (IMGT; D356E, L358M, N384S, K392N, V397M, and V422I by EU).

In one embodiment, the second $C_H3$ region is from a modified human IgG2, and further comprises a modification selected from the group consisting of N44S, K52N, and V82I (IMGT; N384S, K392N, and V422I by EU).

In one embodiment, the second $C_H3$ region is from a modified human IgG4, and further comprises a modification selected from the group consisting of Q15R, N44S, K52N, V57M, R69K, E79Q, and V82I (IMGT; Q355R, N384S, K392N, V397M, R409K, E419Q, and V422I by EU).

One method for making an epitope-binding protein that binds more than one epitope is to immunize a first mouse in accordance with the invention with an antigen that comprises a first epitope of interest, wherein the mouse comprises an endogenous immunoglobulin light chain variable region locus that does not contain an endogenous mouse $V_L$ that is capable of rearranging and forming a light chain, wherein at the endogenous mouse immunglobulin light chain variable region locus is a single rearranged human $V_L$ region operably linked to the mouse endogenous light chain constant region gene, and the rearranged human $V_L$ region is selected from a human Vκ1-39Jκ5 and a human Vκ3-20Jκ1, and the endogenous mouse $V_H$ gene segments have been replaced in whole or in part with human $V_H$ gene segments, such that immunoglobulin heavy chains made by the mouse are solely or substantially heavy chains that comprise human variable domains and mouse constant domains. When immunized, such a mouse will make a reverse chimeric antibody, comprising only one of two human light chain variable domains (e.g., one of human Vκ1-39Jκ5 or human Vκ3-20Jκ1). Once a B cell is identified that encodes a $V_H$ that binds the epitope of interest, the nucleotide sequence of the $V_H$ (and, optionally, the $V_L$) can be retrieved (e.g., by PCR) and cloned into an expression construct in frame with a suitable human immunoglobulin constant domain. This process can be repeated to identify a second $V_H$ domain that binds a second epitope, and a second $V_H$ gene sequence can be retrieved and cloned into an expression vector in frame to a second suitable immunoglobulin constant domain. The first and the second immunoglobulin constant domains can the same or different isotype, and one of the immunoglobulin constant domains (but not the other) can be modified as described herein or in US 2010/0331527A1, and epitope-binding protein can be expressed in a suitable cell and isolated based on its differential affinity for Protein A as compared to a homodimeric epitope-binding protein, e.g., as described in US 2010/0331527A1.

In one embodiment, a method for making a bispecific epitope-binding protein is provided, comprising identifying a first affinity-matured (e.g., comprising one or more somatic hypermutations) human $V_H$ nucleotide sequence ($V_H1$) from a mouse as described herein, identifying a second affinity-matured (e.g., comprising one or more somatic hypermutations) human $V_H$ nucleotide sequence ($V_H2$) from a mouse as described herein, cloning $V_H1$ in frame with a human heavy chain lacking a Protein A-determinant modification as described in US 2010/0331527A1 for form heavy chain 1 (HC1), cloning $V_H2$ in frame with a human heavy chain comprising a Protein A-determinant as described in US 2010/0331527A1 to form heavy chain 2 (HC2), introducing an expression vector comprising HC1 and the same or a different expression vector comprising HC2 into a cell, wherein the cell also expresses a human immunoglobulin light chain that comprises a human Vκ1-39/human Jκ5 or a human Vκ3-20/human Jκ1 fused to a human light chain constant domain, allowing the cell to express a bispecific epitope-binding protein comprising a $V_H$ domain encoded by $V_H1$ and a $V_H$ domain encoded by $V_H2$, and isolating the bispecific epitope-binding protein based on its differential ability to bind Protein A as compared with a monospecific homodimeric epitope-binding protein. In a specific embodiment, HC1 is an IgG1, and HC2 is an IgG1 that comprises the modification H95R (IMGT; H435R by EU) and further comprises the modification Y96F (IMGT; Y436F by EU). In one embodiment, the VH domain encoded by $V_H1$, the $V_H$ domain encoded by $V_H2$, or both, are somatically mutated.

Human $V_H$ Genes that Express with a Common Human $V_L$

A variety of human variable regions from affinity-matured antibodies raised against four different antigens were expressed with either their cognate light chain, or at least one of a human light chain selected from human Vκ1-39Jκ5, human Vκ3-20Jκ1, or human VpreBJλ5 (see Example 10). For antibodies to each of the antigens, somatically mutated high affinity heavy chains from different gene families paired successfully with rearranged human germline Vκ1-39Jκ5 and Vκ3-20Jκ1 regions and were secreted from cells expressing the heavy and light chains. For Vκ1-39Jκ5 and Vκ3-20Jκ1, $V_H$ domains derived from the following human $V_H$ gene families expressed favorably: 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, and 6-1. Thus, a mouse that is engineered to express a limited repertoire of human $V_L$ domains from one or both of Vκ1-39Jκ5 and Vκ3-20Jκ1 will generate a diverse population of somatically mutated human $V_H$ domains from a $V_H$ locus modified to replace mouse $V_H$ gene segments with human $V_H$ gene segments.

Mice genetically engineered to express reverse chimeric (human variable, mouse constant) immunoglobulin heavy chains associated with a single rearranged light chain (e.g., a Vκ1-39/J or a Vκ3-20/J), when immunized with an antigen of interest, generated B cells that comprised a diversity of human $V_H$ rearrangements and expressed a diversity of high-affinity antigen-specific antibodies with diverse properties with respect to their ability to block binding of the antigen to its ligand, and with respect to their ability to bind variants of the antigen (see Examples 14 through 15).

Thus, the mice and methods described herein are useful in making and selecting human immunoglobulin heavy chain variable domains, including somatically mutated human heavy chain variable domains, that result from a diversity of rearrangements, that exhibit a wide variety of affinities (including exhibiting a $K_D$ of about a nanomolar or less), a wide variety of specificities (including binding to different epitopes of the same antigen), and that associate and express with the same or substantially the same human immunoglobulin light chain variable region.

In one aspect, a first mouse comprising a humanized heavy chain variable region locus is bred with a second mouse comprising a nucleic acid sequence encoding a common, or universal, light chain locus as described herein. In one embodiment, the first or the second mouse comprises an ectopic nucleic acid sequence encoding a mouse ADAM6 or ortholog or homolog or functional fragment thereof. Progeny are bred to obtain mice homozygous for a humanized heavy chain locus, and homozygous for the universal light chain locus. In one embodiment, the first mouse or the second mouse comprises a modification of an endogenous mouse light chain locus to render the endogenous mouse light chain locus nonfunctional (e.g., a deletion or a knock-out of, e.g., a λ and/or κ endogenous locus). In one embodiment, the first mouse comprises a replacement of all or substantially all functional endogenous mouse V, D, and J gene segments with one or more unrearranged human V, D, and J gene segments (e.g., all or substantially all functional human V, D, and J gene segments); and the mouse comprises a replacement of all or substantially all functional light chain V and J gene segments with no more than one or no more than two rearranged light chain V/J sequences. In one embodiment the first mouse further comprises an ectopic nucleic acid sequence that encodes a mouse ADAM6 or ortholog or homolog or functional fragment thereof. In one embodiment, the ectopic nucleic acid sequence is at a humanized immunoglobulin heavy chain locus.

In one embodiment, mice that comprise the ectopic sequence and that are homozygous for the universal light chain locus and for the humanized heavy chain locus are immunized with an antigen of interest to generate antibodies that comprise a plurality of somtatically mutated human variable domains that associate and express with a universal light chain. In one embodiment, human heavy chain variable domain nucleic acid sequences identified in the mouse are employed in an expression system to make a fully human antibody comprising the human heavy chain variable domain and a light chain comprising a universal light chain sequence of the mouse.

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is indicated in Celsius, and pressure is at or near atmospheric.

EXAMPLES

Example I

Humanization of Mouse Immunoglobulin Genes

Human and mouse bacterial artificial chromsomes (BACs) were used to engineer 13 different BAC targeting vectors (BACvecs) for humanization of the mouse immunoglobulin heavy chain and κ light chain loci. Tables 1 and 2 set forth detailed descriptions of the steps performed for the construction of all BACvecs employed for the humanization of the mouse immunoglobulin heavy chain and κ light chain loci, respectively.

Identification of Human and Mouse BACs.

Mouse BACs that span the 5' and 3' ends of the immunoglobulin heavy chain and K light chain loci were identified by hybridization of filters spotted with BAC library or by PCR screening mouse BAC library DNA pools. Filters were hybridized under standard conditions using probes that corresponded to the regions of interest. Library pools were screened by PCR using unique primer pairs that flank the targeted region of interest. Additional PCR using the same primers was performed to deconvolute a given well and isolate the corresponding BAC of interest. Both BAC filters and library pools were generated from 129 SvJ mouse ES cells (Incyte Genomics/Invitrogen). Human BACs that cover the entire immunoglobulin heavy chain and κ light chain loci were identified either by hybridization of filters spotted with BAC library (Caltech B, C, or D libraries & RPCI-11 library, Research Genetics/Invitrogen) through screening human BAC library pools (Caltech library, invitrogen) by a PCR-based method or by using a BAC end sequence database (Caltech D library, TIGR).

Construction of BACvecs (Tables 1 and 2).

Bacterial homologous recombination (BHR) was performed as described (Valenzuela et al., 2003; Zhang, Y., et al. (1998). A new logic for DNA engineering using recombination in *Escherichia coli. Nat Genet* 20, 123-128). In most cases, linear fragments were generated by ligating PCR-derived homology boxes to cloned cassettes followed by gel isolation of ligation products and electroporation into BHR-competent bacteria harboring the target BAC. After selection on appropriate antibiotic petri dishes, correctly recombined BACs were identified by PCR across both novel junctions followed by restriction analysis on pulsed-field gels (Schwartz, D.C., and Cantor, C. R. (1984) Separation of yeast chromosome-sized DNAs by pulsed field gradient gel electrophoresis. *Cell* 37, 67-75) and spot-checking by PCR using primers distributed across the human sequences.

Figure 4A:
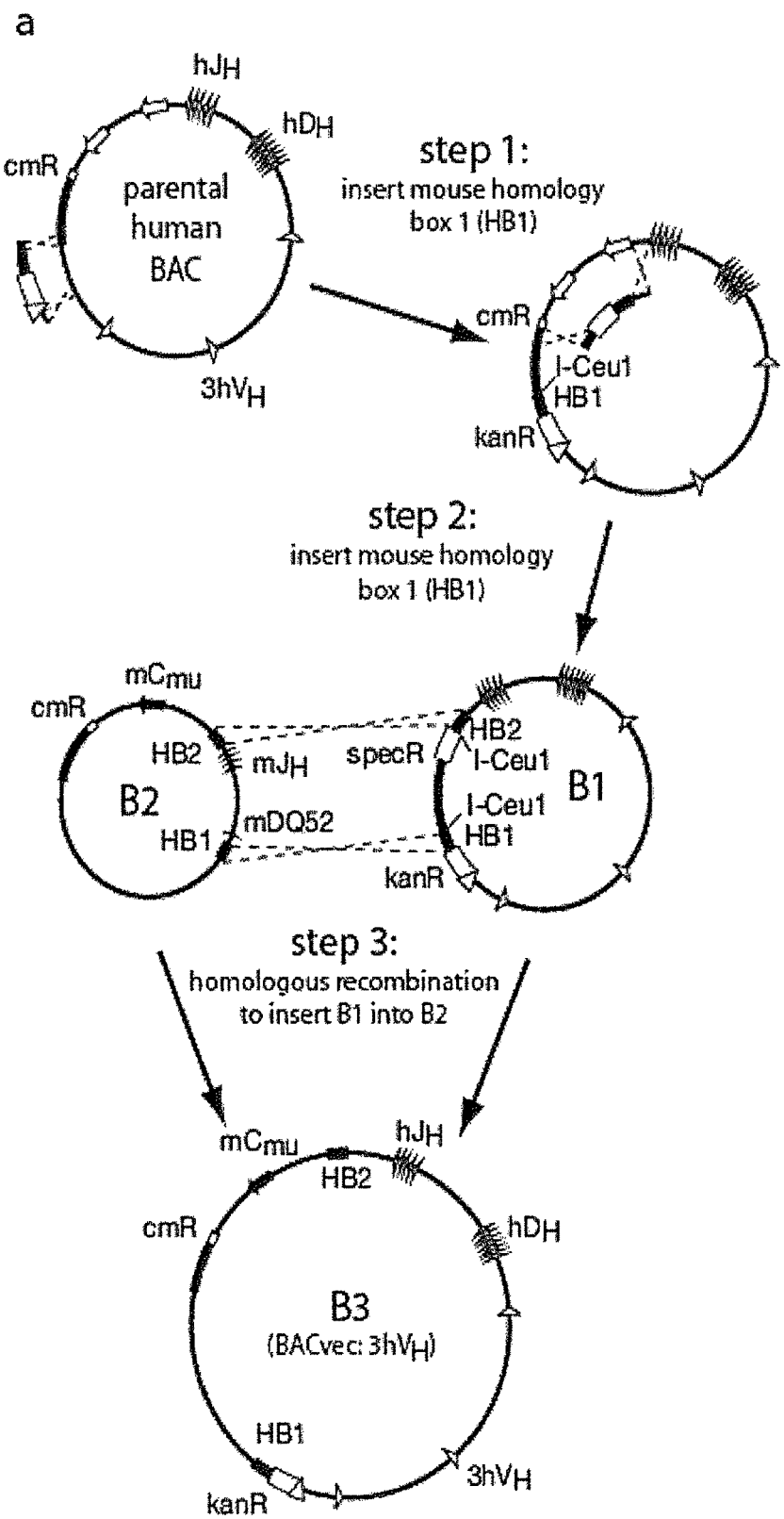
FIG. 4A shows an illustration of the three steps employed for the construction of the $3hV_H$ BACvec by bacterial homologous recombination (BHR). Human (open symbols) and mouse (closed symbols) immunoglobulin gene segments, selection cassettes (open rectangles) and site-specific recombination sites (open triangles) inserted from targeting vectors are shown.
Figure 4B:
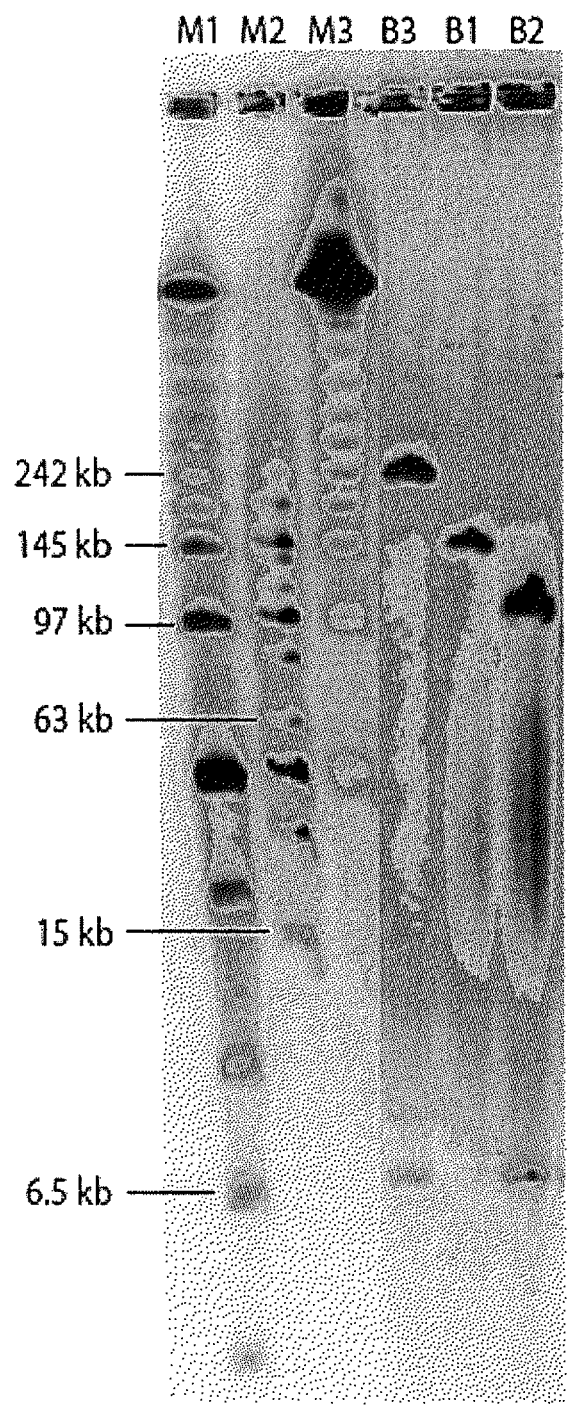
FIG. 4B shows pulse-field gel electrophoresis (PFGE) of three BAC clones (B1, B2 and B3) after NotI digestion. Markers M1, M2 and M3 are low range, mid range and lambda ladder PFG markers, respectively (New England BioLabs, Ipswich, Mass.).

A $3hV_H$ BACvec was constructed using three sequential BHR steps for the initial step of humanization of the immunoglobulin heavy chain locus (FIG. 4A and Table 1). In the first step (Step 1), a cassette was introduced into a human parental BAC upstream from the human $V_H1$-3 gene segment that contains a region of homology to the mouse immunoglobulin heavy chain locus (HB1), a gene that confers kanamycin resistance in bacteria and G418 resistance in animals cells (kanR) and a site-specific recombination site (e.g., loxP). In the second step (Step 2), a second cassette was introduced just downstream from the last $J_H$ segment that contains a second region of homology to the mouse immunoglobulin heavy chain locus (HB2) and a gene that confers resistance in bacteria to spectinomycin (specR). This second step included deleting human immunoglobulin heavy chain locus sequences downstream from $J_H6$ and the BAC vector chloramphenicol resistance gene (cmR). In the third step (Step 3), the doubly modified human BAC (B1) was then linearized using I-CeuI sites that had been added during the first two steps and integrated into a mouse BAC (B2) by BHR through the two regions of homology (HB1 and HB2). The drug selections for first (cm/kan), second (spec/kan) and third (cm/kan) steps were designed to be specific for the desired products. Modified BAC clones were analyzed by pulse-filed gel electrophoresis (PFGE) after digestion with restriction enzymes to determine appropriate construction (FIG. 4B).

In a similar fashion, 12 additional BACvecs were engineered for humanization of the heavy chain and κ light chain loci. In some instances, BAC ligation was performed in lieu of BHR to conjoin two large BACs through introduction of rare restriction sites into both parental BACvecs by BHR along with careful placement of selectable markers. This allowed for the survival of the desired ligation product upon selection with specific drug marker combinations. Recombinant BACs obtained by ligation after digestion with rare restriction enzymes were identified and screened in a similar fashion to those obtained by BHR (as described above).

TABLE 1

| BACvec | Step | Description | Process |
|---|---|---|---|
| $3hV_H$ | 1 | Insert upstream mouse homology box into human proximal BAC CTD-2572o2 | BHR |
| | 2 | Insert downstream mouse homology box into human proximal BAC CTD-2572o2 | BHR |
| | 3 | Insert $3hV_H/27hD_H/9hJ_H$ into mouse proximal BAC CT7-302a07 to create $3hV_H$ BACvec | BHR |
| DC | 1 | Insert cassette at distal end of mouse IgH locus using mouse BAC CT7-253i20 | BHR |
| $18hV_H$ | 1 | Insert specR marker at downstream end of $3hV_H$ insertion using human BAC CTD-2572o2 | BHR |
| | 2 | Insert I-CeuI and Not sites flanking puroR at upstream end of $3hV_H$ insertion | BHR |
| | 3 | Insert Not site at downstream end of ReI2-408p02 BAC (≈10 kb downstream of $V_H2$-5) | BHR |
| | 4 | Insert I-Ceu1 site at upstream end of ReI2-408p02 BAC (≈23 kb upstream of $V_H 1$-18) | BHR |
| | 5 | Ligate 184 kb fragment from step 4 into 153 kb vector from step 2 | Ligation |
| | 6 | Trim human homology from CTD-2572o2 BAC deleting ≈85 kb and leaving 65 kb homology to $3hV_H$ | BHR |
| | 7 | Insert cassette and Not site at distal end of mouse IgH locus in CT7-253i20 BAC | BHR |
| | 8 | Subclone mouse distal homology arm for insertion upstream from human BACs | Ligation |
| | 9 | Insert 20 kb mouse arm upstream of ReI2-408p02 | BHR |
| | 10 | Swap selection cassette from hygR to neoR to create $18hV_H$ BACvec | BHR |
| $39hV_H$ | 1 | Insert I-CeuI and PI-SceI sites flanking hygR into distal end of human BAC CTD-2534n10 | BHR |
| | 2 | Insert CmR at proximal end of CTD-2534n10 BAC to allow for selection for ligation to RP11-72n10 BAC | BHR |
| | 3 | Insert PI-SceI site into RP11-72n10 BAC for ligation to CTD-2534n10 BAC | BHR |
| | 4 | Insert I-CeuI and AscI sites flanking puroR at distal end of RP11-72n10 BAC | BHR |
| | 5 | Ligate 161 kb fragment from construct of step 4 into construct of step 2 replacing hygR | Ligation |
| | 6 | Insert neoR and AscI site at proximal end of mouse distal homology arm using CT7-253i20 BAC | BHR |
| | 7 | Insert specR and I-CeuI site at distal end of mouse distal homology arm | BHR |
| | 8 | Ligate mouse distal homology arm onto human insert from step 5 | Ligation |
| | 9 | Swap selection cassette from neo to hyg using UbCp and pA as homolgy boxes to create $39hV_H$ BACvec | BHR |

TABLE 1-continued

| BACvec | Step | Description | Process |
|---|---|---|---|
| 53hV$_H$ | 1 | Insert specR at proximal end of human CTD-3074b5 BAC | BHR |
| | 2 | Insert AscI site at distal end of human CTD-3074b5 BAC | BHR |
| | 3 | Insert hygR and AscI site at proximal end of mouse distal homology arm using CT7-253i20 BAC | BHR |
| | 4 | Ligate mouse distal homology arm onto construct from step 2 | Ligation |
| | 5 | Swap selection cassette from hyg to neo using UbCp and pA as homolgy boxes to create 53hV$_H$ BACvec | BHR |
| 70hV$_H$ | 1 | Insert PI-SceI and I-CeuI sites flanking spec at distal end of human CTD-2195p5 BAC | BHR |
| | 2 | Insert I-CeuI site at proximal end of RP11-926p12 BAC for ligation to CTD-2195p5 BAC | BHR |
| | 3 | Insert PI-SceI and AscI sites at distal end of RP11-926p12 BAC for ligation of mouse arm | BHR |
| | 4 | Ligate mouse distal homology arm onto construct from step 3 | Ligation |
| | 5 | Ligate mouse distal homology arm and hIgH fragment from RP11-926p12 BAC onto CTD-2195p5 BAC to create 70 hV$_H$ BACvec | Ligation |
| 80hV$_H$ | 1 | Insert I-CeuI and AscI sites flanking hygR at distal end of CTD-2313e3 BAC | BHR |
| | 2 | Ligate mouse dista homology arm onto human CTD-2313e3 BAC from step 1 to create 80hV$_H$ BACvec | Ligation |

TABLE 2

| BACvec | Step | Description | Process |
|---|---|---|---|
| Igκ-PC | 1 | Insert loxP site within mouse J-C intron using CT7-254m04 BAC | BHR |
| Igκ-DC | 1 | Insert loxP site at distal end of mouse IgK locus using CT7-302g12 BAC | BHR |
| 6hVκ | 1 | Insert PI-Scel site ≈400 bp downstream from hJκ5 in CTD-2366j12 BAC | BHR |
| | 2 | Insert I-CeuI and AscI sites flanking hygR at distal end of CTD-2366j12 BAC | BHR |
| | 3 | Insert I-CeuI and PI-SceI sites flanking puroR ≈xxbp downstream from mJκx using CT7-254m04 BAC | BHR |
| | 4 | Insert hIgVκ/Jκ upstream from mouse Enhκ/Cκ using construct from step 3 | Ligation |
| | 5 | Replace cmR in construct of step 4 with specR | BHR |
| | 6 | Insert Neo selection cassette at distal end of mouse Igκ locus using CT7-302g12 BAC | BHR |
| | 7 | Ligate mouse distal homology arm upstream of human insert in construct of step 6 to create 6hVκ BACvec | Ligation |
| 16hVκ | 1 | Insert NeoR at distal end of RP11-1061b13 BAC | BHR |
| | 2 | Replace cmR in construct of step 1 with specR | BHR |
| | 3 | Insert Hyg selection cassette at distal end of mouse Igκ locus using CT7-302g12 BAC | BHR |
| | 4 | Ligate mouse distal homology arm upstream of human insert from construct of step 2 to create 16hVκ BACvec | Ligation |
| 30hVκ | 1 | Insert HygR at distal end of RP11-99g6 BAC | BHR |
| | 2 | Replace cmR in construct of step 1 with specR | BHR |
| | 3 | Insert Neo selection cassette at distal end of mouse Igκ locus using CT7-302g12 BAC | BHR |
| | 4 | Ligate mouse distal homology arm upstream of human insert from construct of step 2 to create 30hVκ BACvec | Ligation |
| 40hVκ | 1 | Insert NeoR at distal end of hIgH locus in CTD-2559d6 BAC | BHR |
| | 2 | Replace cmR in construct of step 1 with specR | BHR |
| | 3 | Ligate mouse distal homology arm upstream of hIgH locus in construct of step 2 to create 40hVκ BACvec | Ligation |

Modification of Embryonic Stem (ES) Cells and Generation of Mice.

ES cell (F1H4) targeting was performed using the VELOCIGENE® genetic engineering method as described (Valenzuela et. al., 2003). Derivation of mice from modified ES cells by either blastocyst (Valenzuela at al., 2003) or 8-cell injection (Poueymirou et al., 2007) was as described. Targeted ES cells and mice were confirmed by screening DNA from ES cells or mice with unique sets of probes and primers in a PCR based assay (e.g., FIGS. 3A, 3B and 3C). All mouse studies were overseen and approved by Regeneron's Institutional Animal Care and Use Committee (IACUC).

Karyotype Analysis and Fluorescent In Situ Hybridization (FISH).

Karyotype Analysis was performed by Coriell Cell Repositories (Coriell Institute for Medical Research, Camden, N.J.). FISH was performed on targeted ES cells as described (Valenzuela et al., 2003). Probes corresponding to either mouse BAC DNA or human BAC DNA were labeled by nick translation (Invitrogen) with the fluorescently labeled dUTP nucleotides spectrum orange or spectrum green (Vysis).

Immunoglobulin Heavy Chain Variable Gene Locus.

Humanization of the variable region of the heavy chain locus was achieved in nine sequential steps by the direct replacement of about three million base pairs (Mb) of contiguous mouse genomic sequence containing all $V_H$, $D_H$ and $J_H$ gene segments with about one Mb of contiguous human genomic sequence containing the equivalent human gene segments (FIG. 1A and Table 1) using VELOCI-GENE® genetic engineering technology (see, e.g., U.S. Pat. No. 6,586,251 and Valenzuela et al., 2003).

The intron between $J_H$ gene segments and constant region genes (the J-C intron) contains a transcriptional enhancer (Neuberger, M. S. (1983) Expression and regulation of immunoglobulin heavy chain gene transfected into lymphoid cells. EMBO J. 2, 1373-1378) followed by a region of simple repeats required for recombination during isotype switching (Kataoka, T. et al. (1980) Rearrangement of immunoglobulin gamma 1-chain gene and mechanism for heavy-chain class switch. Proc Natl Acad Sci USA 77, 919-923). The junction between human $V_H$-$D_H$-$J_H$ region and the mouse $C_H$ region (the proximal junction) was chosen to maintain the mouse heavy chain intronic enhancer and switch domain in order preserve both efficient expression and class switching of the humanized heavy chain locus within the mouse. The exact nucleotide position of this and subsequent junctions in all the replacements was possible by use of the VELOCIGENE® genetic engineering method (supra), which employed bacterial homologous recombination driven by synthesized oligonucleotides. Thus, the proximal junction was placed about 200 bp downstream from the last $J_H$ gene segment and the distal junction was placed several hundred upstream of the most 5' $V_H$ gene segment of the human locus and about 9 kb downstream from the mouse $V_H$1-86 gene segment, also known as J558.55. The mouse $V_H$1-86 (J558.55) gene segment is the most distal heavy chain variable gene segment, reported to be a pseudogene in C57BL/6 mice, but potentially active, albeit with a poor RSS sequence, in the targeted 129 allele. The distal end of the mouse heavy chain locus reportedly may contain control elements that regulate locus expression and/or rearrangement (Pawlitzky et al., 2006).

Figure 2A:
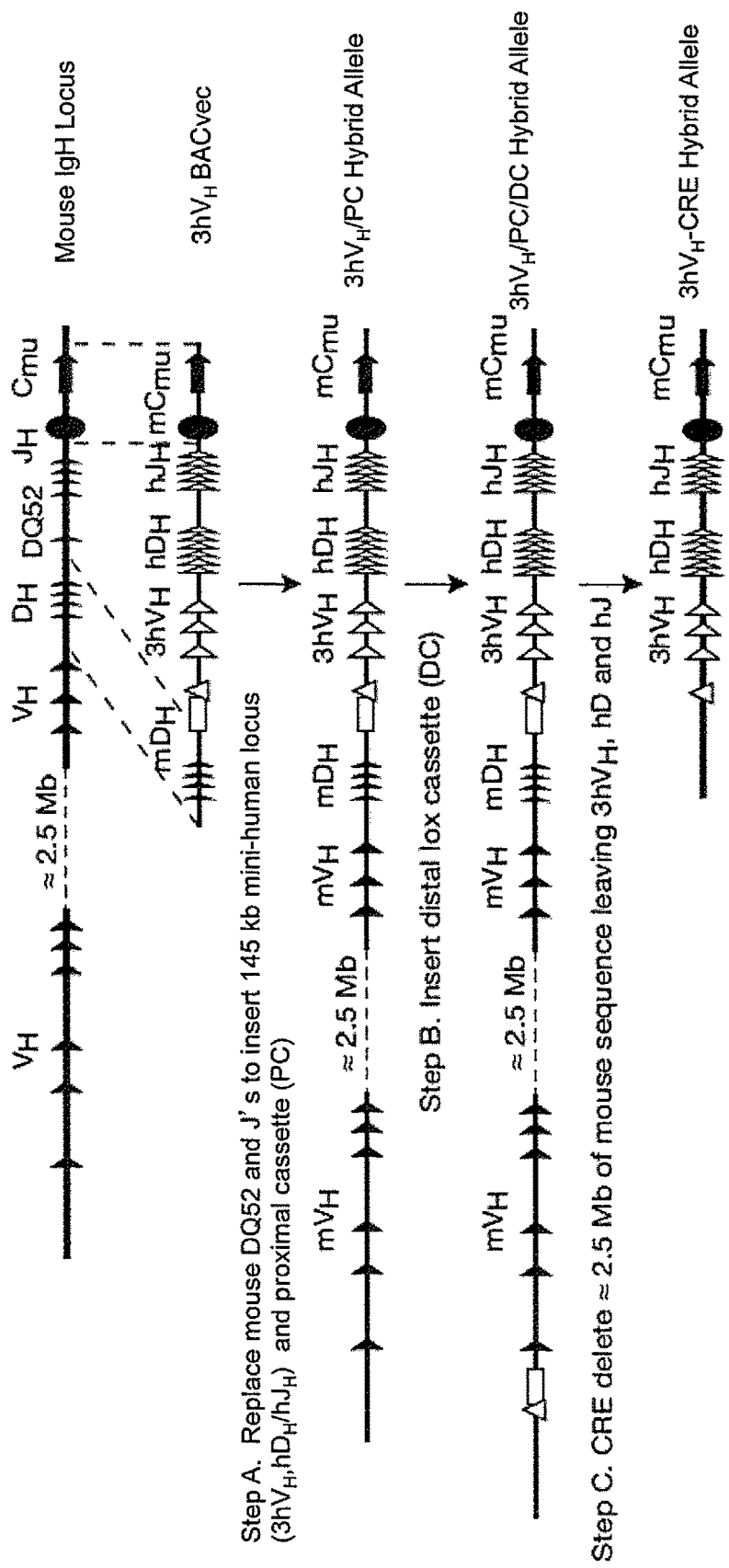
FIG. 2A shows a detailed illustration, not to scale, for three initial steps (A-C) for direct genomic replacement of the mouse immunoglobulin heavy chain variable gene locus that results in deletion of all mouse $V_H$, $D_H$ and $J_H$ gene segments and replacement with three human $V_H$, all human DH and $J_H$ gene segments. A targeting vector for the first insertion of human immunoglobulin heavy chain gene segments is shown (3hV$_N$ BACvec) with a 67 kb 5' mouse homology arm, a selection cassette (open rectangle), a site-specific recombination site (open triangle), a 145 kb human genomic fragment and an 8 kb 3' mouse homology arm. Human (open symbols) and mouse (closed symbols) immunoglobulin gene segments, additional selection cassettes (open rectangles) and site-specific recombination sites (open triangles) inserted from subsequent targeting vectors are shown.
Figure 3A:
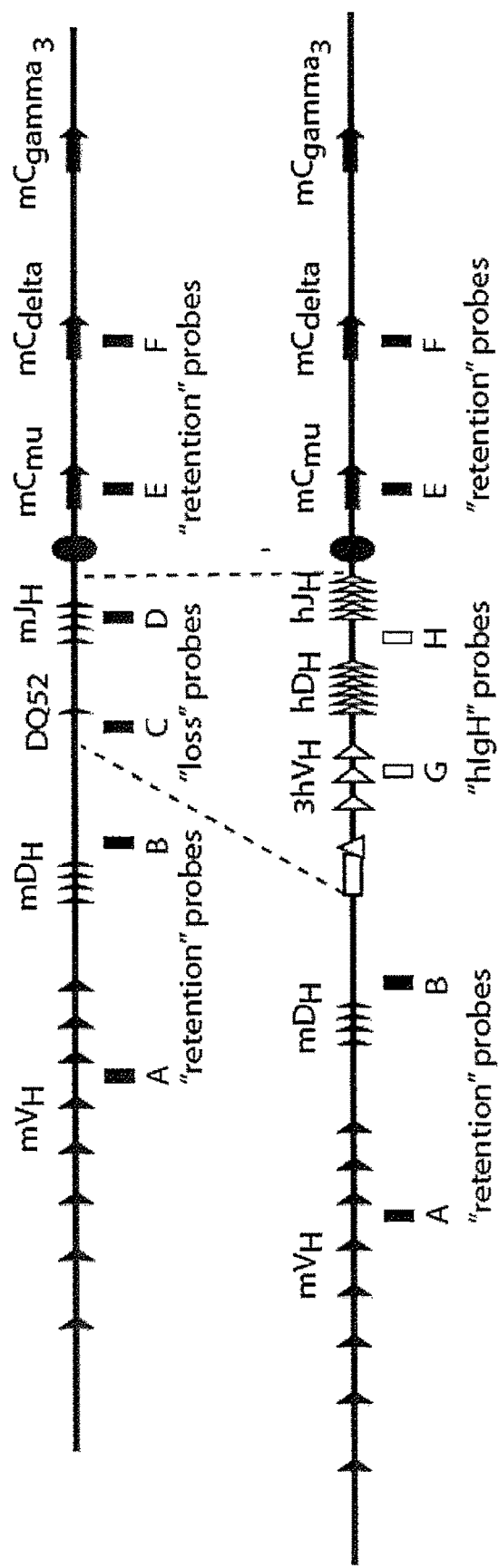
FIG. 3A shows a general illustration of the locations of quantitative PCR (qPCR) primer/probe sets for screening ES cells for insertion of human heavy chain gene sequences and loss of mouse heavy chain gene sequences. The screening strategy in ES cells and mice for the first human heavy gene insertion is shown with qPCR primer/probe sets for the deleted region ("loss" probes C and D), the region inserted ("hIgH" probes G and H) and flanking regions ("retention" probes A, B, E and F) on an unmodified mouse chromosome (top) and a correctly targeted chromosome (bottom).

A first insertion of human immunoglobulin DNA sequence into the mouse was achieved using 144 kb of the proximal end of the human heavy chain locus containing 3 $V_H$, all 27 $D_H$ and 9 $J_H$ human gene segments inserted into the proximal end of the mouse IgH locus, with a concomitant 16.6 kb deletion of mouse genomic sequence, using about 75 kb of mouse homology arms (Step A, FIG. 2A; Tables 1 and 3, 3h$V_H$). This large 144 kb insertion and accompanying 16.6 kb deletion was performed in a single step (Step A) that occurred with a frequency of 0.2% (Table 3). Correctly targeted ES cells were scored by a loss-of-native-allele (LONA) assay (Valenzuela et al., 2003) using probes within and flanking the deleted mouse sequence and within the inserted human sequence, and the integrity of the large human insert was verified using multiple probes spanning the entire insertion (FIGS. 3A, 3B and 3C). Because many rounds of sequential ES cell targeting were anticipated, targeted ES cell clones at this, and all subsequent, steps were subjected to karyotypic analysis (supra) and only those clones showing normal karyotypes in at least 17 of 20 spreads were utilized for subsequent steps.

Targeted ES cells from Step A were re-targeted with a BACvec that produced a 19 kb deletion at the distal end of the heavy chain locus (Step B, FIG. 2A). The Step B BACvec contained a hygromycin resistance gene (hyg) in contrast to the neomycin resistance gene (neo) contained on the BACvec of Step A. The resistance genes from the two BACvecs were designed such that, upon successful targeting to the same chromosome, approximately three Mb of the mouse heavy chain variable gene locus containing all of the mouse $V_H$ gene segments other than $V_H$1-86 and all of the $D_H$ gene segments other than DQ52, as well as the two resistance genes, were flanked by loxP sites; DQ52 and all of the mouse $J_H$ chain gene segments were deleted in Step A. ES cell clones doubly targeted on the same chromosome were identified by driving the 3h$V_H$ proximal cassette to homozygosity in high G418 (Mortensen, R. M. et al. (1992) Production of homozygous mutant ES cells with a single targeting construct. Mol Cell Biol 12:2391-2395) and following the fate of the distal hyg cassette. Mouse segments up to four Mb in size, having been modified in a manner to be flanked by loxP sites, have been successfully deleted in ES cells by transient expression of CRE recombinase with high efficiencies (up to ≈11%) even in the absence of drug selection (Zheng, B., et al. (2000). Engineering mouse chromosomes with Cre-loxP: range, efficiency, and somatic applications. Mol Cell Biol 20:648-655). In a similar manner, the inventors achieved a three Mb deletion in 8% of ES cell clones following transient Cre expression (Step C, FIG. 2A; Table 3). The deletion was scored by the LONA assay using probes at either end of the deleted mouse sequence, as well as the loss of neo and hyg and the appearance of a PCR product across the deletion point containing the sole remaining loxP site. Further, the deletion was confirmed by fluorescence in situ hybridization (data not shown).

Figure 2B:
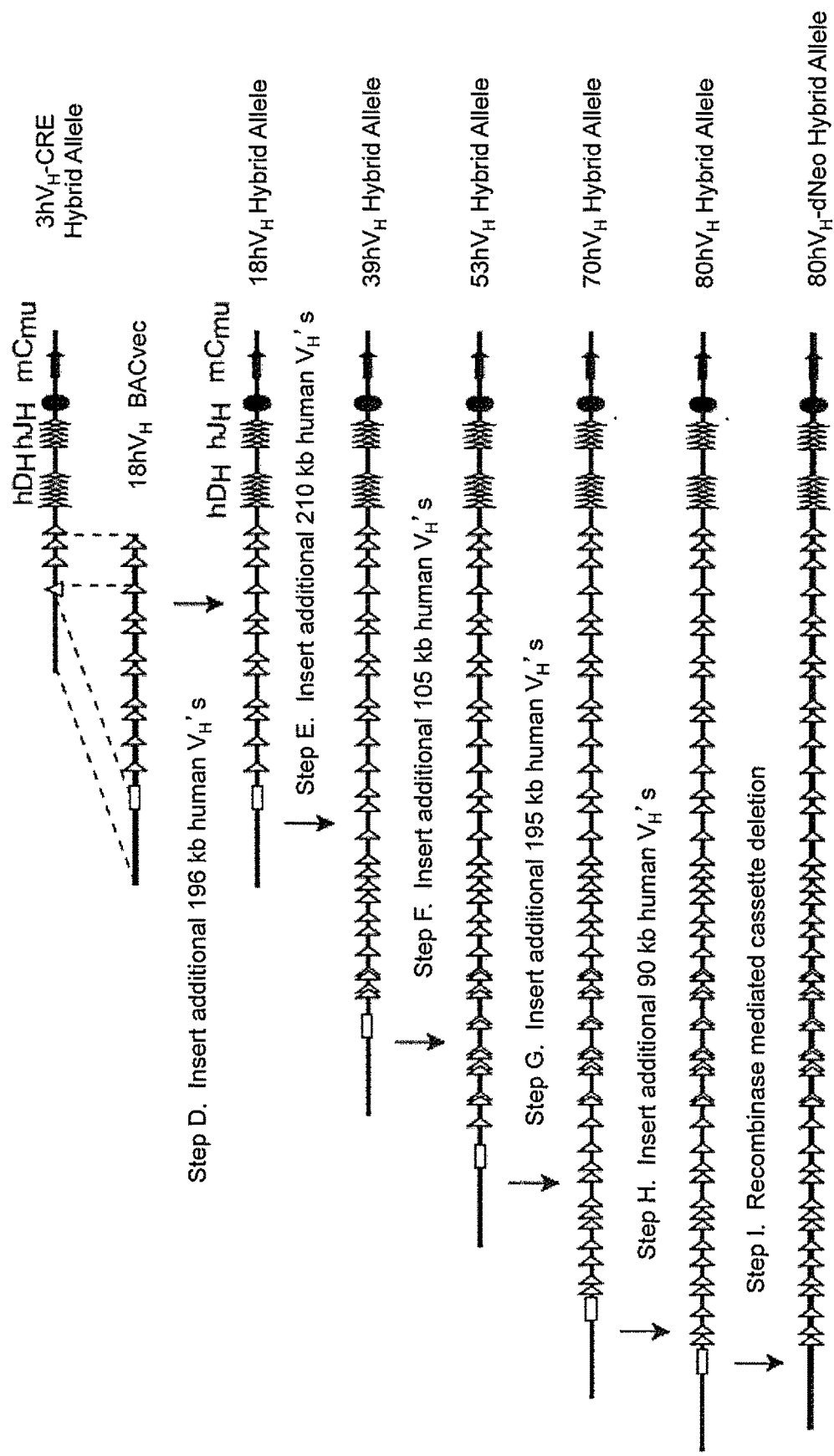
FIG. 2B shows a detailed illustration, not to scale, for six additional steps (D-I) for direct genomic replacement of the mouse immunoglobulin heavy chain variable gene locus that results in the insertion of 77 additional human $V_H$ gene segments and removal of the final selection cassette. A targeting vector for insertion of additional human $V_H$ gene segments (18hV$_H$ BACvec) to the initial insertion of human heavy chain gene segments (3hV$_H$-CRE Hybrid Allele) is shown with a 20 kb 5' mouse homology arm, a selection cassette (open rectangle), a 196 kb human genomic fragment and a 62 kb human homology arm that overlaps with the 5' end of the initial insertion of human heavy chain gene segments which is shown with a site-specific recombination site (open triangle) located 5' to the human gene segments. Human (open symbols) and mouse (closed symbols) immunoglobulin gene segments and additional selection cassettes (open rectangles) inserted by subsequent targeting vectors are shown.

The remainder of the human heavy chain variable region was added to the 3h$V_H$ allele in a series of 5 steps using the VELOCIGENE® genetic engineering method (Steps E-H, FIG. 2B), with each step involving precise insertion of up to 210 kb of human gene sequences. For each step, the proximal end of each new BACvec was designed to overlap the most distal human sequences of the previous step and the distal end of each new BACvec contained the same distal region of mouse homology as used in Step A. The BACvecs of steps D, F and H contained neo selection cassettes, whereas those of steps E and G contained hyg selection cassettes, thus selections were alternated between G418 and hygromycin. Targeting in Step D was assayed by the loss of the unique PCR product across the distal loxP site of 3h$V_H$ Hybrid Allele. Targeting for Steps E through I was assayed by loss of the previous selection cassette. In the final step (Step 1, FIG. 2B), the neo selection cassette, flanked by Frt sites (McLeod, M. et al. (1986) Identification of the crossover site during FLP-mediated recombination in the *Saccharomyces cerevisiae* plasmid 2 microns circle. Mol Cell Biol 6, 3357-3367), was removed by transient FLPe expression (Buchholz, F. et al. (1998) Improved properties of FLP recombinase evolved by cycling mutagenesis. Nat Biotechnol 16, 657-662). The human sequences of the BACvecs for Steps D, E and G were derived from two parental human BACs each, whereas those from Steps F and H were from single BACs. Retention of human sequences was confirmed at every step using multiple probes spanning the inserted human sequences (as described above, e.g. FIGS. 3A, 3B and 3C). Only those clones with normal karyotype and germline potential were carried forward in each step. ES cells from the final step were still able to contribute to the germline after nine sequential manipulations (Table Mice homozygous for each of the heavy chain alleles were viable, appeared healthy and demonstrated an essentially wild-type humoral immune system (see Example 3).

TABLE 3

| Hybrid Allele | Human sequence | Targeting construct | Targeting efficiency | % usage | Total $V_H$ | Functional $V_H$ |
|---|---|---|---|---|---|---|
| 3h$V_H$ | 144 kb | 240 kb | 0.2% | 5 | 3 | 3 |
| 3h$V_H$/DC | 144 kb | 110 kb | 0.1% | 5 | 3 | 3 |
| 3h$V_H$-CRE | 144 kb | — | 8% | 5 | 3 | 3 |
| 18h$V_H$ | 340 kb | 272 kb | 0.1% | 25 | 18 | 12 |
| 39h$V_H$ | 550 kb | 282 kb | 0.2% | 60 | 39 | 25 |
| 53h$V_H$ | 655 kb | 186 kb | 0.4% | 65 | 53 | 29 |
| 70h$V_H$ | 850 kb | 238 kb | 0.5% | 90 | 70 | 39 |
| 80h$V_H$ | 940 kb | 124 kb | 0.2% | 100 | 80 | 43 |
| 80h$V_H$dNeo | 940 kb | — | 2.6% | 100 | 80 | 43 |

Immunoglobulin κ Light Chain Variable Gene Locus.

Figure 1B:
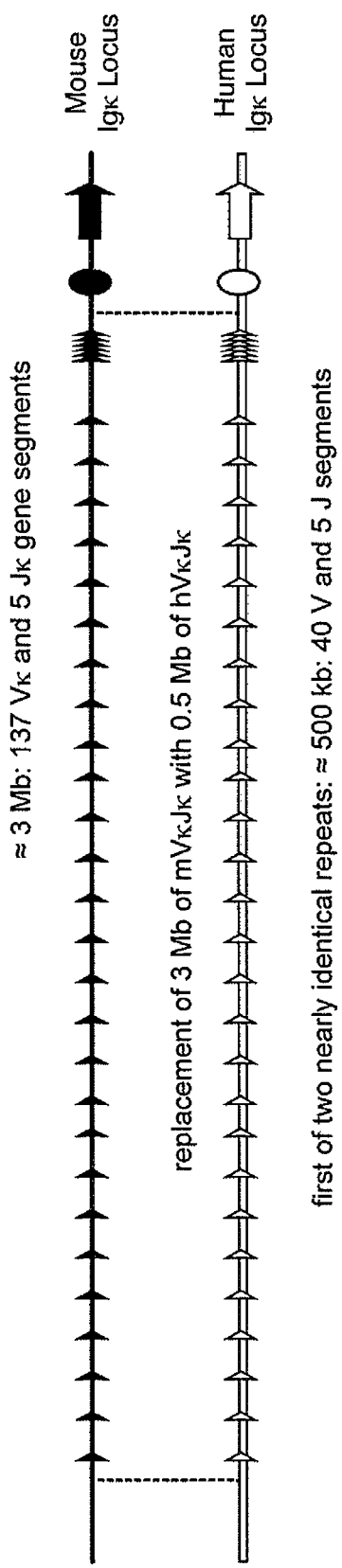
FIG. 1B shows a general illustration, not to scale, for direct genomic replacement of about three megabases (Mb) of the mouse immunoglobulin κ light chain variable gene locus (closed symbols) with about 0.5 megabases (Mb) of the first, or proximal, of two nearly identical repeats of the human immunoglobulin κ light chain variable gene locus (open symbols).

The κ light chain variable region was humanized in eight sequential steps by the direct replacement of about three Mb of mouse sequence containing all Vκ and Jκ gene segments with about 0.5 Mb of human sequence containing the proximal human Vκ and Jκ gene segments in a manner similar to that of the heavy chain (FIG. 1B; Tables 2 and 4).

Figure 2C:
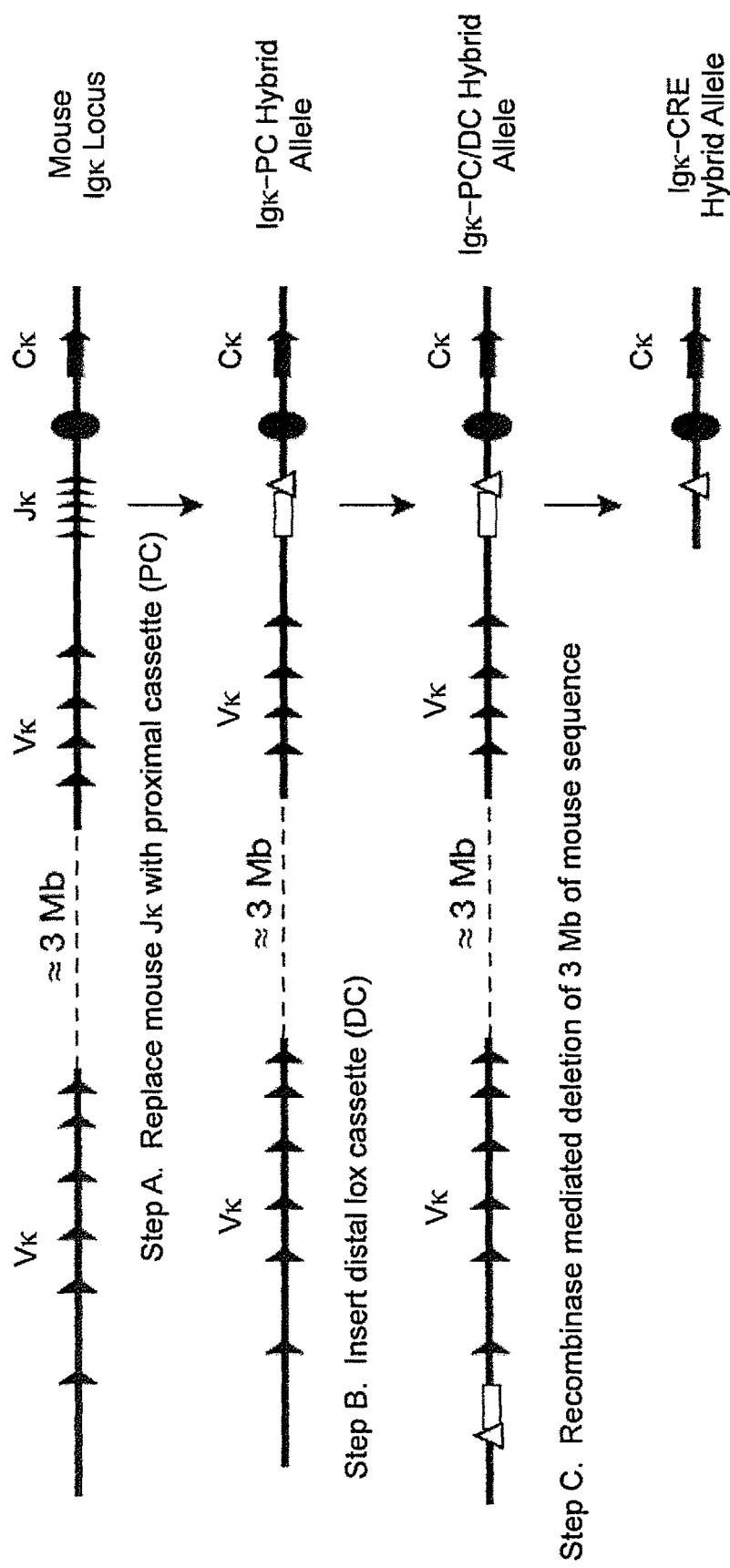
FIG. 2C shows a detailed illustration, not to scale, for three initial steps (A-C) for direct genomic replacement of the mouse immunoglobulin κ light chain variable gene locus that results in deletion of all mouse Vκ, and Jκ gene segments (Igκ-CRE Hybrid Allele). Selection cassettes (open rectangles) and site-specific recombination sites (open triangles) inserted from the targeting vectors are shown.

The variable region of the human κ light chain locus contains two nearly identical 400 kb repeats separated by a 800 kb spacer (Weichhold, G. M. et al. (1993) The human immunoglobulin kappa locus consists of two copies that are organized in opposite polarity, Genomics 16:503-511). Because the repeats are so similar, nearly all of the locus diversity can be reproduced in mice by using the proximal repeat. Further, a natural human allele of the κ light chain locus missing the distal repeat has been reported (Schaible, G. et al. (1993) The immunoglobulin kappa locus: polymorphism and haplotypes of Caucasoid and non-Caucasoid individuals, Hum Genet 91:261-267). About three Mb of mouse κ light chain variable gene sequence were replaced with about 0.5 Mb of human κ light chain variable gene sequence to effectively replace all of the mouse Vκ and Jκ gene segments with the proximal human Vκ and all of the human Jκ gene segments (FIGS. 2C and 2D; Tables 2 and 4). In contrast to the method described in Example 1 for the heavy chain locus, the entire mouse Vκ gene region, containing all Vκ and Jκ gene segments, was deleted in a three-step process before any human sequence was added. First, a neo cassette was introduced at the proximal end of the variable region (Step A, FIG. 2C). Next, a hyg cassette was inserted at the distal end of the κ locus (Step B, FIG. 2C). LoxP sites were again situated within each selection cassette such that Cre treatment induced deletion of the remaining 3 Mb of the mouse Vκ region along with both resistance genes (Step C, FIG. 2C).

Figure 2D:
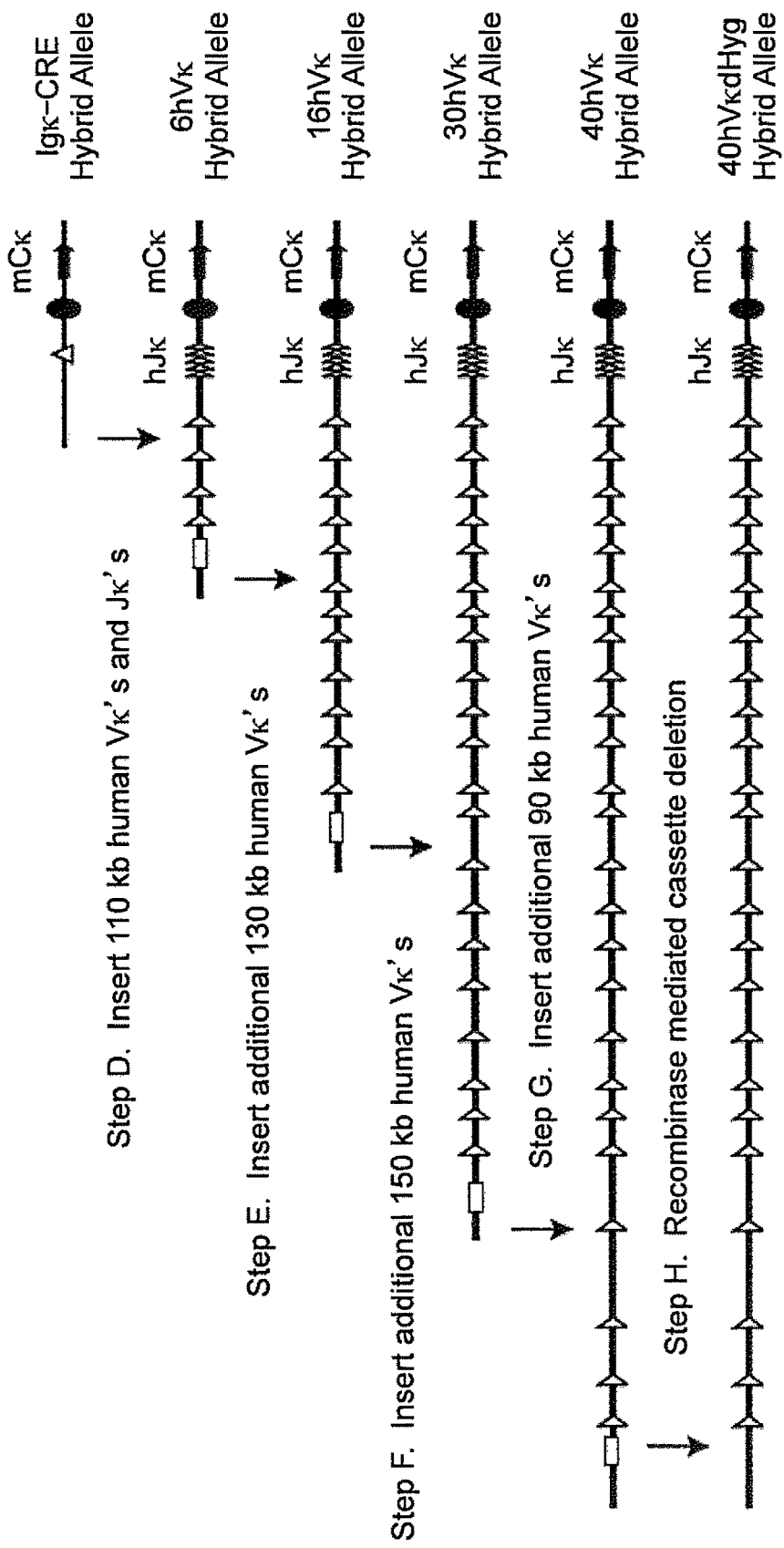
FIG. 2D shows a detailed illustration, not to scale, for 5 additional steps (D-H) for direct genomic replacement of the mouse immunoglobulin κ light chain variable gene locus that results in the insertion of all human Vκ and Jκ gene segments in the proximal repeat and deletion of the final selection cassette (40hVκdHyg Hybrid Allele). Human (open symbols) and mouse (closed symbols) immunoglobulin gene segments and additional selection cassettes (open rectangles) inserted by subsequent targeting vectors are shown.

A human genomic fragment of about 480 kb in size containing the entire immunoglobulin κ light chain variable region was inserted in four sequential steps (FIG. 2D; Tables 2 and 4), with up to 150 kb of human immunoglobulin κ light chain sequence inserted in a single step, using methods similar to those employed for the heavy chain (see Example 1). The final hygromycin resistance gene was removed by transient FLPe expression. As with the heavy chain, targeted ES cell clones were evaluated for integrity of the entire human insert, normal karyotype and germ-line potential after every step. Mice homozygous for each of the κ light chain chain alleles were generated and found to be healthy and of normal appearance.

TABLE 4

| Hybrid Allele | Human sequence | Targeting construct | Targeting efficiency | % usage | Total Vκ | Functional Vκ |
|---|---|---|---|---|---|---|
| Igκ-PC | 0 | 132 kb | 1.1% | — | — | — |
| Igκ-PC/DC | 0 | 90 kb | 0.4% | — | — | — |
| Igκ-CRE | 0 | — | 1% | — | — | — |
| 6hVκ | 110 kb | 122 kb | 0.3% | 14 | 6 | 4 |
| 16hVκ | 240 kb | 203 kb | 0.4% | 47 | 16 | 11 |
| 30hVκ | 390 kb | 193 kb | 0.1% | 70 | 30 | 18 |
| 40hVκ | 480 kb | 185 kb | 0.2% | 100 | 40 | 25 |
| 40hVκdHyg | 480 kb | — | 0.7% | 100 | 40 | 25 |

Example II

Figure 5A:
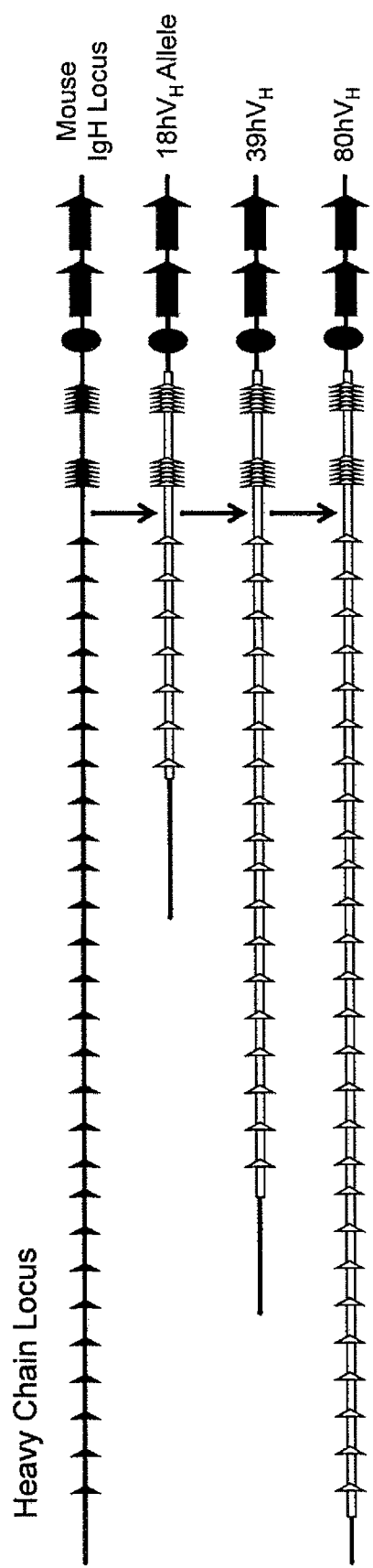
FIG. 5A shows a schematic illustration, not to scale, of sequential modifications of the mouse immunoglobulin heavy chain locus with increasing amounts of human immunoglobulin heavy chain gene segments. Homozygous mice were made from each of the three different stages of heavy chain humanization. Open symbols reflect human sequence; closed symbols reflect mouse sequence.
Figure 5B:
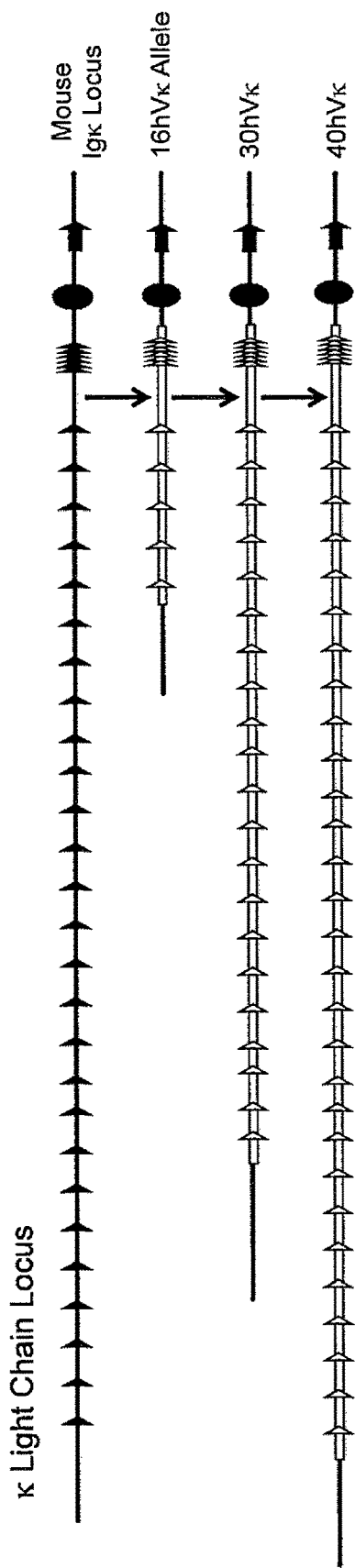
FIG. 5B shows a schematic illustration, not to scale, of sequential modifications of the mouse immunoglobulin κ light chain locus with increasing amounts of human immunoglobulin κ light chain gene segments. Homozygous mice were made from each of the three different stages of κ light chain humanization. Open symbols reflect human sequence; closed symbols reflect mouse sequence.

Generation of Fully Humanized Mice by Combination of Multiple Humanized Immunoglobulin Alleles At several points, ES cells bearing a portion of the human immunoglobulin heavy chain or κ light chain variable repertoires as described in Example 1 were microinjected and the resulting mice bred to create multiple versions of VELOCIMMUNE® humanized mice with progressively larger fractions of the human germline immunoglobulin repertoires (Table 5; FIGS. 5A and 5B). VELOCIMMUNE® 1 (V1) humanized mice possess 18 human $V_H$ gene segments and all of the human $D_H$ and $J_H$ gene segments combined with 16 human Vκ gene segments and all the human Jκ gene segments. VELOCIMMUNE® 2 (V2) humanized mice and VELOCIMMUNE® (V3) humanized mice have increased variable repertoires bearing a total of 39 $V_H$ and 30 Vκ, and 80 $V_H$ and 40 Vκ, respectively. Since the genomic regions encoding the mouse $V_H$, $D_H$ and $J_H$ gene segments, and Vκ and Jκ gene segments, have been completely replaced, antibodies produced by any version of VELOCIMMUNE® humanized mice contain human variable regions linked to mouse constant regions. The mouse λ light chain loci remain intact in all versions of the VELOCIMMUNE® humanized mice and serve as a comparator for efficiency of expression of the various VELOCIMMUNE® humanized κ light chain foci.

Mice doubly homozygous for both immunoglobulin heavy chain and κ light chain humanizations were generated from a subset of the alleles described in Example 1. All genotypes observed during the course of breeding to generate the doubly homozygous mice occurred in roughly Mendelian proportions. Male progeny homozygous for each of the human heavy chain alleles showed reduced fertility. Reduced fertility resulted from loss of mouse ADAM6 activity. The mouse heavy chain variable gene locus contains two embedded functional ADAM6 genes (ADAM6a and ADAM6b). During humanization of the mouse heavy chain variable gene locus, the inserted human genomic sequence contained an ADAM6 pseudogene. Mouse ADAM6 may be required for fertility, and thus lack of mouse ADAM6 genes in humanized heavy chain variable gene loci might lead to reduced fertility in these mice notwithstanding the presence of the human pseudogene.

Examples 7-9 describe the precise replacement of deleted mouse ADAM6 genes back into a humanized heavy chain variable gene locus, and restoration of a wild-type level of fertility in mice with a humanized heavy chain immunoglobulin locus.

TABLE 5

| Version of VELOCIMMUNE® Mouse | Heavy Chain | | | κ Light Chain | | |
|---|---|---|---|---|---|---|
| | Human $V_H$ | Allele | 5' $V_H$ gene | Human Vκ | Allele | 5' Vκ gene |
| V1 | 18 | 18h$V_H$ | $V_H$1-18 | 16 | 16hVκ | Vκ1-16 |
| V2 | 39 | 39h$V_H$ | $V_H$4-39 | 30 | 30hVκ | Vκ2-29 |
| V3 | 80 | 80h$V_H$ | $V_H$3-74 | 40 | 40hVκ | Vκ2-40 |

Example III

Lymphocyte Populations in Mice with Humanized Immunoglobulin Genes

Mature B cell populations in the three different versions of VELOCIMMUNE® mice were evaluated by flow cytometry.

Briefly, cell suspensions from bone marrow, spleen and thymus were made using standard methods. Cells were resuspended at 5×10⁵ cells/mL in BD Pharmingen FACS staining buffer, blocked with anti-mouse CD16/32 (BD Pharmingen), stained with the appropriate cocktail of antibodies and fixed with BD CYTOFIX™ all according to the manufacturer's instructions. Final cell pellets were resuspended in 0.5 mL staining buffer and analyzed using BD FACSCALIBUR™ and BD CELLQUEST PRO™ software. All antibodies (BD Pharmingen) were prepared in a mass dilution/cocktail and added to a final concentration of 0.5 mg/10⁵ cells. Antibody cocktails for bone marrow (A-D) staining were as follows: A: anti-mouse IgM$^b$-FITC, anti-mouse IgM$^a$-PE, anti-mouse CD45R(B220)-APC; B: anti-mouse CD43(S7)-PE, anti-mouse CD45R(B220)-APC; C: anti-mouse CD24(HSA)-PE; anti-mouse CD45R(B220)-APC; D: anti-mouse BP-1-PE, anti-mouse CD45R(B220)-APC. Antibody cocktails for spleen and inguinal lymph node (E-H) staining were as follows: E: anti-mouse IgM$^b$-FITC, anti-mouse IgM$^a$-PE, anti-mouse CD45R(B220)-APC; F: anti-mouse Ig, λ1, λ2, λ3 Light Chain-FITC, anti mouse Igκ Light Chain-PE, anti-mouse CD45R(B220)-APC; G: anti-mouse Ly6G/C-FITC, anti-mouse CD49b (DX5)-PE, anti-mouse CD11b-APC; H: anti-mouse CD4 (L3T4)-FITC, anti-mouse CD45R(B220)-PE, anti-mouse CD8a-APC. Results are shown in FIG. 6.

Figure 6:
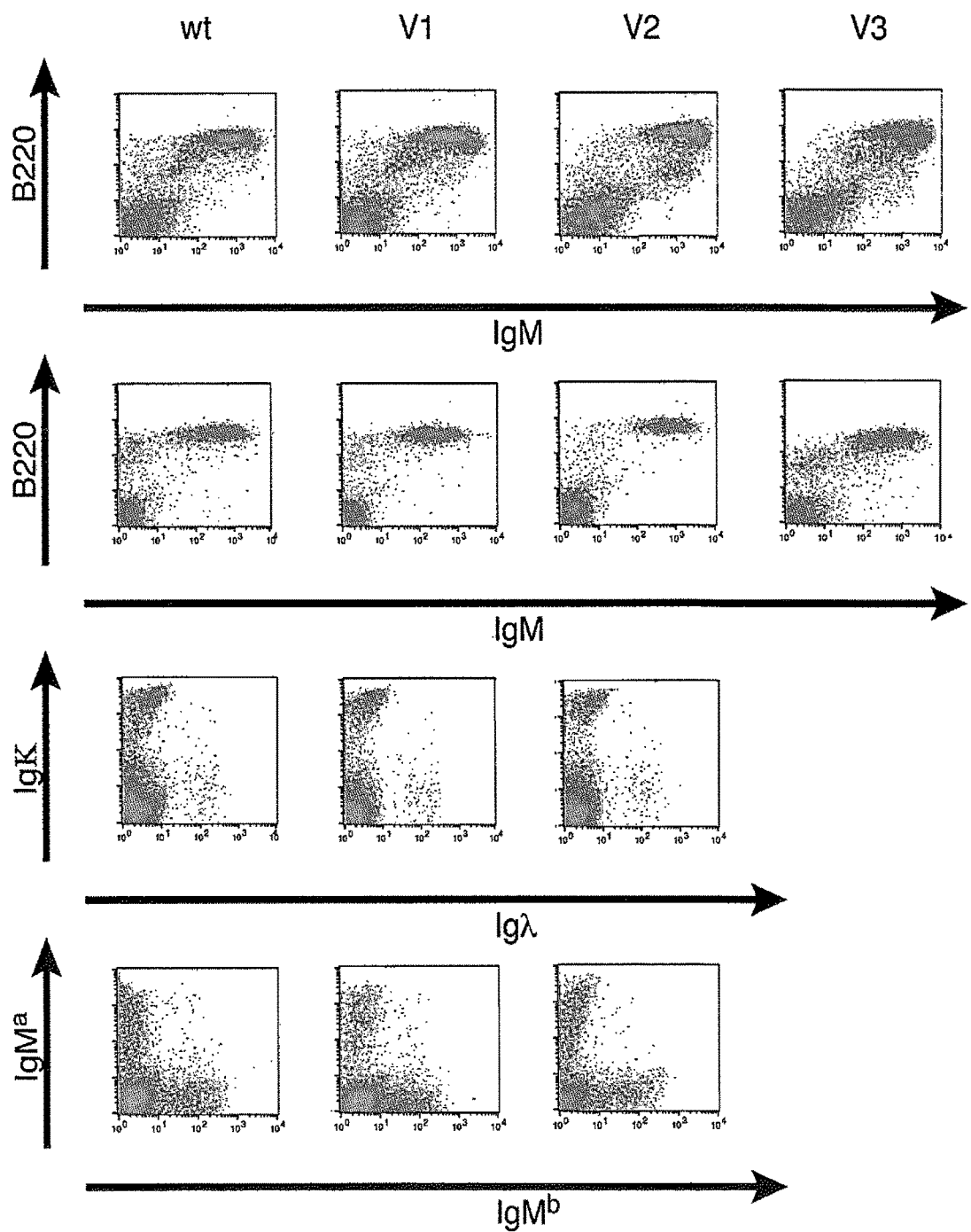
FIG. 6 shows FACS dot plots of B cell populations in wild type and VELOCIMMUNE® humanized mice. Cells from spleen (top row, third row from top and bottom row) or inguinal lymph node (second row from top) of wild type (wt) or VELOCIMMUNE® 1 (V1), VELOCIMMUNE® 2 (V2) or VELOCIMMUNE® 3 (V3) mice were stained for surface IgM expressing B cells (top row, and second row from top), surface immunoglobulin containing either κ or λ light chains (third row from top) or surface IgM of specific haplotypes (bottom row), and populations separated by FACS.

Lymphocytes isolated from spleen or lymph node of homozygous VELOCIMMUNE® humanized mice were stained for surface expression of the markers B220 and IgM and analyzed using flow cytometry (FIG. 6). The sizes of the B220⁺IgM⁺ mature B cell populations in all versions of VELOCIMMUNE® humanized mice tested were virtually identical to those of wild type mice, regardless of the number of $V_H$ gene segments they contained. In addition, mice containing homozygous hybrid humanized immunoglobulin heavy chain loci, even those with only 3 $V_H$ gene segments but normal mouse immunoglobulin κ light chain loci or mice containing homozygous hybrid humanized κ light chain loci with normal mouse immunoglobulin heavy chain loci, also had normal numbers of B220⁺IgM⁺ cells in their peripheral compartments (not shown). These results indicate that chimeric loci with human variable gene segments and mouse constant regions can fully populate the mature B cell compartment. Further, the number of variable gene segments at either the heavy chain or K light chain loci, and thus the theoretical diversity of the antibody repertoire, does not correlate with the ability to generate wild type populations of mature B cells. In contrast, mice with randomly integrated fully-human immunoglobulin transgenes and inactivated mouse immunoglobulin loci have reduced numbers of B cells in these compartments, with the severity of the deficit depending on the number of variable gene segments included in the transgene (Green, L. L., and Jakobovits, A. (1998) Regulation of B cell development by variable gene complexity in mice reconstituted with human immunoglobulin yeast artificial chromosomes, J Exp Med 188:483-495). This demonstrates that the "in situ genetic humanization" strategy results in a fundamentally different functional outcome than the randomly integrated transgenes achieved in the "knockout-plus-transgenic" approach.

Allelic Exclusion and Locus Choice.

The ability to maintain allelic exlusion was examined in mice heterozygous for different versions of the humanized immunoglobulin heavy chain locus.

The humanization of the immunoglobulin loci was carried out in an F1 ES line (F1H4 (Valenzuela et al., 2003)), derived from 129S6/SvEvTac and C57BL/6NTac heterozygous embryos. The human heavy chain germline variable gene sequences are targeted to the 12956 allele, which carries the IgM$^a$ haplotype, whereas the unmodified mouse C576BL/6N allele bears the IgM$^b$ haplotype. These allelic forms of IgM can be distinguished by flow cytometry using antibodies specific to the polymorphisms found in the IgM$^a$ or IgM$^b$ alleles. As shown in FIG. 6 (bottom row), the B cells identified in mice heterozygous for each version of the humanized heavy chain locus only express a single allele, either IgM$^a$ (the humanized allele) or IgM$^b$ (the wild type allele). This demonstrates that the mechanisms involved in allelic exclusion are intact in VELOCIMMUNE® humanized mice. In addition, the relative number of B cells positive for the humanized allele (IgM$^a$) is roughly proportional to the number of $V_H$ gene segments present. The humanized immunoglobulin locus is expressed in approximately 30% of the B cells in VELOCIMMUNE® 1 humanized heterozygote mice, which have 18 human $V_H$ gene segments, and in 50% of the B cells in VELOCIMMUNE® 2 and 3 (not shown) humanized heterozygote mice, with 39 and 80 human $V_H$ gene segments, respectively. Notably, the ratio of cells expressing the humanized versus wild type mouse allele (0.5 for VELOCIMMUNE® 1 humanized mice and 0.9 for VELOCIMMUNE® 2 humanized mice) is greater than the ratio of the number of variable gene segments contained in the humanized versus wild type loci (0.2 for VELOCIMMUNE® 1 humanized mice and 0.4 for VELOCIMMUNE® 2 humanized mice). This may indicate that the probability of allele choice is intermediate between a random choice of one or the other chromosome and a random choice of any particular V segment RSS. Further, there may be a fraction of B-cells, but not all, in which one allele becomes accessible for recombination, completes the process and shuts down recombination before the other allele becomes accessible. In addition, the even distribution of cells that have surface IgM (sIgM) derived from either the hybrid humanized heavy chain locus or the wild type mouse heavy chain locus is evidence that the hybrid locus is operating at a normal level. In contrast, randomly integrated human immunoglobulin transgenes compete poorly with wild type mouse immunoglobulin loci (Bruggemann, M., et al. (1989) A repertoire of monoclonal antibodies with human heavy chains from transgenic mice. PNAS 86, 6709-6713; Green et al. (1994); Tuaillon, N. et al (1993) Human immunoglobulin heavy-chain minilocus recombination in transgenic mice: gene-segment use in mu and gamma transcripts, Proc Natl Acad Sci USA 90:3720-3724). This further demonstrates the immunoglobulins produced by VELOCIMMUNE® humanized mice are functionally different than those produced by randomly integrated transgenes in mice made by "knockout-plus-transgenic" approaches.

Polymorphisms of the Cκ regions are not available in 129S6 or C57BL/6N to examine allelic exclusion of humanized versus non-humanized κ light chain loci. However, VELOCIMMUNE® humanized mice all possess wild type mouse λ light chain loci, therefore, it is possible to observe whether rearrangement and expression of humanized κ light chain loci can prevent mouse λ light chain expression. The ratio of the number of cells expressing the humanized κ light chain relative to the number of cells expressing mouse λ light chain was relatively unchanged in VELOCIMMUNE® humanized mice compared with wild type mice, regardless of the number of human Vκ gene segments inserted at the κ light chain locus (FIG. 6, third row from top). In addition there was no increase in the number of double positive (κ plus λ) cells, indicating that productive recombination at the hybrid κ light chain loci results in appropriate suppression of recombination of the mouse λ light chain loci. In contrast, mice containing randomly integrated κ light chain transgenes with inactivated mouse κ light chain loci—but wild type mouse λ light chain loci—exhibit dramatically increased λ/κ ratios (Jakobovits, 1998), implying that the introduced κ light chain transgenes do not function well in such mice. This further demonstrates the different functional outcome observed in immunoglobulins made by VELOCIMMUNE® humanized mice as compared to those made by "knockout-plus-transgenic" mice.

B Cell Development.

Because the mature B cell populations in VELOCIMMUNE® humanized mice resemble those of wild type mice (described above), it is possible that defects in early B cell differentiation are compensated for by the expansion of mature B cell populations. The various stages of B cell differentiation were examined by analysis of B cell populations using flow cytometry. Table 6 sets forth the ratio of the fraction of cells in each B cell lineage defined by FACs, using specific cell surface markers, in VELOCIMMUNE® humanized mice compared to wild type littermates.

Early B cell development occurs in the bone marrow, and different stages of B cell differentiation are characterized by changes in the types and amounts of cell surface marker expression. These differences in surface expression correlate with the molecular changes occurring at the immunoglobulin loci inside the cell. The pro-B to pre-B cell transition requires the successful rearrangement and expression of functional heavy chain protein, while transition from the pre-B to mature B stage is governed by the correct rearrangement and expression of a κ or λ light chain. Thus, inefficient transition between stages of B cell differentiation can be detected by changes in the relative populations of B cells at a given stage.

TABLE 6

| Version of VELOCIMMUNE ® Mice | Bone Marrow | | | | Spleen | |
|---|---|---|---|---|---|---|
| | | | | | Emerging | |
| | pro-B $CD43^{hi}$ $B220^{lo}$ | pre-B $CD24^{hi}$ $B220^{lo}$ | Immature $B220^{lo}$ $IgM^+$ | Mature $B220^{hi}$ $IgM^+$ | $B220^{hi}$ $IgM^+$ $IgD^+$ | Mature B220hi IgM+ |
| V1 | 1.1 | 1.0 | 0.9 | 1.0 | 1.1 | 1.0 |
| V2 | 1.0 | 1.0 | 1.0 | 1.0 | 1.0 | 1.0 |
| V3 | 1.0 | 1.0 | 1.1 | 1.0 | 1.0 | 1.1 |

No major defects were observed in B cell differentiation in any of the VELOCIMMUNE® humanized mice. The introduction of human heavy chain gene segments does not appear to affect the pro-B to pre-B transition, and introduction of human κ light chain gene segments does not affect the pre-B to B transition in VELOCIMMUNE® humanized mice. This demonstrates that "reverse chimeric" immunoglobulin molecules possessing human variable regions and mouse constants function normally in the context of B cell signaling and co-receptor molecules leading to appropriate B cell differentiation in a mouse environment. In contrast, the balance between the different populations during B cell differentiation are perturbed to varying extents in mice that contain randomly integrated immunoglobulin transgenes and inactivated endogenous heavy chain or κ light chain loci (Green and Jakobovits (1998)).

Example IV

Variable Gene Repertoire in Humanized Immunoglobulin Mice

Usage of human variable gene segments in the humanized antibody repertoire of VELOCIMMUNE® humanized mice was analyzed by reverse transcriptase-polymerase chain reaction (RT-PCR) of human variable regions from multiple sources including splenocytes and hybridoma cells. Variable region sequence, gene segment usage, somatic hypermutation, and junctional diversity of rearranged variable region gene segments were determined.

Briefly, total RNA was extracted from $1 \times 10^7$-$2 \times 10^7$ splenocytes or about $10^4$-$10^5$ hybridoma cells using TRIZOL™ (Invitrogen) or Qiagen RNEASY™ Mini Kit (Qiagen) and primed with mouse constant region specific primers using the SUPERSCRIPT™ III One-Step RT-PCR system (Invitrogen). Reactions were carried out with 2-5 µL of RNA from each sample using the aforementioned 3' constant specific primers paired with pooled leader primers for each family of human variable regions for both the heavy chain and κ light chain, separately. Volumes of reagents and primers, and RT-PCR/PCR conditions were performed according to the manufacturer's instructions. Primers sequences were based upon multiple sources (Wang, X. and Stollar, B. D. (2000) Human immunoglobulin variable region gene analysis by single cell RT-PCR, J Immunol Methods 244:217-225; Ig-primer sets, Novagen). Where appropriate, nested secondary PCR reactions were carried out with pooled family-specific framework primers and the same mouse 3' immunoglobulin constant-specific primer used in the primary reaction. Aliquots (5 µL) from each reaction were analyzed by agarose electrophoresis and reaction products were purified from agarose using a MONTAGE™ Gel Extraction Kit (Millipore). Purified products were cloned using the TOPO™ TA Cloning System (Invitrogen) and transformed into DH10β E. coli cells by electroporation. Individual clones were selected from each transformation reaction and grown in 2 mL LB broth cultures with antibiotic selection overnight at 37° C. Plasmid DNA was purified from bacterial cultures by a kit-based approach (Qiagen).

Immunoglobulin Variable Gene Usage.

Plasmid DNA of both heavy chain and κ light chain clones were sequenced with either T7 or M13 reverse primers on the ABI 3100 Genetic Analyzer (Applied Biosystems). Raw sequence data were imported into SEQUENCHER™ (v4.5, Gene Codes). Each sequence was assembled into contigs and aligned to human immunoglobulin sequences using IMGT V-Quest (Brochet, X. et al., (2008) IMGT/V-QUEST: the highly customized and integrated system for IG and TR standardized V-J and V-D-J sequence analysis. Nucleic Acids Res 36:W503-508) search function to identify human $V_H$, $D_H$, $J_H$ and Vκ, Jκ segment usage. Sequences were compared to germline sequences for somatic hypermutation and recombination junction analysis.

Mice were generated from ES cells containing the initial heavy chain modification ($3hV_H$-CRE Hybrid Allele, bottom of FIG. 2A) by RAG complementation (Chen, J. et al. (1993) RAG-2-deficient blastocyst complementation: an assay of gene function in lymphocyte development, Proc Natl Aced Sci USA 90:4528-4532), and cDNA was prepared from splenocyte RNA. The cDNA was amplified using primer sets (described above) specific for the predicted chimeric heavy chain mRNA that would arise by V(D)J recombination within the inserted human gene segments and subsequent splicing to either mouse IgM or IgG constant domains. Sequences derived from these cDNA clones (not shown) demonstrated that proper V(D)J recombination had occurred within the human variable gene sequences, that the rearranged human V(D)J gene segments were properly spliced in-frame to mouse constant domains and that class-switch recombination had occurred. Further sequence analysis of mRNA products of subsequent hybrid immunoglobulin loci was performed.

In a similar experiment, B cells from non-immunized wild type and VELOCIMMUNE® humanized mice were separated by flow cytometry based upon surface expression of B220 and IgM or IgG. The $B220^+IgM^+$ or surface $IgG^+$ ($sIgG^+$) cells were pooled and $V_H$ and Vκ sequences were obtained following RT-PCR amplification and cloning (described above). Representative gene usage in a set of RT-PCR amplified cDNAs from unimmunized VELOCIMMUNE® 1 humanized mice (Table 7) and VELOCIMMUNE® 3 humanized mice (Table 8) was recorded (*defective RSS; \missing or pseudogene).

TABLE 7

| $V_H$ | Observed |
|---|---|
| 1-18 | 3 |
| 1-17P | 0 |
| 3-16* | 0 |
| 3-15 | 13 |
| 3-13 | 9 |
| 3-11 | 6 |
| 3-9 | 8 |
| 1-8 | 6 |
| 3-7 | 2 |
| 2-5 | 2 |
| 1-3 | 0 |
| 1-2 | 11 |
| 6-1 | 5 |

| $J_H$ | Observed |
|---|---|
| 1 | 2 |
| 2 | 1 |
| 3 | 8 |
| 4 | 33 |
| 5 | 5 |
| 6 | 16 |

| $D_H$ | Observed |
|---|---|
| 1-1 | 1 |
| 2-2 | 2 |
| 3-3 | 4 |
| 4-4 | 0 |
| 5-5 | 0 |
| 5-18 | 4 |
| 6-6 | 5 |
| 1-7 | 7 |
| 2-8 | 0 |
| 3-9 | 4 |
| 3-10 | 2 |
| 4-11 | 1 |
| 5-12 | 1 |
| 6-13 | 3 |
| 1-14 | 0 |
| 2-15 | 0 |
| 3-16 | 1 |
| 4-17 | 0 |
| 6-19 | 2 |
| 1-20 | 2 |
| 2-21 | 1 |
| 3-22 | 0 |
| 4-23 | 2 |
| 5-24 | 1 |
| 6-25 | 1 |
| 1-26 | 6 |
| 7-27 | 10 |

| Vκ | Observed |
|---|---|
| 1-16 | 2 |
| 3-15 | 1 |
| 1-12 | 5 |
| 3-11 | 1 |
| 1-9 | 5 |
| 1-8 | 2 |
| 3-7* | 0 |
| 1-6 | 5 |
| 1-5 | 8 |
| 5-2 | 6 |
| 4-1 | 8 |

| Jκ | Observed |
|---|---|
| 1 | 12 |
| 2 | 10 |
| 3 | 5 |
| 4 | 10 |
| 5 | 0 |

TABLE 8

| $V_H$ | Observed |
|---|---|
| 7-81† | 0 |
| 3-74† | 0 |
| 3-73 | 1 |
| 3-72 | 2 |
| 2-70 | 2 |
| 1-69 | 3 |
| 3-66 | 1 |
| 3-64 | 1 |
| 4-61 | 1 |
| 4-59 | 10 |
| 1-58 | 0 |
| 3-53 | 0 |
| 5-51 | 5 |
| 3-49 | 2 |
| 3-48 | 7 |
| 1-46 | 1 |
| 1-45 | 0 |
| 3-43 | 10 |
| 4-39 | 4 |
| 3-38* | 0 |
| 3-35* | 0 |
| 4-34 | 8 |
| 3-33 | 14 |
| 4-31 | 4 |
| 3-30 | 13 |
| 4-28 | 0 |
| 2-26 | 0 |
| 1-24 | 3 |
| 3-23 | 18 |
| 3-21 | 0 |
| 3-20 | 0 |
| 1-18 | 4 |
| 1-17P | 1 |
| 3-16* | 0 |
| 3-15 | 13 |
| 3-13 | 6 |
| 3-11 | 5 |
| 3-9 | 31 |
| 1-8 | 7 |
| 3-7 | 11 |
| 2-5 | 1 |
| 1-3 | 0 |
| 1-2 | 6 |
| 6-1 | 9 |

| $D_H$ | Observed |
|---|---|
| 1-1 | 7 |
| 2-2 | 8 |
| 3-3 | 9 |
| 4-4 | 4 |
| 5-5 | 6 |
| 5-18 | 6 |
| 6-6 | 29 |
| 1-7 | 30 |
| 2-8 | 4 |
| 3-9 | 8 |
| 3-10 | 10 |
| 4-11 | 4 |
| 5-12 | 5 |
| 6-13 | 17 |
| 1-14 | 2 |
| 2-15 | 3 |
| 3-16 | 4 |
| 4-17 | 3 |
| 6-19 | 8 |
| 1-20 | 3 |
| 2-21 | 1 |
| 3-22 | 5 |
| 4-23 | 2 |
| 5-24 | 2 |
| 6-25 | 2 |
| 1-26 | 17 |
| 7-27 | 7 |

| $J_H$ | Observed |
|---|---|
| 1 | 2 |
| 2 | 8 |
| 3 | 26 |
| 4 | 95 |
| 5 | 11 |
| 6 | 58 |

| Vκ | Observed |
|---|---|
| 2-40 | 1 |
| 1-39 | 34 |
| 1-37 | 2 |
| 1-33 | 35 |
| 2-30 | 8 |
| 2-29 | 2 |
| 2-28 | 7 |
| 1-27 | 5 |
| 2-24 | 7 |
| 6-21* | 3 |
| 3-20 | 10 |
| 1-17 | 13 |
| 1-16 | 10 |
| 3-15 | 13 |
| 1-12 | 13 |
| 3-11 | 13 |
| 1-9 | 11 |
| 1-8 | 1 |
| 3-7* | 0 |
| 1-6 | 6 |
| 1-5 | 7 |
| 5-2 | 0 |
| 4-1 | 21 |

| Jκ | Observed |
|---|---|
| 1 | 50 |
| 2 | 37 |
| 3 | 28 |
| 4 | 64 |
| 5 | 22 |

As shown in Tables 7 and 8, nearly all of the functional human $V_H$, $D_H$, $J_H$, Vκ and Jκ gene segments are utilized. Of the functional variable gene segments described but not detected in the VELOCIMMUNE® humanized mice of this experiment, several have been reported to possess defective recombination signal sequences (RSS) and, thus, would not be expected to be expressed (Feeney, A. J. (2000) Factors that influence formation of B cell repertoire. Immunol Res 21:195-202). Analysis of several other sets of immunoglobulin sequences from various VELOCIMMUNE® humanized mice, isolated from both naïve and immunized repertoires, has shown usage of these gene segments, albeit at lower frequencies (data not shown). Aggregate gene usage data has shown that all functional human $V_H$, Vκ, and Jκ gene segments contained in VELOCIMMUNE® humanized mice have been observed in various naïve and immunized repertoires (data not shown). Although the human $V_H$7-81 gene segment has been identified in the analysis of human heavy chain locus sequences (Matsuda, F. et al., (1998) The complete nucleotide sequence of the human immunoglobulin heavy chain variable region locus, J Exp Med 188:2151-2162), it is not present in the VELOCIMMUNE® humanized mice as confirmed by re-sequencing of the entire VELOCIMMUNE® 3 humanized mouse genome.

Sequences of heavy and light chains of antibodies are known to show exceptional variability, especially in short polypeptide segments within the rearranged variable domain. These regions, known as hypervariable regions or complementary determining regions (CDRs) create the binding site for antigen in the structure of the antibody molecule. The intervening polypeptide sequences are called framework regions (FRs). There are three CDRs (CDR1, CDR2, CDR3) and 4 FRs (FR1, FR2, FR3, FR4) in both heavy and light chains. One CDR, CDR3, is unique in that this CDR is created by recombination of both the $V_H$, $D_H$ and $J_H$ and Vκ and Jκ gene segments and generates a significant amount of repertoire diversity before antigen is encountered. This joining is imprecise due to both nucleotide deletions via exonuclease activity and non-template encoded additions via terminal deoxynucleotidyl transferase (TdT) and, thus, allows for novel sequences to result from the recombination process. Although FRs can show substantial somatic mutation due to the high mutability of the variable region as a whole, variability is not, however, distributed evenly across the variable region. CDRs are concentrated and localized regions of high variability in the surface of the antibody molecule that allow for antigen binding. Heavy chain and light chain sequences of selected antibodies from VELOCIMMUNE® humanized mice around the CDR3 junction demonstrating junctional diversity are shown in FIGS. 7A and 7B, respectively.

As shown in FIG. 7A, non-template encoded nucleotide additions (N-additions) are observed at both the $V_H$-$D_H$ and $D_H$-$J_H$ joint in antibodies from VELOCIMMUNE® humanized mice, indicating proper function of TdT with the human segments. The endpoints of the $V_H$, $D_H$ and $J_H$ segments relative to their germline counterparts indicate that exonuclease activity has also occurred. Unlike the heavy chain locus, the human κ light chain rearrangements exhibit little or no TdT additions at CDR3, which is formed by the recombination of the Vκ and Jκ segments (FIG. 7B). This is expected due to the lack of TdT expression in mice during light chain rearrangements at the pre-B to B cell transition. The diversity observed in the CDR3 of rearranged human Vκ regions is introduced predominantly through exonuclease activity during the recombination event.

Somatic Hypermutation.

Additional diversity is added to the variable regions of rearranged immunoglobulin genes during the germinal center reaction by a process termed somatic hypermutation. B cells expressing somatically mutated variable regions compete with other B cells for access to antigen presented by the follicular dendritic cells. Those B cells with higher affinity for the antigen will further expand and undergo class switching before exiting to the periphery. Thus, B cells expressing switched isotypes typically have encountered antigen and undergone germinal center reactions and will have increased numbers of mutations relative to naïve B cells. Further, variable region sequences from predominantly naïve sIgM$^+$ B cells would be expected to have relatively fewer mutations than variable sequences from sIgG$^+$ B cells which have undergone antigen selection.

Sequences from random $V_H$ or Vκ clones from sIgM$^+$ or sIgG$^+$ B cells from non-immunized VELOCIMMUNE® humanized mice or sIgG$^+$ B cells from immunized mice were compared with their germline variable gene segments and changes relative to the germline sequence annotated. The resulting nucleotide sequences were translated in silico and mutations leading to amino acid changes also annotated. The data were collated from all the variable regions and the percent change at a given position was calculated (FIG. 8).

Figure 8:
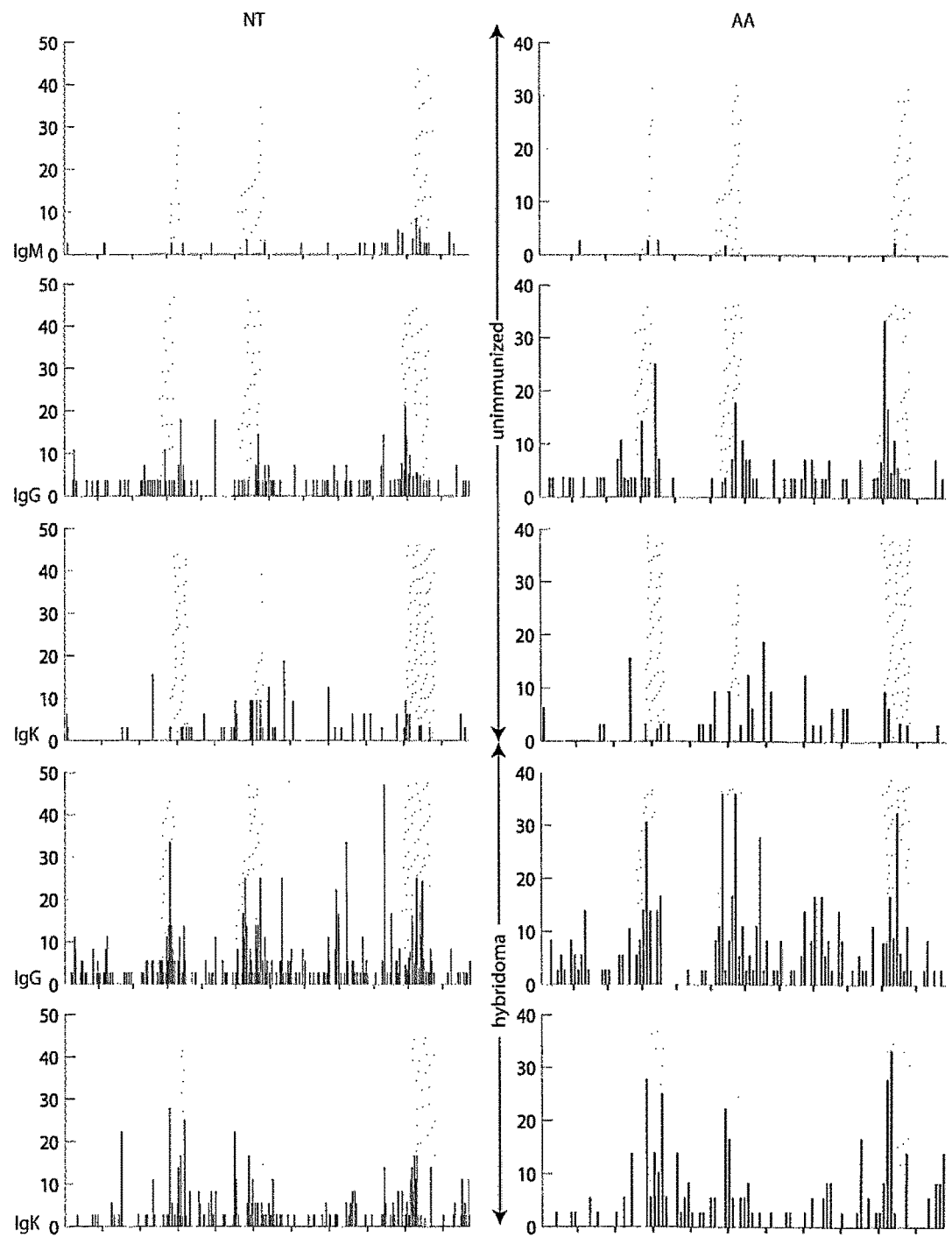
FIG. 8 shows somatic hypermutation frequencies of heavy and light chains of VELOCIMMUNE® antibodies scored (after alignment to matching germline sequences) as percent of sequences changed at each nucleotide (NT; left column) or amino acid (AA; right column) position among sets of 38 (unimmunized IgM), 28 (unimmunized IgG), 32 (unimmunized Igκ from IgG), 36 (immunized IgG) or 36 (immunized Igκ from IgG) sequences. Shaded bars indicate the locations of CDRs.

As shown in FIG. 8, human heavy chain variable regions derived from sIgG$^+$ B cells from non-immunized VELOCIMMUNE® humanized mice exhibit many more nucleotides relative to sIgM$^+$ B cells from the same splenocyte pools, and heavy chain variable regions derived from immunized mice exhibit even more changes. The number of changes is increased in the complementarity-determining regions (CDRs) relative to the framework regions, indicating antigen selection. The corresponding amino acid sequences from the human heavy chain variable regions also exhibit significantly higher numbers of mutations in IgG vs IgM and even more in immunized IgG. These mutations again appear to be more frequent in the CDRs compared with the framework sequences, suggesting that the antibodies were antigen-selected in vivo. A similar increase in the number the nucleotide and amino acid mutations are seen in the Vκ sequences derived from IgG$^+$ B cells from immunized mice.

The gene usage and somatic hypermutation observed in VELOCIMMUNE® humanized mice demonstrate that essentially all gene segments present are capable of rearrangement to form fully functionally reverse chimeric antibodies in these mice. Further, VELOCIMMUNE® humanized mouse derived antibodies fully participate within the mouse immune system to undergo affinity selection and maturation to create fully mature human antibodies that can effectively neutralize their target antigen. VELOCIMMUNE® humanized mice are able to mount robust immune responses to multiple classes of antigens that result in usage of a wide range of human antibodies that are both high affinity and suitable for therapeutic use (data not shown).

Example V

Analysis of Lymphoid Structure and Serum Isotypes

The gross structures of spleen, inguinal lymph nodes, Peyer's patches and thymus of tissue samples from wild type or VELOCIMMUNE® humanized mice stained with H&E were examined by light microscopy. The levels of immunoglobulin isotypes in serum collected from wild-type and VELOCIMMUNE® humanized mice were analyzed using LUMINEx™ technology.

Lymphoid Organ Structure.

The structure and function of the lymphoid tissues are in part dependent upon the proper development of hematopoietic cells. A defect in B cell development or function may be exhibited as an alteration in the structure of the lymphoid tissues. Upon analysis of stained tissue sections, no significant difference in appearance of secondary lymphoid organs between wild type and VELOCIMMUNE® humanized mice was identified (data not shown).

Serum Immunoglobulin Levels.

Figure 9A:
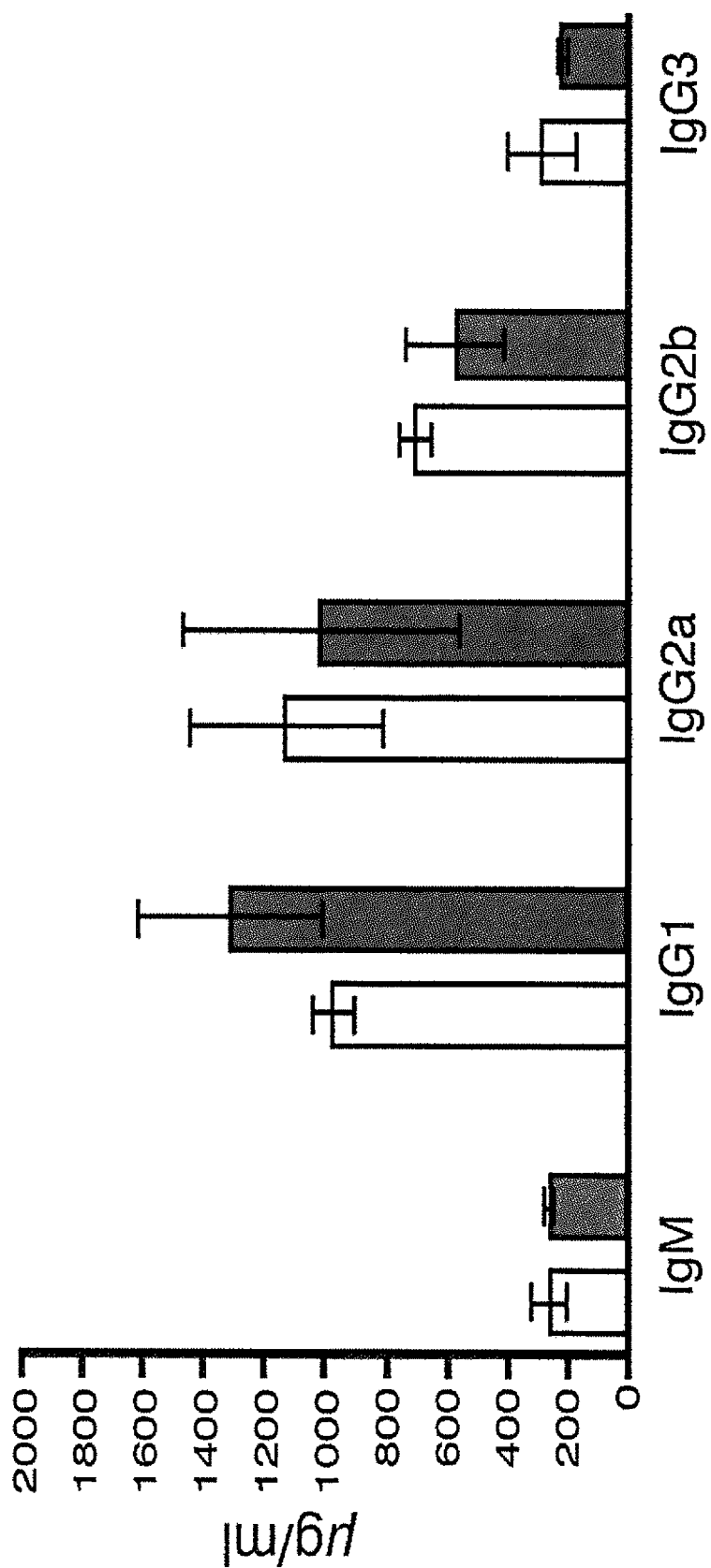
FIG. 9A shows levels of serum immunoglobulin for IgM and IgG isotypes in wild type (open bars) or VELOCIMMUNE® mice (closed bars).
Figure 9C:
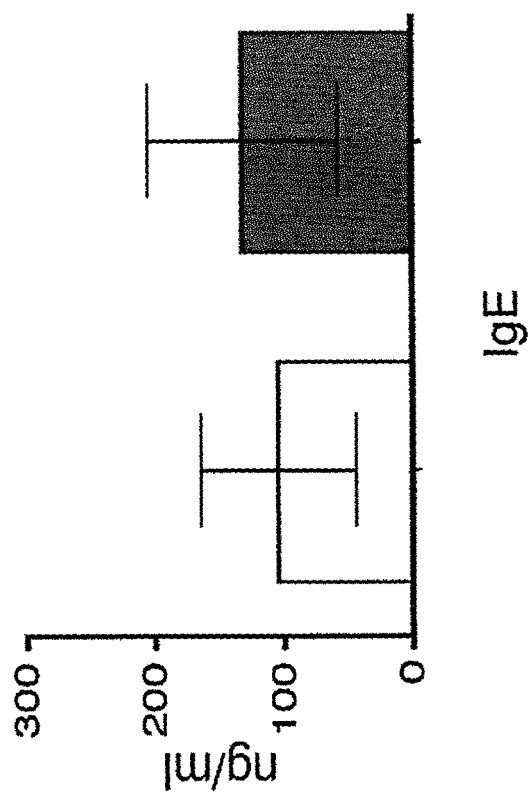
FIG. 9C shows levels of serum immunoglobulin for IgE isotype in wild type (open bars) or VELOCIMMUNE® mice (closed bars).

The level of expression of each isotype is similar in wild type and VELOCIMMUNE® humanized mice (FIGS. 9A, 9B and 9C). This demonstrates that humanization of the variable gene segments had no apparent adverse effect upon class switching or immunoglobulin expression and secretion and therefore apparently maintain all the endogenous mouse sequences necessary for these functions.

Example VI

Immunization and Antibody Production in Humanized Immunoglobulin Mice

Different versions of VELOCIMMUNE® humanized mice were immunized with antigen to examine the humoral response to foreign antigen challenge.

Immunization and Hybridoma Development.

VELOCIMMUNE® humanized and wild-type mice can be immunized with an antigen in the form of protein, DNA, a combination of DNA and protein, or cells expressing the antigen. Animals are typically boosted every three weeks for a total of two to three times. Following each antigen boost, serum samples from each animal are collected and analyzed for antigen-specific antibody responses by serum titer determination. Prior to fusion, mice received a final pre-fusion boost of 5 µg protein or DNA, as desired, via intra-peritoneal and/or intravenous injections. Splenocytes are harvested and fused to Ag8.653 myeloma cells in an electrofusion chamber according to the manufacture's suggested protocol (Cyto Pulse Sciences Inc., Glen Burnie, Md.). Ten days after culture, hybridomas are screened for antigen specificity using an ELISA assay (Harlow, E. and Lane, D. (1988) Antibodies: A Laboratory Manual. Cold Spring Harbor Press, New York). Alternatively, antigen specific B cells are isolated directly from immunized VELOCIMMUNE® humanized mice and screened using standard techniques, including those described here, to obtain human antibodies specific for an antigen of interest.

Serum Titer Determination.

To monitor animal anti-antigen serum response, serum samples are collected about 10 days after each boost and the titers are determined using antigen specific ELISA. Briefly, Nunc MAXISORP™ 96 well plates are coated with 2 µg/mL antigen overnight at 4° C. and blocked with bovine serum albumin (Sigma, St. Louis, Mo.). Serum samples in a serial 3 fold dilutions are allowed to bind to the plates for one hour at room temperature. The plates are then washed with PBS containing 0.05% Tween-20 and the bound IgG are detected using HRP-conjugated goat anti-mouse Fc (Jackson Immuno Research Laboratories, Inc., West Grove, Pa.) for total IgG titer, or biotin-labeled isotype specific or light chain specific polyclonal antibodies (SouthernBiotech Inc.) for isotype specific titers, respectively. For biotin-labeled antibodies, following plate wash, HRP-conjugated streptavidin (Pierce, Rockford, Ill.) is added. All plates are developed using colorimetric substrates such as BD OPTEIA™ (BD Biosciences Pharmingen, San Diego, Calif.). After the reaction is stopped with 1 M phosphoric acid, optical absorptions at 450 nm are recorded and the data are analyzed using PRISM™ software from Graph Pad. Dilutions required to obtain two-fold of background signal are defined as titer.

In one experiment, VELOCIMMUNE® humanized mice were immunized with human interleukin-6 receptor (hIL-6R). A representative set of serum titers for VELOCIMMUNE® and wild type mice immunized with hIL-6R is shown in FIGS. 10A and 10B.

Figure 10A:
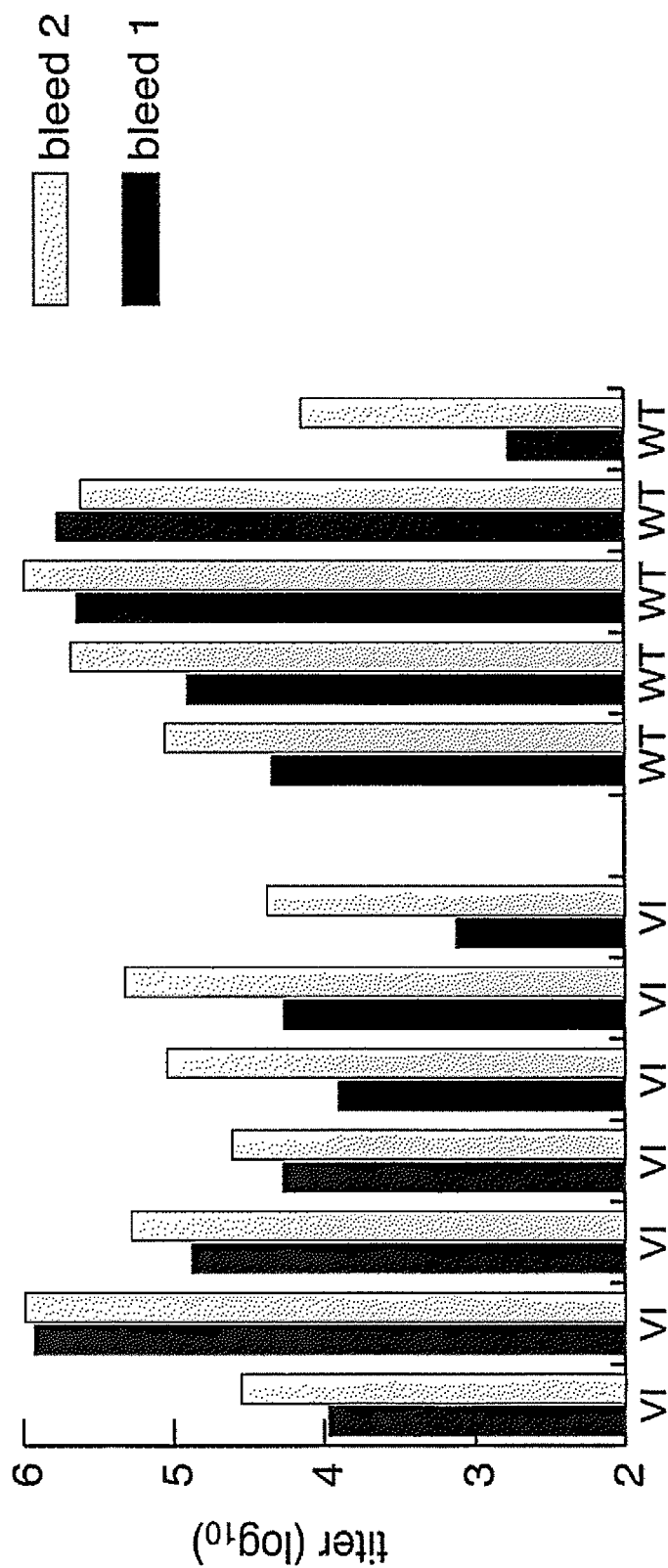
FIG. 10A shows antigen specific IgG titers against interleukin-6 receptor of serum from seven VELOCIMMUNE® (VI) and five wild type (WT) mice after two (bleed 1) or three (bleed 2) rounds of immunization with interleukin-6 receptor ectodomain.
Figure 10B:
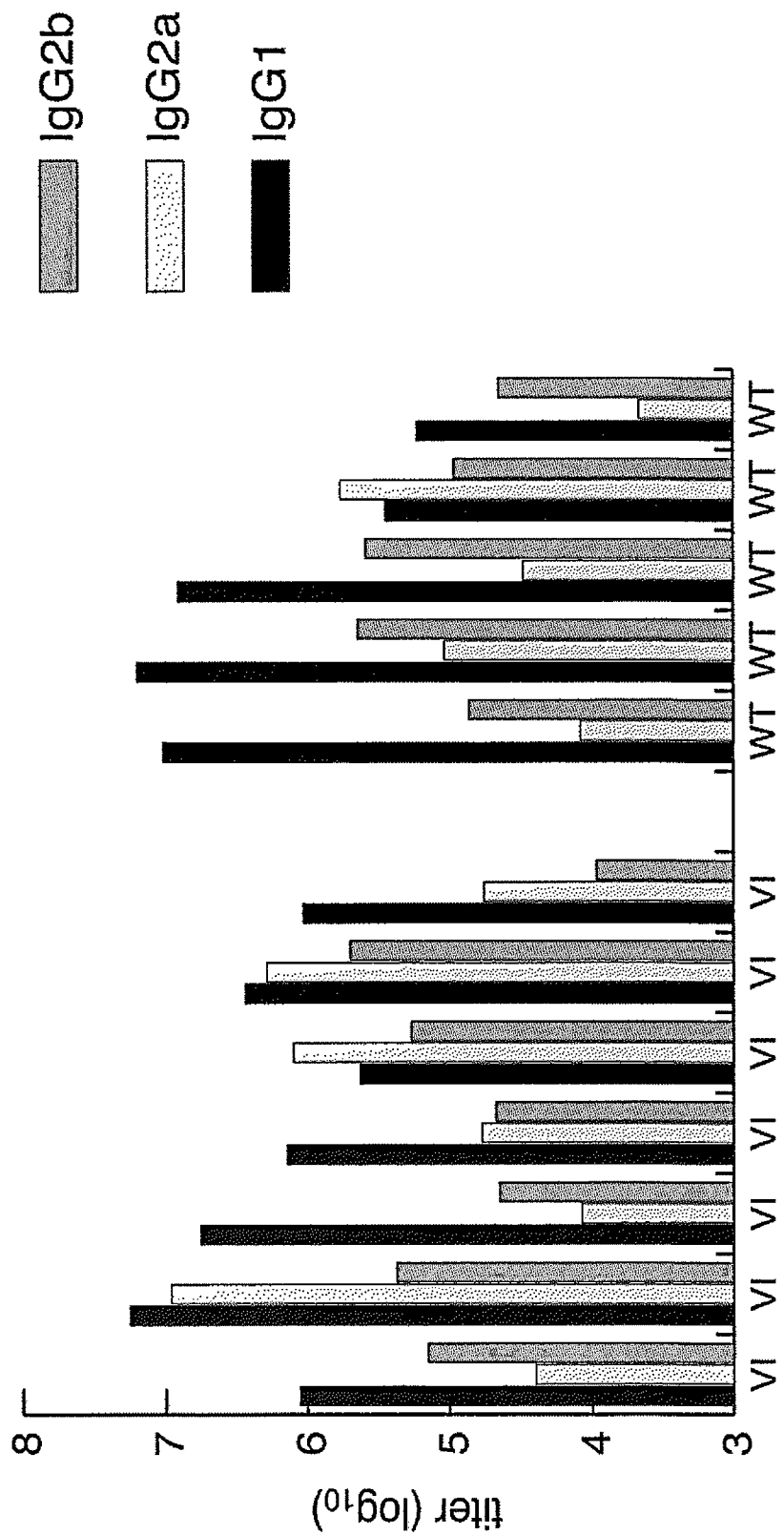
FIG. 10B shows anti-interleukin-6 receptor-specific IgG isotype-specific titers from seven VELOCIMMUNE® (VI) and five wild type (WT) mice.

VELOCIMMUNE® humanized and wild-type mice mounted strong responses towards the IL-6R with similar titer ranges (FIG. 10A). Several mice from the VELOCIMMUNE® humanized and wild-type cohorts reached a maximal response after a single antigen boost. These results indicate that the immune response strength and kinetics to this antigen were similar in the VELOCIMMUNE® humanized and wild type mice. These antigen-specific antibody responses were further analyzed to examine the particular isotypes of the antigen-specific antibodies found in the sera. Both VELOCIMMUNE® humanized and wild type groups predominantly elicited an IgG1 response (FIG. 10B), suggesting that class switching during the humoral response is similar in mice of each type.

Affinity Determination of Antibody Binding to Antigen in Solution.

An ELISA-based solution competition assay is typically designed to determine antibody-binding affinity to the antigen.

Briefly, antibodies in conditioned medium are premixed with serial dilutions of antigen protein ranging from 0 to 10 mg/mL. The solutions of the antibody and antigen mixture are then incubated for two to four hours at room temperature to reach binding equilibria. The amounts of free antibody in the mixtures are then measured using a quantitative sandwich ELISA. Ninety-six well MAISORB™ plates (VWR, West Chester, Pa.) are coated with 1 µg/mL antigen protein in PBS solution overnight at 4° C. followed by BSA nonspecific blocking. The antibody-antigen mixture solutions are then transferred to these plates followed by one-hour incubation. The plates are then washed with washing buffer and the plate-bound antibodies were detected with an HRP-conjugated goat anti-mouse IgG polyclonal antibody reagent (Jackson Immuno Research Lab) and developed using colorimetric substrates such as BD OPTEIA™ (BD Biosciences Pharmingen, San Diego, Calif.). After the reaction is stopped with 1 M phosphoric acid, optical absorptions at 450 nm are recorded and the data are analyzed using PRISM™ software from Graph Pad. The dependency of the signals on the concentrations of antigen in solution are analyzed with a 4 parameter fit analysis and reported as $IC_{50}$, the antigen concentration required to achieve 50% reduction of the signal from the antibody samples without the presence of antigen in solution.

In one experiment, VELOCIMMUNE® humanized mice were immunized with hIL-6R (as described above). FIGS. 11A and 11B show a representative set of affinity measurements for anti-hIL6R antibodies from VELOCIMMUNE® humanized and wild-type mice.

After immunized mice receive a third antigen boost, serum titers are determined by ELISA. Splenocytes are isolated from selected wild type and VELOCIMMUNE® humanized mouse cohorts and fused with Ag8.653 myeloma cells to form hybridomas and grown under selection (as described above). Out of a total of 671 anti-IL-6R hybridomas produced, 236 were found to express antigen-specific antibodies. Media harvested from antigen positive wells was used to determine the antibody affinity of binding to antigen using a solution competition ELISA. Antibodies derived from VELOCIMMUNE® humanized mice exhibit a wide range of affinity in binding to antigen in solution (FIG. 11A). Furthermore, 49 out of 236 anti-IL-6R hybridomas were found to block IL-6 from binding to the receptor in an in vitro bioassay (data not shown). Further, these 49 anti-IL-6R blocking antibodies exhibited a range of high solution affinities similar to that of blocking antibodies derived from the parallel immunization of wild type mice (FIG. 11B).

Example VII

Construction of a Mouse ADAM6 Targeting Vector

A targeting vector for insertion of mouse ADAM6a and ADAM6b genes into a humanized heavy chain locus was constructed using VELOCIGENE® genetic engineering technology (supra) to modify a Bacterial Artificial Chromosome (BAC) 929d24 obtained from Dr. Fred Alt (Havard University). 929d24 BAC DNA was engineered to contain genomic fragments containing the mouse ADAM6a and ADAM6b genes and a hygromycin cassette for targeted deletion of a human ADAM6 pseudogene (hADAM6Ψ) located between human $V_H1-2$ and $V_H6-1$ gene segments of a humanized heavy chain locus (FIG. 12).

First, a genomic fragment containing the mouse ADAM6b gene, ~800 bp of upstream (5') sequence and ~4800 bp of downstream (3') sequence was subcloned from the 929d24 BAC clone. A second genomic fragment containing the mouse ADAM6a gene, ~300 bp of upstream (5') sequence and ~3400 bp of downstream (3') sequence, was separately subcloned from the 929d24 BAC clone. The two genomic fragments containing the mouse ADAM6b and ADAM6a genes were ligated to a hygromycin cassette flanked by Frt recombination sites to create the targeting vector (Mouse ADAM6 Targeting Vector, FIG. 20; SEQ ID NO:3). Different restriction enzyme sites were engineered onto the 5' end of the targeting vector following the mouse ADAM6b gene and onto the 3' end following the mouse ADAM6a gene (bottom of FIG. 12) for ligation into the humanized heavy chain locus.

Figure 13:
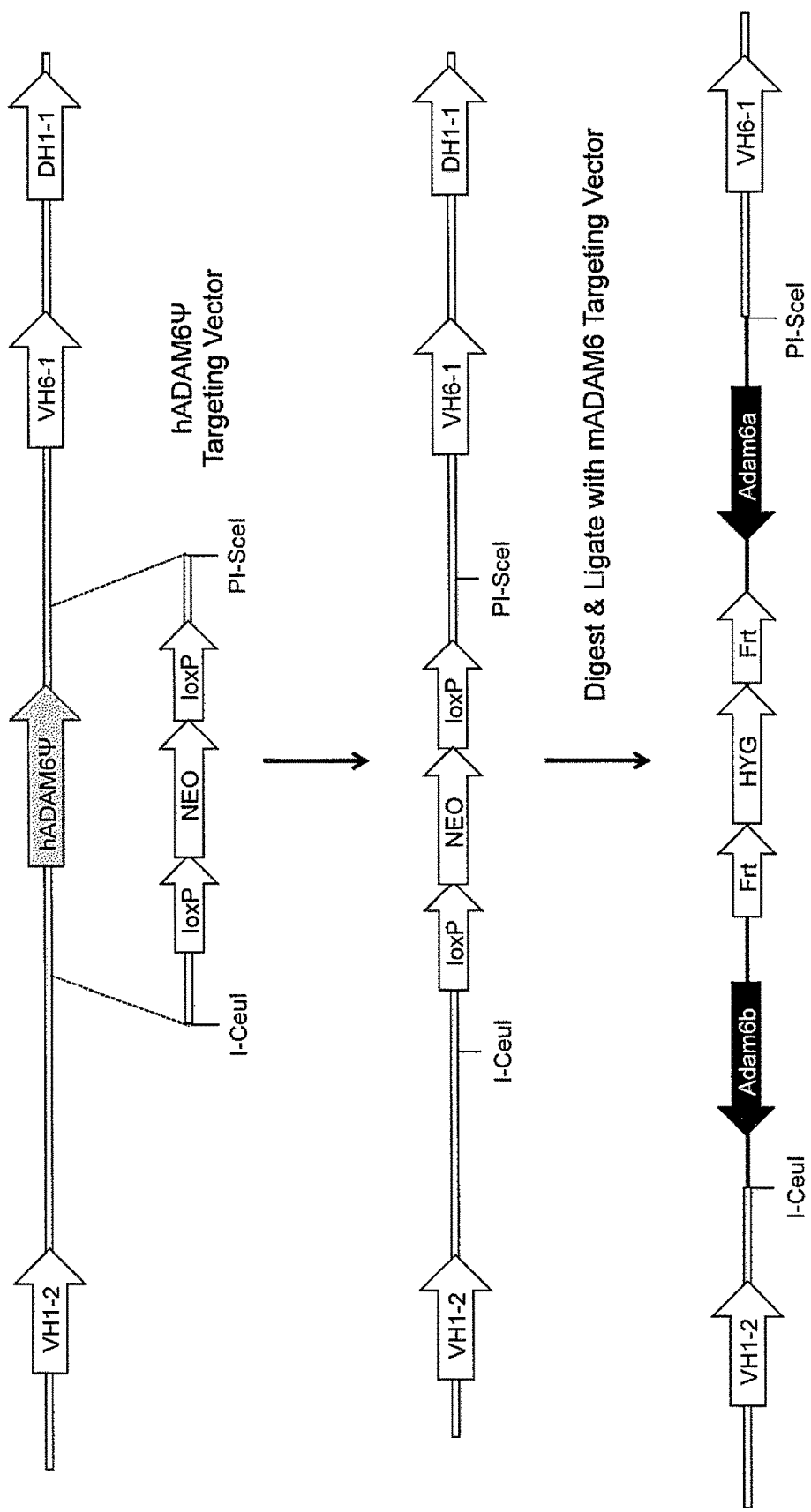
FIG. 13 shows a schematic illustration, not to scale, of a human ADAM6 pseudogene (hADAM6Ψ) located between human heavy chain variable gene segments 1-2 ($V_H$1-2) and 6-1 ($V_H$6-1). A targeting vector for bacterial homologous recombination (hADAM6Ψ Targeting Vector) to delete a human ADAM6 pseudogene and insert unique restriction sites into a human heavy chain locus is shown with a selection cassette (NEO: neomycin) flanked by site-specific recombination sites (loxP) including engineered restriction sites on the 5' and 3' ends. An illustration, not to scale, of the resulting targeted humanized heavy chain locus containing a genomic fragment that encodes for the mouse ADAM6a and ADAM6b genes including a selection cassette flanked by site-specific recombination sites is shown.
Figure 14A:
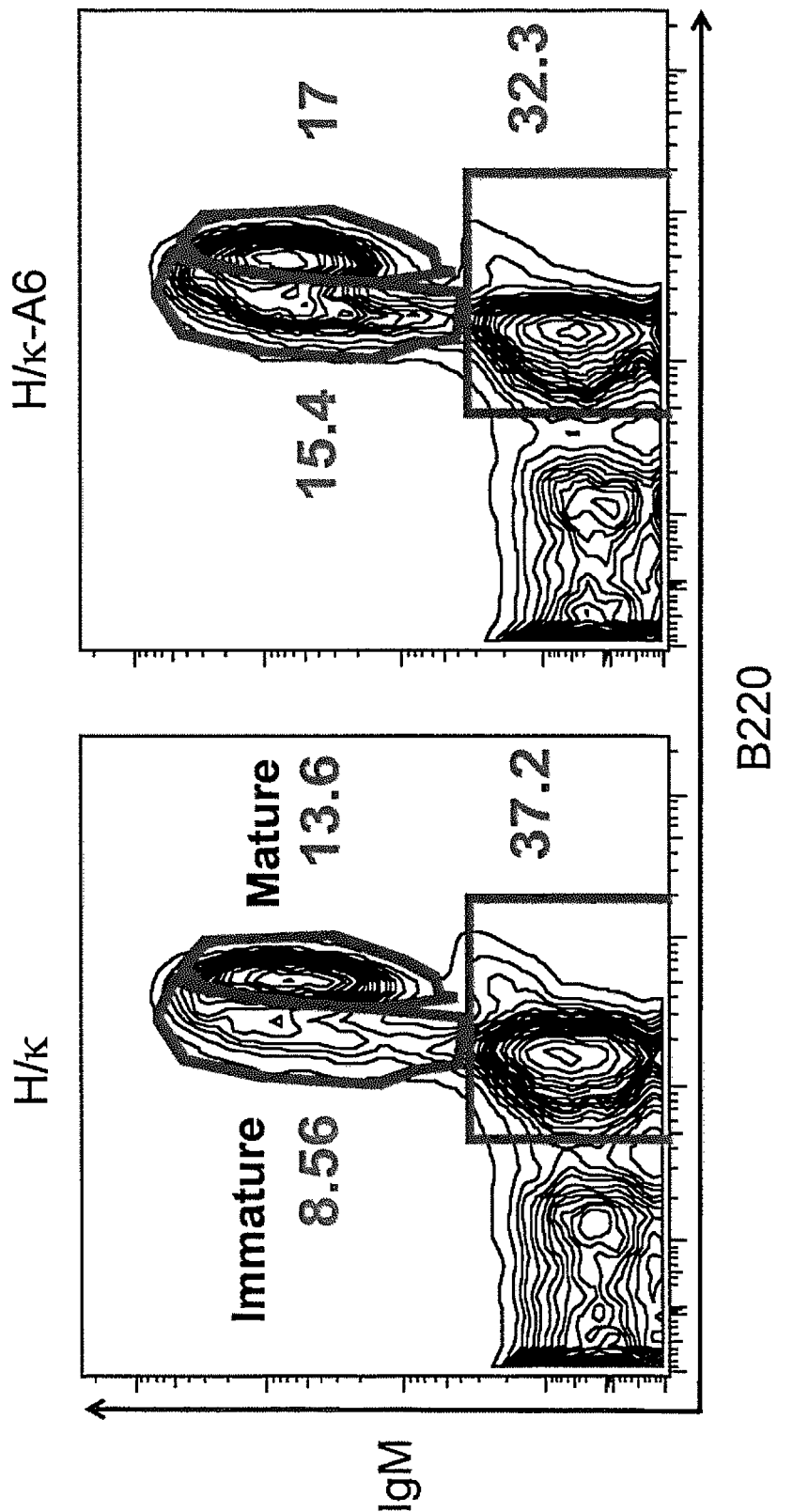
FIG. 14A shows FACS contour plots of lymphocytes gated on singlets for surface expression of IgM and B220 in the bone marrow for mice homozygous for human heavy and human κ light chain variable gene loci (H/κ) and mice homozygous for human heavy and human κ light chain variable gene loci having an inserted mouse genomic fragment comprising mouse ADAM6 genes (H/κ-A6). Percentage of immature (B220$^{int}$IgM$^+$) and mature (B220$^{high}$IgM$^+$) B cells is noted in each contour plot.
Figure 14B:
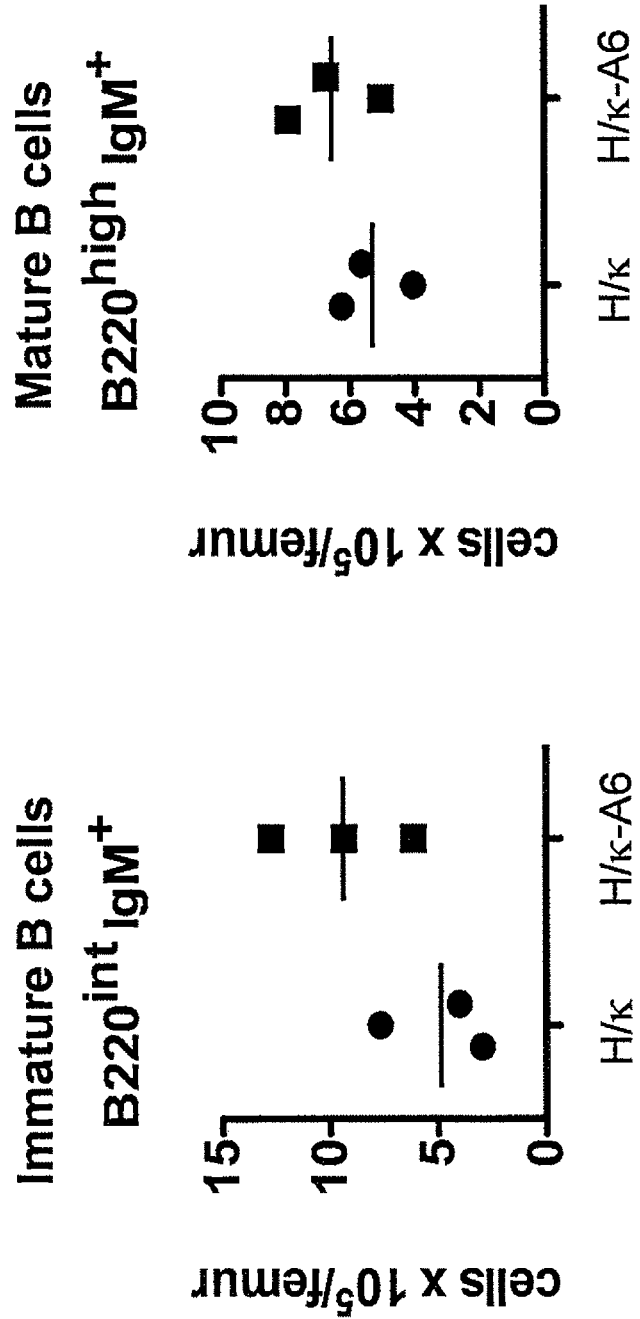
FIG. 14B shows the total number of immature (B220$^{int}$IgM$^+$) and mature (B220$^{high}$IgM$^+$) B cells in the bone marrow isolated from femurs of mice homozygous for human heavy and human κ light chain variable gene loci (H/κ) and mice homozyogous for human heavy and human κ light chain variable gene loci having an ectopic mouse genomic fragment encoding for mouse ADAM6 genes (H/κ-A6).
Figure 15A:
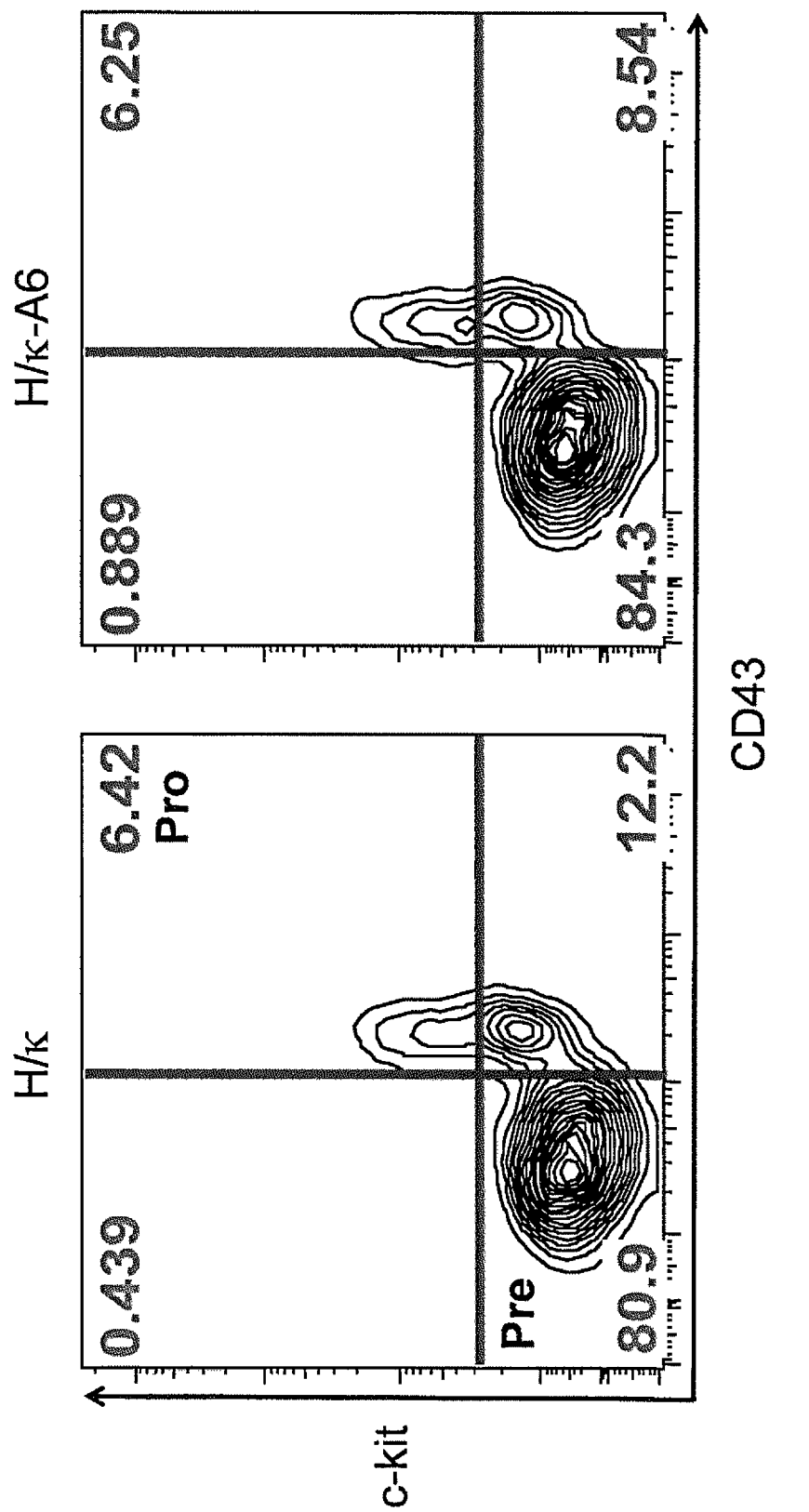
FIG. 15A shows FACS contour plots of CD19$^+$-gated B cells for surface expression of c-kit and CD43 in the bone marrow for mice homozygous for human heavy and human κ light chain variable gene loci (H/κ) and mice homozyogous for human heavy and human κ light chain variable gene loci having an ectopic mouse genomic fragment encoding for mouse ADAM6 genes (H/κ-A6). Percentage of pro-B (CD19$^+$CD43$^+$ckit$^+$) and pre-B (CD19$^+$CD43$^-$ckit$^-$) cells is noted in the upper right and lower left quadrants, respectively, of each contour plot.
Figure 15B:
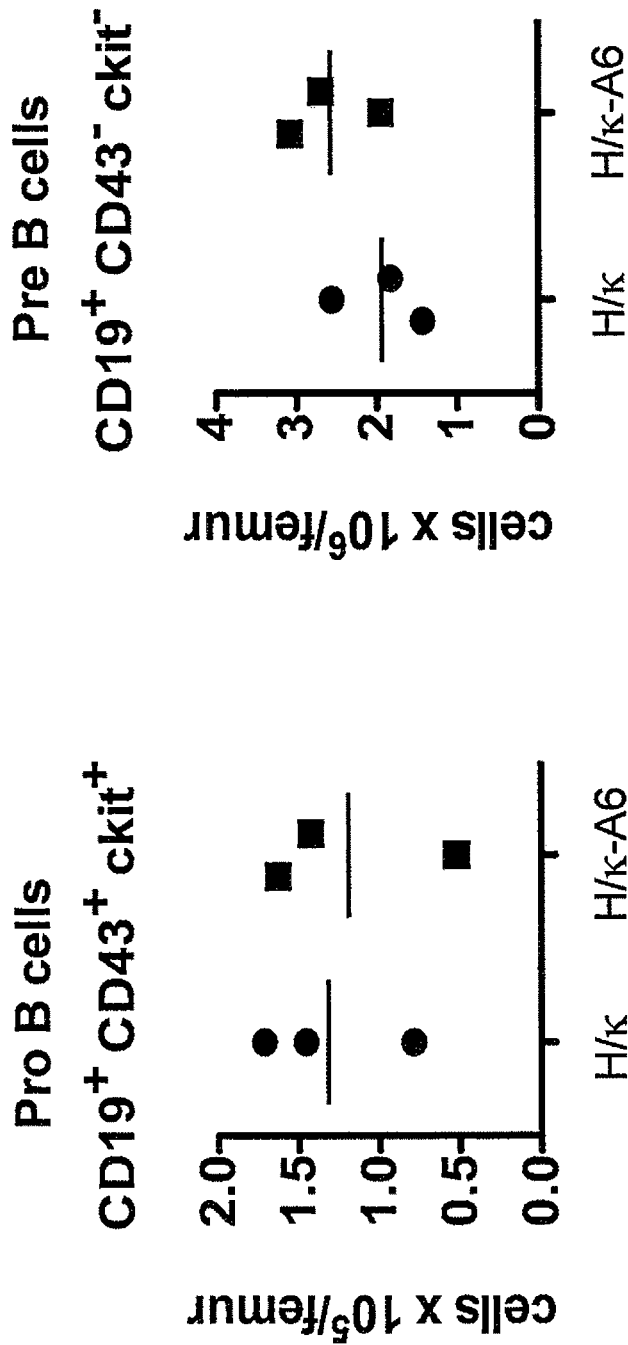
FIG. 15B shows the total number of pro-B cells (CD19$^+$CD43$^+$ckit$^+$) and pre-B cells (CD19$^+$CD43$^-$ckit$^-$) in the bone marrow isolated from femurs of mice homozygous for human heavy and human κ light chain variable gene loci (H/κ) and mice homozygous for human heavy and human κ light chain variable gene loci having an ectopic mouse genomic fragment comprising mouse ADAM6 genes (H/κ-A6).

A separate modification was made to a BAC clone containing a replacement of the mouse heavy chain locus with the human heavy chain locus, including the human ADAM6 pseudogene located between the human $V_H1$-2 and $V_H6$-1 gene segments of the humanized locus for the subsequent ligation of the mouse ADAM6 targeting vector (FIG. 13).

Briefly, a neomycin cassette flanked by loxP recombination sites was engineered to contain homology arms containing human genomic sequence at positions 3' of the human $V_H1$-2 gene segment (5' with respect to hADAM6Ψ) and 5' of human $V_H6$-1 gene segment (3' with respect to hADAM6Ψ; see middle of FIG. 13). The location of the insertion site of this targeting construct was about 1.3 kb 5' and ~350 bp 3' of the human ADAM6 pseudogene. The targeting construct also included the same restriction sites as the mouse ADAM6 targeting vector to allow for subsequent BAC ligation between the modified BAC clone containing the deletion of the human ADAM6 pseudogene and the mouse ADAM6 targeting vector.

Following digestion of BAC DNA derived from both constructs, the genomic fragments were ligated together to construct an engineered BAC clone containing a humanized heavy chain locus containing an ectopically placed genomic sequence comprising mouse ADAM6a and ADAM6b nucleotide sequences. The final targeting construct for the deletion of a human ADAM6 gene within a humanized heavy chain locus and insertion of mouse ADAM6a and ADAM6b sequences in ES cells contained, from 5' to 3', a 5' genomic fragment containing ~13 kb of human genomic sequence 3' of the human $V_H1$-2 gene segment, ~800 bp of mouse genomic sequence downstream of the mouse ADAM6b gene, the mouse ADAM6b gene, ~4800 bp of genomic sequence upstream of the mouse ADAM6b gene, a 5' Frt site, a hygromycin cassette, a 3' Frt site, ~300 bp of mouse genomic sequence downstream of the mouse ADAM6a gene, the mouse ADAM6a gene, ~3400 bp of mouse genomic sequence upstream of the mouse ADAM6a gene, and a 3' genomic fragment containing ~30 kb of human genomic sequence 5' of the human $V_H6$-1 gene segment (bottom of FIG. 13).

The engineered BAC clone (described above) was used to electroporate mouse ES cells that contained a humanized heavy chain locus to created modified ES cells comprising a mouse genomic sequence ectopically placed that comprises mouse ADAM6a and ADAM6b sequences within a humanized heavy chain locus. Positive ES cells containing the ectopic mouse genomic fragment within the humanized heavy chain locus were identified by a quantitative PCR assay using TAQMAN™ probes (Lie, Y. S. and Petropoulos, C. J. (1998) Advances in quantitative PCR technology: 5' nuclease assays. Curr Opin Biotechnol 9(1):43-48). The upstream and downstream regions outside of the modified portion of the humanized heavy chain locus were confirmed by PCR using primers and probes located within the modified region to confirm the presence of the ectopic mouse genomic sequence within the humanized heavy chain locus as well as the hygromycin cassette. The nucleotide sequence across the upstream insertion point included the following, which indicates human heavy chain genomic sequence upstream of the insertion point and an I-Ceu I restriction site (contained within the parentheses below) linked contiguously to mouse genomic sequence present at the insertion point: (CCAGCTTCAT TAGTAATCGT TCATCTGTGG TAAAAAGGCA GGATTTGAAG CGATGGAAGA TGGGAGTACG GGGCGTTGGA AGACAAAGTG CCA-CACAGCG CAGCCTTCGT CTAGACCCCC GGGCTAACTA TAACGGTCCT AAGGTAGCGA G) GGGATGACAG ATTCTCTGTT CAGTGCACTC AGGGTCTGCC TCCACGAGAA TCACCATGCC CTTTCTCAAG ACTGTGTTCT GTGCAGTGCC CTGTCAGTGG (SEQ ID NO:4). The nucleotide sequence across the downstream insertion point at the 3' end of the targeted region included the following, which indicates mouse genomic sequence and a Pl-Sce I restriction site (contained within the parentheses below) linked contiguously with human heavy chain genomic sequence downstream of the insertion point: (AGGGGTCGAG GGGGAATTTT ACAAAGAACA AAGAAGCGGG CATCTGCTGA CATGAGGGCC GAAGTCAGGC TCCA-GGCAGC GGGAGCTCCA CCGCGGTGGC GCCATTTCAT TACCTCTTTC TCCGCACCCG ACATA-GATAAAGCTT) ATCCCCCACC AAGCAAATCC CCCTACCTGG GGCCGAGCTT CCCGTATGTG GGAAAATGAA TCCCTGAGGT CGATTGCTGC ATG-CAATGAA ATTCAACTAG (SEQ ID NO:5).

Targeted ES cells described above were used as donor ES cells and introduced into an 8-cell stage mouse embryo by the VELOCIMOUSE® mouse engineering method (see, e.g., U.S. Pat. Nos. 7,6598,442, 7,576,259, 7,294,754). Mice bearing a humanized heavy chain locus containing an ectopic mouse genomic sequence comprising mouse ADAM6a and ADAM6b sequences were identified by genotyping using a modification of allele assay (Valenzuela et al., 2003) that detected the presence of the mouse ADAM6a and ADAM6b genes within the humanized heavy chain locus.

Mice bearing a humanized heavy chain locus that contains mouse ADAM6a and ADAM6b genes are bred to a FLPe deletor mouse strain (see, e.g., Rodríguez, C. I. et al. (2000) High-efficiency deletor mice show that FLPe is an alternative to Cre-loxP. Nature Genetics 25:139-140) in order to remove any FRTed hygromycin cassette introduced by the targeting vector that is not removed, e.g., at the ES cell stage or in the embryo. Optionally, the hygromycin cassette is retained in the mice.

Pups are genotyped and a pup heterozygous for a humanized heavy chain locus containing an ectopic mouse genomic fragment that comprises mouse ADAM6a and ADAM6b sequences is selected for characterizing mouse ADAM6 gene expression and fertility.

Example VIII

Characterization of ADAM6 Rescue Mice

Flow Cytometry.

Three mice at age 25 weeks homozygous for human heavy and human κ light chain variable gene loci (H/κ) and three mice at age 18-20 weeks homozygous for human heavy and human κ light chain having the ectopic mouse genomic fragment encoding the mouse ADAM6a and ADAM6b genes within both alleles of the human heavy chain locus (H/κ-A6) were sacrificed for identification and analysis of lymphocyte cell populations by FACs on the BD LSR II System (BD Bioscience). Lymphocytes were gated for specific cell lineages and analyzed for progression through various stages of B cell development. Tissues collected from the animals included blood, spleen and bone marrow. Blood was collected into BD microtainer tubes with EDTA (BD Biosciences). Bone marrow was collected from femurs by flushing with complete RPMI medium supplemented with fetal calf serum, sodium pyruvate, HEPES, 2-mercaptoethanol, non-essential amino acids, and gentamycin. Red blood cells from blood, spleen and bone marrow preparations were lysed with an ammonium chloride-based lysis buffer (e.g., ACK lysis buffer), followed by washing with complete RPMI medium.

For staining of cell populations, $1\times10^6$ cells from the various tissue sources were incubated with anti-mouse CD16/CD32 (2.4G2, BD Biosciences) on ice for 10 minutes, followed by labeling with one or a combination of the following antibody cocktails for 30 min on ice.

Bone marrow: anti-mouse FITC-CD43 (1B11, BioLegend), PE-ckit (2B8, BioLegend), PeCy7-IgM (II/41, eBioscience), PerCP-Cy5.5-IgD (11-26c.2a, BioLegend), APC-eFluor780-B220 (RA3-682, eBioscience), A700-CD19 (1D3, BD Biosciences).

Peripheral blood and spleen: anti-mouse FITC-κ (187.1, BD Biosciences), PE-λ (RML-42, BioLegend), PeCy7-IgM (II/41, eBioscience), PerCP-Cy5.5-IgD (11-26c.2a, BioLegend), APC-CD3 (145-2C11, BD), A700-CD19 (1D3, BD), APC-eFluor780-B220 (RA3-6B2, eBioscience). Following incubation with the labeled antibodies, cells were washed and fixed in 2% formaldehyde. Data acquisition was performed on an LSRII flow cytometer and analyzed with FlowJo. Results from a representative H/κ and H/κ-A6 mouse are shown in FIGS. 14-18.

Figure 16A:
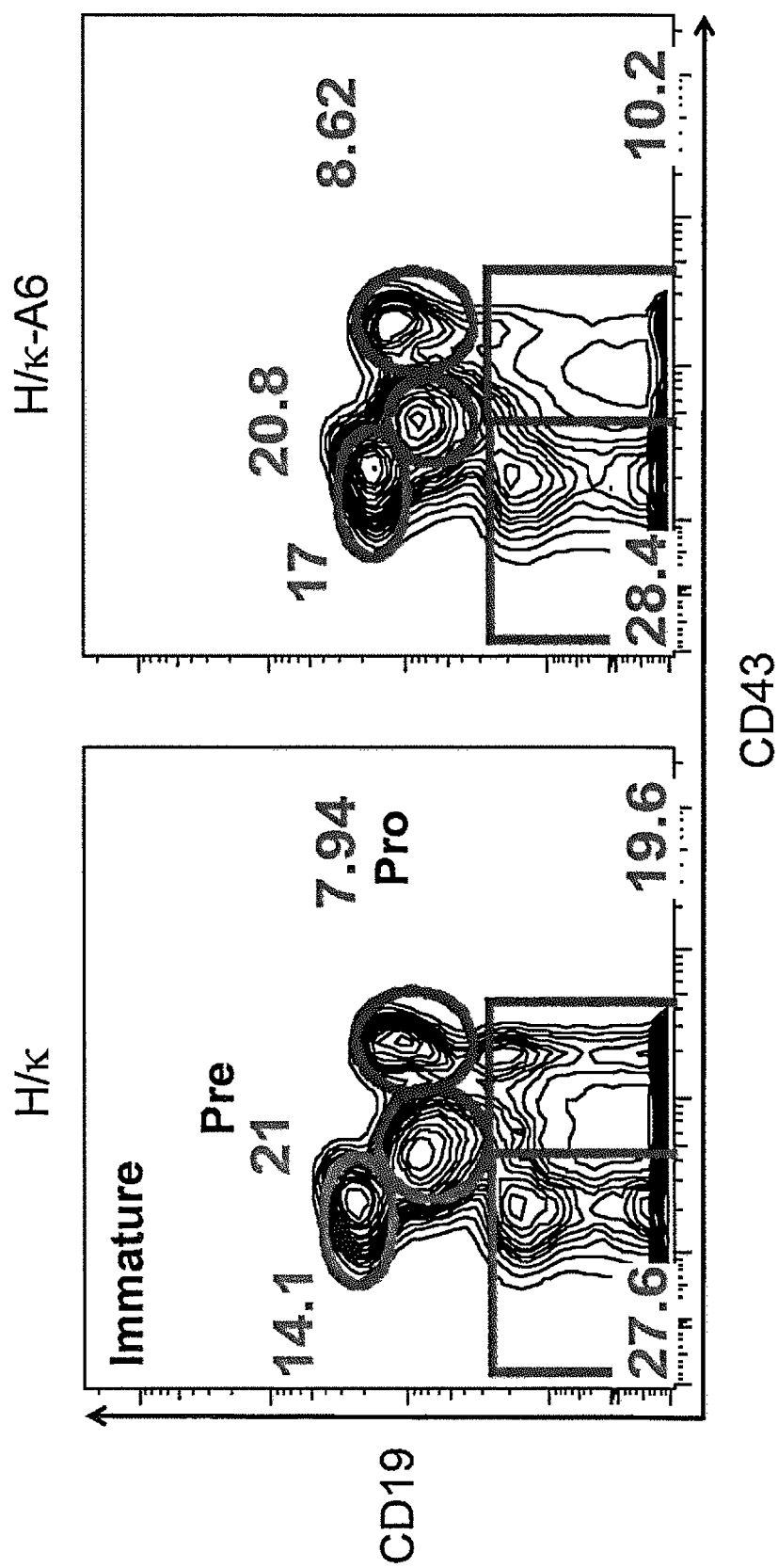
FIG. 16A shows FACS contour plots of lymphocytes gated on singlets for surface expression of CD19 and CD43 in the bone marrow for mice homozygous for human heavy and human κ light chain variable gene loci (H/κ) and mice homozygous for human heavy and human κ light chain variable gene loci having an ectopic mouse genomic fragment encoding for mouse ADAM6 genes (H/κ-A6). Percentage of immature B (CD19$^+$CD43$^-$), pre-B (CD19$^+$CD43$^{int}$) and pro-B (CD19$^+$CD43$^+$) cells is noted in each contour plot.
Figure 16B:
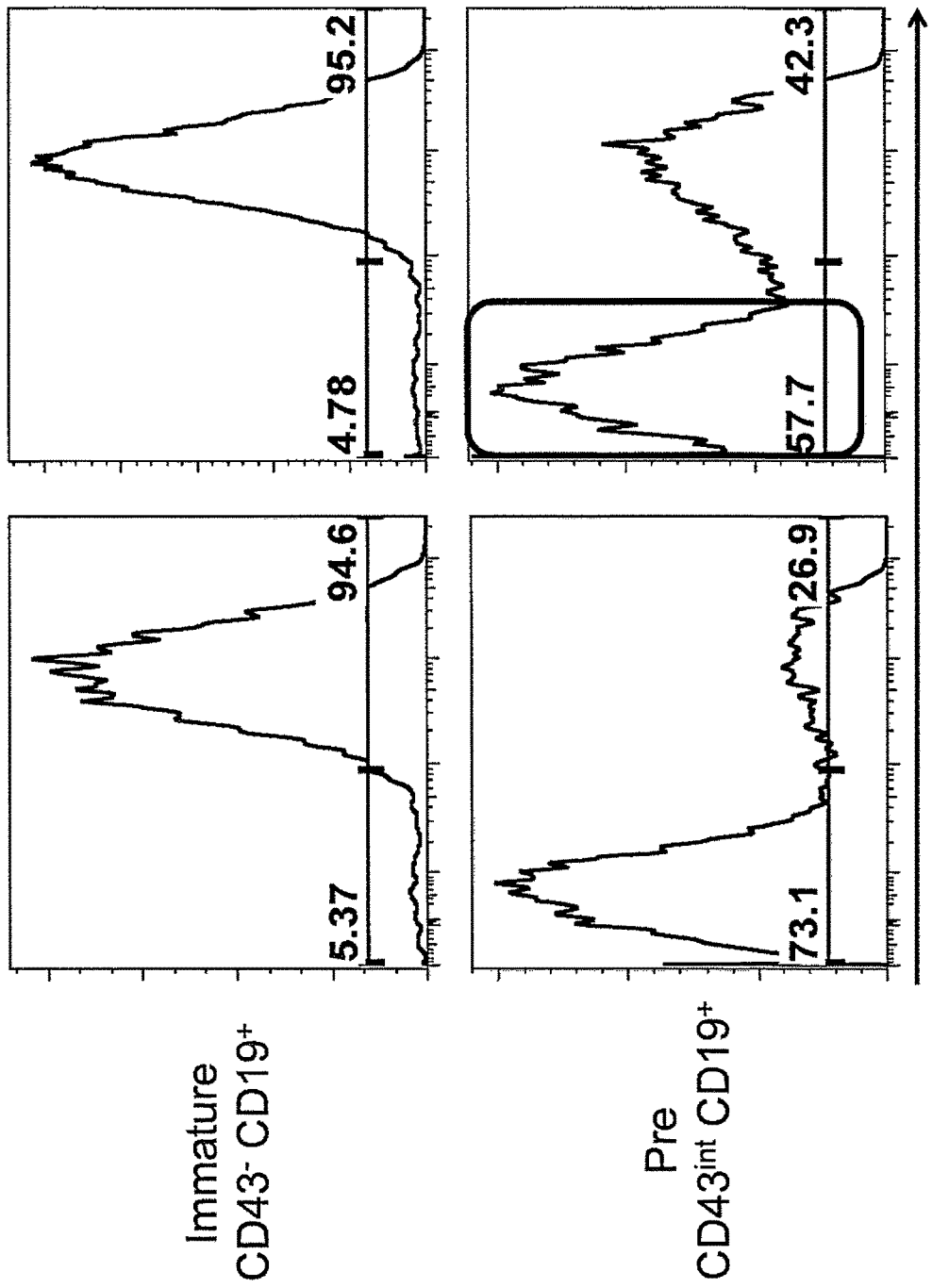
FIG. 16B shows histograms of immature B (CD19$^+$CD43$^-$) and pre-B (CD19$^+$CD43$^{int}$) cells in the bone marrow of mice homozygous for human heavy and human κ light chain variable gene loci (H/κ) and mice homozygous for human heavy and human κ light chain variable gene loci having an ectopic mouse genomic fragment encoding for mouse ADAM6 genes (H/κ-A6).
Figure 17A:
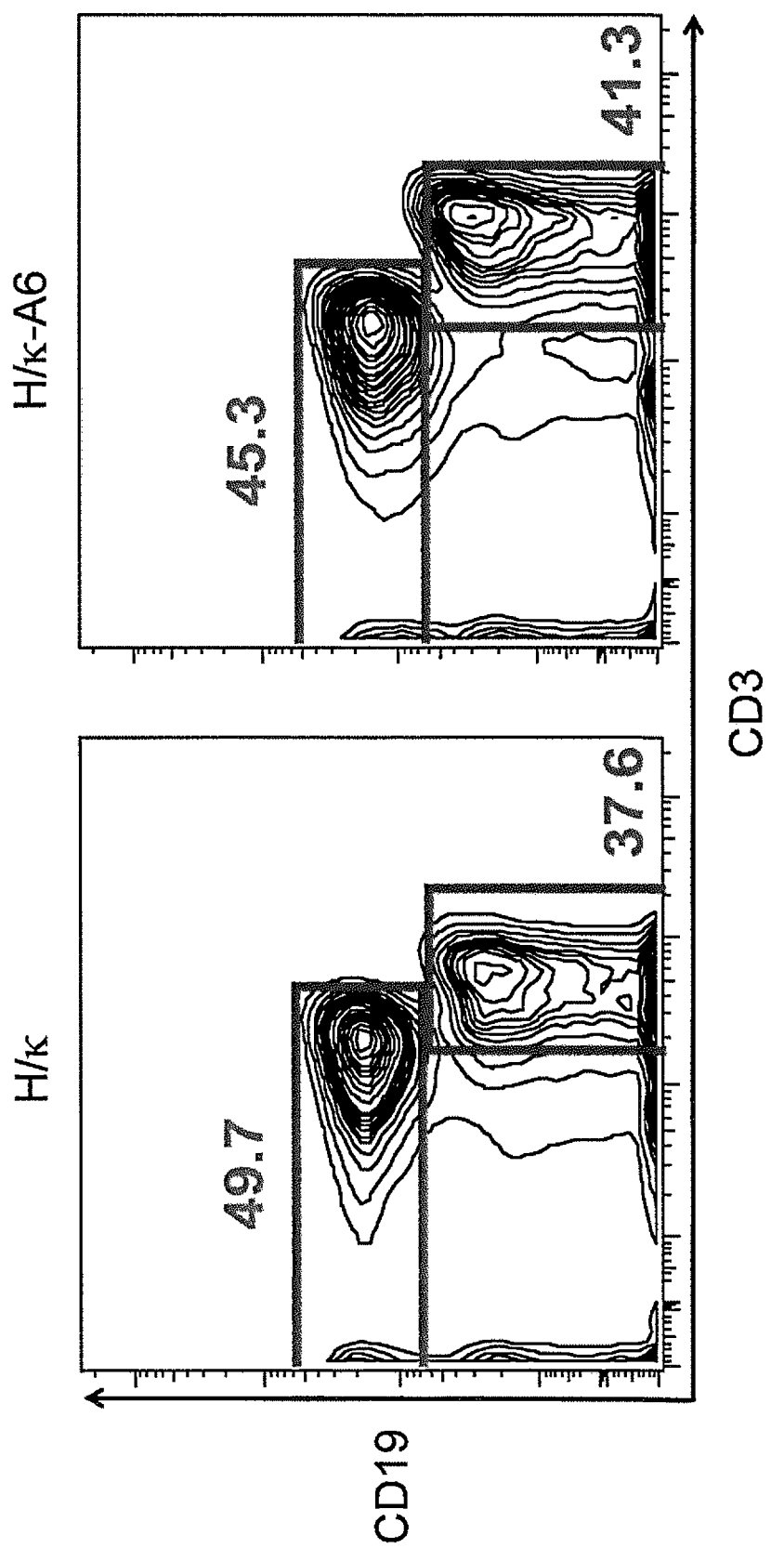
FIG. 17A shows FACS contour plots of lymphocytes gated on singlets for surface expression of CD19 and CD3 in splenocytes for mice homozygous for human heavy and human κ light chain variable gene loci (H/κ) and mice homozygous for human heavy and human κ light chain variable gene loci having an ectopic mouse genomic fragment encoding for mouse ADAM6 genes (H/κ-A6). Percentage of B (CD19$^+$CD3$^-$) and T (CD19$^-$CD3') cells is noted in each contour plot.
Figure 17B:
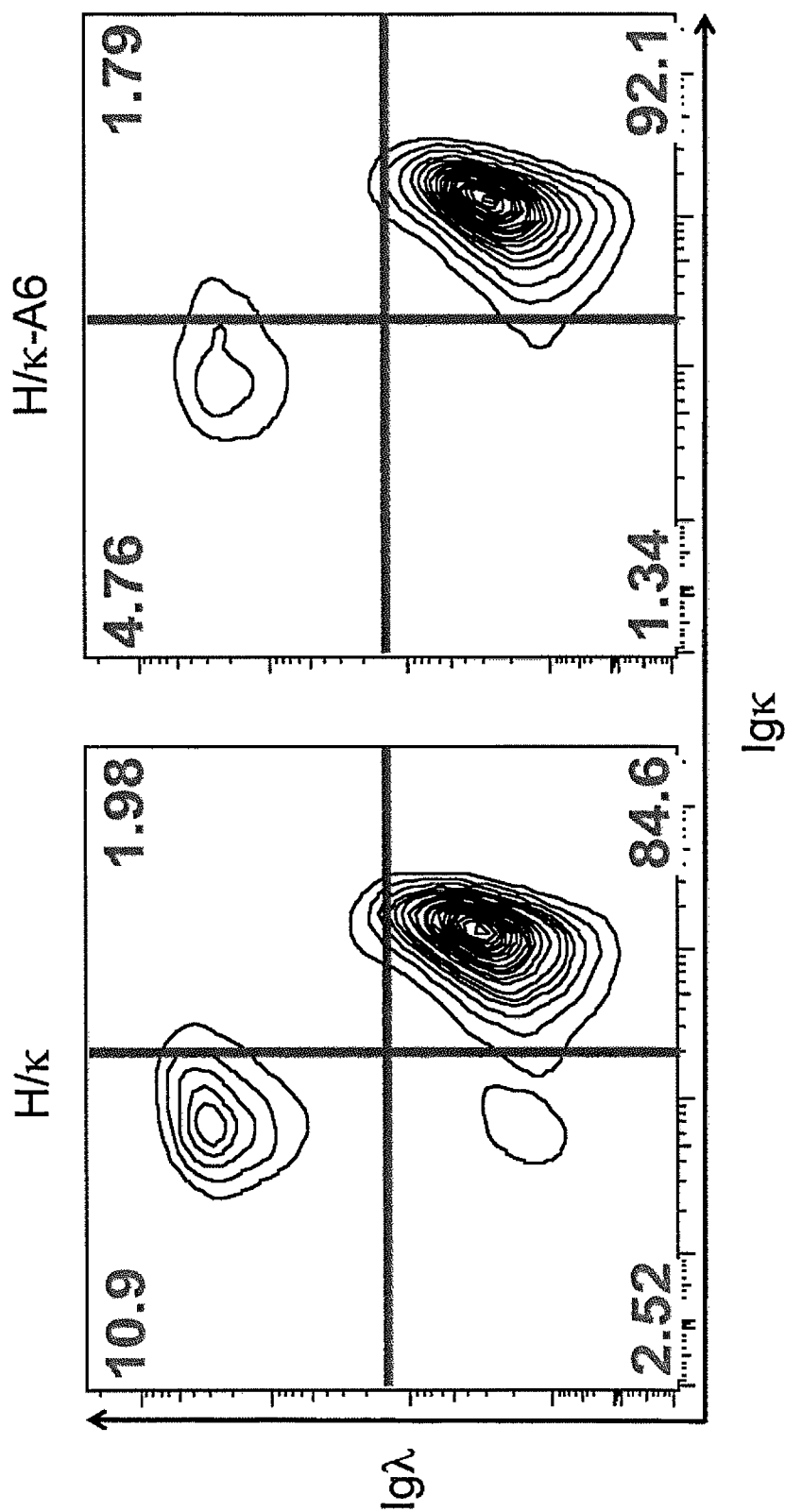
FIG. 17B shows FACs contour plots for CD19$^+$-gated B cells for surface expression of Igλ and Igκ light chain in the spleen of mice homozygous for human heavy and human κ light chain variable gene loci (H/κ) and mice homozygous for human heavy and human κ light chain variable gene loci having an ectopic mouse genomic fragment comprising mouse ADAM6 genes (H/κ-A6). Percentage of Igλ$^+$ (upper left quadrant) and Igκ$^+$ (lower right quadrant) B cells is noted in each contour plot.
Figure 17C:
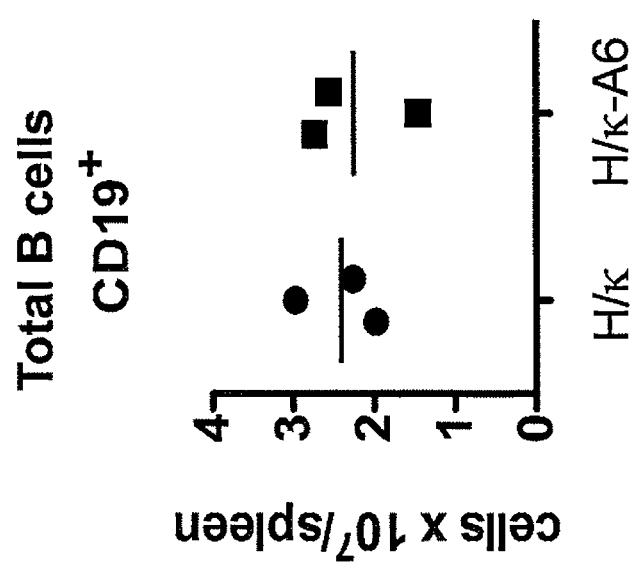
FIG. 17C shows the total number of CD19$^+$ B cells in the spleen of mice homozygous for human heavy and human κ light chain variable gene loci (H/κ) and mice homozygous for human heavy and human κ light chain variable gene loci having an ectopic mouse genomic fragment comprising mouse ADAM6 genes (H/κ-A6).
Figure 18A:
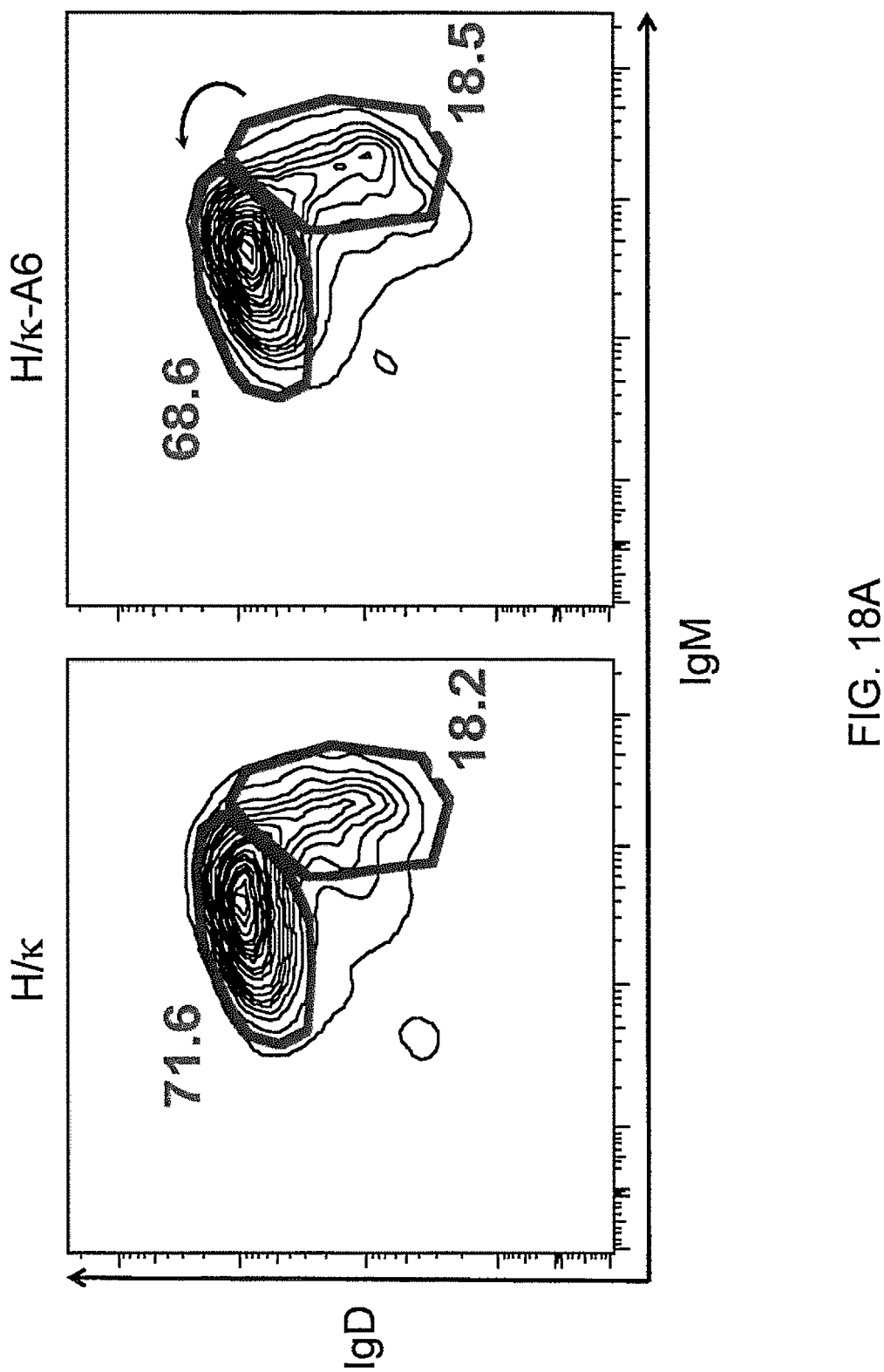
FIG. 18A shows FACs contour plots of CD19$^+$-gated B cells for surface expression of IgD and IgM in the spleen of mice homozygous for human heavy and human κ light chain variable gene loci (H/κ) and mice homozygous for human heavy and human κ light chain variable gene loci having an ectopic mouse genomic fragment comprising mouse ADAM6 genes (H/κ-A6). Percentage of mature B cells (CD19$^+$IgD$^{high}$IgM$^{Int}$) is noted for each contour plot. The arrow on the right contour plot illustrates the process of maturation for B cells in relation to IgM and IgD surface expression.
Figure 18B:
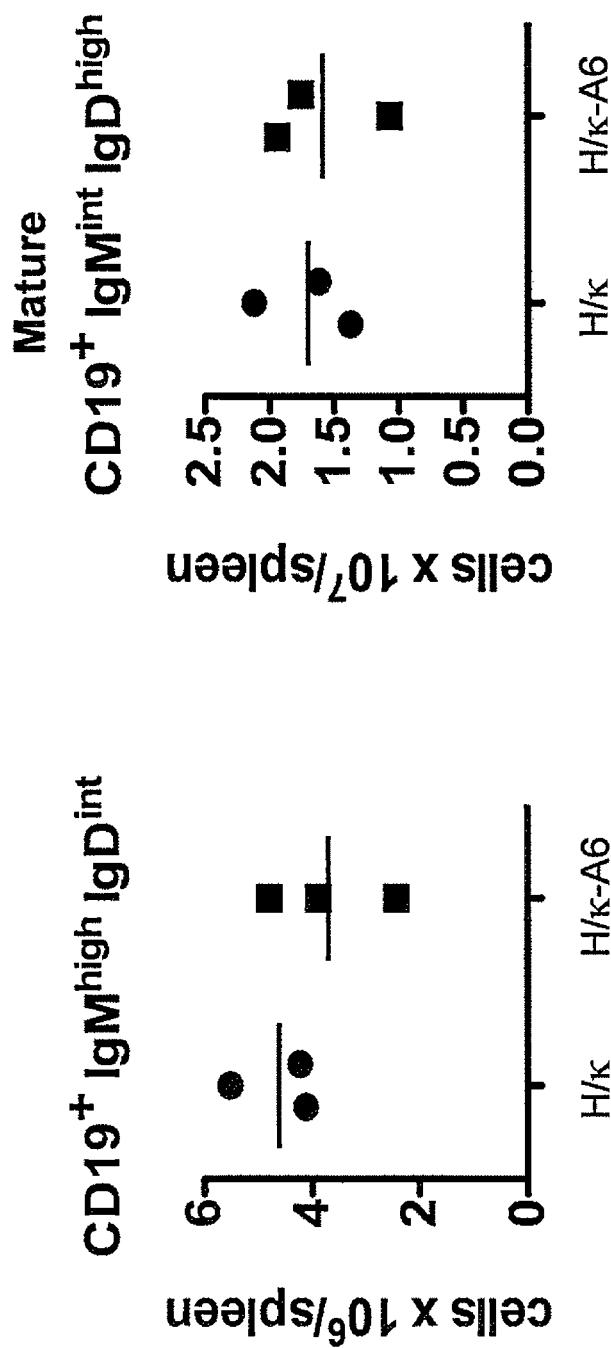
FIG. 18B shows the total number of B cells in the spleen of mice homozygous for human heavy and human κ light chain variable gene loci (H/κ) and mice homozygous for human heavy and human κ light chain variable gene loci having an ectopic mouse genomic fragment encoding for mouse ADAM6 genes (H/κ-A6) during maturation from CD19$^+$IgM$^{high}$IgD$^{int}$ to CD19$^+$IgM$^{int}$IgD$^{high}$.

The results demonstrate that B cells of H/κ-A6 mice progress through the stages of B cell development in a similar fashion to H/κ mice in the bone marrow and peripheral compartments, and show normal patterns of maturation once they enter the periphery. H/κ-A6 mice demonstrated an increased CD43$^{int}$CD19$^+$ cell population as compared to H/κ mice (FIG. 16B). This may indicate an accelerated IgM expression from the humanized heavy chain locus containing an ectopic mouse genomic fragment comprising the mouse ADAM6a and ADAM6b sequences in H/κ-A6 mice. In the periphery, B and T cell populations of H/κ-A6 mice appear normal and similar to H/κ mice.

Testis Morphology and Sperm Characterization.

To determine if infertility in mice having humanized immunoglobulin heavy chain variable loci is due to testis and/or sperm production defects, testis morphology and sperm content of the epididymis was examined.

Briefly, testes from two groups of five mice per group (Group 1: mice homozygous for human heavy and κ light chain variable gene loci, mADAM6$^{-/-}$; Group 2: mice heterozygous for human heavy chain variable gene loci and homozygous for κ light chain variable gene loci, mADAM6$^{+/-}$) were dissected with the epididymis intact and weighed. The specimens were then fixed, embedded in paraffin, sectioned and stained with hematoxylin and eosin (HE) stain. Testis sections (2 testes per mouse, for a total of 20) were examined for defects in morphology and evidence of sperm production, while epididymis sections were examined for presence of sperm.

In this experiment, no differences in testis weight or morphology was observed between mADAM6$^{-/-}$ mice and mADAM6$^{+/-}$ mice. Sperm was observed in all genotypes, both in the testes and the epididymis. These results establish that the absence of mouse ADAM6a and ADAM6b genes does not lead to detectable changes in testis morphology, and that sperm is produced in mice in the presence and absence of these two genes. Defects in fertility of male ADAM6$^{-/-}$ mice are therefore not likely to be due to low sperm production.

Sperm Motility and Migration.

Mice that lack other ADAM gene family members are infertile due to defects in sperm motility or migration. Sperm migration is defined as the ability of sperm to pass from the uterus into the oviduct, and is normally necessary for fertilization in mice. To determine if the deletion of mouse ADAM6a and ADAM6b affects this process, sperm migration was evaluated in mADAM6$^{-/-}$ mice. Sperm motility was also examined.

Briefly, sperm was obtained from testes of (1) mice heterozygous for human heavy chain variable gene loci and homozygous for human κ light chain variable gene locui (ADAM6$^{+/-}$); (2) mice homozyogous for human heavy chain variable gene loci and homozygous for human κ light chain variable gene loci (ADAM6$^{-/-}$); (3) mice homozygous for human heavy chain variable gene loci and homozygous for wild-type κ light chain (ADAM6$^{-/-}$ mκ); and, (4) wild-type C57 BL/6 mice (WT). No significant abnormalities were observed in sperm count or overall sperm motility by inspection. For all mice, cumulus dispersal was observed, indicating that each sperm sample was able to penetrate the cumulus cells and bind the zona pellucida in vitro. These results establish that ADAM6$^{-/-}$ mice have sperm that are capable of penetrating the cumulus and binding the zona pellucida.

Fertilization of mouse ova in vitro (IVF) was done using sperm from mice as described above. A slightly lower number of cleaved embryos were present for ADAM6$^{-/-}$ the day following IVF, as well as a reduced number of sperm bound to the eggs. These results establish that sperm from ADAM6$^{-/-}$ mice, once exposed to an ovum, are capable of penetrating the cumulus and binding the zona pellucida.

In another experiment, the ability of sperm from ADAM6$^{-/-}$ mice to migrate from the uterus and through the oviduct was determined in a sperm migration assay.

Briefly, a first group of five superovulated female mice were set up with five ADAM6$^{-/-}$ males. A second group of five superovulated female mice were set up with five ADAM6$^{+/-}$ males. The mating pairs were observed for copulation, and five to six hours post-copulation the uterus and attached oviduct from all females were removed and flushed for analysis. Flush solutions were checked for eggs to verify ovulation and obtain a sperm count. Sperm migration was evaluated in two different ways. First, both oviducts were removed from the uterus, flushed with saline, and any sperm identified were counted. The presence of eggs was also noted as evidence of ovulation. Second, oviducts were left attached to the uterus and both tissues were fixed, embedded in paraffin, sectioned and stained (as described above). Sections were examined for presence of sperm, in both the uterus and in both oviducts.

For the five females mated with the five ADAM6$^{-/-}$ males, very little sperm was found in the flush solution from the oviduct. Flush solutions from oviducts of the five females mated with the five ADAM6$^{+/-}$ males exhibited a sperm level about 25- to 30-fold higher (avg, n=10 oviducts) than present in flush solutions from the oviducts of the five females mated with the five ADAM6$^{-/-}$ males.

Histological sections of uterus and oviduct were prepared. The sections were examined for sperm presence in the uterus and the oviduct (the colliculus tubarius). Inspection of histological sections of oviduct and uterus revealed that for female mice mated with ADAM6$^{-/-}$ mice, sperm was found in the uterus but not in the oviduct. Further, sections from females mated with ADAM6$^{-/-}$ mice revealed that sperm was not found at the uterotubal junction (UTJ). In sections from females mated with ADAM6$^{-/-}$ mice, sperm was identified in the UTJ and in the oviduct.

These results establish that mice lacking ADAM6a and ADAM6b genes make sperm that exhibit an in viva migration defect. In all cases, sperm was observed within the uterus, indicating that copulation and sperm release apparently occur as normal, but little to no sperm was observed within the oviducts after copulation as measured either by sperm count or histological observation. These results establish that mice lacking ADAM6a and ADAM6b genes produce sperm that exhibit an inability to migrate from the uterus to the oviduct. This defect apparently leads to infertility because sperm are unable to cross the uterine-tubule junction into the oviduct, where eggs are fertilized. Taken together, all of these results converge to the support the hypothesis that mouse ADAM6 genes help direct sperm with normal motility to migrate out of the uterus, through the uterotubal junction and the oviduct, and thus approach an egg to achieve the fertilization event. The mechanism by which ADAM6 achieves this may be directly by action of the ADAM6 proteins, or through coordinate expression with other proteins, e.g., other ADAM proteins, in the sperm cell, as described below.

ADAM Gene Family Expression.

A complex of ADAM proteins are known to be present as a complex on the surface of maturing sperm. Mice lacking other ADAM gene family members lose this complex as sperm mature, and exhibit a reduction of multiple ADAM proteins in mature sperm. To determine if a lack of ADAM6a and ADAM6b genes affects other ADAM proteins in a similar manner, Western blots of protein extracts from testis (immature sperm) and epididymis (maturing sperm) were analyzed to determine the expression levels of other ADAM gene family members.

In this experiment, protein extracts were analyzed from four ADAM6$^{-/-}$ and four ADAM6$^{+/-}$ mice. The results showed that expression of ADAM2 and ADAM3 were not affected in testis extracts. However, both ADAM2 and ADAM3 were dramatically reduced in epididymis extracts. This demonstrates that the absence of ADAM6a and ADAM6b in sperm of ADAM6$^{-/-}$ mice may have a direct affect on the expression and perhaps function of other ADAM proteins as sperm matures (e.g., ADAM2 and ADAM3). This suggests that ADAM6a and ADAM6b are part of an ADAM protein complex on the surface of sperm, which might be critical for proper sperm migration.

Example IX

Human Heavy Chain Variable Gene Usage in ADAM6 Rescue Mice

Selected human heavy chain variable gene usage was determined for mice homozygous for human heavy and κ light chain variable gene loci either lacking mouse ADAM6a and ADAM6b genes (mADAM6$^{-/-}$ or containing an ectopic genomic fragment encoding for mouse ADAM6a and ADAM6b genes (ADAM6$^{+/+}$; see Example 1) by a quantitative PCR assay using TAQMAN™ probes (as described above).

Briefly, CD19$^+$ B cells were purified from the spleens of mADAM6$^{-/-}$ and mADAM6$^{+/+}$ mice using mouse CD19 Microbeads (Miltenyi Biotec) and total RNA was purified using the RNEASY™ Mini kit (Qiagen). Genomic RNA was removed using a RNase-free DNase on-column treatment (Qiagen). About 200 ng mRNA was reverse-transcribed into cDNA using the First Stand cDNA Synthesis kit (Invitrogen) and then amplified with the TAQMAN™ Universal PCR Master Mix (Applied Biosystems) using the ABI 7900 Sequence Detection System (Applied Biosystems). Relative expression of each gene was normalized to the mouse K Constant (mCκ). Table 9 sets forth the sense/antisense/TAQMAN™ MGB probe combinations used in this experiment.

TABLE 9

| Human $V_H$ | Sequence (5'-3') | SEQ ID NOs: |
|---|---|---|
| $V_H$6-1 | Sense: CAGGTACAGCTGCAGCAGTCA | 6 |
|  | Anti-sense: GGAGATGGCACAGGTGAGTGA | 7 |
|  | Probe: TCCAGGACTGGTGAAGC | 8 |
| $V_H$1-2 | Sense: TAGTCCCAGTGATGAGAAAGAGAT | 9 |
|  | Anti-sense: GAGAACACAGAAGTGGATGAGATC | 10 |
|  | Probe: TGAGTCCAGTCCAGGGA | 11 |
| $V_H$3-23 | Sense: AAAAATTGAGTGTGAATGGATAAGAGTG | 12 |
|  | Anti-sense: AACCCTGGTCAGAAACTGCCA | 13 |
|  | Probe: AGAGAAACAGTGGATACGT | 14 |
| $V_H$1-69 | Sense: AACTACGCACAGAAGTTCCAGG | 15 |
|  | Anti-sense: GCTCGTGGATTTGTCCGC | 16 |
|  | Probe: CAGAGTCACGATTACC | 17 |
| mCκ | Sense: TGAGCAGCACCCTCACGTT | 18 |
|  | Anti-sense: GTGGCCTCACAGGTATAGCTGTT | 19 |
|  | Probe: ACCAAGGACGAGTATGAA | 20 |

In this experiment, expression of all four human $V_H$ genes was observed in the samples analyzed. Further, the expression levels were comparable between mADAM6$^{-/-}$ and ADAM6$^{+/+}$ mice. These results demonstrate that human $V_H$ genes that were both distal to the modification site ($V_H$3-23 and $V_H$1-69) and proximal to the modification site ($V_H$1-2 and $V_H$6-1) were all able to recombine to form a functionally expressed human heavy chain. These results demonstrate that the ectopic genomic fragment comprising mouse ADAM6a and ADAM6b sequences inserted into a human heavy chain genomic sequence did not affect V(D)J recombination of human heavy chain gene segments within the locus, and these mice are able to recombine human heavy chain gene segments in normal fashion to produce functional heavy chain immunoglobulin proteins.

Example X

Identification of Human Heavy Chain Variable Regions that Associate with Selected Human Light Chain Variable Regions An in vitro expression system was constructed to determine if a single rearranged human germline light chain could be co-expressed with human heavy chains from antigen-specific human antibodies.

Methods for generating human antibodies in genetically modified mice are known (see e.g., U.S. Pat. No. 6,596,541, Regeneron Pharmaceuticals, VELOCIMMUNE® humanized mouse). The VELOCIMMUNE® humanized mouse technology involves generation of a genetically modified mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibodies produced from a VELOCIMMUNE® humanized mouse are fully human. Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate a fully human antibody containing a non-IgM isotype, for example, wild type or modified IgG1, IgG2, IgG3 or IgG4. While the constant region selected may vary according to specific use, high affinity antigen-binding and target specificity characteristics reside in the variable region.

A VELOCIMMUNE® humanized mouse was immunized with a growth factor that promotes angiogenesis (Antigen C) and antigen-specific human antibodies were isolated and sequenced for V gene usage using standard techniques recognized in the art. Selected antibodies were cloned onto human heavy and light chain constant regions and 69 heavy chains were selected for pairing with one of three human light chains: (1) the cognate κ light chain linked to a human κ constant region, (2) a rearranged human germline Vκ1-39Jκ5 linked to a human κ constant region, or (3) a rearranged human germline Vκ3-20Jκ1 linked to a human κ constant region. Each heavy chain and light chain pair were co-transfected in CHO-K1 cells using standard techniques. Presence of antibody in the supernatant was detected by anti-human IgG in an ELISA assay. Antibody titer (ng/ml) was determined for each heavy chain/light chain pair and titers with the different rearranged germline light chains were compared to the titers obtained with the parental antibody molecule (i.e., heavy chain paired with cognate light chain) and percent of native titer was calculated (Table 10). $V_H$: Heavy chain variable gene. ND: no expression detected under current experimental conditions.

TABLE 10

| $V_H$ | Antibody Titer (ng/mL) | | | Percent of Native Titer | |
| --- | --- | --- | --- | --- | --- |
| | Cognate LC | Vκ1-39Jκ5 | Vκ3-20Jκ1 | Vκ1-39Jκ5 | Vκ3-20Jκ1 |
| 3-15 | 63 | 23 | 11 | 36.2 | 17.5 |
| 1-2 | 103 | 53 | ND | 51.1 | — |
| 3-23 | 83 | 60 | 23 | 72.0 | 27.5 |
| 3-33 | 15 | 77 | ND | 499.4 | — |
| 4-31 | 22 | 69 | 17 | 309.4 | 76.7 |
| 3-7 | 53 | 35 | 28 | 65.2 | 53.1 |
| — | 22 | 32 | 19 | 148.8 | 89.3 |
| 1-24 | 3 | 13 | ND | 455.2 | — |
| 3-33 | 1 | 47 | ND | 5266.7 | — |
| 3-33 | 58 | 37 | ND | 63.1 | — |
| — | 110 | 67 | 18 | 60.6 | 16.5 |
| 3-23 | 127 | 123 | 21 | 96.5 | 16.3 |
| 3-33 | 28 | 16 | 2 | 57.7 | 7.1 |
| 3-23 | 32 | 50 | 38 | 157.1 | 119.4 |
| — | 18 | 45 | 18 | 254.3 | 101.7 |
| 3-9 | 1 | 30 | 23 | 2508.3 | 1900.0 |
| 3-11 | 12 | 26 | 6 | 225.9 | 48.3 |
| 1-8 | 16 | ND | 13 | — | 81.8 |
| 3-33 | 54 | 81 | 10 | 150.7 | 19.1 |
| — | 34 | 9 | ND | 25.9 | — |
| 3-20 | 7 | 14 | 54 | 203.0 | 809.0 |
| 3-33 | 19 | 38 | ND | 200.5 | — |
| 3-11 | 48 | ND | 203 | — | 423.6 |
| — | 11 | 23 | 8 | 212.7 | 74.5 |
| 3-33 | 168 | 138 | 182 | 82.0 | 108.2 |
| 3-20 | 117 | 67 | 100 | 57.5 | 86.1 |
| 3-23 | 86 | 61 | 132 | 70.7 | 154.1 |

TABLE 10-continued

| $V_H$ | Antibody Titer (ng/mL) | | | Percent of Native Titer | |
| --- | --- | --- | --- | --- | --- |
| | Cognate LC | Vκ1-39Jκ5 | Vκ3-20Jκ1 | Vκ1-39Jκ5 | Vκ3-20Jκ1 |
| 3-33 | 20 | 12 | 33 | 60.9 | 165.3 |
| 4-31 | 69 | 92 | 52 | 133.8 | 75.0 |
| 3-23 | 87 | 78 | 62 | 89.5 | 71.2 |
| 1-2 | 31 | 82 | 51 | 263.0 | 164.6 |
| 3-23 | 53 | 93 | 151 | 175.4 | 285.4 |
| — | 11 | 8 | 17 | 75.7 | 151.4 |
| 3-33 | 114 | 36 | 27 | 31.6 | 23.4 |
| 3-15 | 73 | 39 | 44 | 53.7 | 59.6 |
| 3-33 | 1 | 34 | 16 | 5600.0 | 2683.3 |
| 3-9 | 58 | 112 | 57 | 192.9 | 97.6 |
| 3-33 | 67 | 20 | 105 | 30.1 | 157.0 |
| 3-33 | 34 | 21 | 24 | 62.7 | 70.4 |
| 3-20 | 10 | 49 | 91 | 478.4 | 888.2 |
| 3-33 | 66 | 32 | 25 | 48.6 | 38.2 |
| 3-23 | 17 | 59 | 56 | 342.7 | 329.8 |
| — | 58 | 108 | 19 | 184.4 | 32.9 |
| — | 68 | 54 | 20 | 79.4 | 29.9 |
| 3-33 | 42 | 35 | 32 | 83.3 | 75.4 |
| — | 29 | 19 | 13 | 67.1 | 43.9 |
| 3-9 | 24 | 34 | 29 | 137.3 | 118.4 |
| 3-30/33 | 17 | 33 | 7 | 195.2 | 43.1 |
| 3-7 | 25 | 70 | 74 | 284.6 | 301.6 |
| 3-33 | 87 | 127 | ND | 145.1 | — |
| 6-1 | 28 | 56 | ND | 201.8 | — |
| 3-33 | 56 | 39 | 20 | 69.9 | 36.1 |
| 3-33 | 10 | 53 | 1 | 520.6 | 6.9 |
| 3-33 | 20 | 67 | 10 | 337.2 | 52.3 |
| 3-33 | 11 | 36 | 18 | 316.8 | 158.4 |
| 3-23 | 12 | 42 | 32 | 356.8 | 272.9 |
| 3-33 | 66 | 95 | 15 | 143.6 | 22.5 |
| 3-15 | 55 | 68 | ND | 123.1 | — |
| — | 32 | 68 | 3 | 210.9 | 10.6 |
| 1-8 | 28 | 48 | ND | 170.9 | — |
| 3-33 | 124 | 192 | 21 | 154.3 | 17.0 |
| 3-33 | 0 | 113 | ND | 56550.0 | — |
| 3-33 | 10 | 157 | 1 | 1505.8 | 12.5 |
| 3-33 | 6 | 86 | 15 | 1385.5 | 243.5 |
| 3-23 | 70 | 115 | 22 | 163.5 | 31.0 |
| 3-7 | 71 | 117 | 21 | 164.6 | 29.6 |
| 3-33 | 82 | 100 | 47 | 122.7 | 57.1 |
| 3-7 | 124 | 161 | 41 | 130.0 | 33.5 |

In a similar experiment, VELOCIMMUNE® humanized mice were immunized with several different antigens and selected heavy chains of antigen specific human antibodies were tested for their ability to pair with different rearranged human germline light chains (as described above). The antigens used in this experiment included an enzyme involved in cholesterol homeostasis (Antigen A), a serum hormone involved in regulating glucose homeostasis (Antigen B), a growth factor that promotes angiogenesis (Antigen C) and a cell-surface receptor (Antigen D). Antigen specific antibodies were isolated from mice of each immunization group and the heavy chain and light chain variable regions were cloned and sequenced. From the sequence of the heavy and light chains, V gene usage was determined and selected heavy chains were paired with either their cognate light chain or a rearranged human germline Vκ1-39Jκ5 region. Each heavy/light chain pair was co-transfected in CHO-K1 cells and the presence of antibody in the supernatant was detected by anti-human IgG in an ELISA assay. Antibody titer (μg/ml) was determined for each heavy chain/light chain pairing and titers with the different rearranged human germline light chains were compared to the titers obtained with the parental antibody molecule (i.e., heavy chain paired with cognate light chain) and percent of native titer was calculated (Table 11). $V_H$: Heavy chain variable gene. Vκ:κ light chain variable gene. ND: no expression detected under current experimental conditions.

TABLE 11

| Antigen | Antibody | $V_H$ | Vκ | $V_H$ Alone | $V_H$ + Vκ | $V_H$ + Vκ1-39Jκ5 | Percent of Native Titer |
|---|---|---|---|---|---|---|---|
| A | 320 | 1-18 | 2-30 | 0.3 | 3.1 | 2.0 | 66 |
|   | 321 | 2-5 | 2-28 | 0.4 | 0.4 | 1.9 | 448 |
|   | 334 | 2-5 | 2-28 | 0.4 | 2.7 | 2.0 | 73 |
|   | 313 | 3-13 | 3-15 | 0.5 | 0.7 | 4.5 | 670 |
|   | 316 | 3-23 | 4-1 | 0.3 | 0.2 | 4.1 | 2174 |
|   | 315 | 3-30 | 4-1 | 0.3 | 0.2 | 3.2 | 1327 |
|   | 318 | 4-59 | 1-17 | 0.3 | 4.6 | 4.0 | 86 |
| B | 257 | 3-13 | 1-5 | 0.4 | 3.1 | 3.2 | 104 |
|   | 283 | 3-13 | 1-5 | 0.4 | 5.4 | 3.7 | 69 |
|   | 637 | 3-13 | 1-5 | 0.4 | 4.3 | 3.0 | 70 |
|   | 638 | 3-13 | 1-5 | 0.4 | 4.1 | 3.3 | 82 |
|   | 624 | 3-23 | 1-17 | 0.3 | 5.0 | 3.9 | 79 |
|   | 284 | 3-30 | 1-17 | 0.3 | 4.6 | 3.4 | 75 |
|   | 653 | 3-33 | 1-17 | 0.3 | 4.3 | 0.3 | 7 |
|   | 268 | 4-34 | 1-27 | 0.3 | 5.5 | 3.8 | 69 |
|   | 633 | 4-34 | 1-27 | 0.6 | 6.9 | 3.0 | 44 |
| C | 730 | 3-7 | 1-5 | 0.3 | 1.1 | 2.8 | 249 |
|   | 728 | 3-7 | 1-5 | 0.3 | 2.0 | 3.2 | 157 |
|   | 691 | 3-9 | 3-20 | 0.3 | 2.8 | 3.1 | 109 |
|   | 749 | 3-33 | 3-15 | 0.3 | 3.8 | 2.3 | 62 |
|   | 750 | 3-33 | 1-16 | 0.3 | 3.0 | 2.8 | 92 |
|   | 724 | 3-33 | 1-17 | 0.3 | 2.3 | 3.4 | 151 |
|   | 706 | 3-33 | 1-16 | 0.3 | 3.6 | 3.0 | 84 |
|   | 744 | 1-18 | 1-12 | 0.4 | 5.1 | 3.0 | 59 |
|   | 696 | 3-11 | 1-16 | 0.4 | 3.0 | 2.9 | 97 |
|   | 685 | 3-13 | 3-20 | 0.3 | 0.5 | 3.4 | 734 |
|   | 732 | 3-15 | 1-17 | 0.3 | 4.5 | 3.2 | 72 |
|   | 694 | 3-15 | 1-5 | 0.4 | 5.2 | 2.9 | 55 |
|   | 743 | 3-23 | 1-12 | 0.3 | 3.2 | 0.3 | 10 |
|   | 742 | 3-23 | 2-28 | 0.4 | 4.2 | 3.1 | 74 |
|   | 693 | 3-23 | 1-12 | 0.5 | 4.2 | 4.0 | 94 |
| D | 136 | 3-23 | 2-28 | 0.4 | 5.0 | 2.7 | 55 |
|   | 155 | 3-30 | 1-16 | 0.4 | 1.0 | 2.2 | 221 |
|   | 163 | 3-30 | 1-16 | 0.3 | 0.6 | 3.0 | 506 |
|   | 171 | 3-30 | 1-16 | 0.3 | 1.0 | 2.8 | 295 |
|   | 145 | 3-43 | 1-5 | 0.4 | 4.4 | 2.9 | 65 |
|   | 49 | 3-48 | 3-11 | 0.3 | 1.7 | 2.6 | 155 |
|   | 51 | 3-48 | 1-39 | 0.1 | 1.9 | 0.1 | 4 |
|   | 159 | 3-7 | 6-21 | 0.4 | 3.9 | 3.6 | 92 |
|   | 169 | 3-7 | 6-21 | 0.3 | 1.3 | 3.1 | 235 |
|   | 134 | 3-9 | 1-5 | 0.4 | 5.0 | 2.9 | 58 |
|   | 141 | 4-31 | 1-33 | 2.4 | 4.2 | 2.6 | 63 |
|   | 142 | 4-31 | 1-33 | 0.4 | 4.2 | 2.8 | 67 |

The results obtained from these experiments demonstrate that somatically mutated, high affinity heavy chains from different gene families are able to pair with rearranged human germline Vκ1-39Jκ5 and Vκ3-20Jκ1 regions and be secreted from the cell as a normal antibody molecule. As shown in Table 10, antibody titer was increased for about 61% (42 of 69) heavy chains when paired with the rearranged human Vκ1-39Jκ5 light chain and about 29% (20 of 69) heavy chains when paired with the rearranged human Vκ3-20Jκ1 light chain as compared to the cognate light chain of the parental antibody. For about 20% (14 of 69) of the heavy chains, both rearranged human germline light chains conferred an increase in expression as compared to the cognate light chain of the parental antibody. As shown in Table 11, the rearranged human germline Vκ1-39Jκ5 region conferred an increase in expression of several heavy chains specific for a range of different classes of antigens as compared to the cognate light chain for the parental antibodies. Antibody titer was increased by more than two-fold for about 35% (15/43) of the heavy chains as compared to the cognate light chain of the parental antibodies. For two heavy chains (315 and 316), the increase was greater than ten-fold as compared to the parental antibody. Within all the heavy chains that showed increase expression relative to the cognate light chain of the parental antibody, family three ($V_H$3) heavy chains are over represented in comparison to other heavy chain variable region gene families. This demonstrates a favorable relationship of human $V_H$3 heavy chains to pair with rearranged human germline Vκ1-39Jκ5 and Vκ3-20Jκ1 light chains.

Example XI

Generation of a Rearranged Human Germline Light Chain Locus

Various rearranged human germline light chain targeting vectors were made using VELOCIGENE® genetic engineering technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify mouse genomic Bacterial Artificial Chromosome (BAC) clones 302g12 and 254 m04 (Invitrogen). Using these two BAC clones, genomic constructs were engineered to contain a single rearranged human germline light chain region and inserted into an endogenous κ light chain locus that was previously modified to delete the endogenous κ variable and joining gene segments.

Construction of Rearranged Human Germline Light Chain Targeting Vectors.

Three different rearranged human germline light chain regions were made using standard molecular biology techniques recognized in the art. The human variable gene segments used for constructing these three regions included rearranged human Vκ1-39Jκ5 sequence, a rearranged human Vκ3-20Jκ1 sequence and a rearranged human VpreBJl5 sequence.

A DNA segment containing exon 1 (encoding the leader peptide) and intron 1 of the mouse Vκ3-7 gene was made by de novo DNA synthesis (Integrated DNA Technologies). Part of the 5' untranslated region up to a naturally occurring BlpI restriction enzyme site was included. Exons of human Vκ1-39 and Vκ3-20 genes were PCR amplified from human genomic BAC libraries. The forward primers had a 5' extension containing the splice acceptor site of intron 1 of the mouse Vκ3-7 gene. The reverse primer used for PCR of the human Vκ1-39 sequence included an extension encoding human Jκ5, whereas the reverse primer used for PCR of the human Vκ3-20 sequence included an extension encoding human Jκ1. The human VpreBJλ5 sequence was made by de novo DNA synthesis (Integrated DNA Technologies). A portion of the human Jκ-Cκ intron including the splice donor site was PCR amplified from plasmid pBS-296-HA18-PIS-cel. The forward PCR primer included an extension encoding part of either a human Jκ5, Jκ1, or Jλ5 sequence. The reverse primer included a PI-SceI site, which was previously engineered into the intron.

The mouse Vκ3-7 exon1/intron 1, human variable light chain exons, and human Jκ-Cκ intron fragments were sewn together by overlap extension PCR, digested with BlpI and PI-SceI, and ligated into plasmid pBS-296-HA18-PlSceI, which contained the promoter from the human Vκ3-15 variable gene segment. A loxed hygromycin cassette within plasmid pBS-296-HA18-PlSceI was replaced with a FRTed hygromycin cassette flanked by NotI and AscI sites. The NotI/PI-SceI fragment of this plasmid was ligated into modified mouse BAC 254 m04, which contained part of the mouse Jκ-Cκ intron, the mouse Cκ exon, and about 75 kb of genomic sequence downstream of the mouse κ locus which provided a 3' homology arm for homologous recombination in mouse ES cells. The NotI/AscI fragment of this BAC was then ligated into modified mouse BAC 302g12, which contained a FRTed neomycin cassette and about 23 kb of genomic sequence upstream of the endogenous κ locus for homologous recombination in mouse ES cells.

Figure 19:
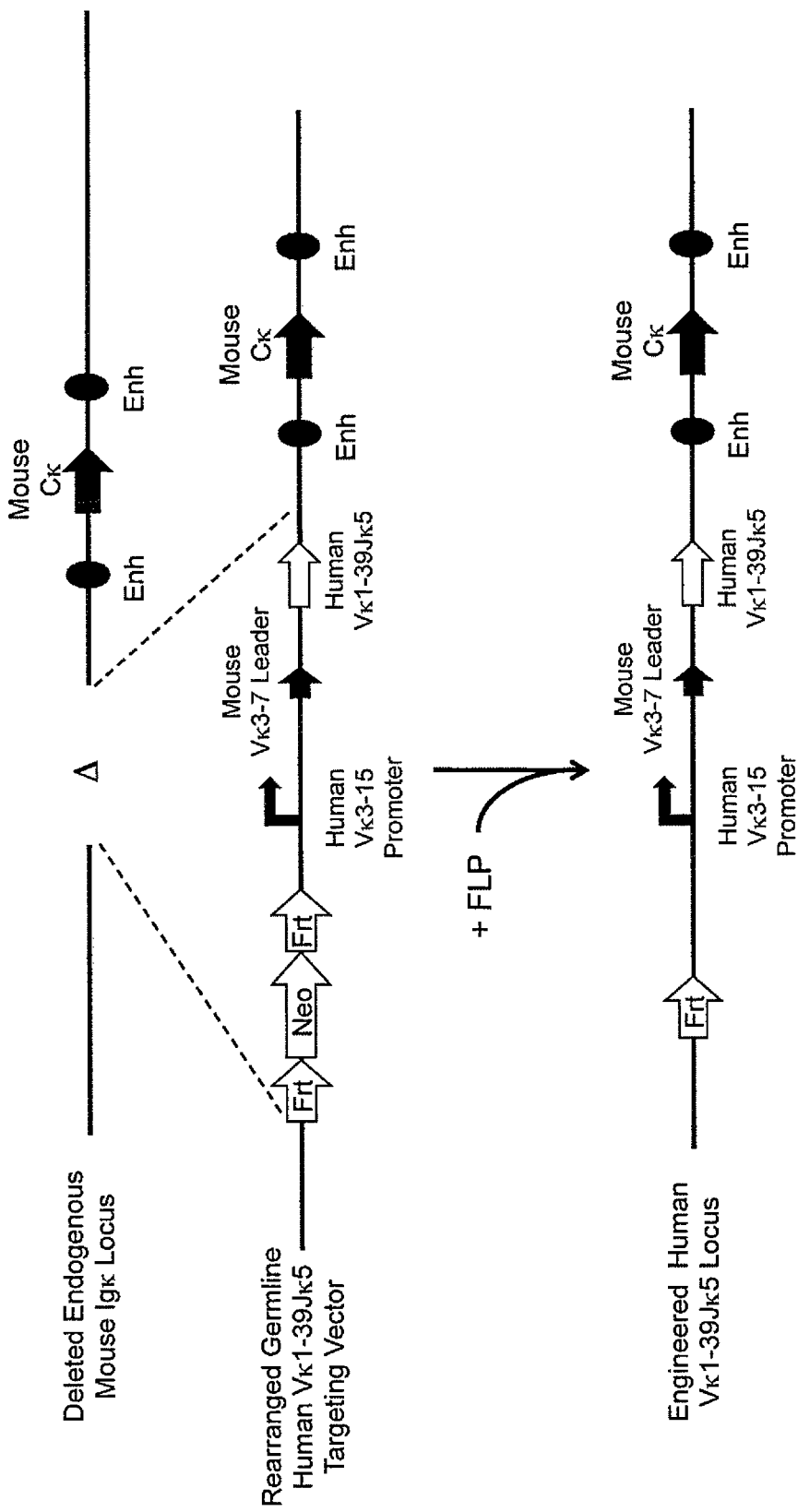
FIG. 19 illustrates a targeting strategy for replacing endogenous mouse immunoglobulin light chain variable region gene segments with a human Vκ1-39Jκ5 gene region.

Rearranged Human Germline Vκ1-39Jκ5 Targeting Vector (FIG. 19).

Restriction enzyme sites were introduced at the 5' and 3' ends of an engineered light chain insert for cloning into a targeting vector: an AscI site at the 5' end and a Pl-SceI site at the 3' end. Within the 5' AscI site and the 3' Pl-SceI site the targeting construct from 5' to 3' included a 5' homology arm containing sequence 5' to the endogenous mouse κ light chain locus obtained from mouse BAC clone 302g12, a FRTed neomycin resistance gene, a genomic sequence including the human Vκ3-15 promoter, a leader sequence of the mouse Vκ3-7 variable gene segment, a intron sequence of the mouse Vκ3-7 variable gene segment, an open reading frame of a rearranged human germline Vκ1-39Jκ5 region, a genomic sequence containing a portion of the human Jκ-Cκ intron, and a 3' homology arm containing sequence 3' of the endogenous mouse Jκ5 gene segment obtained from mouse BAC clone 254 m04 (FIG. 19, middle). Genes and/or sequences upstream of the endogenous mouse κ light chain locus and downstream of the most 3' Jκ gene segment (e.g., the endogenous 3' enhancer) were unmodified by the targeting construct (see FIG. 19). The sequence of the engineered human Vκ1-39Jκ5 locus is shown in SEQ ID NO:59.

Targeted insertion of the rearranged human germline Vκ1-39Jκ5 region into BAC DNA was confirmed by polymerase chain reaction (PCR) using primers located at sequences within the rearranged human germline light chain region. Briefly, the intron sequence 3' to the mouse Vκ3-7 leader sequence was confirmed with primers ULC-m1F (AGGTGAGGGT ACAGATAAGT GTTATGAG; SEQ ID NO:60) and ULC-m1R (TGACAAATGC CCTAATTATA GTGATCA; SEQ ID NO:61). The open reading frame of the rearranged human germline Vκ1-39Jκ5 region was confirmed with primers 1633-h2F (GGGCAAGTCA GAG-CATTAGC A; SEQ ID NO:62) and 1633-h2R (TG-CAAACTGG ATGCAGCATA G; SEQ ID NO:63). The neomycin cassette was confirmed with primers neoF (ggtggagagg ctattcggc; SEQ ID NO:64) and neoR (gaacacggcg gcatcag; SEQ ID NO:65). Targeted BAC DNA was then used to electroporate mouse ES cells to created modified ES cells for generating chimeric mice that express a rearranged human germline Vκ1-39Jκ5 region.

Positive ES cell clones were confirmed by Taqman™ screening and karyotyping using probes specific for the engineered Vκ1-39Jκ5 light chain region inserted into the endogenous locus. Briefly, probe neoP (TGGGCACAAC AGACAATCGG CTG; SEQ ID NO:66) which binds within the neomycin marker gene, probe ULC-m1P (CCATTAT-GAT GCTCCATGCC TCTCTGTTC; SEQ ID NO:67) which binds within the intron sequence 3' to the mouse Vκ3-7 leader sequence, and probe 1633h2P (ATCAGCA-GAA ACCAGGGAAA GCCCCT; SEQ ID NO:68) which binds within the rearranged human germline Vκ1-39Jκ5 open reading frame. Positive ES cell clones were then used to implant female mice to give rise to a litter of pups expressing the germline Vκ1-39Jκ5 light chain region.

Alternatively, ES cells bearing the rearranged human germline Vκ1-39Jκ5 light chain region are transfected with a constuct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice.

Figure 20:
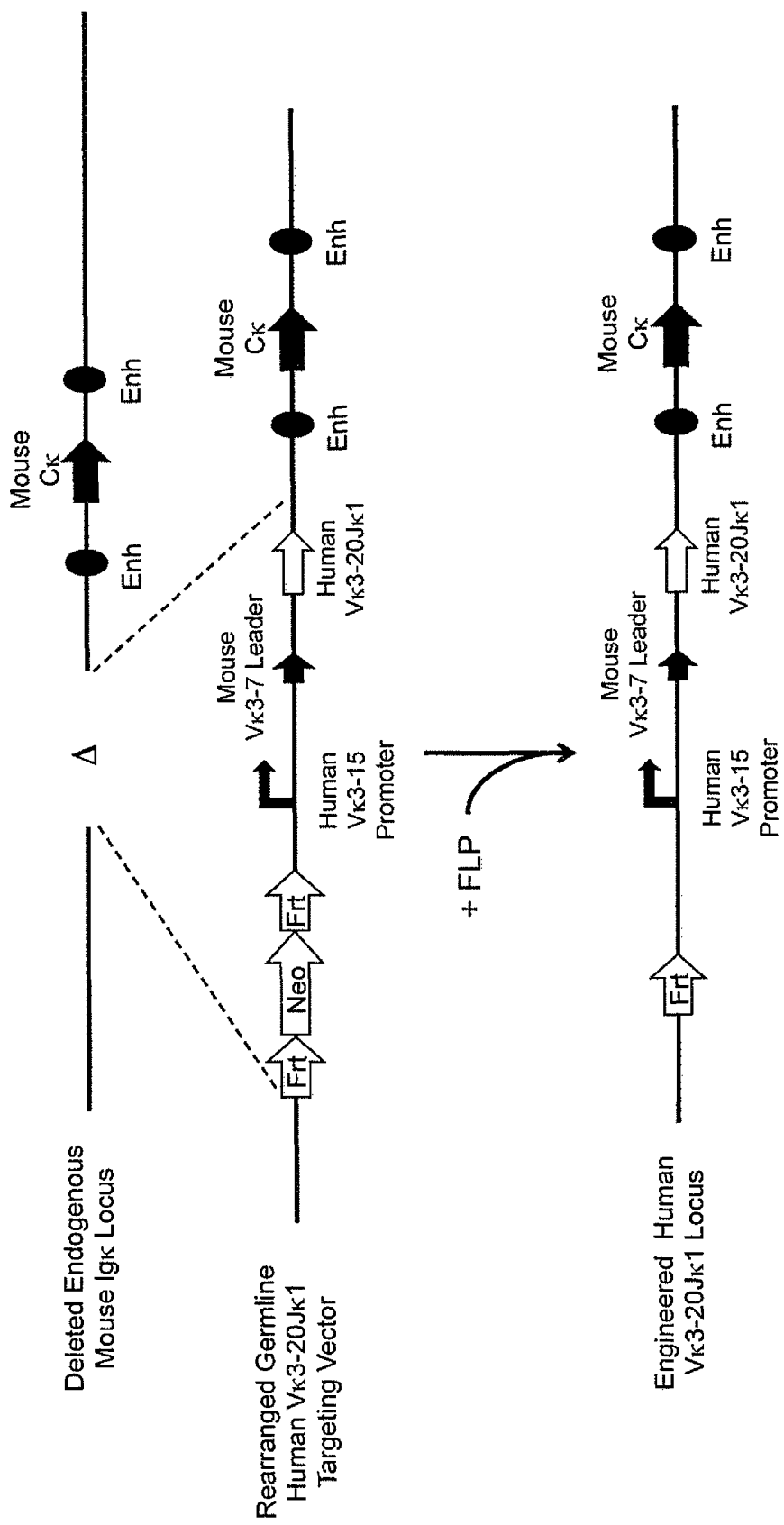
FIG. 20 illustrates a targeting strategy for replacing endogenous mouse immunoglobulin light chain variable region gene segments with a human Vκ3-20Jκ1 gene region.

Rearranged Human Germline Vκ3-20Jκ1 Targeting Vector (FIG. 20).

In a similar fashion, an engineered light chain locus expressing a rearranged human germline Vκ3-20Jκ1 region was made using a targeting construct including, from 5' to 3', a 5' homology arm containing sequence 5' to the endogenous mouse κ light chain locus obtained from mouse BAC clone 302g12, a FRTed neomycin resistance gene, a genomic sequence including the human Vκ3-15 promoter, a leader sequence of the mouse Vκ3-7 variable gene segment, an intron sequence of the mouse Vκ3-7 variable gene segment, an open reading frame of a rearranged human germline Vκ3-20Jκ1 region, a genomic sequence containing a portion of the human Jκ-Cκ intron, and a 3' homology arm containing sequence 3' of the endogenous mouse Jκ5 gene segment obtained from mouse BAC clone 254 m04 (FIG. 20, middle). The sequence of the engineered human Vκ3-20Jκ1 locus is shown in SEQ ID NO:69.

Targeted insertion of the rearranged human germline Vκ3-20Jκ1 region into BAC DNA was confirmed by polymerase chain reaction (PCR) using primers located at sequences within the rearranged human germline Vκ3-20Jκ1 light chain region. Briefly, the intron sequence 3' to the mouse Vκ3-7 leader sequence was confirmed with primers ULC-m1F (SEQ ID NO:60) and ULC-m1R (SEQ ID NO:61). The open reading frame of the rearranged human germline Vκ3-20Jκ1 region was confirmed with primers 1635-h2F (TCCAGGCACC CTGTCTTTG; SEQ ID NO:70) and 1635-h2R (AAGTAGCTGC TGCTAACACT CTGACT; SEQ ID NO:71). The neomycin cassette was confirmed with primers neoF (SEQ ID NO:64) and neoR (SEQ ID NO:65). Targeted BAC DNA was then used to electroporate mouse ES cells to created modified ES cells for generating chimeric mice that express the rearranged human germline Vκ3-20Jκ1 light chain.

Positive ES cell clones were confirmed by Taqman™ screening and karyotyping using probes specific for the engineered Vκ3-20Jκ1 light chain region inserted into the endogenous κ light chain locus. Briefly, probe neoP (SEQ ID NO:66) which binds within the neomycin marker gene, probe ULC-m1P (SEQ ID NO:67) which binds within the mouse Vκ3-7 leader sequence, and probe 1635h2P (AAAGAGCCAC CCTCTCCTGC AGGG; SEQ ID NO:72) which binds within the human Vκ3-20Jκ1 open reading frame. Positive ES cell clones were then used to implant female mice. A litter of pups expressing the human germline Vκ3-20Jκ1 light chain region.

Alternatively, ES cells bearing human germline Vκ3-20Jκ1 light chain region can be transfected with a constuct that expresses FLP in order to remove the FRTed neomycin cassette introduced by the targeting construct. Optionally, the neomycin cassette may be removed by breeding to mice that express FLP recombinase (e.g., U.S. Pat. No. 6,774, 279). Optionally, the neomycin cassette is retained in the mice.

Figure 21:
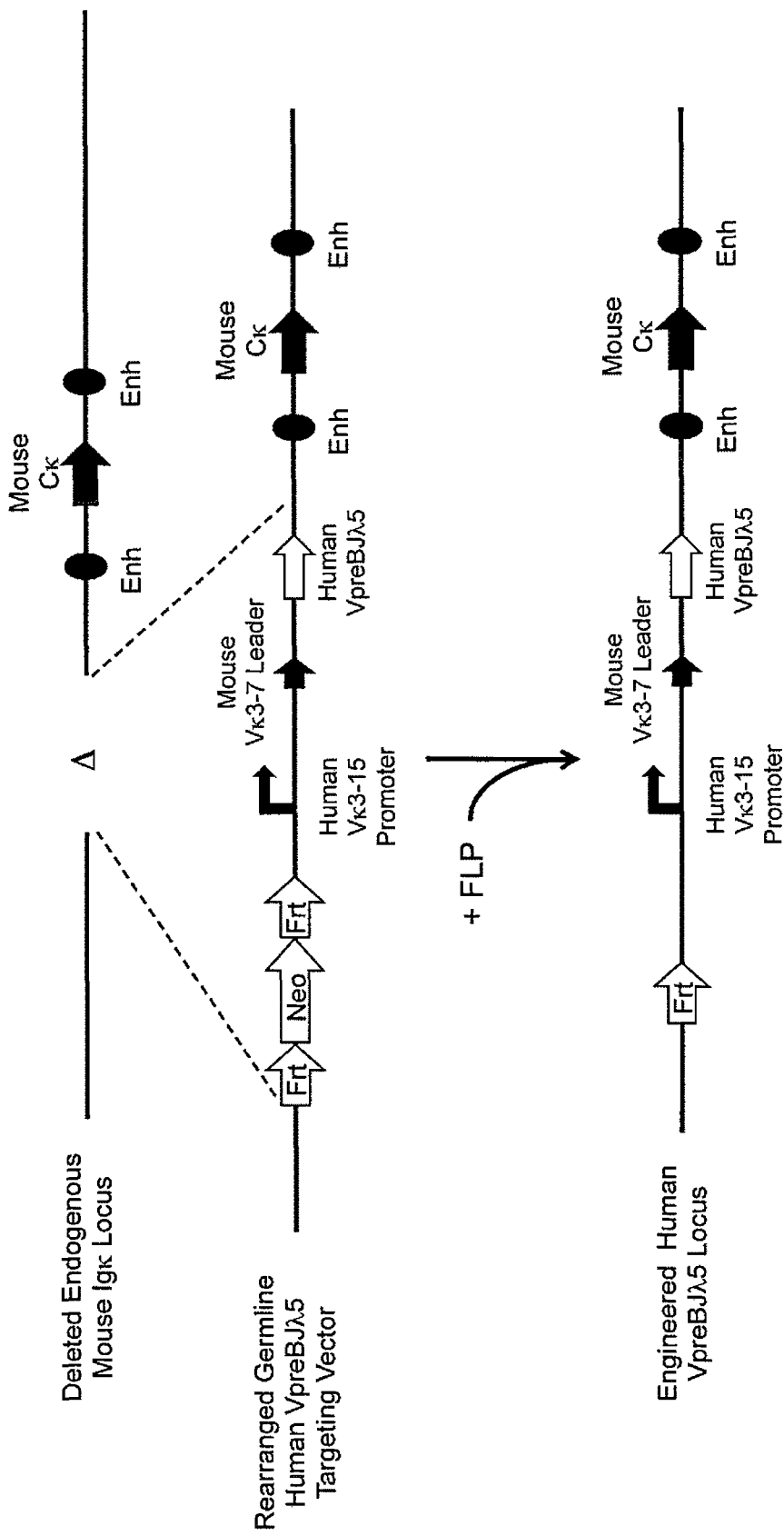
FIG. 21 illustrates a targeting strategy for replacing endogenous mouse immunoglobulin light chain variable region gene segments with a human VpreB/Jλ5 gene region.

Rearranged Human Germline VpreBJl5 Targeting Vector (FIG. 21).

In a similar fashion, an engineered light chain locus expressing a rearranged human germline VpreBJl5 region was made using a targeting construct including, from 5' to 3', a 5' homology arm containing sequence 5' to the endogenous mouse κ light chain locus obtained from mouse BAC clone 302g12, a FRTed neomycin resistance gene, an genomic sequence including the human Vκ3-15 promoter, a leader sequence of the mouse Vκ3-7 variable gene segment, an intron sequence of the mouse Vκ3-7 variable gene segment, an open reading frame of a rearranged human germline VpreBJλ5 region, a genomic sequence containing a portion of the human Jκ-Cκ intron, and a 3' homology arm containing sequence 3' of the endogenous mouse Jκ5 gene segment obtained from mouse BAC clone 254 m04 (FIG. 21, middle). The sequence of the engineered human VpreBJl5 locus is shown in SEQ ID NO:73.

Targeted insertion of the rearranged human germline VpreBJλ5 region into BAC DNA was confirmed by polymerase chain reaction (PCR) using primers located at sequences within the rearranged human germline VpreBJλ5 region light chain region. Briefly, the intron sequence 3' to the mouse Vκ3-7 leader sequence was confirmed with primers ULC-m1F (SEQ ID NO:60 and ULC-m1R (SEQ ID NO:61). The open reading frame of the rearranged human germline VpreBJλ5 region was confirmed with primers 1616-h1F (TGTCCTCGGC CCTTGGA; SEQ ID NO:74) and 1616-h1R(CCGATGTCAT GGTCGTTCCT; SEQ ID NO:75). The neomycin cassette was confirmed with primers neoF (SEQ ID NO:64) and neoR (SEQ ID NO:65). Targeted BAC DNA was then used to electroporate mouse ES cells to created modified ES cells for generating chimeric mice that express the rearranged human germline VpreBJλ5 light chain.

Positive ES cell clones are confirmed by Taqman™ screening and karyotyping using probes specific for the engineered VpreBJλ5 light chain region inserted into the endogenous κ light chain locus. Briefly, probe neoP (SEQ ID NO:66) which binds within the neomycin marker gene, probe ULC-m1P (SEQ ID NO:67) which binds within the mouse IgVκ3-7 leader sequence, and probe 1616h1P (ACAATCCGCC TCACCTGCAC CCT; SEQ ID NO:76) which binds within the human VpreBJλ5 open reading frame. Positive ES cell clones are then used to implant female mice to give rise to a litter of pups expressing a germline light chain region.

Alternatively, ES cells bearing the rearranged human germline VpreBJl5 light chain region are transfected with a construct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice.

Example XII

Generation of Mice Expressing a Single Rearranged Human Light Chain

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses, Nature Biotech. 25(1):91-99. VELOCIMICE® independently bearing an engineered human germline Vκ1-39Jκ5 light chain region, a Vκ3-20Jκ1 light chain region or a VpreBJλ75 light chain region are identified by genotyping using a modification of allele assay (Valenzuela et al., supra) that detects the presence of the unique rearranged human-germline light chain region.

Pups are genotyped and a pup heterozygous or homozygous for the unique rearranged human germline light chain region are selected for characterizing expression of the rearranged human germline light chain region.

Flow Cytometry.

Expression of the rearranged human light chain region in the normal antibody repertoire of common light chain mice was validated by analysis of immunoglobulin κ and λ expression in splenocytes and peripheral blood of common light chain mice. Cell suspensions from harvested spleens and peripheral blood of wild type (n=5), Vκ1-39Jκ5 common light chain heterozygote (n=3), Vκ1-39Jκ5 common light chain homozygote (n=3), Vκ3-20Jκ1 common light chain heterozygote (n=2), and Vκ3-20Jκ1 common light chain homozygote (n=2) mice were made using standard methods and stained with CD19⁺, Igl⁺ and Igk⁺ using fluorescently labeled antibodies (BD Pharmigen).

Figure 22:
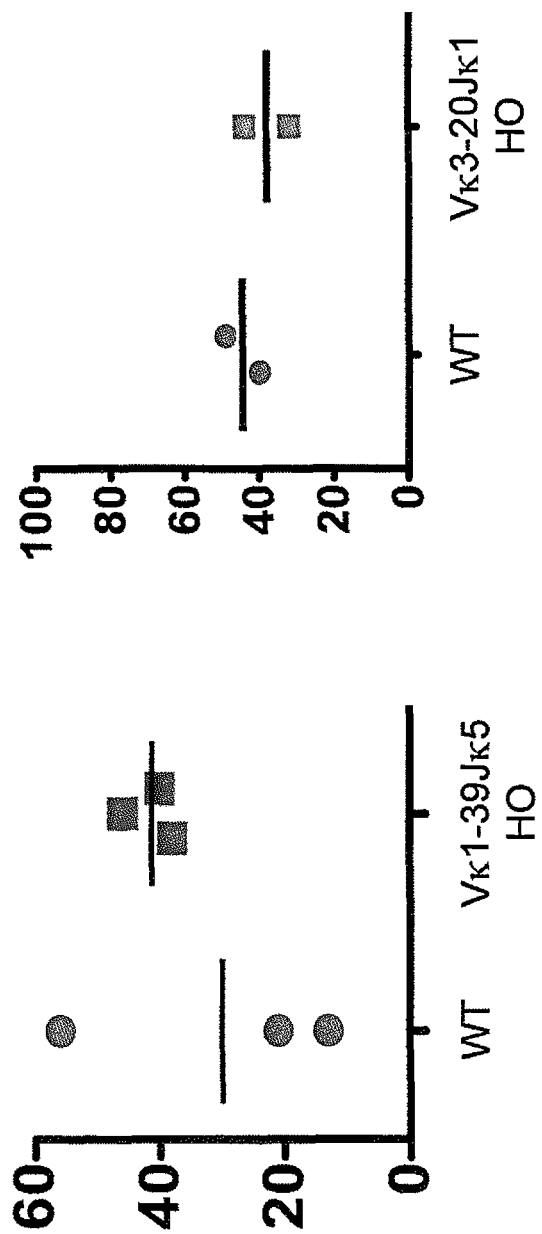
FIG. 22 shows the percent of CD19$^+$ B cells (y-axis) from peripheral blood for wild type mice (WT), mice homozygous for an engineered human rearranged Vκ1-39Jκ5 light chain region (Vκ1-39Jκ5 HO) and mice homozygous for an engineered human rearranged Vκ3-20Jκ1 light chain region (Vκ3-20Jκ1 HO).

Briefly, $1 \times 10^6$ cells were incubated with anti-mouse CD16/CD32 (clone 2.4G2, BD Pharmigen) on ice for 10 minutes, followed by labeling with the following antibody cocktail for 30 minutes on ice: APC conjugated anti-mouse CD19 (clone 1D3, BD Pharmigen), PerCP-Cy5.5 conjugated anti-mouse CD3 (clone 17A2, BioLegend), FITC conjugated anti-mouse Igκ (clone 187.1, BD Pharmigen), PE conjugated anti-mouse Igλ, (clone RML-42, BioLegend). Following staining, cells were washed and fixed in 2% formaldehyde. Data acquisition was performed on an LSRII flow cytometer and analyzed with FlowJo™. Gating: total B cells (CD19⁺CD3⁻), Igk⁺ B cells (Igk⁺Igl⁻CD19⁺CD3⁻), Igl⁺ B cells (Igκ⁻Igl⁺CD19⁺CD3⁻). Data gathered from blood and splenocyte samples demonstrated similar results. Table 12 sets forth the percent positive CD19⁺ B cells from peripheral blood of one representative mouse from each group that are Igl⁺, Igk⁺, or Igl⁺Igk⁺. Percent of CD19⁺ B cells in peripheral blood from wild type (WT) and mice homozygous for either the Vκ1-39Jκ5 or Vκ3-20Jκ1 common light chain are shown in FIG. 22.

TABLE 12

| Mouse Genotype | CD19⁺ B cells | | |
|---|---|---|---|
| | Igl⁺ | Igk⁺ | Igl⁺Igk⁺ |
| wild type | 4.8 | 93 | 0.53 |
| Vκ1-39Jκ5 | 1.4 | 93 | 2.6 |
| Vκ3-20Jκ1 | 4.2 | 88 | 6 |

Common Light Chain Expression.

Expression of each common light chain (Vκ1-39Jκ5 and Vκ3-20Jκ1) was analyzed in heterozygous and homozygous mice using a quantitative PCR assay (e.g. Taqman™).

Figure 23A:
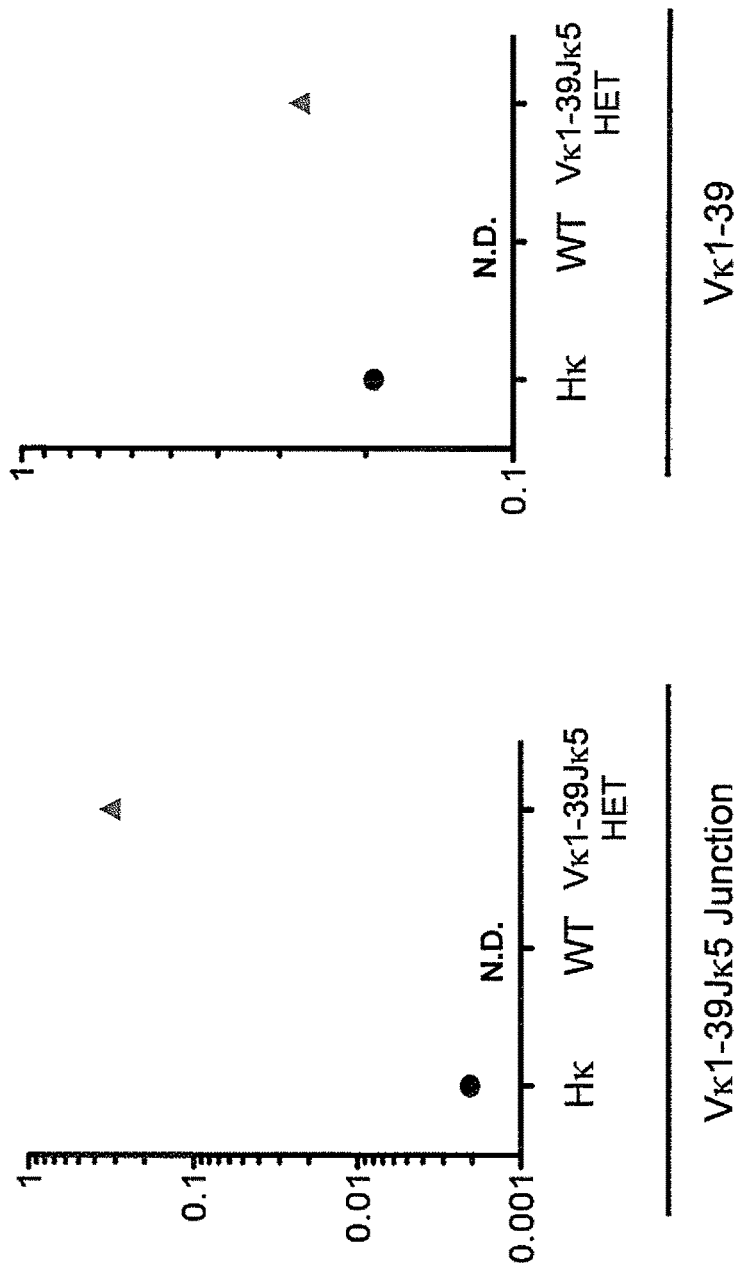
FIG. 23A shows the relative mRNA expression (y-axis) of a Vκ1-39-derived light chain in a quantitative PCR assay using probes specific for the junction of an engineered human rearranged Vκ1-39Jκ5 light chain region (Vκ1-39Jκ5 Junction Probe) and the human Vκ1-39 gene segment (Vκ1-39 Probe) in a mouse homozygous for a replacement of the endogenous Vκ and Jκ gene segments with human Vκ and Jκ gene segments (Hκ), a wild type mouse (WT), and a mouse heterozygous for an engineered human rearranged Vκ1-39Jκ5 light chain region (Vκ1-39Jκ5 HET). Signals are normalized to expression of mouse Cκ. N.D.: not detected.
Figure 23B:
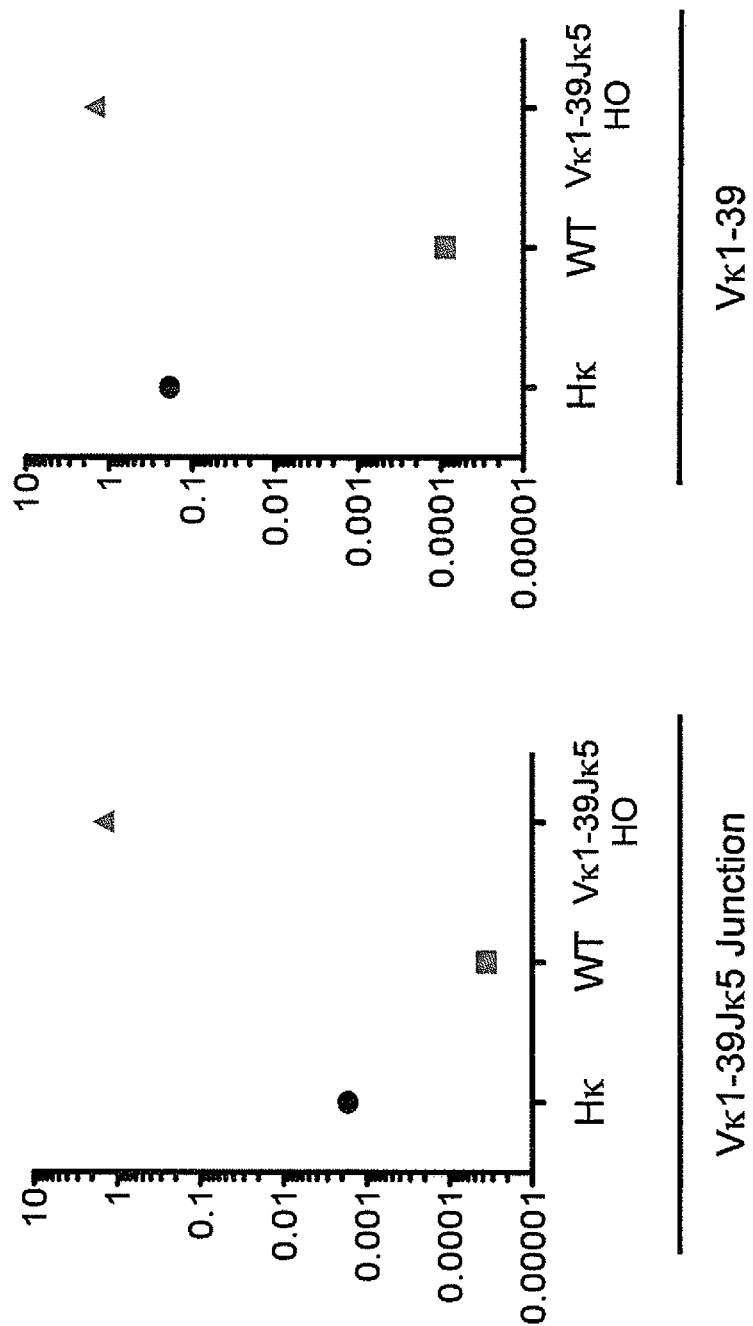
FIG. 23B shows the relative mRNA expression (y-axis) of a Vκ1-39-derived light chain in a quantitative PCR assay using probes specific for the junction of an engineered human rearranged Vκ1-39Jκ5 light chain region (Vκ1-39Jκ5 Junction Probe) and the human Vκ1-39 gene segment (Vκ1-39 Probe) in a mouse homozygous for a replacement of the endogenous Vκ and Jκ gene segments with human Vκ and Jκ gene segments (Hκ), a wild type mouse (WT), and a mouse homozygous for an engineered human rearranged Vκ1-39Jκ5 light chain region (Vκ1-39Jκ5 HO). Signals are normalized to expression of mouse Cκ.
Figure 23C:
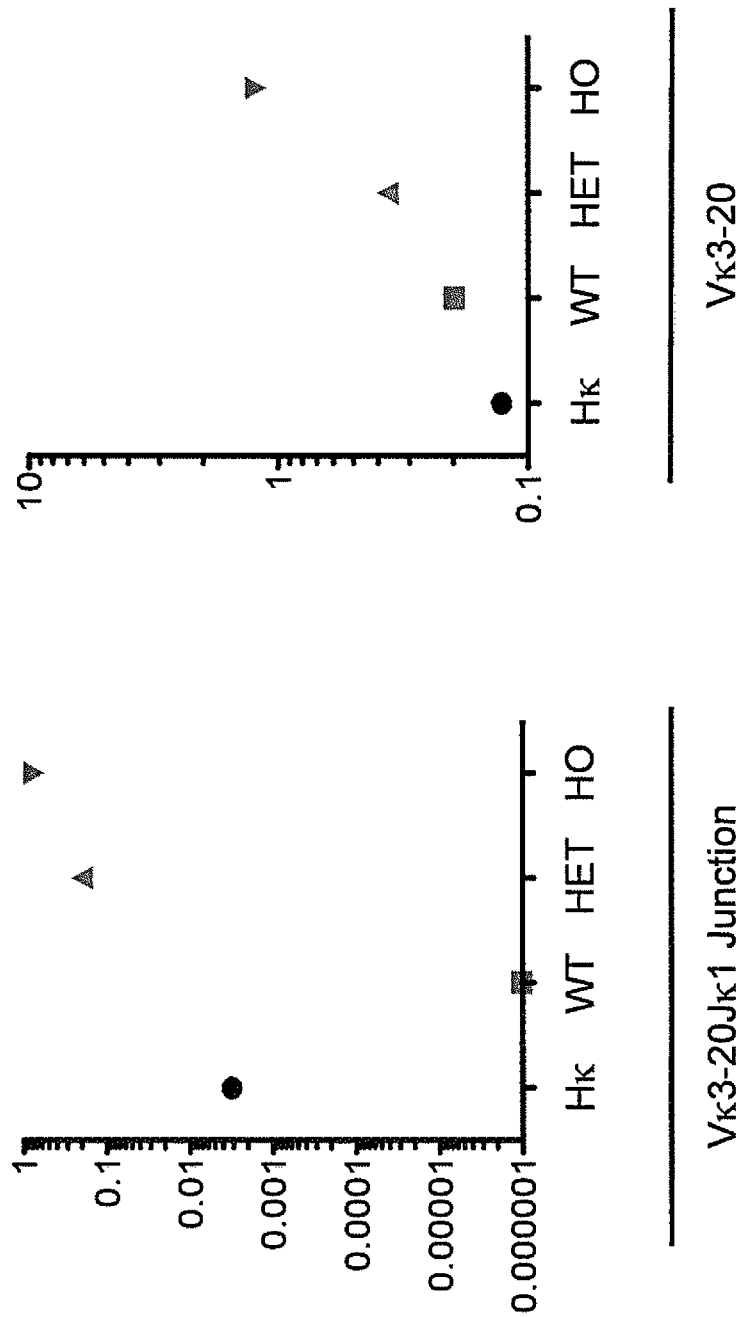
FIG. 23C shows the relative mRNA expression (y-axis) of a Vκ3-20-derived light chain in a quantitative PCR assay using probes specific for the junction of an engineered human rearranged Vκ3-20Jκ1 light chain region (Vκ3-20Jκ1 Junction Probe) and the human Vκ3-20 gene segment (Vκ3-20 Probe) in a mouse homozygous for a replacement of the endogenous Vκ and Jκ gene segments with human Vκ and Jκ gene segments (Hκ), a wild type mouse (WT), and a mouse heterozygous (HET) and homozygous (HO) for an engineered human rearranged Vκ3-20Jκ1 light chain region. Signals are normalized to expression of mouse Cκ.

Briefly, CD19⁺ B cells were purified from the spleens of wild type, mice homozygous for a replacement of the mouse heavy chain and κ light chain variable region loci with corresponding human heavy chain and κ light chain variable region loci (HK), as well as mice homozygous and heterozygous for each rearranged human light chain region (Vκ1-39Jκ5 or Vκ3-20Jκ1) using mouse CD19 Microbeads (Miltenyi Biotec) according to manufacturer's specifications. Total RNA was purified from CD19⁺ B cells using RNeasy™ Mini kit (Qiagen) according to the manufacturer's specifications and genomic RNA was removed using a RNase-free DNase on-column treatment (Qiagen). 200 ng mRNA was reverse-transcribed into cDNA using the First Stand cDNA Synthesis kit (Invitrogen) and the resulting cDNA was amplified with the Taqman™ Universal PCR Master Mix (Applied Biosystems). All reactions were performed using the ABI 7900 Sequence Detection System (Applied Biosystems) using primers and Taqman™ MGB probes spanning (1) the Vκ-Jκ junction for both common light chains, (2) the Vκ gene alone (i.e. Vκ1-39 and Vκ3-20), and (3) the mouse Cκ region. Table 13 sets forth the sequences of the primers and probes employed for this assay. Relative expression was normalized to expression of the mouse Cκ region. Results are shown in FIGS. 23A, 23B and 23C.

TABLE 13

| Region | Primer/Probe Description (5'-3') | SEQ ID NOs: |
|---|---|---|
| Vκ1-39Jκ5 Junction | (sense) AGCAGTCTGC AACCTGAAGA TTT | 77 |
| | (anti-sense) GTTTAATCTC CAGTCGTGTC CCTT | 78 |
| | (probe) CCTCCGATCA CCTTC | 79 |
| Vκ1-39 | (sense) AAACCAGGGA AAGCCCCTAA | 80 |
| | (anti-sense) ATGGGACCCC ACTTTGCA | 81 |
| | (probe) CTCCTGATCT ATGCTGCAT | 82 |
| Vκ3-20Jκ1 Junction | (sense) CAGCAGACTG GAGCCTGAAG A | 83 |
| | (anti-sense) TGATTTCCAC CTTGGTCCCT T | 84 |
| | (probe) TAGCTCACCT TGGACGTT | 85 |
| Vκ3-20 | (sense) CTCCTCATCT ATGGTGCATC CA | 86 |
| | (anti-sense) GACCCACTGC CACTGAACCT | 87 |
| | (probe) CCACTGGCAT CCC | 88 |
| Mouse Cκ | (sense) TGAGCAGCAC CCTCACGTT | 89 |
| | (anti-sense) GTGGCCTCAC AGGTATAGCT GTT | 90 |
| | (probe) ACCAAGGACG AGTATGAA | 91 |

Antigen Specific Common Light Chain Antibodies.

Common light chain mice bearing either a Vκ1-39Jκ5 or Vκ3-20Jκ1 common light chain at the endogenous mouse κ light chain locus were immunized with β-galactosidase and antibody titer was measured.

Figure 24A:
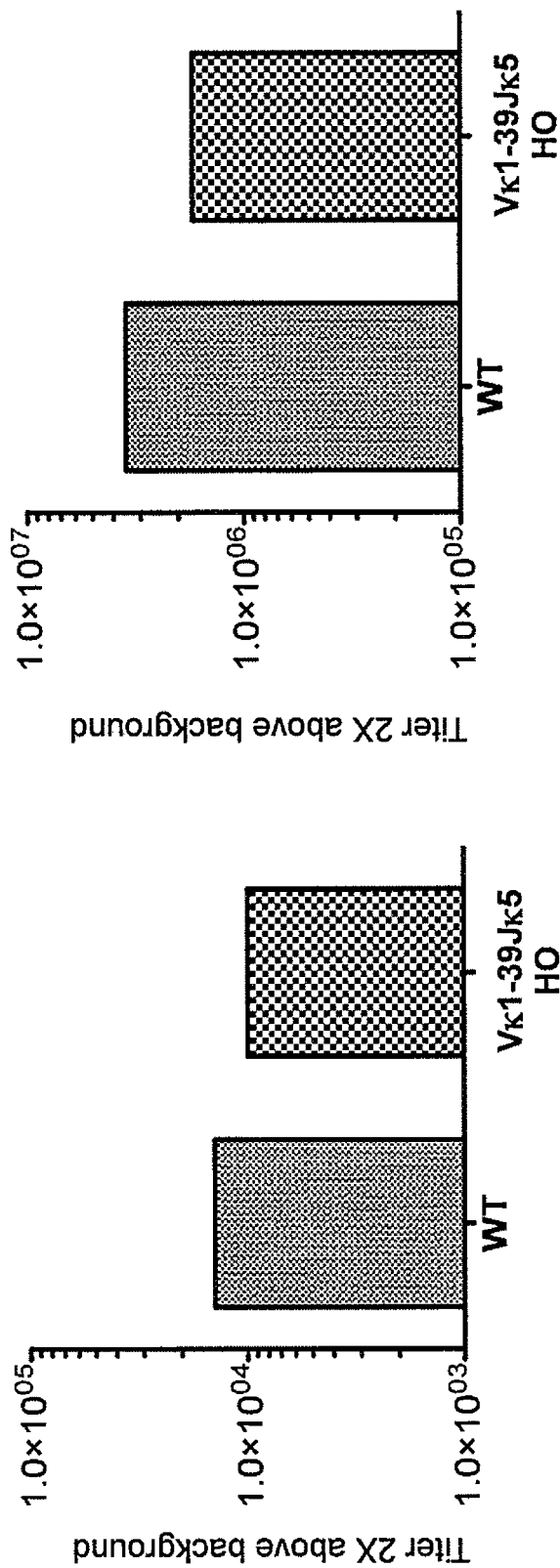
FIG. 24A shows IgM (left) and IgG (right) titer in wild type (WT; N=2) and mice homozygous for an engineered human rearranged Vκ1-39Jκ5 light chain region (Vκ1-39Jκ5 HO; N=2) immunized with β-galatosidase.
Figure 24B:
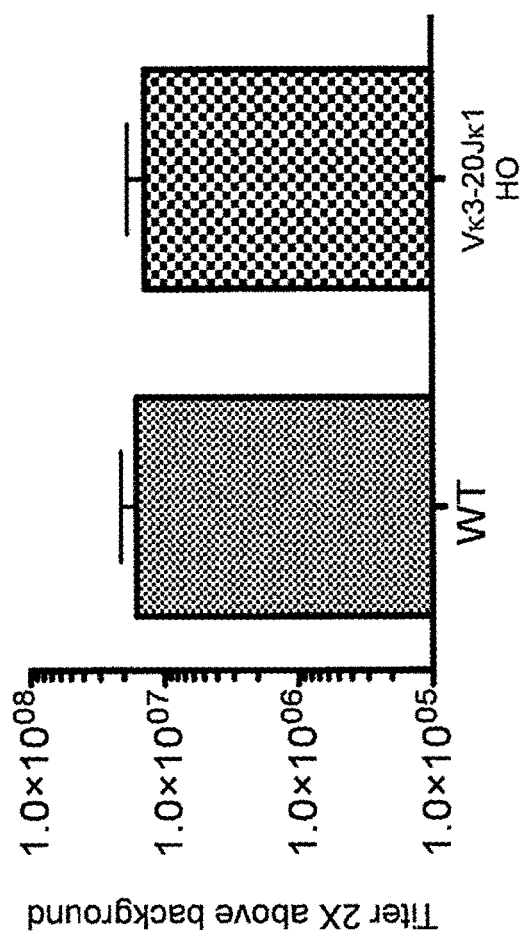
FIG. 24B shows total immunoglobulin (IgM, IgG, IgA) titer in wild type (WT; N=5) and mice homozygous for an engineered human rearranged Vκ3-20Jκ1 light chain region (Vκ3-20Jκ1 HO; N=5) immunized with β-galatosidase.

Briefly, β-galactosidase (Sigma) was emulsified in TITERMAX™ adjuvant (Sigma), as per the manufacturer's instructions. Wild type (n=7), Vκ1-39Jκ5 common light chain homozgyotes (n=2) and Vκ3-20Jκ1 common light chain homozygotes (n=5) were immunized by subcutaneous injection with 100 μg β-galactosidase/TITERMAX™. Mice were boosted by subcutaneous injection two times, 3 weeks apart, with 50 μg β-galactosidase/TITERMAX™. After the second boost, blood was collected from anaesthetized mice using a retro-orbital bleed into serum separator tubes (BD Biosciences) as per the manufacturer's instructions. To measure anti-β-galactosidase IgM or IgG antibodies, ELISA plates (Nunc) were coated with 1 μg/mL β-galactosidase overnight at 4° C. Excess antigen was washed off before blocking with PBS with 1% BSA for one hour at room temperature. Serial dilutions of serum were added to the plates and incubated for one hour at room temperature before washing. Plates were then incubated with HRP conjugated anti-19M (Southern Biotech) or anti-IgG (Southern Biotech) for one hour at room temperature. Following another wash, plates were developed with TMB substrate (BD Biosciences). Reactions were stopped with 1N sulfuric acid and $OD_{450}$ was read using a Victor X5 Plate Reader (Perkin Elmer). Data was analyzed with GRAPHPAD™ Prism and signal was calculated as the dilution of serum that is two times above background. Results are shown in FIGS. 24A and 24B.

As shown in this Example, the ratio of κ/λ B cells in both the splenic and peripheral compartments of Vκ1-39Jκ5 and Vκ3-20Jκ1 common light chain mice demonstrated a near wild type pattern (Table 12 and FIG. 22). VpreBJλ5 common light chain mice, however, demonstrated fewer peripheral B cells, of which about 1-2% express the engineered human light chain region (data not shown). The expression levels of the Vκ1-39Jκ5 and Vκ3-20Jκ1 rearranged human light chain regions from the endogenous κ light chain locus were elevated in comparison to an endogenous κ light chain locus containing a complete replacement of mouse Vκ and Jκ gene segments with human Vκ and Jκ gene segments (FIGS. 23A, 23B and 23C). The expression levels of the VpreBJλ5 rearranged human light chain region demonstrated similar high expression from the endogenous κ light chain locus in both heterozygous and homozygous mice (data not shown). This demonstrates that in direct competition with the mouse λ, κ, or both endogenous light chain loci, a single rearranged human $V_L/J_L$ sequence can yield better than wild type level expression from the endogenous k light chain locus and give rise to normal splenic and blood B cell frequency. Further, the presence of an engineered κ light chain locus having either a human Vκ1-39Jκ5 or human Vκ3-20Jκ1 sequence was well tolerated by the mice and appear to function in wild type fashion by representing a substantial portion of the light chain repertoire in the humoral component of the immune response (FIGS. 24A and 24B).

Example XIII

Breeding of Mice Expressing a Single Rearranged Human Germline Light Chain

This Example describes several other genetically modified mouse strains that can be bred to any one of the common light chain mice described herein to create multiple genetically modified mouse strains harboring multiple genetically modified immunoglobulin loci.

Endogenous Igλ Knockout (KO).

To optimize the usage of the engineered light chain locus, mice bearing one of the rearranged human germline light chain regions are bred to another mouse containing a deletion in the endogenous λ light chain locus. In this manner, the progeny obtained will express, as their only light chain, the rearranged human germline light chain region as described in Example 11. Breeding is performed by standard techniques recognized in the art and, alternatively, by a commercial breeder (e.g., The Jackson Laboratory). Mouse strains bearing an engineered light chain locus and a deletion of the endogenous λ light chain locus are screened for presence of the unique light chain region and absence of endogenous mouse λ light chains.

Humanized Endogenous Heavy Chain Locus.

Mice bearing an engineered human germline light chain locus are bred with mice that contain a replacement of the endogenous mouse heavy chain variable gene locus with the human heavy chain variable gene locus (see U.S. Pat. No. 6,596,541; the VELOCIMMUNE® humanized mouse, Regeneron Pharmaceuticals, Inc.). The VELOCIMMUNE® humanized mouse comprises a genome comprising human heavy chain variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies is isolated and operably linked to DNA encoding the human heavy chain constant regions. The DNA is then expressed in a cell capable of expressing the fully human heavy chain of the antibody.

Mice bearing a replacement of the endogenous mouse $V_H$ locus with the human $V_H$ locus and a single rearranged human germline $V_L$ region at the endogenous κ light chain locus are obtained. Reverse chimeric antibodies containing somatically mutated heavy chains (human $V_H$ and mouse $C_H$) with a single human light chain (human $V_L$ and mouse $C_L$) are obtained upon immunization with an antigen of interest. $V_H$ and $V_L$ nucleotide sequences of B cells expressing the antibodies are identified and fully human antibodies are made by fusion the $V_H$ and $V_L$ nucleotide sequences to human $C_H$ and $C_L$ nucleotide sequences in a suitable expression system.

Example XIV

Generation of Antibodies from Mice Expressing Human Heavy Chains and a Rearranged Human Germline Light Chain Region After breeding mice that contain the engineered human light chain region to various desired strains containing modifications and deletions of other endogenous Ig loci (as described in Example 12), selected mice can be immunized with an antigen of interest.

Generally, a VELOCIMMUNE® humanized mouse containing one of the single rearranged human germline light chain regions is challenged with an antigen, and lymphatic cells (such as B-cells) are recovered from serum of the animals. The lymphatic cells are fused with a myeloma cell line to prepare immortal hybridoma cell lines, and such hybridoma cell lines are screened and selected to identify hybridoma cell lines that produce antibodies containing human heavy chain variables and a rearranged human germline light chains which are specific to the antigen used for immunization. DNA encoding the variable regions of the heavy chains and the light chain are isolated and linked to desirable isotypic constant regions of the heavy chain and light chain. Due to the presence of the endogenous mouse sequences and any additional cis-acting elements present in the endogenous locus, the single light chain of each antibody may be somatically mutated. This adds additional diversity to the antigen-specific repertoire comprising a single light chain and diverse heavy chain sequences. The resulting cloned antibody sequences are subsequently expressed in a cell, such as a CHO cell. Alternatively, DNA encoding the antigen-specific chimeric antibodies or the variable domains of the light and heavy chains are identified directly from antigen-specific lymphocytes.

Initially, high affinity chimeric antibodies are isolated having a human variable region and a mouse constant region. As described above, the antibodies are characterized and selected for desirable characteristics, including affinity, selectivity, epitope, etc. The mouse constant regions are replaced with a desired human constant region to generate the fully human antibody containing a somatically mutated human heavy chain and a single light chain derived from a rearranged human germline light chain region of the invention. Suitable human constant regions include, for example wild type or modified IgG1 or IgG4.

Separate cohorts of VELOCIMMUNE® humanized mice containing a replacement of the endogenous mouse heavy chain locus with human $V_H$, $D_H$, and $J_H$ gene segments and a replacement of the endogenous mouse κ light chain locus with either the engineered germline Vκ1-39Jκ5 human light chain region or the engineered germline Vκ3-20Jκ1 human light chain region (described above) were immunized with a human cell surface receptor protein (Antigen E). Antigen E is administered directly onto the hind footpad of mice with six consecutive injections every 3-4 days. Two to three micrograms of Antigen E are mixed with 10 μg of CpG oligonucleotide (Cat # tlrl-modn—ODN1826 oligonucleotide; InVivogen, San Diego, Calif.) and 25 μg of Adju-Phos (Aluminum phosphate gel adjuvant, Cat# H-71639-250; Brenntag Biosector, Frederikssund, Denmark) prior to injection. A total of six injections are given prior to the final antigen recall, which is given 3-5 days prior to sacrifice. Bleeds after the 4th and 6th injection are collected and the antibody immune response is monitored by a standard antigen-specific immunoassay.

When a desired immune response is achieved splenocytes are harvested and fused with mouse myeloma cells to preserve their viability and form hybridoma cell lines. The hybridoma cell lines are screened and selected to identify cell lines that produce Antigen E-specific common light chain antibodies. Using this technique several anti-Antigen E-specific common light chain antibodies (i.e., antibodies possessing human heavy chain variable domains, the same human light chain variable domain, and mouse constant domains) are obtained.

Alternatively, anti-Antigen E common light chain antibodies are isolated directly from antigen-positive B cells without fusion to myeloma cells, as described in U.S. 2007/0280945A1, herein specifically incorporated by reference in its entirety. Using this method, several fully human anti-Antigen E common light chain antibodies (i.e., antibodies possessing human heavy chain variable domains, either an engineered human Vκ1-39Jκ5 light chain or an engineered human Vκ3-20Jκ1 light chain region, and human constant domains) were obtained.

The biological properties of the exemplary anti-Antigen E common light chain antibodies generated in accordance with the methods of this Example are described in detail below.

Example XV

Heavy Chain Gene Segment Usage in Antigen-Specific Common Light Chain Antibodies To analyze the structure of the human anti-Antigen E common light chain antibodies produced, nucleic acids encoding heavy chain antibody variable regions were cloned and sequenced. From the nucleic acid sequences and predicted amino acid sequences of the antibodies, gene usage was identified for the heavy chain variable region (HCVR) of selected common light chain antibodies obtained from immunized VELOCIMMUNE® humanized mice containing either the engineered human Vκ1-39Jκ5 light chain or engineered human Vκ3-20Jκ1 light chain region. Results are shown in Tables 14 and 15, which demonstrate that mice according to the invention generate antigen-specific common light chain antibodies from a variety of human heavy chain gene segments, due to a variety of rearrangements, when employing either a mouse that expresses a light chain from only a human Vκ1-39- or a human Vκ3-20-derived light chain. Human $V_H$ gene segments of the 2, 3, 4, and 5 families rearranged with a variety of human $D_H$ segments and human $J_H$ segments to yield antigen-specific antibodies.

TABLE 14

Vκ1-39Jκ5
Common Light Chain Antibodies

| Antibody | HCVR V_H | D_H | J_H |
|---|---|---|---|
| 2952 | 2-5 | 6-6 | 1 |
| 5978 | 2-5 | 6-6 | 1 |
| 5981 | 2-5 | 3-22 | 1 |
| 6027 | 3-13 | 6-6 | 5 |
| 3022 | 3-23 | 3-10 | 4 |
| 3028 | 3-23 | 3-3 | 4 |
| 5999 | 3-23 | 6-6 | 4 |
| 6009 | 3-23 | 2-8 | 4 |
| 6011 | 3-23 | 7-27 | 4 |
| 5980 | 3-30 | 1-1 | 4 |
| 3014 | 3-30 | 1-7 | 4 |
| 3015 | 3-30 | 1-7 | 4 |
| 3023 | 3-30 | 1-7 | 4 |
| 3024 | 3-30 | 1-7 | 4 |
| 3032 | 3-30 | 1-7 | 4 |
| 6024 | 3-30 | 1-7 | 4 |
| 6025 | 3-30 | 1-7 | 4 |
| 6031 | 3-30 | 1-7 | 4 |
| 6007 | 3-30 | 3-3 | 4 |
| 2982 | 3-30 | 3-22 | 5 |
| 6001 | 3-30 | 3-22 | 5 |
| 6005 | 3-30 | 3-22 | 5 |
| 6035 | 3-30 | 5-5 | 2 |
| 3013 | 3-30 | 5-12 | 4 |
| 3042 | 3-30 | 5-12 | 4 |
| 2955 | 3-30 | 6-6 | 1 |
| 3043 | 3-30 | 6-6 | 3 |
| 3018 | 3-30 | 6-6 | 4 |
| 2949 | 3-30 | 6-6 | 5 |
| 2950 | 3-30 | 6-6 | 5 |
| 2954 | 3-30 | 6-6 | 5 |
| 2978 | 3-30 | 6-6 | 5 |
| 3016 | 3-30 | 6-6 | 5 |
| 3017 | 3-30 | 6-6 | 5 |
| 3033 | 3-30 | 6-6 | 5 |
| 3041 | 3-30 | 6-6 | 5 |
| 5979 | 3-30 | 6-6 | 5 |
| 5998 | 3-30 | 6-6 | 5 |
| 6004 | 3-30 | 6-6 | 5 |
| 6010 | 3-30 | 6-6 | 5 |
| 6019 | 3-30 | 6-6 | 5 |
| 6021 | 3-30 | 6-6 | 5 |
| 6022 | 3-30 | 6-6 | 5 |
| 6023 | 3-30 | 6-6 | 5 |
| 6030 | 3-30 | 6-6 | 5 |
| 6032 | 3-30 | 6-6 | 5 |
| 2985 | 3-30 | 6-13 | 4 |
| 2997 | 3-30 | 6-13 | 4 |
| 3011 | 3-30 | 6-13 | 4 |
| 3047 | 3-30 | 6-13 | 4 |
| 5982 | 3-30 | 6-13 | 4 |
| 6002 | 3-30 | 6-13 | 4 |
| 6003 | 3-30 | 6-13 | 4 |
| 6012 | 3-30 | 6-13 | 4 |
| 6013 | 3-30 | 6-13 | 4 |
| 6014 | 3-30 | 6-13 | 4 |
| 6015 | 3-30 | 6-13 | 4 |
| 6016 | 3-30 | 6-13 | 4 |
| 6017 | 3-30 | 6-13 | 4 |
| 6020 | 3-30 | 6-13 | 4 |
| 6034 | 3-30 | 6-13 | 4 |
| 2948 | 3-30 | 7-27 | 4 |
| 2987 | 3-30 | 7-27 | 4 |
| 2996 | 3-30 | 7-27 | 4 |
| 3005 | 3-30 | 7-27 | 4 |
| 3012 | 3-30 | 7-27 | 4 |
| 3020 | 3-30 | 7-27 | 4 |
| 3021 | 3-30 | 7-27 | 4 |
| 3025 | 3-30 | 7-27 | 4 |
| 3030 | 3-30 | 7-27 | 4 |
| 3036 | 3-30 | 7-27 | 4 |
| 5997 | 3-30 | 7-27 | 4 |
| 6033 | 3-30 | 7-27 | 4 |

TABLE 14-continued

Vκ1-39Jκ5
Common Light Chain Antibodies

| Antibody | HCVR V_H | D_H | J_H |
|---|---|---|---|
| 3004 | 3-30 | 7-27 | 5 |
| 6028 | 3-30 | 7-27 | 6 |
| 3010 | 4-59 | 3-16 | 3 |
| 3019 | 4-59 | 3-16 | 3 |
| 6018 | 4-59 | 3-16 | 3 |
| 6026 | 4-59 | 3-16 | 3 |
| 6029 | 4-59 | 3-16 | 3 |
| 6036 | 4-59 | 3-16 | 3 |
| 6037 | 4-59 | 3-16 | 3 |
| 2964 | 4-59 | 3-22 | 3 |
| 3027 | 4-59 | 3-16 | 4 |
| 3046 | 5-51 | 5-5 | 3 |
| 6000 | 1-69 | 6-13 | 4 |
| 6006 | 1-69 | 6-6 | 5 |
| 6008 | 1-69 | 6-13 | 4 |

TABLE 15

Vκ3-20Jκ1
Common Light Chain Antibodies

| Antibody | HCVR V_H | D_H | J_H |
|---|---|---|---|
| 5989 | 3-30 | 3-3 | 3 |
| 5994 | 3-33 | 1-7 | 4 |
| 5985 | 3-33 | 2-15 | 4 |
| 5987 | 3-33 | 2-15 | 4 |
| 5995 | 3-33 | 2-15 | 4 |
| 2968 | 4-39 | 1-26 | 3 |
| 5988 | 4-39 | 1-26 | 3 |
| 5990 | 4-39 | 1-26 | 3 |
| 5992 | 4-39 | 1-26 | 3 |
| 2975 | 5-51 | 6-13 | 5 |
| 2972 | 5-51 | 3-16 | 6 |
| 5986 | 5-51 | 3-16 | 6 |
| 5993 | 5-51 | 3-16 | 6 |
| 5996 | 5-51 | 3-16 | 6 |
| 5984 | 3-53 | 1-1 | 4 |

Example XVI

Determination of Blocking Ability of
Antigen-Specific Common Light Chain Antibodies
by LUMINEX™ Assay Ninety-eight human common light chain antibodies raised against Antigen E were tested for their ability to block binding of Antigen E's natural ligand (Ligand Y) to Antigen E in a bead-based assay.

The extracellular domain (ECD) of Antigen E was conjugated to two myc epitope tags and a 6× histidine tag (Antigen E-mmH) and amine-coupled to carboxylated microspheres at a concentration of 20 μg/mL in MES buffer. The mixture was incubated for two hours at room temperature followed by bead deactivation with 1M Tris pH 8.0 followed by washing in PBS with 0.05% (v/v) Tween-20. The beads were then blocked with PBS (Irvine Scientific, Santa Ana, Calif.) containing 2% (w/v) BSA (Sigma-Aldrich Corp., St. Louis, Mo.). In a 96-well filter plate, supernatants containing Antigen E-specific common light chain antibodies, were diluted 1:15 in buffer. A negative control containing a mock supernatant with the same media components as for the antibody supernatant was prepared. Antigen E-labeled beads were added to the supernatants and incubated overnight at 4° C. Biotinylated-Ligand Y protein was added to a final concentration of 0.06 nM and incubated for two hours at room temperature. Detection of biotinylated-Ligand Y bound to Antigen E-myc-myc-6His labeled beads was determined with R-Phycoerythrin conjugated to Streptavidin (Moss Inc, Pasadena, Md.) followed by measurement in a LUMINEX™ flow cytometry-based analyzer. Background Mean Fluorescence Intensity (MFI) of a sample without Ligand Y was subtracted from all samples. Percent blocking was calculated by division of the background-subtracted MFI of each sample by the adjusted negative control value, multiplying by 100 and subtracting the resulting value from 100.

In a similar experiment, the same 98 human common light chain antibodies raised against Antigen E were tested for their ability to block binding of Antigen E to Ligand Y-labeled beads.

Briefly, Ligand Y was amine-coupled to carboxylated microspheres at a concentration of 20 μg/mL diluted in MES buffer. The mixture and incubated two hours at room temperature followed by deactivation of beads with 1M Tris pH 8 then washing in PBS with 0.05% (v/v) Tween-20. The beads were then blocked with PBS (Irvine Scientific, Santa Ana, Calif.) containing 2% (w/v) BSA (Sigma-Aldrich Corp., St. Louis, Mo.). In a 96-well filter plate, supernatants containing Antigen E-specific common light chain antibodies were diluted 1:15 in buffer. A negative control containing a mock supernatant with the same media components as for the antibody supernatant was prepared. A biotinylated-Antigen E-mmH was added to a final concentration of 0.42 nM and incubated overnight at 4° C. Ligand Y-labeled beads were then added to the antibody/Antigen E mixture and incubated for two hours at room temperature. Detection of biotinylated-Antigen E-mmH bound to Ligand Y-beads was determined with R-Phycoerythrin conjugated to Streptavidin (Moss Inc, Pasadena, Md.) followed by measurement in a LUMINEX™ flow cytometry-based analyzer, Background Mean Fluorescence Intensity (MFI) of a sample without Antigen E was subtracted from all samples. Percent blocking was calculated by division of the background-subtracted MFI of each sample by the adjusted negative control value, multiplying by 100 and subtracting the resulting value from 100.

Tables 16 and 17 show the percent blocking for all 98 anti-Antigen E common light chain antibodies tested in both LUMINEX™ assays. ND: not determined under current experimental conditions.

TABLE 16

| Vκ1-39Jκ5 Common Light Chain Antibodies | | |
|---|---|---|
| Antibody | % Blocking of Antigen E-Labeled Beads | % Blocking of Antigen E In Solution |
| 2948 | 81.1 | 47.8 |
| 2948G | 38.6 | ND |
| 2949 | 97.6 | 78.8 |
| 2949G | 97.1 | 73.7 |
| 2950 | 96.2 | 81.9 |
| 2950G | 89.8 | 31.4 |
| 2952 | 96.1 | 74.3 |
| 2952G | 93.5 | 39.9 |
| 2954 | 93.7 | 70.1 |
| 2954G | 91.7 | 30.1 |
| 2955 | 75.8 | 30.0 |
| 2955G | 71.8 | ND |
| 2964 | 92.1 | 31.4 |
| 2964G | 94.6 | 43.0 |
| 2978 | 98.0 | 95.1 |
| 2978G | 13.9 | 94.1 |
| 2982 | 92.8 | 78.5 |
| 2982G | 41.9 | 52.4 |
| 2985 | 39.5 | 31.2 |
| 2985G | 2.0 | 5.0 |
| 2987 | 81.7 | 67.8 |
| 2987G | 26.6 | 29.3 |
| 2996 | 87.3 | 55.3 |
| 2996G | 95.9 | 38.4 |
| 2997 | 93.4 | 70.6 |
| 2997G | 9.7 | 7.5 |
| 3004 | 79.0 | 48.4 |
| 3004G | 60.3 | 40.7 |
| 3005 | 97.4 | 93.5 |
| 3005G | 77.5 | 75.6 |
| 3010 | 98.0 | 82.6 |
| 3010G | 97.9 | 81.0 |
| 3011 | 87.4 | 42.8 |
| 3011G | 83.5 | 41.7 |
| 3012 | 91.0 | 60.8 |
| 3012G | 52.4 | 16.8 |
| 3013 | 80.3 | 65.8 |
| 3013G | 17.5 | 15.4 |
| 3014 | 63.4 | 20.7 |
| 3014G | 74.4 | 28.5 |
| 3015 | 89.1 | 55.7 |
| 3015G | 58.8 | 17.3 |
| 3016 | 97.1 | 81.6 |
| 3016G | 93.1 | 66.4 |
| 3017 | 94.8 | 70.2 |
| 3017G | 87.9 | 40.8 |
| 3018 | 85.4 | 54.0 |
| 3018G | 26.1 | 12.7 |
| 3019 | 99.3 | 92.4 |
| 3019G | 99.3 | 88.1 |
| 3020 | 96.7 | 90.3 |
| 3020G | 85.2 | 41.5 |
| 3021 | 74.5 | 26.1 |
| 3021G | 81.1 | 27.4 |
| 3022 | 65.2 | 17.6 |
| 3022G | 67.2 | 9.1 |
| 3023 | 71.4 | 28.5 |
| 3023G | 73.8 | 29.7 |
| 3024 | 73.9 | 32.6 |
| 3024G | 89.0 | 10.0 |
| 3025 | 70.7 | 15.6 |
| 3025G | 76.7 | 24.3 |
| 3027 | 96.2 | 61.6 |
| 3027G | 98.6 | 75.3 |
| 3028 | 92.4 | 29.0 |
| 3028G | 87.3 | 28.8 |
| 3030 | 6.0 | 10.6 |
| 3030G | 41.3 | 14.2 |
| 3032 | 76.5 | 31.4 |
| 3032G | 17.7 | 11.0 |
| 3033 | 98.2 | 86.1 |
| 3033G | 93.6 | 64.0 |
| 3036 | 74.7 | 32.7 |
| 3036G | 90.1 | 51.2 |
| 3041 | 95.3 | 75.9 |
| 3041G | 92.4 | 51.6 |
| 3042 | 88.1 | 73.3 |
| 3042G | 60.9 | 25.2 |
| 3043 | 90.8 | 65.8 |
| 3043G | 92.8 | 60.3 |

TABLE 17

Vκ3-20Jκ1
Common Light Chain Antibodies

| Antibody | % Blocking of Antigen E-Labeled Beads | % Blocking of Antigen E In Solution |
|---|---|---|
| 2968 | 97.1 | 73.3 |
| 2968G | 67.1 | 14.6 |
| 2969 | 51.7 | 20.3 |
| 2969G | 37.2 | 16.5 |
| 2970 | 92.2 | 34.2 |
| 2970G | 92.7 | 27.2 |
| 2971 | 23.4 | 11.6 |
| 2971G | 18.8 | 18.9 |
| 2972 | 67.1 | 38.8 |
| 2972G | 64.5 | 39.2 |
| 2973 | 77.7 | 27.0 |
| 2973G | 51.1 | 20.7 |
| 2974 | 57.8 | 12.4 |
| 2974G | 69.9 | 17.6 |
| 2975 | 49.4 | 18.2 |
| 2975G | 32.0 | 19.5 |
| 2976 | 1.0 | 1.0 |
| 2976G | 50.4 | 20.4 |

In the first LUMINEX™ experiment described above, 80 common light chain antibodies containing the Vκ1-39Jκ5 engineered light chain were tested for their ability to block Ligand Y binding to Antigen E-labeled beads. Of these 80 common light chain antibodies, 68 demonstrated >50% blocking, while 12 demonstrated <50% blocking (6 at 25-50% blocking and 6 at <25% blocking). For the 18 common light chain antibodies containing the Vκ3-20Jκ1 engineered light chain, 12 demonstrated >50% blocking, while 6 demonstrated <50% blocking (3 at 25-50% blocking and 3 at <25% blocking) of Ligand Y binding to Antigen E-labeled beads.

In the second LUMINEX™ experiment described above, the same 80 common light chain antibodies containing the Vκ1-39Jκ5 engineered light chain were tested for their ability to block binding of Antigen E to Ligand Y-labeled beads. Of these 80 common light chain antibodies, 36 demonstrated >50% blocking, while 44 demonstrated <50% blocking (27 at 25-50% blocking and 17 at <25% blocking). For the 18 common light chain antibodies containing the Vκ3-20Jκ1 engineered light chain, 1 demonstrated >50% blocking, while 17 demonstrated <50% blocking (5 at 25-50% blocking and 12 at <25% blocking) of Antigen E binding to Ligand Y-labeled beads.

The data of Tables 16 and 17 establish that the rearrangements described in Tables 14 and 15 generated anti-Antigen E-specific common light chain antibodies that blocked binding of Ligand Y to its cognate receptor Antigen E with varying degrees of efficacy, which is consistent with the anti-Antigen E common light chain antibodies of Tables 14 and 15 comprising antibodies with overlapping and non-overlapping epitope specificity with respect to Antigen E.

Example XVII

Determination of Blocking Ability of Antigen-Specific Common Light Chain Antibodies by ELISA Human common light chain antibodies raised against Antigen E were tested for their ability to block Antigen E binding to a Ligand Y-coated surface in an ELISA assay.

Ligand Y was coated onto 96-well plates at a concentration of 2 μg/mL diluted in PBS and incubated overnight followed by washing four times in PBS with 0.05% Tween-20. The plate was then blocked with PBS (Irvine Scientific, Santa Ana, Calif.) containing 0.5% (w/v) BSA (Sigma-Aldrich Corp., St. Louis, Mo.) for one hour at room temperature. In a separate plate, supernatants containing anti-Antigen E common light chain antibodies were diluted 1:10 in buffer. A mock supernatant with the same components of the antibodies was used as a negative control. Antigen E-mmH (described above) was added to a final concentration of 0.150 nM and incubated for one hour at room temperature. The antibody/Antigen E-mmH mixture was then added to the plate containing Ligand Y and incubated for one hour at room temperature. Detection of Antigen E-mmH bound to Ligand Y was determined with Horse-Radish Peroxidase (HRP) conjugated to anti-Penta-His antibody (Qiagen, Valencia, Calif.) and developed by standard calorimetric response using tetramethylbenzidine (TMB) substrate (BD Biosciences, San Jose, Calif.) neutralized by sulfuric acid. Absorbance was read at OD450 for 0.1 sec. Background absorbance of a sample without Antigen E was subtracted from all samples. Percent blocking was calculated by division of the background-subtracted MFI of each sample by the adjusted negative control value, multiplying by 100 and subtracting the resulting value from 100.

Tables 18 and 19 show the percent blocking for all 98 anti-Antigen E common light chain antibodies tested in the ELISA assay. ND: not determined under current experimental conditions.

TABLE 18

| Vκ1-39Jκ5 Common Light Chain Antibodies | |
|---|---|
| Antibody | % Blocking of Antigen E In Solution |
| 2948 | 21.8 |
| 2948G | 22.9 |
| 2949 | 79.5 |
| 2949G | 71.5 |
| 2950 | 80.4 |
| 2950G | 30.9 |
| 2952 | 66.9 |
| 2952G | 47.3 |
| 2954 | 55.9 |
| 2954G | 44.7 |
| 2955 | 12.1 |
| 2955G | 25.6 |
| 2964 | 34.8 |
| 2964G | 47.7 |
| 2978 | 90.0 |
| 2978G | 90.2 |
| 2982 | 59.0 |
| 2982G | 20.4 |
| 2985 | 10.5 |
| 2985G | ND |
| 2987 | 31.4 |
| 2987G | ND |
| 2996 | 29.3 |
| 2996G | ND |
| 2997 | 48.7 |
| 2997G | ND |
| 3004 | 16.7 |
| 3004G | 3.5 |
| 3005 | 87.2 |
| 3005G | 54.3 |
| 3010 | 74.5 |
| 3010G | 84.6 |
| 3011 | 19.4 |
| 3011G | ND |
| 3012 | 45.0 |
| 3012G | 12.6 |
| 3013 | 39.0 |
| 3013G | 9.6 |

TABLE 18-continued Vκ1-39Jκ5
Common Light Chain Antibodies

| Antibody | % Blocking of Antigen E In Solution |
|---|---|
| 3014 | 5.2 |
| 3014G | 17.1 |
| 3015 | 23.7 |
| 3015G | 10.2 |
| 3016 | 78.1 |
| 3016G | 37.4 |
| 3017 | 61.6 |
| 3017G | 25.2 |
| 3018 | 40.6 |
| 3018G | 14.5 |
| 3019 | 94.6 |
| 3019G | 92.3 |
| 3020 | 80.8 |
| 3020G | ND |
| 3021 | 7.6 |
| 3021G | 20.7 |
| 3022 | 2.4 |
| 3022G | 15.0 |
| 3023 | 9.1 |
| 3023G | 19.2 |
| 3024 | 7.5 |
| 3024G | 15.2 |
| 3025 | ND |
| 3025G | 13.9 |
| 3027 | 61.4 |
| 3027G | 82.7 |
| 3028 | 40.3 |
| 3028G | 12.3 |
| 3030 | ND |
| 3030G | 9.5 |
| 3032 | ND |
| 3032G | 13.1 |
| 3033 | 77.1 |
| 3033G | 32.9 |
| 3036 | 17.6 |
| 3036G | 24.6 |
| 3041 | 59.3 |
| 3041G | 30.7 |
| 3042 | 39.9 |
| 3042G | 16.1 |
| 3043 | 57.4 |
| 3043G | 46.1 |

TABLE 19

Vκ3-20Jκ1
Common Light Chain Antibodies

| Antibody | % Blocking of Antigen E In Solution |
|---|---|
| 2968 | 68.9 |
| 2968G | 15.2 |
| 2969 | 10.1 |
| 2969G | 23.6 |
| 2970 | 34.3 |
| 2970G | 41.3 |
| 2971 | 6.3 |
| 2971G | 27.1 |
| 2972 | 9.6 |
| 2972G | 35.7 |
| 2973 | 20.7 |
| 2973G | 23.1 |
| 2974 | ND |
| 2974G | 22.0 |
| 2975 | 8.7 |
| 2975G | 19.2 |
| 2976 | 4.6 |
| 2976G | 26.7 |

As described in this Example, of the 80 common light chain antibodies containing the Vκ1-39Jκ5 engineered light chain tested for their ability to block Antigen E binding to a Ligand Y-coated surface, 22 demonstrated >50% blocking, while 58 demonstrated <50% blocking (20 at 25-50% blocking and 38 at <25% blocking). For the 18 common light chain antibodies containing the Vκ3-20Jκ1 engineered light chain, one demonstrated >50% blocking, while 17 demonstrated <50% blocking (5 at 25-50% blocking and 12 at <25% blocking) of Antigen E binding to a Ligand Y-coated surface.

These results are also consistent with the Antigen E-specific common light chain antibody pool comprising antibodies with overlapping and non-overlapping epitope specificity with respect to Antigen E.

Example XVIII

BIACORE™ Affinity Determination for Antigen-Specific Common Light Chain Antibodies Equilibrium dissociation constants ($K_D$) for selected antibody supernatants were determined by SPR (Surface Plasmon Resonance) using a BIAcore™ T100 instrument (GE Healthcare). All data was obtained using HBS-EP (10 mM HEPES, 150 mM NaCl, 0.3 mM EDTA, 0.05% Surfactant P20, pH 7.4) as both the running and sample buffers, at 25° C. Antibodies were captured from crude supernatant samples on a CM5 sensor chip surface previously derivatized with a high density of anti-human Fc antibodies using standard amine coupling chemistry. During the capture step, supernatants were injected across the anti-human Fc surface at a flow rate of 3 µL/min, for a total of 3 minutes. The capture step was followed by an injection of either running buffer or analyte at a concentration of 100 nM for 2 minutes at a flow rate of 35 µL/min. Dissociation of antigen from the captured antibody was monitored for 6 minutes. The captured antibody was removed by a brief injection of 10 mM glycine, pH 1.5. All sensorgrams were double referenced by subtracting sensorgrams from buffer injections from the analyte sensorgrams, thereby removing artifacts caused by dissociation of the antibody from the capture surface. Binding data for each antibody was fit to a 1:1 binding model with mass transport using BIACORE™ T100 Evaluation software v2.1. Results are shown in Tables 20 and 21.

TABLE 20

Vκ1-39Jκ5
Common Light Chain Antibodies

| Antibody | 100 nM Antigen E | |
|---|---|---|
| | $K_D$ (nM) | $T_{1/2}$ (min) |
| 2948 | 8.83 | 28 |
| 2948G | 95.0 | 1 |
| 2949 | 3.57 | 18 |
| 2949G | 6.37 | 9 |
| 2950 | 4.91 | 17 |
| 2950G | 13.6 | 5 |
| 2952 | 6.25 | 7 |
| 2952G | 7.16 | 4 |
| 2954 | 2.37 | 24 |
| 2954G | 5.30 | 9 |
| 2955 | 14.4 | 6 |
| 2955G | 12.0 | 4 |
| 2964 | 14.8 | 6 |
| 2964G | 13.0 | 9 |
| 2978 | 1.91 | 49 |
| 2978G | 1.80 | 58 |
| 2982 | 6.41 | 19 |
| 2982G | 16.3 | 9 |

TABLE 20-continued

Vκ1-39Jκ5
Common Light Chain Antibodies

| Antibody | 100 nM Antigen E | |
|---|---|---|
| | $K_D$ (nM) | $T_{1/2}$ (min) |
| 2985 | 64.4 | 9 |
| 2985G | 2.44 | 8 |
| 2987 | 21.0 | 11 |
| 2987G | 37.6 | 4 |
| 2996 | 10.8 | 9 |
| 2996G | 24.0 | 2 |
| 2997 | 7.75 | 19 |
| 2997G | 151 | 1 |
| 3004 | 46.5 | 14 |
| 3004G | 1.93 | 91 |
| 3005 | 2.35 | 108 |
| 3005G | 6.96 | 27 |
| 3010 | 4.13 | 26 |
| 3010G | 2.10 | 49 |
| 3011 | 59.1 | 5 |
| 3011G | 41.7 | 5 |
| 3012 | 9.71 | 20 |
| 3012G | 89.9 | 2 |
| 3013 | 20.2 | 20 |
| 3013G | 13.2 | 4 |
| 3014 | 213 | 4 |
| 3014G | 36.8 | 3 |
| 3015 | 29.1 | 11 |
| 3015G | 65.9 | 0 |
| 3016 | 4.99 | 17 |
| 30160 | 18.9 | 4 |
| 3017 | 9.83 | 8 |
| 3017G | 55.4 | 2 |
| 3018 | 11.3 | 36 |
| 3018G | 32.5 | 3 |
| 3019 | 1.54 | 59 |
| 3019G | 2.29 | 42 |
| 3020 | 5.41 | 39 |
| 3020G | 41.9 | 6 |
| 3021 | 50.1 | 6 |
| 3021G | 26.8 | 4 |
| 3022 | 25.7 | 17 |
| 3022G | 20.8 | 12 |
| 3023 | 263 | 9 |
| 3023G | 103 | 5 |
| 3024 | 58.8 | 7 |
| 3024G | 7.09 | 10 |
| 3025 | 35.2 | 6 |
| 3025G | 42.5 | 8 |
| 3027 | 7.15 | 6 |
| 3027G | 4.24 | 18 |
| 3028 | 6.89 | 37 |
| 3028G | 7.23 | 22 |
| 3030 | 46.2 | 7 |
| 3030G | 128 | 3 |
| 3032 | 53.2 | 9 |
| 3032G | 13.0 | 1 |
| 3033 | 4.61 | 17 |
| 3033G | 12.0 | 5 |
| 3036 | 284 | 12 |
| 3036G | 18.2 | 10 |
| 3041 | 6.90 | 12 |
| 3041G | 22.9 | 2 |
| 3042 | 9.46 | 34 |
| 3042G | 85.5 | 3 |
| 3043 | 9.26 | 29 |
| 3043G | 13.1 | 22 |

TABLE 21

Vκ3-20Jκ1
Common Light Chain Antibodies

| Antibody | 100 nM Antigen E | |
|---|---|---|
| | $K_D$ (nM) | $T_{1/2}$ (min) |
| 2968 | 5.50 | 8 |
| 2968G | 305 | 0 |
| 2969 | 34.9 | 2 |
| 2969G | 181 | 1 |
| 2970G | 12.3 | 3 |
| 2971G | 32.8 | 22 |
| 2972 | 6.02 | 13 |
| 2972G | 74.6 | 26 |
| 2973 | 5.35 | 39 |
| 2973G | 11.0 | 44 |
| 2974 | 256 | 0 |
| 2974G | 138 | 0 |
| 2975 | 38.0 | 2 |
| 2975G | 134 | 1 |
| 2976 | 6.73 | 10 |
| 2976G | 656 | 8 |

The binding affinities of common light chain antibodies comprising the rearrangements shown in Tables 14 and 15 vary, with nearly all exhibiting a $K_D$ in the nanomolar range. The affinity data is consistent with the common light chain antibodies resulting from the combinatorial association of rearranged variable domains described in Tables 14 and 15 being high-affinity, clonally selected, and somatically mutated. Coupled with data previously shown, the common light chain antibodies described in Tables 14 and 15 comprise a collection of diverse, high-affinity antibodies that exhibit specificity for one or more epitopes on Antigen E.

Example XIX

Determination of Binding Specificities of Antigen-Specific Common Light Chain Antibodies by LUMINEX™ Assay Selected anti-Antigen E common light chain antibodies were tested for their ability to bind to the ECD of Antigen E and Antigen E ECD variants, including the cynomolgous monkey ortholog (Mf Antigen E), which differs from the human protein in approximately 10% of its amino acid residues; a deletion mutant of Antigen E lacking the last 10 amino acids from the C-terminal end of the ECD (Antigen E-ΔCT); and two mutants containing an alanine substitution at suspected locations of interaction with Ligand Y (Antigen E-Ala1 and AntigenE-Ala2). The Antigen E proteins were produced in CHO cells and each contained a myc-myc-His C-terminal tag.

For the binding studies, Antigen E ECD protein or variant protein (described above) from 1 mL of culture medium was captured by incubation for 2 hr at room temperature with $1\times10^6$ microsphere (Luminex™) beads covalently coated with an anti-myc monoclonal antibody (MAb 9E10, hybridoma cell line CRL-1729™; ATCC, Manassas, Va.). The beads were then washed with PBS before use. Supernatants containing anti-Antigen E common light chain antibodies were diluted 1:4 in buffer and added to 96-well filter plates. A mock supernatant with no antibody was used as negative control. The beads containing the captured Antigen E proteins were then added to the antibody samples (3000 beads per well) and incubated overnight at 4° C. The following day, the sample beads were washed and the bound common light chain antibody was detected with a R-phycoerythrin-conjugated anti-human IgG antibody. The fluorescence intensity of the beads (approximately 100 beads counted for each antibody sample binding to each Antigen E protein) was measured with a Luminex™ flow cytometry-based analyzer, and the median fluorescence intensity (MFI) for at least 100 counted beads per bead/antibody interaction was recorded. Results are shown in Tables 22 and 23.

TABLE 22

Vκ1-39Jκ5 Common Light Chain Antibodies

| Antibody | Mean Fluorescence Intensity (MFI) | | | | |
|---|---|---|---|---|---|
| | Antigen E-ECD | Antigen E-ΔCT | Antigen E-Ala1 | Antigen E-Ala2 | Mf Antigen E |
| 2948 | 1503 | 2746 | 4953 | 3579 | 1648 |
| 2948G | 537 | 662 | 2581 | 2150 | 863 |
| 2949 | 3706 | 4345 | 8169 | 5678 | 5142 |
| 2949G | 3403 | 3318 | 7918 | 5826 | 5514 |
| 2950 | 3296 | 4292 | 7756 | 5171 | 4749 |
| 2950G | 2521 | 2408 | 7532 | 5079 | 3455 |
| 2952 | 3384 | 1619 | 1269 | 168 | 911 |
| 2952G | 3358 | 1001 | 108 | 55 | 244 |
| 2954 | 2808 | 3815 | 7114 | 5039 | 3396 |
| 2954G | 2643 | 2711 | 7620 | 5406 | 3499 |
| 2955 | 1310 | 2472 | 4738 | 3765 | 1637 |
| 2955G | 1324 | 1802 | 4910 | 3755 | 1623 |
| 2964 | 5108 | 1125 | 4185 | 346 | 44 |
| 2964G | 4999 | 729 | 4646 | 534 | 91 |
| 2978 | 6986 | 2800 | 14542 | 10674 | 8049 |
| 2978G | 5464 | 3295 | 11652 | 8026 | 6452 |
| 2982 | 4955 | 2388 | 13200 | 9490 | 6772 |
| 2982G | 3222 | 2013 | 8672 | 6509 | 4949 |
| 2985 | 1358 | 832 | 4986 | 3892 | 1669 |
| 2985G | 43 | 43 | 128 | 244 | 116 |
| 2987 | 3117 | 1674 | 7646 | 5944 | 2546 |
| 2987G | 3068 | 1537 | 9202 | 6004 | 4744 |
| 2996 | 4666 | 1917 | 12875 | 9046 | 6459 |
| 2996G | 2752 | 1736 | 8742 | 6150 | 4873 |
| 2997 | 5164 | 2159 | 12167 | 8361 | 5922 |
| 2997G | 658 | 356 | 3392 | 2325 | 1020 |
| 3004 | 2794 | 1397 | 8542 | 6268 | 3083 |
| 3004G | 2753 | 1508 | 8267 | 5808 | 4345 |
| 3005 | 5683 | 2221 | 12900 | 9864 | 5868 |
| 3005G | 4344 | 2732 | 10669 | 7125 | 5880 |
| 3010 | 4829 | 1617 | 2642 | 3887 | 44 |
| 3010G | 3685 | 1097 | 2540 | 3022 | 51 |
| 3011 | 2859 | 2015 | 7855 | 5513 | 3863 |
| 3011G | 2005 | 1072 | 6194 | 4041 | 3181 |
| 3012 | 3233 | 2221 | 8543 | 5637 | 3307 |
| 3012G | 968 | 378 | 3115 | 2261 | 1198 |
| 3013 | 2343 | 1791 | 6715 | 4810 | 2528 |
| 3013G | 327 | 144 | 1333 | 1225 | 370 |
| 3014 | 1225 | 1089 | 5436 | 3621 | 1718 |
| 3014G | 1585 | 851 | 5178 | 3705 | 2411 |
| 3015 | 3202 | 2068 | 8262 | 5554 | 3796 |
| 3015G | 1243 | 531 | 4246 | 2643 | 1611 |
| 3016 | 4220 | 2543 | 8920 | 5999 | 5666 |
| 3016G | 2519 | 1277 | 6344 | 4288 | 4091 |
| 3017 | 3545 | 2553 | 8700 | 5547 | 5098 |
| 3017G | 1972 | 1081 | 5763 | 3825 | 3038 |
| 3018 | 2339 | 1971 | 6140 | 4515 | 2293 |
| 3018G | 254 | 118 | 978 | 1020 | 345 |
| 3019 | 5235 | 1882 | 7108 | 4249 | 54 |
| 3019G | 4090 | 1270 | 4769 | 3474 | 214 |
| 3020 | 3883 | 3107 | 8591 | 6602 | 4420 |
| 3020G | 2165 | 1209 | 6489 | 4295 | 2912 |
| 3021 | 1961 | 1472 | 6872 | 4641 | 2742 |
| 3021G | 2091 | 1005 | 6430 | 3988 | 2935 |
| 3022 | 2418 | 793 | 7523 | 2679 | 36 |
| 3022G | 2189 | 831 | 6182 | 3051 | 132 |
| 3023 | 1692 | 1411 | 5788 | 3898 | 2054 |
| 3023G | 1770 | 825 | 5702 | 3677 | 2648 |
| 3024 | 1819 | 1467 | 6179 | 4557 | 2450 |
| 3024G | 100 | 87 | 268 | 433 | 131 |
| 3025 | 1853 | 1233 | 6413 | 4337 | 2581 |
| 3025G | 1782 | 791 | 5773 | 3871 | 2717 |
| 3027 | 4131 | 1018 | 582 | 2510 | 22 |

TABLE 22-continued

Vκ1-39Jκ5 Common Light Chain Antibodies

| Antibody | Mean Fluorescence Intensity (MFI) | | | | |
|---|---|---|---|---|---|
| | Antigen E-ECD | Antigen E-ΔCT | Antigen E-Ala1 | Antigen E-Ala2 | Mf Antigen E |
| 3027G | 3492 | 814 | 1933 | 2596 | 42 |
| 3028 | 4361 | 2545 | 9884 | 5639 | 975 |
| 3028G | 2835 | 1398 | 7124 | 3885 | 597 |
| 3030 | 463 | 277 | 1266 | 1130 | 391 |
| 3030G | 943 | 302 | 3420 | 2570 | 1186 |
| 3032 | 2083 | 1496 | 6594 | 4402 | 2405 |
| 3032G | 295 | 106 | 814 | 902 | 292 |
| 3033 | 4409 | 2774 | 8971 | 6331 | 5825 |
| 3033G | 2499 | 1234 | 6745 | 4174 | 4210 |
| 3036 | 1755 | 1362 | 6137 | 4041 | 1987 |
| 3036G | 2313 | 1073 | 6387 | 4243 | 3173 |
| 3041 | 3674 | 2655 | 8629 | 5837 | 4082 |
| 3041G | 2519 | 1265 | 6468 | 4274 | 3320 |
| 3042 | 2653 | 2137 | 7277 | 5124 | 3325 |
| 3042G | 1117 | 463 | 4205 | 2762 | 1519 |
| 3043 | 3036 | 2128 | 7607 | 5532 | 3366 |
| 3043G | 2293 | 1319 | 6573 | 4403 | 3228 |

TABLE 23

Vκ3-20Jκ1 Common Light Chain Antibodies

| Antibody | Mean Fluorescence Intensity (MFI) | | | | |
|---|---|---|---|---|---|
| | Antigen E-ECD | Antigen E-ΔCT | Antigen E-Ala1 | Antigen E-Ala2 | Mf Antigen E |
| 2968 | 6559 | 3454 | 14662 | 3388 | 29 |
| 2968G | 2149 | 375 | 9109 | 129 | 22 |
| 2969 | 2014 | 1857 | 7509 | 5671 | 3021 |
| 2969G | 1347 | 610 | 6133 | 4942 | 2513 |
| 2970 | 5518 | 1324 | 14214 | 607 | 32 |
| 2970G | 4683 | 599 | 12321 | 506 | 31 |
| 2971 | 501 | 490 | 2506 | 2017 | 754 |
| 2971G | 578 | 265 | 2457 | 2062 | 724 |
| 2972 | 2164 | 2158 | 8408 | 6409 | 3166 |
| 2972G | 1730 | 992 | 6364 | 4602 | 2146 |
| 2973 | 3527 | 1148 | 3967 | 44 | 84 |
| 2973G | 1294 | 276 | 1603 | 28 | 44 |
| 2974 | 1766 | 722 | 8821 | 241 | 19 |
| 2974G | 2036 | 228 | 8172 | 135 | 26 |
| 2975 | 1990 | 1476 | 8669 | 6134 | 2468 |
| 2975G | 890 | 315 | 4194 | 3987 | 1376 |
| 2976 | 147 | 140 | 996 | 1079 | 181 |
| 2976G | 1365 | 460 | 6024 | 3929 | 1625 |

The anti-Antigen E common light chain antibody supernatants exhibited high specific binding to the beads linked to Antigen E-ECD. For these beads, the negative control mock supernatant resulted in negligible signal (<10 MFI) when combined with the Antigen E-ECD bead sample, whereas the supernatants containing anti-Antigen E common light chain antibodies exhibited strong binding signal (average MFI of 2627 for 98 antibody supernatants; MFI>500 for 91/98 antibody samples).

As a measure of the ability of the selected anti-Antigen E common light chain antibodies to identify different epitopes on the ECD of Antigen E, the relative binding of the antibodies to the variants were determined. All four Antigen E variants were captured to the anti-myc LUMINEX™ beads as described above for the native Antigen E-ECD binding studies, and the relative binding ratios ($MFI_{variant}/MFI_{Antigen\ E\text{-}ECD}$) were determined. For 98 tested common light chain antibody supernatants shown in Tables 21 and 22, the average ratios ($MFI_{variant}/MFI_{Antigen\ E\text{-}ECD}$) differed for each variant, likely reflecting different capture amounts of proteins on the beads (average ratios of 0.61, 2.9, 2.0, and 1.0 for Antigen E-ΔCT, Antigen E-Ala1, Antigen E-Ala2, and Mf Antigen E, respectively). For each protein variant, the binding for a subset of the 98 tested common light chain antibodies showed greatly reduced binding, indicating sensitivity to the mutation that characterized a given variant. For example, 19 of the common light chain antibody samples bound to the Mf Antigen E with $MFI_{variant}/MFI_{Antigen\ E\text{-}ECD}$ of <8%. Since many in this group include high or moderately high affinity antibodies (5 with $K_D$<5 nM, 15 with $K_D$<50 nM), it is likely that the lower signal for this group results from sensitivity to the sequence (epitope) differences between native Antigen E-ECD and a given variant rather than from lower affinities.

These data establish that the common light chain antibodies described in Tables 14 and 15 represent a diverse group of Antigen-E-specific common light chain antibodies that specifically recognize more than one epitope on Antigen E.

We claim:

1. A male mouse whose germline genome comprises:
(a) an insertion comprising at least one unrearranged human $V_H$ gene segment, at least one unrearranged human $D_H$ gene segment, and at least one unrearranged human $J_H$ gene segment, wherein the at least one unrearranged human $V_H$ gene segment, at least one human $D_H$ gene segment, and at least one unrearranged human $J_H$ gene segment are operably linked to a heavy chain constant region gene, wherein the insertion disrupts the function of an endogenous ADAM6 protein, and wherein the disruption of the endogenous ADAM6 function is associated with a reduction in fertility in male mice;
(b) an insertion comprising no more than one, or no more than two, rearranged human light chain V/J sequences, wherein the no more than one, or no more than two, rearranged human light chain V/J sequences are operably linked to a light chain constant region gene; and,
(c) an insertion comprising an ectopic nucleic acid sequence that encodes a functional mouse ADAM6 protein, wherein the functional mouse ADAM6 protein is expressed and the male mouse has wild-type fertility.

2. The mouse according to claim 1, wherein the ectopic nucleic acid sequence is at a locus other than the immunoglobulin heavy chain variable locus.

3. The mouse according to claim 1, wherein the heavy chain constant region gene is a mouse gene.

4. The mouse according to claim 1, wherein the light chain constant region gene is a mouse gene.

5. A mouse cell obtained from the mouse of claim 1.

6. The mouse cell of claim 5, wherein the heavy chain constant gene is a non-human heavy chain constant gene.

7. The mouse cell of claim 5, wherein the light chain constant gene is a non-human light chain constant gene.

8. The mouse cell of claim 5, wherein the cell is a B cell that expresses:
a chimeric immunoglobulin heavy chain comprising an immunoglobulin heavy chain variable domain that is derived from a rearrangement of one of the at least one unrearranged human $V_H$ gene segment, one of the at least one unrearranged human $D_H$ gene segment, and one of the at least one unrearranged human $J_H$ gene segment, wherein the immunoglobulin heavy chain variable domain is operably linked to a non-human heavy chain constant region; and
a chimeric immunoglobulin light chain comprising an immunoglobulin light chain variable domain that is expressed from one of the no more than one, or no more than two, rearranged human light chain V/J sequences, or a somatically hypermutated variant thereof, and
wherein the immunoglobulin light chain variable domain is fused operably linked to a non-human light chain constant region.

9. The mouse cell of claim 5, wherein the cell is an embryonic stem (ES) cell.

10. The mouse cell of claim 5, wherein the immunoglobulin light chain variable domain is expressed from:
(a) a rearranged human Vκ1-39/Jκ sequence, or
(b) a rearranged human Vκ3-20/Jκ sequence.

11. The mouse cell of claim 10, wherein the rearranged human Vκ1-39/Jκ sequence is a rearranged human Vκ1-39/Jκ5 sequence.

12. The mouse cell of claim 10, wherein the rearranged human Vκ3-20/Jκ sequence is a rearranged human Vκ3-20/Jκ1 sequence.

13. The mouse of claim 1, wherein the no more than one, or no more than two, rearranged human light chain V/J sequences are:
(a) a rearranged human Vκ1-39/Jκ sequence, and/or
(b) a rearranged human Vκ3-20/Jκ sequence.

14. The mouse of claim 13, wherein the rearranged human Vκ1-39/Jκ sequence is a rearranged human Vκ1-39/1κ5 sequence.

15. The mouse of claim 13, wherein the rearranged human Vκ3-20/Jκ sequence is a rearranged human Vκ3-20/Jκ1 sequence.

16. The mouse of claim 1, wherein the mouse lacks an endogenous mouse κ immunoglobulin light chain variable region locus that is capable of rearranging and forming a gene that encodes a mouse κ variable region.

17. The mouse of claim 1, wherein the mouse lacks an endogenous mouse λ immunoglobulin light chain variable region locus that is capable of rearranging and forming a gene that encodes a mouse λ variable region.

18. The mouse of claim 1, wherein the at least one unrearranged human $V_H$ gene segment comprises a gene segment selected from the group consisting of $V_H$1-2, $V_H$1-8, $V_H$1-24, $V_H$1-69, $V_H$2-5, $V_H$3-7, $V_H$3-9, $V_H$3-11, $V_H$3-13, $V_H$3-15, $V_H$3-20, $V_H$3-23, $V_H$3-30, $V_H$3-33, $V_H$3-43, $V_H$3-48, $V_H$4-31, $V_H$4-39, $V_H$4-59, $V_H$5-51 and $V_H$6-1.

19. The mouse of claim 1, wherein the insertion of (b) comprises a single rearranged human light chain V/J sequence, and wherein the single rearranged human light chain V/J sequence is operably linked to a light chain constant region gene.

* * * * *